(12) United States Patent
Woodward et al.

(10) Patent No.: US 10,399,974 B2
(45) Date of Patent: *Sep. 3, 2019

(54) N2-PHENYL-PYRIDO[3,4-D]PYRIMIDINE-2, 8-DIAMINE DERIVATIVES AND THEIR USE AS MPS1 INHIBITORS

(71) Applicant: Cancer Research Technology Limited, London (GB)

(72) Inventors: Hannah Woodward, London (GB); Paolo Innocenti, London (GB); Sebastien Naud, London (GB); Julian Blagg, London (GB); Swen Hoelder, London (GB)

(73) Assignee: Cancer Research Technology Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/861,287

(22) Filed: Jan. 3, 2018

(65) Prior Publication Data

US 2018/0194761 A1    Jul. 12, 2018

Related U.S. Application Data

(63) Continuation of application No. 15/121,432, filed as application No. PCT/GB2015/050590 on Feb. 27, 2015, now Pat. No. 9,902,721.

(30) Foreign Application Priority Data

Feb. 28, 2014   (GB) .................................. 1403536.4

(51) Int. Cl.
*A61K 31/519*   (2006.01)
*C07D 471/04*   (2006.01)
*C07D 519/00*   (2006.01)

(52) U.S. Cl.
CPC .......... *C07D 471/04* (2013.01); *A61K 31/519* (2013.01); *C07D 519/00* (2013.01)

(58) Field of Classification Search
CPC ..................... A61K 31/519; C07D 471/04
USPC ...................... 514/264.11; 544/279
See application file for complete search history.

(56) References Cited

U.S. PATENT DOCUMENTS

| | | | |
|---|---|---|---|
| 2,697,710 A | 12/1954 | Hitchings et al. | |
| 3,021,332 A | 2/1962 | Hitchings et al. | |
| 6,653,332 B2 | 11/2003 | Jaen et al. | |
| 6,831,175 B2 | 12/2004 | Li et al. | |
| 7,939,551 B2 | 5/2011 | Jaen et al. | |
| 9,409,907 B2 | 8/2016 | Hoelder et al. | |
| 9,834,552 B2 | 12/2017 | Hoelder et al. | |
| 9,890,157 B2 * | 2/2018 | Hoelder ............... | C07D 401/14 |
| 9,902,721 B2 * | 2/2018 | Woodward ........... | C07D 519/00 |
| 2003/0073668 A1 | 4/2003 | Booth et al. | |
| 2003/0105115 A1 | 6/2003 | Metcalf et al. | |
| 2004/0092521 A1 | 5/2004 | Altenbach et al. | |
| 2005/0256118 A1 | 11/2005 | Altenbach et al. | |
| 2005/0272728 A1 | 12/2005 | Altenbach et al. | |
| 2011/0257196 A1 | 10/2011 | Lu et al. | |
| 2012/0122838 A1 | 5/2012 | Ren et al. | |
| 2012/0258857 A1 | 10/2012 | Pham et al. | |
| 2015/0031672 A1 | 1/2015 | Ren et al. | |
| 2018/0141944 A1 | 5/2018 | Hoelder et al. | |
| 2018/0194761 A1 | 7/2018 | Woodward et al. | |

FOREIGN PATENT DOCUMENTS

| | | |
|---|---|---|
| EP | 1463505 A2 | 10/2004 |
| JP | 2005/263596 A | 9/2005 |
| JP | 2015/013283 A | 1/2015 |
| WO | WO-1996/015128 A2 | 5/1996 |
| WO | WO-2001/055147 A1 | 8/2001 |
| WO | WO-2002/090360 A1 | 11/2002 |
| WO | WO-2003/051366 A2 | 6/2003 |
| WO | WO-2003/074530 A1 | 9/2003 |
| WO | WO-2004/043458 A1 | 5/2004 |
| WO | WO-2004/065378 A1 | 8/2004 |
| WO | WO-2007/000240 A1 | 1/2007 |
| WO | WO-2007/117607 A2 | 10/2007 |
| WO | WO-2007/125405 A2 | 11/2007 |
| WO | WO-2007/140222 A2 | 12/2007 |
| WO | WO-2008/079988 A2 | 7/2008 |
| WO | WO-2008/135232 A1 | 11/2008 |
| WO | WO-2009/032694 A1 | 3/2009 |
| WO | WO-2009/084695 A1 | 7/2009 |
| WO | WO-2009/103966 A1 | 8/2009 |
| WO | WO-2010/007374 A1 | 1/2010 |
| WO | WO-2010/129816 A2 | 11/2010 |

(Continued)

OTHER PUBLICATIONS

Aguilera et al., "c-Jun N-terminal Phosphorylation Antagonises Recruitment of the Mbd3/NuRD Repressor Complex," Nature, 469(7329): 231-236 (2011).

(Continued)

*Primary Examiner* — Jeffrey H Murray
(74) *Attorney, Agent, or Firm* — Foley Hoag LLP; David P. Halstead; Lucas P. Watkins

(57) ABSTRACT

The present invention relates to compounds of formula I:

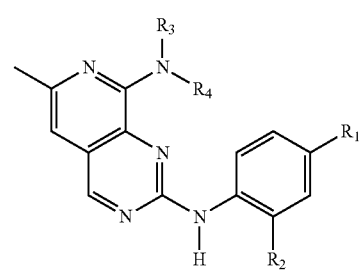

wherein $R_1$, $R_2$, $R_3$ and $R_4$ are all as defined herein. The compounds of the present invention are known to inhibit the spindle checkpoint function of Monospindle 1 (Mps1—also known as TTK) kinases either directly or indirectly via interaction with the Mps1 kinase itself. In particular, the present invention relates to the use of these compounds as therapeutic agents for the treatment and/or prevention of proliferative diseases, such as cancer. The present invention also relates to processes for the preparation of these compounds, and to pharmaceutical compositions comprising them.

4 Claims, No Drawings

(56) References Cited

FOREIGN PATENT DOCUMENTS

| WO | WO-2011/090738 A2 | 7/2011 |
|---|---|---|
| WO | WO-2012/013557 A1 | 2/2012 |
| WO | WO-2012/028756 A1 | 3/2012 |
| WO | WO-2012/052540 A1 | 4/2012 |
| WO | WO-2012/064973 A2 | 5/2012 |
| WO | WO-2012/080284 A2 | 6/2012 |
| WO | WO-2012/088438 A1 | 6/2012 |
| WO | WO-2012/092471 A2 | 7/2012 |
| WO | WO-2012/101032 A1 | 8/2012 |
| WO | WO-2012/123745 A1 | 9/2012 |
| WO | WO-2014/037750 A1 | 3/2014 |
| WO | WO-2014/037751 A1 | 3/2014 |

OTHER PUBLICATIONS

Alajarin et al., "Unprecedented Intramolecular [3+2] Cycloadditions of Azido-ketenimines and Azido-Carboiimides. Synthesis of Indol[1,2-a]quinazolines and Tetrazolo[5,1-b]quinazolines," Org Biomol Chem, 9(19): 6741-6749 (2011).

Balog et al., "Novel fluorescent isoquinoline derivatives obtained via Buchwald-Hartwig coupling of isoquinolin-3-amines", *Arkivoc*, vol. 5, 109-119 (2012).

Bathini et al., "2-Aminoquinazoline inhibitors of cyclin-dependent kinases", *Bioorg. Med. Chem. Lett.* vol. 15(17), 3881-3885 (2005).

Cabarello et al., "2D Autocorrelation, CoMFA, and CoMSIA modeling of protein tyrosine kinases' inhibition by substituted pyrido[2,3-d]pyrimidine derivatives", *Bioorg. Med. Chem.*, vol. 16(2), 810-821 (2008).

Database PubChem Compounds [Online] Dec. 1, 2012, Database accession No. CID 70113665, abstract.

Database PubChem Compounds [Online] Jul. 13, 2005, Database accession No. CID 2000835, abstract.

Database PubChem Compounds [Online] Jul. 13, 2005, Database accession No. CID 2004801, abstract.

Database PubChem Compounds [Online] Jul. 13, 2005, Database accession No. CID 2019230, abstract.

Database PubChem Compounds [Online] Jul. 9, 2005, Database accession No. CID 940974, abstract.

Database PubChem Compounds [Online] Jul. 9, 2005, Database accession No. CID 945107, abstract.

Database PubChem Compounds [Online] Jul. 9, 2005, Database accession No. CID 945815, abstract.

Database PubChem Compounds [Online] NCBI; Dec. 1, 2012 Database accession No. CID 69975764, abstract.

Database PubChem Compounds [Online] NCBI; Sep. 13, 2005, Database accession No. CID 4000352, abstract.

Database Registry [Online] Chemical Abstracts Service, Columbus, Ohio, US; Jan. 19, 2004, Database accession No. 639005-15-5, abstract.

He et al., "Synthesis and SAR of Novel Quinazolines as Potent and Brain-penetrant c-jun N-terminal Kinase (JNK) Inhibitors," Bioorg Med Chem Lett, 21(6): 1719-1723 (2011).

Lainchbury et al., "Discovery of 3-Alkoxyamino-5-(pyridin-2-ylamino)pyrazine-2-carbonitriles as Selective, Orally Bioavailable CHK1 Inhibitors", J. Med. Chem., vol. 55(22), 10229-10240 (2012).

Proisy et al., "Rapid synthesis of 3-aminoisoquinoline-5-sulfonamides using the Buchwald-Hartwig reaction," Synthesis, 4: 561-566 (2009).

Ranjitkar et al., "Affinity-Based Probes Based on Type II Kinase Inhibitors", *J. Am. Chem. Soc.* vol. 134(16), 19017-19025 (2012).

Reader et al., "Structure-Guided Evolution of Potent and Selective CHK1 Inhibitors through Scaffold Morphing," J Med Chem, 54(24): 8328-8342 (2011).

Scifinder Search Report, pp. 1-104, dated Aug. 20, 2012.

Thompson et al., "Synthesis and Structure—Activity Relationships of 7-Substituted 3-(2,6-Dichlorophenyl)-1,6-naphthyridin-2(1H)-ones as Selective Inhibitors of pp. 60", *J. Med. Chem. Lett.*, vol. 43(16), 3134-3147 (2000).

Trumpp-Kallmeyer et al., "Development of a Binding Model to Protein Tyrosine Kinases for Substituted Pyrido[2,3-d]pyrimidine Inhibitors", *J. Med. Chem.*, vol. 41(11), 1752-1763 (1998).

Walton et al., "The Preclinical Pharmacology and Therapeutic Activity of the Novel CHK1 Inhibitor SAR-020106," Mol Cancer Ther, 9: 89 (2010).

Chen et al., "Core-shell $SiO_2$@ LDHs with tuneable size, composition and morphology," Chem Commun, 51(16):3462-3465 (2015).

Chen et al., "Synthesis and characterisation of aqueous miscible organic-layered double hydroxides," J Mater Chem A, 2(36):15102-15110 (2014).

International Search Report and Written Opinion for International Application No. PCT/GB2016/052158 dated Nov. 7, 2016.

* cited by examiner

N2-PHENYL-PYRIDO[3,4-D]PYRIMIDINE-2, 8-DIAMINE DERIVATIVES AND THEIR USE AS MPS1 INHIBITORS

This application is a continuation of U.S. Ser. No. 15/121, 432, filed Aug. 25, 2016, which is the U.S. National Stage of International Patent Application No. PCT/GB2015/050590, filed Feb. 27, 2015, which claims the benefit of and priority to Great Britain Patent Application No. 1403536.4, filed Feb. 28, 2014.

INTRODUCTION

The present invention relates to compounds that inhibit the spindle checkpoint function of monopolar spindle 1 (Mps1—also known as TTK) kinases, either directly or indirectly via interaction with the Mps1 kinase itself. In particular, the present invention relates to compounds for use as therapeutic agents for the treatment and/or prevention of proliferative diseases, such as cancer. The present invention also relates to processes for the preparation of these compounds, and to pharmaceutical compositions comprising them.

BACKGROUND OF THE INVENTION

Cancer is caused by uncontrolled and unregulated cellular proliferation. Precisely what causes a cell to become malignant and proliferate in an uncontrolled and unregulated manner has been the focus of intense research over recent decades. This research has led to the targeting of surveillance mechanisms, such as those responsible for regulating the cell cycle, with anticancer agents. For example, published patent application WO 2009/103966 (CANCER RESEARCH TECHNOLOGY LIMITED) relates to the inhibition of checkpoint kinase 1 (CHK1) kinase function, with bicyclylaryl-aryl-amine compounds, in the treatment of cancer.

The main role of the cell cycle is to enable error-free DNA replication, chromosome segregation and cytokinesis. Surveillance mechanisms, the so-called checkpoint pathways, monitor passage through mitosis at several stages. One of the best characterised is the spindle assembly checkpoint that prevents anaphase onset until the appropriate tension and attachment across kinetochores is achieved (HARDWICK K G, 1998, "The spindle checkpoint", *Trends Genet* 14, 1-4). The majority of proteins involved in the checkpoint exert their functions through protein binding interactions with the involvement of only a small number of kinases (MUSACCHIO A et al, 2007, "The spindle-assembly checkpoint in space and time", Nature Reviews, *Molecular and Cell Biology*, 8, 379-393). A mitotic checkpoint complex (MCC) that contains three checkpoint proteins (Mad2, BubR1/Mad3, Bub3) and the APC/C co-factor, CDC20, concentrates at the kinetochores and acts as a spindle checkpoint effector. Other core proteins required to amplify the checkpoint signal include Mad1 and the kinases Bub1, Mps1 (also known as TTK) and Aurora-B (MUSACCHIO, referenced above).

One of the first components of the spindle assembly checkpoint signal, identified by a genetic screen in budding yeast, was dubbed Mps1 (monopolar spindle 1) for the monopolar spindles produced by Mps1 mutant cells (WEISS E, 1996, "The *Saccharomyces cerevisiae* spindle pole body duplication gene MPS1 is part of a mitotic checkpoint", *J Cell Biol* 132, 111-123), however, it still remains one of the least studied checkpoint components in higher eukaryotes. Subsequently, the Mps1 gene was shown to encode an essential dual-specificity kinase (LAUZE et al, 1995, "Yeast spindle pole body duplication gene MPS1 encodes an essential dual specificity protein kinase", *EMBO J* 14, 1655-1663 and also POCH et al, 1994, "RPK1, an essential yeast protein kinase involved in the regulation of the onset of mitosis, shows homology to mammalian dual-specificity kinases", *Mol Gen Genet* 243, 641-653) conserved from yeast to humans (MILLS et al, 1992, "Expression of TTK, a novel human protein kinase, is associated with cell proliferation", *J Biol Chem* 267, 16000-16006). Mps1 activity peaks at the $G_2$/M transition and is enhanced upon activation of the spindle checkpoint with nocodazole (STUCKE et al, 2002, "Human Mps1 kinase is required for the spindle assembly checkpoint but not for centrosome duplication", *EMBO J* 21, 1723-1732 and also LIU et al, 2003, "Human MPS1 kinase is required for mitotic arrest induced by the loss of CENP-E from kinetochores", *Mol Biol Cell* 14, 1638-1651). The autophosphorylation of Mps1 at Thr676 in the activation loop has been identified and is essential for Mps1 function (MATTISON et al, 2007, "Mps1 activation loop autophosphorylation enhances kinase activity", *J Biol Chem* 282, 30553-30561).

Given the importance of Mps1 in spindle checkpoint activation, the development of Mps1 inhibitors would be an asset, not only as a tool to further investigate its cell cycle-related functions, but also as a form of anticancer treatment. The first generation inhibitors of Mps1 have been described. Cincreasin, caused chromosome mis-segregation and death in yeast cells (DORER et al, 2005, "A small-molecule inhibitor of Mps1 blocks the spindle-checkpoint response to a lack of tension on mitotic chromosomes", *Curr Biol* 15, 1070-1076) and SP600125, a JNK (c-Jun aminoterminal kinase) inhibitor, also disrupts spindle checkpoint function in a JNK-independent manner via the inhibition of Mps1 (SCHMIDT et al, 2005, "Ablation of the spindle assembly checkpoint by a compound targeting Mps1", *EMBO Rep* 6, 866-872). Recently, three small molecule inhibitors of Mps1 were identified (KWIATOWSKI et al, 2010, "Small-molecule kinase inhibitors provide insight into Mps1 cell cycle function", *Nat Chem Biol* 6, 359-368; HEWITT et al, 2010, "Sustained Mps1 activity is required in mitosis to recruit O-Mad2 to the Mad1-C-Mad2 core complex", *J Cell Biol* 190, 25-34; and SANTAGUIDA et al, 2010, "Dissecting the role of MPS1 in chromosome biorientation and the spindle checkpoint through the small molecule inhibitor reversine", *J Cell Biol* 190, 73-87). Chemical inhibition of Mps1 induced premature mitotic exit, gross aneuploidy and death to human cancer cell lines (KWIATOWSKI, above). Mps1 inhibitors AZ3146 and reversine, severely impaired recruitment of Mad1, Mad2 and CENP-E to kinetochores (HEWITT, and SANTAGUIDA, above).

Dysregulation of the mitotic checkpoint is recognised as a feature of the malignant transformation process. Mitotic checkpoint dysfunction in tumors provides an opportunity for developing a therapeutic strategy using small molecules. This is based on the proposition that pharmacologic disruption of an already compromised mitotic checkpoint may selectively sensitize tumors. This observation has led to the hypothesis that inhibition of Mps1 may be of therapeutic benefit.

It is an objective of the present invention to provide compounds that are potent inhibitors of Mps1.

It is a further objective to provide compounds that possess one or more advantageous pharmaceutical properties, such as, for example, advantageous cell and/or in vivo potency, good solubility and/or one or more advantageous DMPK properties (for example, a favourable metabolic stability profile, favourable Cyp inhibition, a favourable hERG profile, a favourable clearance profile, a favourable volume of distribution etc.).

SUMMARY OF THE INVENTION

In one aspect, the present invention provides a compound, or a pharmaceutically acceptable salt or solvate thereof, as defined herein.

In another aspect, the present invention provides a pharmaceutical composition which comprises a compound as defined herein, or a pharmaceutically acceptable salt or solvate thereof, and one or more pharmaceutically acceptable excipients.

In another aspect, the present invention provides a compound as defined herein, or a pharmaceutically acceptable salt or solvate thereof, or a pharmaceutical composition as defined herein for use in therapy.

In another aspect, the present invention provides a compound as defined herein, or a pharmaceutically acceptable salt or solvate thereof, or a pharmaceutical composition as defined herein, for use in the treatment of a proliferative condition.

In another aspect, the present invention provides a compound as defined herein, or a pharmaceutically acceptable salt or solvate thereof, or a pharmaceutical composition as defined herein, for use in the treatment of cancer. In a particular embodiment, the cancer is a human cancer.

In another aspect, the present invention provides a compound as defined herein, or a pharmaceutically acceptable salt or solvate thereof, or a pharmaceutical composition as defined herein, for use in the production of a Mps1 kinase inhibitory effect.

In another aspect, the present invention provides the use of a compound as defined herein, or a pharmaceutically acceptable salt or solvate thereof, in the manufacture of a medicament for use in the treatment of a proliferative condition.

In another aspect, the present invention provides the use of a compound as defined herein, or a pharmaceutically acceptable salt or solvate thereof, in the manufacture of a medicament for use in the treatment of cancer. Suitably, the medicament is for use in the treatment of human cancers.

In another aspect, the present invention provides the use of a compound as defined herein, or a pharmaceutically acceptable salt or solvate thereof, in the manufacture of a medicament for use in the production of an Mps1 kinase inhibitory effect.

In another aspect, the present invention provides a method of inhibiting Mps1 kinase in vitro or in vivo, said method comprising contacting a cell with an effective amount of a compound as defined herein, or a pharmaceutically acceptable salt or solvate thereof.

In another aspect, the present invention provides a method of inhibiting cell proliferation in vitro or in vivo, said method comprising contacting a cell with an effective amount of a compound as defined herein, or a pharmaceutically acceptable salt or solvate thereof.

In another aspect, the present invention provides a method of treating a proliferative disorder in a patient in need of such treatment, said method comprising administering to said patient a therapeutically effective amount of a compound as defined herein, or a pharmaceutically acceptable salt or solvate thereof, or a pharmaceutical composition as defined herein.

In another aspect, the present invention provides a method of treating cancer in a patient in need of such treatment, said method comprising administering to said patient a therapeutically effective amount of a compound as defined herein, or a pharmaceutically acceptable salt or solvate thereof, or a pharmaceutical composition as defined herein.

The present invention further provides a method of synthesising a compound as defined herein, or a pharmaceutically acceptable salt or solvate thereof.

In another aspect, the present invention provides a compound as defined herein, or a pharmaceutically acceptable salt or solvate thereof, obtainable by, or obtained by, or directly obtained by a method of synthesis as defined herein.

In another aspect, the present invention provides novel intermediates defined herein which are suitable for use in any one of the synthetic methods set out herein.

Preferred, suitable, and optional features of any one particular aspect of the present invention are also preferred, suitable, and optional features of any other aspect.

DETAILED DESCRIPTION OF THE INVENTION

Definitions

Unless otherwise stated, the following terms used in the specification and claims have the following meanings set out below.

It is to be appreciated that references to "treating" or "treatment" include prophylaxis as well as the alleviation of established symptoms of a condition. "Treating" or "treatment" of a state, disorder or condition therefore includes: (1) preventing or delaying the appearance of clinical symptoms of the state, disorder or condition developing in a human that may be afflicted with or predisposed to the state, disorder or condition but does not yet experience or display clinical or subclinical symptoms of the state, disorder or condition, (2) inhibiting the state, disorder or condition, i.e., arresting, reducing or delaying the development of the disease or a relapse thereof (in case of maintenance treatment) or at least one clinical or subclinical symptom thereof, or (3) relieving or attenuating the disease, i.e., causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

In this specification the term "alkyl" includes both straight and branched chain alkyl groups. References to individual alkyl groups such as "propyl" are specific for the straight chain version only and references to individual branched chain alkyl groups such as "isopropyl" are specific for the branched chain version only. For example, "(1-6C)alkyl" includes (1-4C)alkyl, (1-3C)alkyl, propyl, isopropyl and t-butyl. A similar convention applies to other radicals, for example "phenyl(1-6C)alkyl" includes phenyl(1-4C)alkyl, benzyl, 1-phenylethyl and 2-phenylethyl.

The term "(m-nC)" or "(m-nC) group" used alone or as a prefix, refers to any group having m to n carbon atoms.

The term "alkylene" is used herein to refer to both straight and branched chain alkylene linker groups. For example, references to (1-4C)alkylene groups include methylene ($—CH_2—$), ethylene ($—CH_2—CH_2—$), propylene ($—CH_2—CH_2—CH_2—$) and butylene ($—CH_2—CH_2—$ CH$_2$—CH$_2$—), as well as branched groups such as, for example, —CH(CH$_3$)—, —C(CH$_3$)$_2$— or —CH$_2$—CH(CH$_3$)—.

The term "(3-8C)cycloalkyl" means a hydrocarbon ring containing from 3 to 8 carbon atoms, for example, cyclopropyl, cyclobutyl, cyclopentyl, cyclohexyl, cycloheptyl or bicycle[2.2.2]octane, bicycle[2.1.1]hexane, bicycle[1.1.1]pentane and bicyclo[2.2.1]heptyl.

The term "(1-8C)heteroalkyl" refers to an alkyl chain comprising 1-8 carbon atoms which additionally comprises one, two or three heteroatoms present within the alkyl chain which are selected from the group consisting of N, O, or S.

The term "halo" refers to fluoro, chloro, bromo and iodo.

The term "fluoroalkyl" is used herein to refer to an alkyl group in which one or more hydrogen atoms have been replaced by fluorine atoms. Examples of fluoroalkyl groups include —CHF$_2$, —CH$_2$CF$_3$, or perfluoroalkyl groups such as —CF$_3$ or —CF$_2$CF$_3$.

The term "fluoroakoxy" is used herein to refer to an alkoxy group in which one or more hydrogen atoms have been replaced by fluorine atoms. Examples of fluoroalkoxy groups include —OCHF$_2$, —OCH$_2$CF$_3$, or perfluoroalkoxy groups such as —OCF$_3$ or —OCF$_2$CF$_3$.

The term "heterocyclyl", "heterocyclic" or "heterocycle" means a non-aromatic saturated or partially saturated monocyclic, fused, bridged, or spiro bicyclic heterocyclic ring system(s). Monocyclic heterocyclic rings contain from about 3 to 12 (suitably from 3 to 7) ring atoms, with from 1 to 5 (suitably 1, 2 or 3) heteroatoms selected from nitrogen, oxygen or sulfur in the ring. Bicyclic heterocycles contain from 7 to 17 member atoms, suitably 7 to 12 member atoms, in the ring. Bicyclic heterocyclic(s) rings may be fused, spiro, or bridged ring systems. Examples of heterocyclic groups include cyclic ethers such as oxiranyl, oxetanyl, tetrahydrofuranyl, dioxanyl, and substituted cyclic ethers. Heterocycles containing nitrogen include, for example, azetidinyl, pyrrolidinyl, piperidinyl, piperazinyl, tetrahydrotriazinyl, tetrahydropyrazolyl, and the like. Typical sulfur containing heterocycles include tetrahydrothienyl, dihydro-1,3-dithiol, tetrahydro-2H-thiopyran, and hexahydrothiepine. Other heterocycles include dihydro-oxathiolyl, tetrahydro-oxazolyl, tetrahydro-oxadiazolyl, tetrahydrodioxazolyl, tetrahydro-oxathiazolyl, hexahydrotriazinyl, tetrahydro-oxazinyl, morpholinyl, thiomorpholinyl, tetrahydropyrimidinyl, dioxolinyl, octahydrobenzofuranyl, octahydrobenzimidazolyl, and octahydrobenzothiazolyl. For heterocycles containing sulfur, the oxidized sulfur heterocycles containing SO or SO$_2$ groups are also included. Examples include the sulfoxide and sulfone forms of tetrahydrothienyl and thiomorpholinyl such as tetrahydrothiene 1,1-dioxide and thiomorpholinyl 1,1-dioxide. A suitable value for a heterocyclyl group which bears 1 or 2 oxo (=O) or thioxo (=S) substituents is, for example, 2-oxopyrrolidinyl, 2-thioxopyrrolidinyl, 2-oxoimidazolidinyl, 2-thioxoimidazolidinyl, 2-oxopiperidinyl, 2,5-dioxopyrrolidinyl, 2,5-dioxoimidazolidinyl or 2,6-dioxopiperidinyl. Particular heterocyclyl groups are saturated monocyclic 3 to 7 membered heterocyclyls containing 1, 2 or 3 heteroatoms selected from nitrogen, oxygen or sulfur, for example azetidinyl, tetrahydrofuranyl, tetrahydropyranyl, pyrrolidinyl, morpholinyl, tetrahydrothienyl, tetrahydrothienyl 1,1-dioxide, thiomorpholinyl, thiomorpholinyl 1,1-dioxide, piperidinyl, homopiperidinyl, piperazinyl or homopiperazinyl. As the skilled person would appreciate, any heterocycle may be linked to another group via any suitable atom, such as via a carbon or nitrogen atom. However, reference herein to piperidino or morpholino refers to a piperidin-1-yl or morpholin-4-yl ring that is linked via the ring nitrogen.

By "bridged ring systems" is meant ring systems in which two rings share more than two atoms, see for example *Advanced Organic Chemistry*, by Jerry March, 4$^{th}$ Edition, Wiley Interscience, pages 131-133, 1992. Examples of bridged heterocyclyl ring systems include, aza-bicyclo[2.2.1]heptane, 2-oxa-5-azabicyclo[2.2.1]heptane, aza-bicyclo[2.2.2]octane, aza-bicyclo[3.2.1]octane and quinuclidine.

By "spiro bi-cyclic ring systems" we mean that the two ring systems share one common spiro carbon atom, i.e. the heterocyclic ring is linked to a further carbocyclic or heterocyclic ring through a single common spiro carbon atom. Examples of spiro ring systems include 6-azaspiro[3.4]octane, 2-oxa-6-azaspiro[3.4]octane, 2-azaspiro[3.3]heptanes, 2-oxa-6-azaspiro[3.3]heptanes, 7-oxa-2-azaspiro[3.5]nonane, 6-oxa-2-azaspiro[3.4]octane, 2-oxa-7-azaspiro[3.5]nonane and 2-oxa-6-azaspiro[3.5]nonane.

"Heterocyclyl(m-nC)alkyl" means a heterocyclyl group covalently attached to a (m-nC)alkylene group, both of which are defined herein.

The term "heteroaryl" or "heteroaromatic" means an aromatic mono-, bi-, or polycyclic ring incorporating one or more (for example 1-4, particularly 1, 2 or 3) heteroatoms selected from nitrogen, oxygen or sulfur. Examples of heteroaryl groups are monocyclic and bicyclic groups containing from five to twelve ring members, and more usually from five to ten ring members. The heteroaryl group can be, for example, a 5- or 6-membered monocyclic ring or a 9- or 10-membered bicyclic ring, for example a bicyclic structure formed from fused five and six membered rings or two fused six membered rings. Each ring may contain up to about four heteroatoms typically selected from nitrogen, sulfur and oxygen. Typically the heteroaryl ring will contain up to 3 heteroatoms, more usually up to 2, for example a single heteroatom. In one embodiment, the heteroaryl ring contains at least one ring nitrogen atom. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of heteroaryl include furyl, pyrrolyl, thienyl, oxazolyl, isoxazolyl, imidazolyl, pyrazolyl, thiazolyl, isothiazolyl, oxadiazolyl, thiadiazolyl, triazolyl, tetrazolyl, pyridyl, pyridazinyl, pyrimidinyl, pyrazinyl, 1,3,5-triazenyl, benzofuranyl, indolyl, isoindolyl, benzothienyl, benzoxazolyl, benzimidazolyl, benzothiazolyl, benzothiazolyl, indazolyl, purinyl, benzofurazanyl, quinolyl, isoquinolyl, quinazolinyl, quinoxalinyl, cinnolinyl, pteridinyl, naphthyridinyl, carbazolyl, phenazinyl, benzisoquinolinyl, pyridopyrazinyl, thieno[2,3-b]furanyl, 2H-furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl. "Heteroaryl" also covers partially aromatic bi- or polycyclic ring systems wherein at least one ring is an aromatic ring and one or more of the other ring(s) is a non-aromatic, saturated or partially saturated ring, provided at least one ring contains one or more heteroatoms selected from nitrogen, oxygen or sulfur. Examples of partially aromatic heteroaryl groups include for example, tetrahydroisoquinolinyl, tetrahydroquinolinyl, 2-oxo-1,2,3,4-tetrahydroquinolinyl, dihydrobenzthienyl, dihydrobenzfuranyl, 2,3-dihydro-benzo[1,4]dioxinyl, benzo[1,3]dioxolyl, 2,2-dioxo-1,3-dihydro-2-benzothienyl, 4,5,6,7-tetrahydrobenzofuranyl, indolinyl, 1,2,3,4-tetrahydro-1,8-naphthyridinyl, 1,2,3,4-tetrahydropyrido[2,3-b]pyrazinyl and 3,4-dihydro-2H-pyrido[3,2-b][1,4]oxazinyl.

Examples of five membered heteroaryl groups include but are not limited to pyrrolyl, furanyl, thienyl, imidazolyl, furazanyl, oxazolyl, oxadiazolyl, oxatriazolyl, isoxazolyl, thiazolyl, isothiazolyl, pyrazolyl, triazolyl and tetrazolyl groups.

Examples of six membered heteroaryl groups include but are not limited to pyridyl, pyrazinyl, pyridazinyl, pyrimidinyl and triazinyl.

A bicyclic heteroaryl group may be, for example, a group selected from:
a) a benzene ring fused to a 5- or 6-membered ring containing 1, 2 or 3 ring heteroatoms;
b) a pyridine ring fused to a 5- or 6-membered ring containing 1, 2 or 3 ring heteroatoms;
c) a pyrimidine ring fused to a 5- or 6-membered ring containing 1 or 2 ring heteroatoms;
d) a pyrrole ring fused to a 5- or 6-membered ring containing 1, 2 or 3 ring heteroatoms;
e) a pyrazole ring fused to a 5- or 6-membered ring containing 1 or 2 ring heteroatoms;
f) a pyrazine ring fused to a 5- or 6-membered ring containing 1 or 2 ring heteroatoms;
g) an imidazole ring fused to a 5- or 6-membered ring containing 1 or 2 ring heteroatoms;
h) an oxazole ring fused to a 5- or 6-membered ring containing 1 or 2 ring heteroatoms;
i) an isoxazole ring fused to a 5- or 6-membered ring containing 1 or 2 ring heteroatoms;
j) a thiazole ring fused to a 5- or 6-membered ring containing 1 or 2 ring heteroatoms;
k) an isothiazole ring fused to a 5- or 6-membered ring containing 1 or 2 ring heteroatoms;
l) a thiophene ring fused to a 5- or 6-membered ring containing 1, 2 or 3 ring heteroatoms;
m) a furan ring fused to a 5- or 6-membered ring containing 1, 2 or 3 ring heteroatoms;
n) a cyclohexyl ring fused to a 5- or 6-membered heteroaromatic ring containing 1, 2 or 3 ring heteroatoms; and
o) a cyclopentyl ring fused to a 5- or 6-membered heteroaromatic ring containing 1, 2 or 3 ring heteroatoms.

Particular examples of bicyclic heteroaryl groups containing a six membered ring fused to a five membered ring include but are not limited to benzofuranyl, benzothiophenyl, benzimidazolyl, benzoxazolyl, benzisoxazolyl, benzothiazolyl, benzisothiazolyl, isobenzofuranyl, indolyl, isoindolyl, indolizinyl, indolinyl, isoindolinyl, purinyl (e.g., adeninyl, guaninyl), indazolyl, benzodioxolyl, pyrrolopyridine, and pyrazolopyridinyl groups.

Particular examples of bicyclic heteroaryl groups containing two fused six membered rings include but are not limited to quinolinyl, isoquinolinyl, chromanyl, thiochromanyl, chromenyl, isochromenyl, chromanyl, isochromanyl, benzodioxanyl, quinolizinyl, benzoxazinyl, benzodiazinyl, pyridopyridinyl, quinoxalinyl, quinazolinyl, cinnolinyl, phthalazinyl, naphthyridinyl and pteridinyl groups.

"Heteroaryl(m-nC)alkyl" means a heteroaryl group covalently attached to a (m-nC)alkylene group, both of which are defined herein. Examples of heteroaralkyl groups include pyridin-3-ylmethyl, 3-(benzofuran-2-yl)propyl, and the like.

The term "aryl" means a cyclic or polycyclic aromatic ring having from 5 to 12 carbon atoms. The term aryl includes both monovalent species and divalent species. Examples of aryl groups include, but are not limited to, phenyl, biphenyl, naphthyl and the like. In particular embodiment, an aryl is phenyl.

The term "aryl(m-nC)alkyl" means an aryl group covalently attached to a (m-nC)alkylene group, both of which are defined herein. Examples of aryl-(m-nC)alkyl groups include benzyl, phenylethyl, and the like.

This specification also makes use of several composite terms to describe groups comprising more than one functionality. Such terms will be understood by a person skilled in the art. For example heterocyclyl(m-nC)alkyl comprises (m-nC)alkyl substituted by heterocyclyl.

The term "optionally substituted" refers to either groups, structures, or molecules that are substituted and those that are not substituted.

Where optional substituents are chosen from "one or more" groups it is to be understood that this definition includes all substituents being chosen from one of the specified groups or the substituents being chosen from two or more of the specified groups.

The phrase "compound of the invention" means those compounds which are disclosed herein, both generically and specifically.

Compounds of the Invention

In one aspect, the present invention provides a compound of formula I shown below:

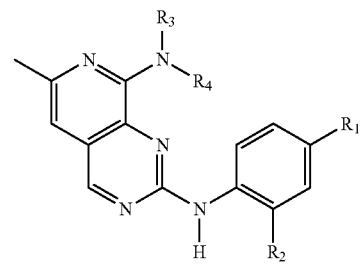

I wherein:
$R_1$ is selected from:
(i) a 5- or 6-membered heteroaryl optionally substituted with one or more substituents independently selected from halo, trifluoromethyl, difluoromethyl, trifluoromethoxy, difluoromethoxy, cyano, nitro, (1-4C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$,
wherein $R_a$ and $R_b$ are each independently selected from H or (1-4C)alkyl, and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, $NR_cR_d$, $OR_c$, $C(O)R_c$, $C(O)OR_c$, $OC(O)R_c$, $N(R_d)OR_c$, $C(O)N(R_d)R_c$, $N(R_d)C(O)R_c$, $S(O)_qR_c$ (where q is 0, 1 or 2), $SO_2N(R_d)R_c$, or $N(R_d)SO_2R_c$, wherein $R_c$ and $R_d$ are each independently selected from H or (1-4C)alkyl;
or
wherein the 5- or 6-membered heteroaryl is optionally fused to a 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-4C)alkyl, $NR_kR_l$, $OR_k$, $C(O)R_k$, $C(O)OR_k$, OC(O)

$R_k$, $N(R_l)OR_k$, $C(O)N(R_l)R_k$, $N(R_l)C(O)R_k$, $S(O)_pR_k$ (where p is 0, 1 or 2), $SO_2N(R_k)R_l$, or $N(R_k)SO_2R_l$, wherein $R_k$ and $R_l$ are each independently selected from H or (1-4C)alkyl, and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, $NR_mR_n$, $OR_m$, $C(O)R_m$, $C(O)OR_m$, $OC(O)R_m$, $N(R_n)OR_m$, $C(O)N(R_n)R_m$, $N(R_n)C(O)R_m$, $S(O)_qR_m$ (where q is 0, 1 or 2), $SO_2N(R_n)R_m$, or $N(R_n)SO_2R_m$, wherein $R_m$ and $R_n$ are each independently selected from H or (1-4C)alkyl; or (ii) a group —$C(O)N(R_f)R_e$— or —$S(O)_2N(R_f)R_e$—;
wherein $R_e$ and $R_f$ are each independently selected from H or (1-4C)alkyl which is optionally substituted by halo or (1-2C)alkoxy;

or $R_e$ and $R_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-4C)alkyl, $NR_gR_h$, $OR_g$, $C(O)R_g$, $C(O)OR_g$, $OC(O)R_g$, $N(R_h)OR_g$, $C(O)N(R_h)R_g$, $N(R_h)C(O)R_g$, $S(O)_pR_h$ (where p is 0, 1 or 2), $SO_2N(R_h)R_g$, or $N(R_h)SO_2R_g$, wherein $R_g$ and $R_h$ are each independently selected from H or (1-4C)alkyl;

$R_2$ is selected from hydrogen, fluoro, chloro, (1-3C)alkoxy or (1-3C)fluoroalkoxy; and either:

(i) $R_3$ is selected from hydrogen or (1-3C)alkyl and $R_4$ is selected from (1-6C)alkyl, (3-9C)cycloalkyl, (3-9C)cycloalkyl-(1-4C)alkyl, aryl, aryl-(1-4C)alkyl, heterocyclyl, heterocyclyl-(1-4C)alkyl, heteroaryl, heteroaryl-(1-4C)alkyl, and wherein $R_4$ is optionally further substituted by one or more substituents selected from hydroxy, fluoro, chloro, cyano, $CF_3$, $CHF_2$, $OCF_3$, $OCHF_2$, (1-4C)alkyl, $NR_oR_p$, $OR_o$, $C(O)R_o$, $C(O)OR_p$, $OC(O)R_o$, $N(R_p)OR_o$, $C(O)N(R_p)R_o$, $N(R_p)C(O)R_o$, $S(O)_pR_o$ (where p is 0, 1 or 2), $SO_2N(R_p)R_o$, or $N(R_p)SO_2R_o$ or (3-6C)cycloalkyl, (3-6C)cycloalkyl-(1-2C)alkyl, a 4, 5 or 6-membered heterocyclyl, a 4, 5 or 6-membered heterocyclyl-(1-2C)alkyl, wherein $R_o$ and $R_p$ are each independently selected from H or (1-4C)alkyl, (3-6C)cycloalkyl or (3-6C)cycloalkyl-(1-4C)alkyl; or (ii) $R_3$ and $R_4$ are linked such that, together with the nitrogen atom to which they are attached, they form a nitrogen-linked 4-, 5-6- or 7-membered heterocyclic ring, wherein said ring is optionally fused to a further 3-, 4-, 5- or 6-membered ring carbocyclic or heterocyclic ring, a 5- or 6-membered heteroaryl ring or a phenyl ring to form a bi-cyclic heterocyclic system, or linked through a spiro carbon atom to a further 4-, 5- or 6-membered ring carbocyclic or heterocyclic ring to form a spiro bicyclic ring system; and wherein the heterocyclic ring, bicyclic ring system or spiro bicyclic ring system is optionally substituted by one or more substituents independently selected from halo, trifluoromethyl, difluoromethyl, trifluoromethoxy, difluoromethoxy, cyano, nitro, (1-4C)alkyl, $NR_iR_j$, $OR_i$, $C(O)R_i$, $C(O)OR_i$, $OC(O)R_i$, $N(R_j)OR_i$, $C(O)N(R_j)R_i$, $N(R_j)C(O)R_i$, $S(O)_qR_i$ (where q is 0, 1 or 2), $SO_2N(R_j)R_i$, or $N(R_j)SO_2R_i$, wherein $R_i$ and $R_j$ are each independently selected from H or (1-4C)alkyl;

or a pharmaceutically acceptable salt or solvate thereof.

In an embodiment, the compound is a compound of formula I defined herein with the proviso that said compound is not one of the following:

N2-(2-methoxy-4-(1-methyl-1H-pyrazol-4-yl)phenyl)-6-methyl-N8-neopentylpyrido[3,4-d]pyrimidine-2,8-diamine;

N2-(4-(1,2-dimethyl-1H-imidazol-5-yl)-2-methoxyphenyl)-N8-(2-methoxy-2-methylpropyl)-6-methylpyrido[3,4-d]pyrimidine-2,8-diamine;

N2-(4-(1,2-dimethyl-1H-imidazol-5-yl)-2-methoxyphenyl)-6-methyl-N8-neopentylpyrido[3,4-d]pyrimidine-2,8-diamine;

N2-(2-methoxy-4-(4-methyl-4H-1,2,4-triazol-3-yl)phenyl)-6-methyl-N8-neopentylpyrido[3,4-d]pyrimidine-2,8-diamine;

N8-(2-methoxy-2-methylpropyl)-N2-(2-methoxy-4-(4-methyl-4H-1,2,4-triazol-3-yl)phenyl)-6-methylpyrido[3,4-d]pyrimidine-2,8-diamine;

N2-(2-methoxy-4-(1-(2-methoxyethyl)-2-methyl-1H-imidazol-5-yl)phenyl)-6-methyl-N8-neopentylpyrido[3,4-d]pyrimidine-2,8-diamine;

N2-(2-ethoxy-4-(4-methyl-4H-1,2,4-triazol-3-yl)phenyl)-6-methyl-N8-neopentylpyrido[3,4-d]pyrimidine-2,8-diamine;

N2-(2-methoxy-4-(4-(methylsulfonyl)piperazin-1-yl)phenyl)-6-methyl-N8-neopentylpyrido[3,4-d]pyrimidine-2,8-diamine;

N2-(4-(1,3-dimethyl-1H-pyrazol-4-yl)-2-methoxyphenyl)-N8-(2-methoxy-2-methylpropyl)-6-methylpyrido[3,4-d]pyrimidine-2,8-diamine;

N-(2-ethoxy-4-(4-methyl-4H-1,2,4-triazol-3-yl)phenyl)-6-methyl-8-(6-oxa-2-azaspiro[3.4]octan-2-yl)pyrido[3,4-d]pyrimidin-2-amine;

N8-(2-methoxy-2-methylpropyl)-N2-(2-methoxy-4-(1-methyl-1H-1,2,4-triazol-5-yl)phenyl)-6-methylpyrido[3,4-d]pyrimidine-2,8-diamine;

N2-(2-(difluoromethoxy)-4-(1-methyl-1H-pyrazol-4-yl)phenyl)-N8-(2-methoxy-2-methylpropyl)-6-methylpyrido[3,4-d]pyrimidine-2,8-diamine;

(4-(3-methoxy-4-((8-((2-methoxy-2-methylpropyl)amino)-6-methylpyrido[3,4-d]pyrimidin-2-yl)amino)phenyl)-1-methyl-1H-pyrazol-5-yl)methanol.

Particular compounds of the invention include, for example, compounds of the formula I, or pharmaceutically acceptable salts or solvates thereof, wherein, unless otherwise stated, each of $R_1$, $R_2$, $R_3$, $R_4$ or $R_{a-o}$ has any of the meanings defined hereinbefore or in any one of paragraphs (1) to (58) hereinafter:—

(1) $R_1$ is selected from:
(i) a 5- or 6-membered heteroaryl optionally substituted with one or more substituents independently selected from halo, trifluoromethyl, difluoromethyl, trifluoromethoxy, difluoromethoxy, cyano, nitro, (1-2C)alkyl, $NR_aR_b$, $OR_a$, $C(O)R_a$, $C(O)OR_a$, $OC(O)R_a$, $N(R_b)OR_a$, $C(O)N(R_b)R_a$, $N(R_b)C(O)R_a$, $S(O)_pR_a$ (where p is 0, 1 or 2), $SO_2N(R_b)R_a$, or $N(R_b)SO_2R_a$, wherein $R_a$ and $R_b$ are each independently selected from H or (1-2C)alkyl, and wherein any alkyl moiety present in the substituent group is optionally further substituted with one or more substituents selected from halo, trifluoromethyl, trifluoromethoxy, difluoromethoxy, cyano, (1-2C)alkyl, 4-7-membered heterocyclyl, $NR_cR_d$, $OR_c$, $C(O)R_c$, $C(O)OR_c$, $OC(O)R_c$, $N(R_d)OR_c$, $C(O)N(R_d)R_c$, N(R$_d$)C(O)R$_c$, S(O)$_q$R$_c$ (where q is 0, 1 or 2), SO$_2$N(R$_d$)R$_c$, or N(R$_d$)SO$_2$R$_c$, wherein R$_c$ and R$_d$ are each independently selected from H or (1-2C)alkyl; or wherein the 5- or 6-membered heteroaryl is optionally fused to a 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-2C)alkyl, NR$_k$R$_l$, OR$_k$, C(O)R$_k$, C(O)OR$_k$, OC(O)R$_k$, N(R$_l$)OR$_k$, C(O)N(R$_l$)R$_k$, N(R$_l$)C(O)R$_k$, S(O)$_p$R$_k$ (where p is 0, 1 or 2), SO$_2$N(R$_k$)R$_l$, or N(R$_k$)SO$_2$R$_l$, wherein R$_k$ and R$_l$ are each independently selected from H or (1-2C)alkyl, and wherein any alkyl moiety present in the substituent group is optionally further substituted with one or more substituents selected from halo, trifluoromethyl, difluoromethyl, trifluoromethoxy, difluoromethoxy, cyano, nitro, (1-2C)alkyl, NR$_m$R$_n$, OR$_m$, C(O)R$_m$, C(O)OR$_m$, OC(O)R$_m$, N(R$_n$)OR$_m$, C(O)N(R$_n$)R$_m$, N(R$_n$)C(O)R$_m$, S(O)$_q$R$_m$ (where q is 0, 1 or 2), SO$_2$N(R$_n$)R$_m$, or N(R$_n$)SO$_2$R$_m$, wherein R$_m$ and R$_n$ are each independently selected from H or (1-2C)alkyl;

(ii) a group —C(O)N(R$_f$)R$_e$— or —S(O)$_2$N(R$_f$)R$_e$—;
wherein R$_e$ and R$_f$ are each independently selected from H or (1-4C)alkyl which is optionally substituted by halo or (1-2C)alkoxy;

or R$_e$ and R$_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-2C)alkyl, NR$_g$R$_h$, OR$_g$, C(O)R$_g$, C(O)OR$_g$, OC(O)R$_g$, N(R$_h$)OR$_g$, C(O)N(R$_h$)R$_g$, N(R$_h$)C(O)R$_g$, S(O)$_p$R$_h$ (where p is 0, 1 or 2), SO$_2$N(R$_h$)R$_g$, or N(R$_h$)SO$_2$R$_g$, wherein R$_g$ and R$_h$ are each independently selected from H or (1-2C)alkyl;

(2) R$_1$ is selected from:
(i) a 5- or 6-membered heteroaryl optionally substituted with one or more substituents independently selected from halo, trifluoromethyl, difluoromethyl, trifluoromethoxy, difluoromethoxy, cyano, nitro, (1-2C)alkyl, NR$_a$R$_b$, OR$_a$, C(O)R$_a$, C(O)OR$_a$, OC(O)R$_a$, N(R$_b$)OR$_a$, C(O)N(R$_b$)R$_a$, N(R$_b$)C(O)R$_a$, S(O)$_p$R$_a$ (where p is 0, 1 or 2), SO$_2$N(R$_b$)R$_a$, or N(R$_b$)SO$_2$R$_a$,
wherein R$_a$ and R$_b$ are each independently selected from H or (1-2C)alkyl;
and wherein any alkyl moiety present in the substituent group is optionally further substituted with one or more substituents selected from halo, cyano, NR$_c$R$_d$, OR$_c$, or S(O)$_q$R$_c$ (where q is 0, 1 or 2), wherein R$_c$ and R$_d$ are each independently selected from H or (1-2C)alkyl;
or
wherein the 5- or 6-membered heteroaryl is optionally fused to a 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-2C)alkyl, NR$_k$R$_l$, OR$_k$, C(O)R$_k$, C(O)OR$_k$, OC(O)R$_k$, N(R$_l$)OR$_k$, C(O)N(R$_l$)R$_k$, N(R$_l$)C(O)R$_k$, S(O)$_p$R$_k$ (where p is 0, 1 or 2), SO$_2$N(R$_k$)R$_l$, or N(R$_k$)SO$_2$R$_l$, wherein R$_k$ and R$_l$ are each independently selected from H or (1-2C)alkyl;

(ii) a group —C(O)N(R$_f$)R$_e$— or —S(O)$_2$N(R$_f$)R$_e$—;
wherein R$_e$ and R$_f$ are each independently selected from H or (1-4C)alkyl which is optionally substituted by halo or (1-2C)alkoxy;
or R$_e$ and R$_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-2C)alkyl, NR$_g$R$_h$, OR$_g$, C(O)R$_g$, C(O)OR$_g$, OC(O)R$_g$, N(R$_h$)OR$_g$, C(O)N(R$_h$)R$_g$, N(R$_h$)C(O)R$_g$, S(O)$_p$R$_h$ (where p is 0, 1 or 2), SO$_2$N(R$_h$)R$_g$, or N(R$_h$)SO$_2$R$_g$, wherein R$_g$ and R$_h$ are each independently selected from H or (1-2C)alkyl;

(3) R$_1$ is selected from:
(i) a 5- or 6-membered heteroaryl optionally substituted with one or more substituents independently selected from halo, trifluoromethyl, difluoromethyl, trifluoromethoxy, difluoromethoxy, cyano, nitro, (1-2C)alkyl, NR$_a$R$_b$, OR$_a$, C(O)R$_a$, or S(O)$_p$R$_a$ (where p is 0, 1 or 2),
wherein R$_a$ and R$_b$ are each independently selected from H or (1-2C)alky, and wherein any alkyl moiety present in the substituent group is optionally further substituted with one or more substituents selected from OR$_c$,
wherein R$_c$ and R$_d$ are each independently selected from H or (1-2C)alkyl; or
wherein the 5- or 6-membered heteroaryl is optionally fused to a 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-2C)alkyl, NR$_k$R$_l$, OR$_k$, C(O)R$_k$, or S(O)$_p$R$_k$ (where p is 0, 1 or 2), wherein R$_k$ and R$_l$ are each independently selected from H or (1-2C)alkyl;

(ii) a group —C(O)N(R$_f$)R$_e$— or —S(O)$_2$N(R$_f$)R$_e$—;
wherein R$_e$ and R$_f$ are each independently selected from H or (1-2C)alkyl; or R$_e$ and R$_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-2C)alkyl, NR$_g$R$_h$, OR$_g$, C(O)R$_g$, or S(O)$_p$R$_h$ (where p is 0, 1 or 2), wherein R$_g$ and R$_h$ are each independently selected from H or (1-2C)alkyl;

(4) R$_1$ is selected from:
(i) a 5- or 6-membered heteroaryl optionally substituted with one or more substituents independently selected from halo, trifluoromethyl, difluoromethyl, trifluoromethoxy, difluoromethoxy, cyano, (1-2C)alkyl, NR$_a$R$_b$, or OR$_a$, wherein R$_a$ and R$_b$ are each independently selected from H or (1-2C)alkyl, and wherein any alkyl moiety present in the substituent group is optionally further substituted with one or more substituents selected from OR$_c$, wherein R$_c$ and R$_d$ are each independently selected from H or (1-2C)alkyl; or
wherein the 5- or 6-membered heteroaryl is optionally fused to a 4-, 5-, or 6-membered heterocyclic ring, wherein the fused ring system is optionally substituted by one or more substituents independently selected from halo, trifluoromethyl, difluoromethyl, trifluoromethoxy, difluoromethoxy, cyano, (1-2C)alkyl, $NR_kR_l$, or $OR_k$, wherein $R_k$ and $R_l$ are each independently selected from H or (1-2C)alkyl;

(ii) a group —C(O)N($R_f$)$R_e$— or —S(O)$_2$N($R_f$)$R_e$—;

wherein $R_e$ and $R_f$ are each independently selected from H or (1-2C)alkyl; or $R_e$ and $R_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-2C)alkyl, $NR_gR_h$, or $OR_g$, wherein $R_g$ and $R_h$ are each independently selected from H or (1-2C)alkyl;

(5) $R_1$ is selected from:
(i) a 5- or 6-membered heteroaryl comprising 1, 2, 3 or 4 nitrogen atoms or 1 or 2 nitrogen atoms and one oxygen atom, said heteroaryl being optionally substituted with one or more substituents independently selected from halo, trifluoromethyl, difluoromethyl, trifluoromethoxy, difluoromethoxy, cyano, (1-2C)alkyl, $NR_aR_b$, or $OR_a$, wherein $R_a$ and $R_b$ are each independently selected from H or (1-2C)alkyl, and wherein any alkyl moiety present in the substituent group is optionally further substituted with one or more substituents selected from $OR_c$, wherein $R_c$ and $R_d$ are each independently selected from H or (1-2C)alkyl; or
wherein the 5- or 6-membered heteroaryl is optionally fused to a 4-, 5-, or 6-membered heterocyclic ring, wherein the fused ring system is optionally substituted by one or more substituents independently selected from halo, trifluoromethyl, difluoromethyl, trifluoromethoxy, difluoromethoxy, cyano, (1-2C) alkyl, $NR_kR_l$, or $OR_k$, wherein $R_k$ and $R_l$ are each independently selected from H or (1-2C)alkyl;
(ii) a group —C(O)N($R_f$)$R_e$— or —S(O)$_2$N($R_f$)$R_e$—;
wherein $R_e$ and $R_f$ are each independently selected from H or (1-2C)alkyl; or $R_e$ and $R_f$ are linked such that, together with the nitrogen atom to which they are attached, they form a 4-, 5- or 6-membered heterocyclic ring comprising one or two further heteroatoms selected from N, O or S, wherein said ring is optionally substituted with one or more substituents independently selected from halo, trifluoromethyl, difluoromethyl, trifluoromethoxy, difluoromethoxy, cyano, nitro, (1-2C)alkyl, $NR_gR_h$, or $OR_g$, wherein $R_g$ and $R_h$ are each independently selected from H or (1-2C)alkyl;

(6) $R_1$ is selected from:
(i) a 5-membered heteroaryl optionally substituted with one or more substituents independently selected from halo, trifluoromethyl, difluoromethyl, trifluoromethoxy, difluoromethoxy, cyano, (1-2C)alkyl, $NR_aR_b$, or $OR_a$, wherein $R_a$ and $R_b$ are each independently selected from H or (1-2C)alkyl, and wherein any alkyl moiety present in the substituent group is optionally further substituted with one or more substituents selected from $OR_c$, wherein $R_c$ and $R_d$ are each independently selected from H or (1-2C)alkyl; or
wherein the 5-membered heteroaryl is optionally fused to a 4-, 5-, or 6-membered heterocyclic ring, wherein the fused ring system is optionally substituted by one or more substituents independently selected from halo, trifluoromethyl, difluoromethyl, trifluoromethoxy, difluoromethoxy, cyano, (1-2C)alkyl, $NR_kR_l$, or $OR_k$, wherein $R_k$ and $R_l$ are each independently selected from H or (1-2C)alkyl;

(ii) a group —C(O)N($R_f$)$R_e$— or —S(O)$_2$N($R_f$)$R_e$—;
wherein $R_e$ and $R_f$ are each independently selected from H or (1-2C)alkyl; or $R_e$ and $R_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-2C)alkyl, $NR_gR_h$, or $OR_g$, wherein $R_g$ and $R_h$ are each independently selected from H or (1-2C)alkyl;

(7) $R_1$ is selected from:
(i) a heteroaryl of the formula:

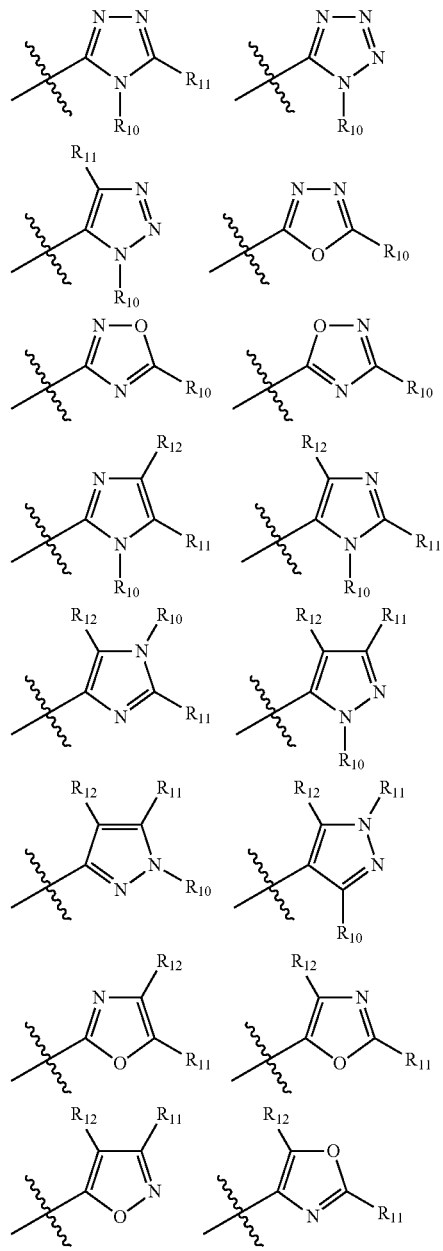

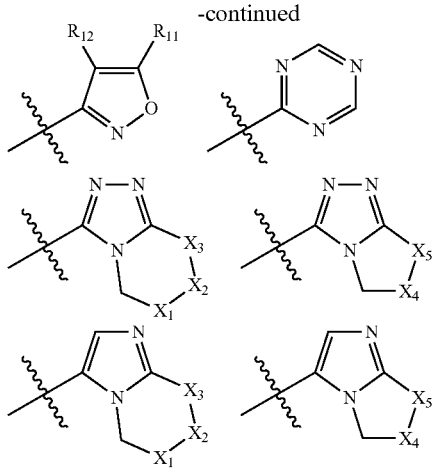

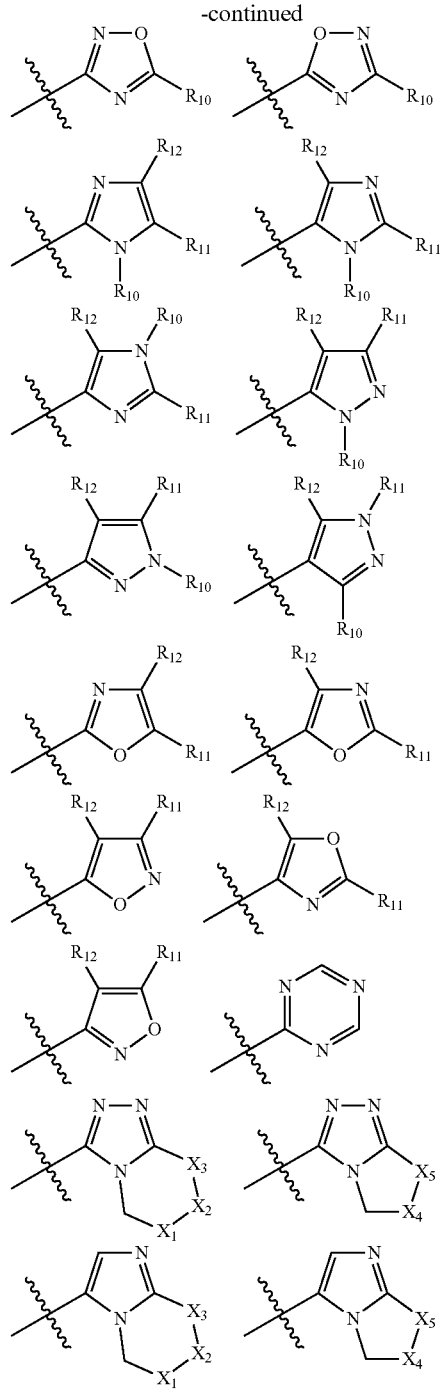

wherein $R_{10}$, $R_{11}$ and $R_{12}$ are each independently selected from hydrogen halo, trifluoromethyl, difluoromethyl, trifluoromethoxy, difluoromethoxy, cyano, nitro, (1-2C)alkyl, $NR_aR_b$, $OR_a$, wherein $R_a$ and $R_b$ are each independently selected from H or (1-2C) alkyl, and wherein any alkyl moiety present in the substituent group is optionally further substituted with one or more substituents selected from halo, cyano, $NR_cR_d$, $OR_c$, wherein $R_c$ and $R_d$ are each independently selected from H or (1-2C)alkyl; and one of $X_1$, $X_2$ and $X_3$ is O or $NR_{13}$, wherein $R_{13}$ is hydrogen or a (1-2C)alkyl group which is optionally substituted by one or more substituents selected from halo, hydroxy and (1-2C)alkoxy;

and one of $X_4$ and $X_5$ is O or $NR_{14}$, wherein $R_{14}$ is hydrogen or a (1-2C)alkyl group which is optionally substituted by one or more substituents selected from halo, hydroxy and (1-2C)alkoxy; or (ii) a group —C(O)N($R_f$)$R_e$— or —S(O)$_2$N($R_f$)$R_e$—;

wherein $R_e$ and $R_f$ are each independently selected from H or (1-2C)alkyl; or $R_e$ and $R_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-2C)alkyl, $NR_gR_h$, or $OR_g$, wherein $R_g$ and $R_h$ are each independently selected from H or (1-2C)alkyl;

(8) $R_1$ is selected from:

(i) a heteroaryl of the formula:

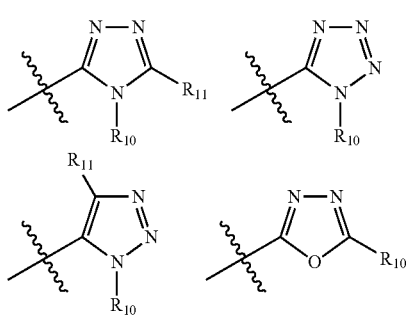

wherein $R_{10}$, $R_{11}$ and $R_{12}$ are each independently selected from hydrogen, cyano or a (1-2C)alkyl group which is optionally substituted by one or more substituents selected from hydroxy and (1-2C) alkoxy;

and one of $X_1$, $X_2$ and $X_3$ is O or $NR_{13}$, wherein $R_{13}$ is hydrogen or a (1-2C)alkyl group;

and one of $X_4$ and $X_5$ is O or $NR_{14}$, wherein $R_{14}$ is hydrogen or a (1-2C)alkyl group; or (ii) a group —C(O)N($R_f$)$R_e$— or —S(O)$_2$N($R_f$)$R_e$—;

wherein $R_e$ and $R_f$ are each independently selected from H or (1-2C)alkyl; or $R_e$ and $R_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-2C)alkyl, $NR_gR_h$, or $OR_g$, wherein $R_g$ and $R_h$ are each independently selected from H or (1-2C)alkyl;

(9) $R_i$ is selected from:

(i) a heteroaryl of the formula:

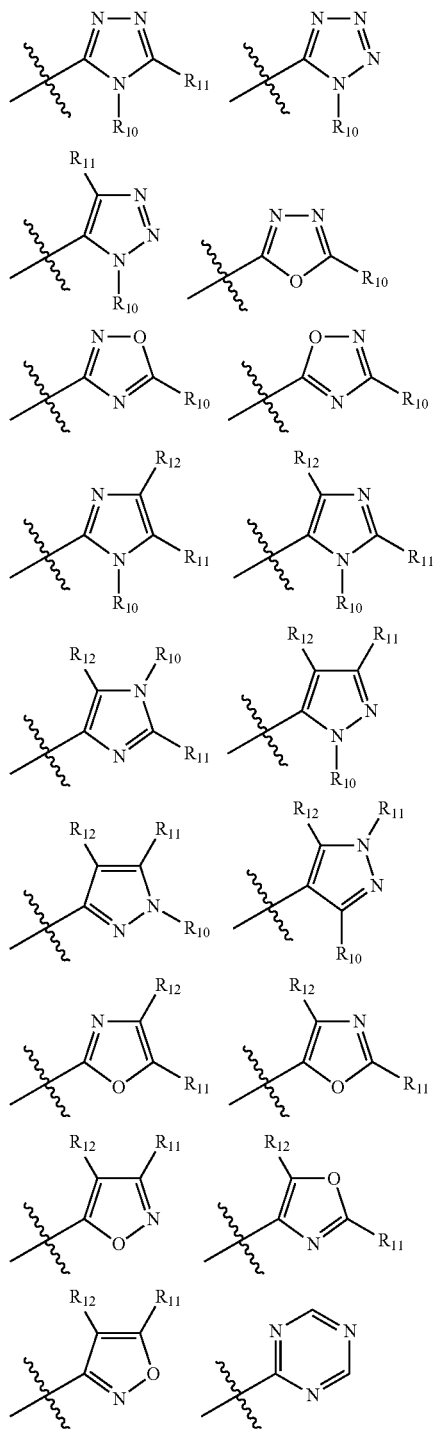

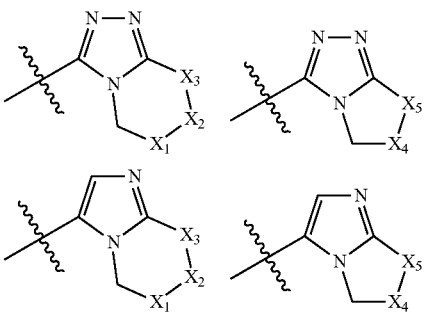

wherein $R_{10}$, $R_{11}$ and $R_{12}$ are each independently selected from hydrogen, cyano or a (1-2C)alkyl group which is optionally substituted by one or more substituents selected from hydroxy and (1-2C) alkoxy;

and one of $X_1$, $X_2$ and $X_3$ is O or $NR_{13}$, wherein $R_{13}$ is hydrogen or a (1-2C)alkyl group;

and one of $X_4$ and $X_5$ is O or $NR_{14}$, wherein $R_{14}$ is hydrogen or a (1-2C)alkyl group; or (ii) a group —C(O)N($R_f$)$R_e$— or —S(O)$_2$N($R_f$)$R_e$—;

wherein $R_e$ and $R_f$ are each independently selected from H or (1-2C)alkyl; or $R_e$ and $R_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-2C)alkyl, $NR_gR_h$, or $OR_g$, wherein $R_g$ and $R_h$ are each independently selected from H or (1-2C)alkyl;

(10) $R_1$ is selected from:

(i) a 5-membered heteroaryl of the formula:

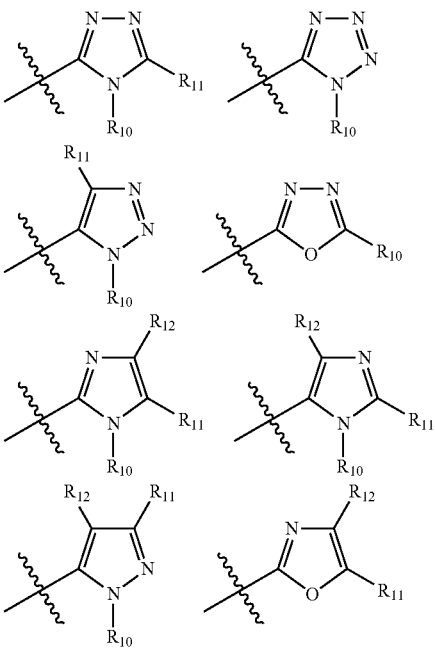

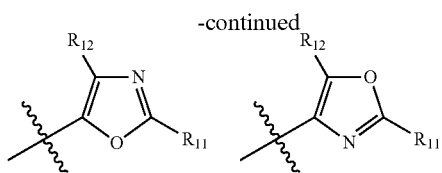

wherein R$_{10}$, R$_{11}$ and R$_{12}$ are each independently selected from hydrogen or a (1-2C)alkyl group which is optionally substituted by one or more substituents selected from hydroxy and (1-2C)alkoxy; or
(ii) a group —C(O)N(R$_f$)R$_e$— or —S(O)$_2$N(R$_f$)R$_e$—;
wherein R$_e$ and R$_f$ are each independently selected from H or (1-2C)alkyl; or R$_e$ and R$_f$ are linked such that, together with the nitrogen atom to which they are attached, they form a 4-, 5- or 6-membered heterocyclic ring, wherein said ring is optionally substituted with one or more substituents independently selected from halo, trifluoromethyl, difluoromethyl, trifluoromethoxy, difluoromethoxy, cyano, nitro, (1-2C)alkyl, NR$_g$R$_h$, or OR$_g$, wherein R$_g$ and R$_h$ are each independently selected from H or (1-2C)alkyl;
(11) R$_1$ is selected from:
(i) a 5-membered heteroaryl of the formula:

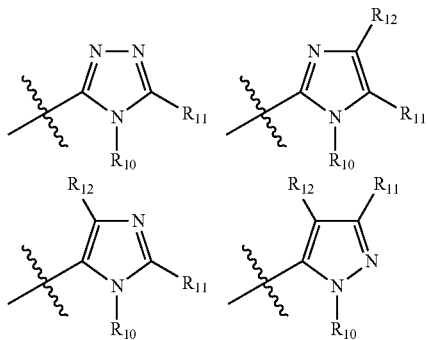

wherein R$_{10}$, R$_{11}$ and R$_{12}$ are each independently selected from hydrogen or a (1-2C)alkyl group which is optionally substituted by one or more substituents selected from hydroxy and (1-2C)alkoxy; or
(ii) a group —C(O)N(R$_f$)R$_e$— or —S(O)$_2$N(R$_f$)R$_e$—;
wherein R$_e$ and R$_f$ are each independently selected from H or (1-2C)alkyl, or R$_e$ and R$_f$ are linked such that, together with the nitrogen atom to which they are attached, they form a 4-, 5- or 6-membered heterocyclic ring;
(12) R$_1$ is a 5- or 6-membered heteroaryl optionally substituted with one or more substituents independently selected from halo, trifluoromethyl, difluoromethyl, trifluoromethoxy, difluoromethoxy, cyano, nitro, (1-2C)alkyl, NR$_a$R$_b$, OR$_a$, C(O)R$_a$, C(O)OR$_a$, OC(O)R$_a$, N(R$_b$)OR$_a$, C(O)N(R$_b$)R$_a$, N(R$_b$)C(O)R$_a$, S(O)$_p$R$_a$ (where p is 0, 1 or 2), SO$_2$N(R$_b$)R$_a$, or N(R$_b$)SO$_2$R$_a$,
wherein R$_a$ and R$_b$ are each independently selected from H or (1-2C)alkyl, and wherein any alkyl moiety present in the substituent group is optionally further substituted with one or more substituents selected from halo, trifluoromethyl, difluoromethyl, trifluoromethoxy, difluoromethoxy, cyano, (1-2C)alkyl, 4-7-membered heterocyclyl, NR$_c$R$_d$, OR$_c$, C(O)R$_c$, C(O)OR$_c$, OC(O)R$_c$, N(R$_d$)OR$_c$, C(O)N(R$_d$)R$_c$, N(R$_d$)C(O)R$_c$, S(O)$_q$R$_c$ (where q is 0, 1 or 2), SO$_2$N(R$_d$)R$_c$, or N(R$_d$)SO$_2$R$_c$, wherein R$_c$ and R$_d$ are each independently selected from H or (1-2C)alkyl;
or wherein the 5- or 6-membered heteroaryl is optionally fused to 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-2C)alkyl, NR$_k$R$_l$, OR$_k$, C(O)R$_k$, C(O)OR$_k$, OC(O)R$_k$, N(R$_l$)OR$_k$, C(O)N(R$_l$)R$_k$, N(R$_l$)C(O)R$_k$, S(O)$_p$R$_k$ (where p is 0, 1 or 2), SO$_2$N(R$_k$)R$_l$, or N(R$_k$)SO$_2$R$_l$; wherein R$_k$ and R$_l$ are each independently selected from H or (1-2C)alkyl;
and wherein any alkyl moiety present in the substituent group is optionally further substituted with one or more substituents selected from halo, trifluoromethyl, difluoromethyl, trifluoromethoxy, difluoromethoxy, cyano, nitro, (1-2C)alkyl, NR$_m$R$_n$, OR$_m$, C(O)R$_m$, C(O)OR$_m$, OC(O)R$_m$, N(R$_n$)OR$_m$, C(O)N(R$_n$)R$_m$, N(R$_n$)C(O)R$_m$, S(O)$_q$R$_m$ (where q is 0, 1 or 2), SO$_2$N(R$_n$)R$_m$, or N(R$_n$)SO$_2$R$_m$, wherein R$_m$ and R$_n$ are each independently selected from H or (1-2C)alkyl;
(13) R$_1$ is a 5- or 6-membered heteroaryl optionally substituted with one or more substituents independently selected from halo, trifluoromethyl, difluoromethyl, trifluoromethoxy, difluoromethoxy, cyano, nitro, (1-2C)alkyl, NR$_a$R$_b$, OR$_a$, C(O)R$_a$, C(O)OR$_a$, OC(O)R$_a$, N(R$_b$)OR$_a$, C(O)N(R$_b$)R$_a$, N(R$_b$)C(O)R$_a$, S(O)$_p$R$_a$ (where p is 0, 1 or 2), SO$_2$N(R$_b$)R$_a$, or N(R$_b$)SO$_2$R$_a$,
wherein R$_a$ and R$_b$ are each independently selected from H or (1-2C)alkyl;
and wherein any alkyl moiety present in the substituent group is optionally further substituted with one or more substituents selected from halo, cyano, NR$_c$R$_d$, OR$_c$, or S(O)$_q$R$_c$ (where q is 0, 1 or 2), wherein R$_c$ and R$_d$ are each independently selected from H or (1-2C)alkyl; or
wherein the 5- or 6-membered heteroaryl is optionally fused to 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-2C)alkyl, NR$_k$R$_l$, OR$_k$, C(O)R$_k$, C(O)OR$_k$, OC(O)R$_k$, N(R$_l$)OR$_k$, C(O)N(R$_l$)R$_k$, N(R$_l$)C(O)R$_k$, S(O)$_p$R$_k$ (where p is 0, 1 or 2), SO$_2$N(R$_k$)R$_l$, or N(R$_k$)SO$_2$R$_l$; wherein R$_k$ and R$_l$ are each independently selected from H or (1-2C)alkyl;
(14) R$_1$ is a 5- or 6-membered heteroaryl optionally substituted with one or more substituents independently selected from halo, trifluoromethyl, difluoromethyl, trifluoromethoxy, difluoromethoxy, cyano, nitro, (1-2C)alkyl, NR$_a$R$_b$, OR$_a$, C(O)R$_a$, or S(O)$_p$R$_a$ (where p is 0, 1 or 2), wherein R$_a$ and R$_b$ are each independently selected from H or (1-2C)alky, and wherein any alkyl moiety present in the substituent group is optionally further substituted with one or more substituents selected from OR$_c$, wherein R$_c$ and R$_d$ are each independently selected from H or (1-2C)alkyl; or
wherein the 5- or 6-membered heteroaryl is optionally fused to 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-2C)alkyl, NR$_k$R$_l$, OR$_k$, C(O)R$_k$, or S(O)$_p$R$_k$ (where p is 0, 1 or 2), wherein R$_k$ and R$_l$ are each independently selected from H or (1-2C)alkyl;
(15) R$_1$ is a 5- or 6-membered heteroaryl optionally substituted with one or more substituents independently selected from halo, trifluoromethyl, difluoromethyl, trifluoromethoxy, difluoromethoxy, cyano, (1-2C)alkyl, $NR_aR_b$, or $OR_a$, wherein $R_a$ and $R_b$ are each independently selected from H or (1-2C)alkyl, and wherein any alkyl moiety present in the substituent group is optionally further substituted with one or more substituents selected from $OR_c$, wherein $R_c$ and $R_d$ are each independently selected from H or (1-2C)alkyl; or wherein the 5- or 6-membered heteroaryl is optionally fused to 4-, 5-, or 6-membered heterocyclic ring, wherein the fused ring system is optionally substituted by one or more substituents independently selected from halo, trifluoromethyl, difluoromethyl, trifluoromethoxy, difluoromethoxy, cyano, (1-2C)alkyl, $NR_kR_l$, or $OR_k$, wherein $R_k$ and $R_l$ are each independently selected from H or (1-2C)alkyl;

(16) $R_1$ is a 5- or 6-membered heteroaryl comprising 1, 2, 3 or 4 nitrogen atoms or 1 or 2 nitrogen atoms and one oxygen atom, said heteroaryl being optionally substituted with one or more substituents independently selected from halo, trifluoromethyl, difluoromethyl, trifluoromethoxy, difluoromethoxy, cyano, (1-2C)alkyl, $NR_aR_b$, or $OR_a$, wherein $R_a$ and $R_b$ are each independently selected from H or (1-2C) alkyl, and wherein any alkyl moiety present in the substituent group is optionally further substituted with one or more substituents selected from $OR_c$, wherein $R_c$ and $R_d$ are each independently selected from H or (1-2C)alkyl; or wherein the 5- or 6-membered heteroaryl is optionally fused to 4-, 5-, or 6-membered heterocyclic ring, wherein the fused ring system is optionally substituted by one or more substituents independently selected from halo, trifluoromethyl, difluoromethyl, trifluoromethoxy, difluoromethoxy, cyano, (1-2C)alkyl, $NR_kR_l$, or $OR_k$, wherein $R_k$ and $R_l$ are each independently selected from H or (1-2C)alkyl;

(17) $R_1$ is a 5-membered heteroaryl optionally substituted with one or more substituents independently selected from halo, trifluoromethyl, difluoromethyl, trifluoromethoxy, difluoromethoxy, cyano, (1-2C)alkyl, $NR_aR_b$, or $OR_a$, wherein $R_a$ and $R_b$ are each independently selected from H or (1-2C)alkyl, and wherein any alkyl moiety present in the substituent group is optionally further substituted with one or more substituents selected from $OR_c$, wherein $R_c$ and $R_d$ are each independently selected from H or (1-2C)alkyl; or wherein the 5-membered heteroaryl is optionally fused to 4-, 5-, or 6-membered heterocyclic ring, wherein the fused ring system is optionally substituted by one or more substituents independently selected from halo, trifluoromethyl, difluoromethyl, trifluoromethoxy, difluoromethoxy, cyano, (1-2C)alkyl, $NR_kR_l$, or $OR_k$, wherein $R_k$ and $R_l$ are each independently selected from H or (1-2C)alkyl;

(18) $R_1$ is a heteroaryl of the formula:

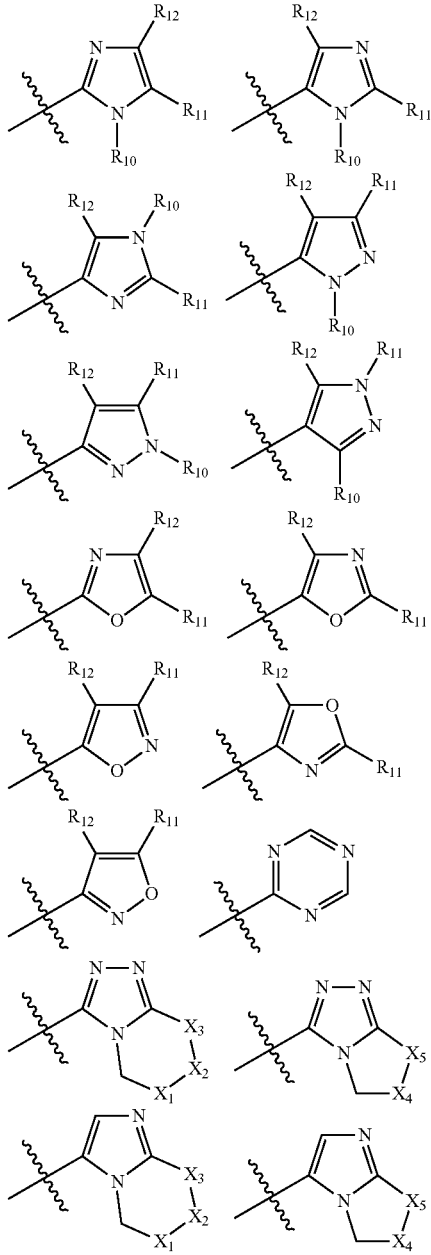

wherein $R_{10}$, $R_{11}$ and $R_{12}$ are each independently selected from hydrogen halo, trifluoromethyl, difluoromethyl, trifluoromethoxy, difluoromethoxy, cyano, nitro, (1-2C)alkyl, $NR_aR_b$, $OR_a$, wherein $R_a$ and $R_b$ are each independently selected from H or (1-2C)alkyl, and wherein any alkyl moiety present in the substituent group is optionally further substituted with one or more substituents selected from halo, cyano, $NR_cR_d$, $OR_c$, wherein $R_c$ and $R_d$ are each independently selected from H or (1-2C)alkyl; and one of $X_1$, $X_2$ and $X_3$ is O or $NR_{13}$, wherein $R_{13}$ is hydrogen or a (1-2C)alkyl group which is optionally substituted by one or more substituents selected from halo, hydroxy and (1-2C)alkoxy;

and one of $X_4$ and $X_5$ is O or $NR_{14}$, wherein $R_{14}$ is hydrogen or a (1-2C)alkyl group which is optionally substituted by one or more substituents selected from halo, hydroxy and (1-2C)alkoxy;

(19) $R_1$ is a heteroaryl of the formula:

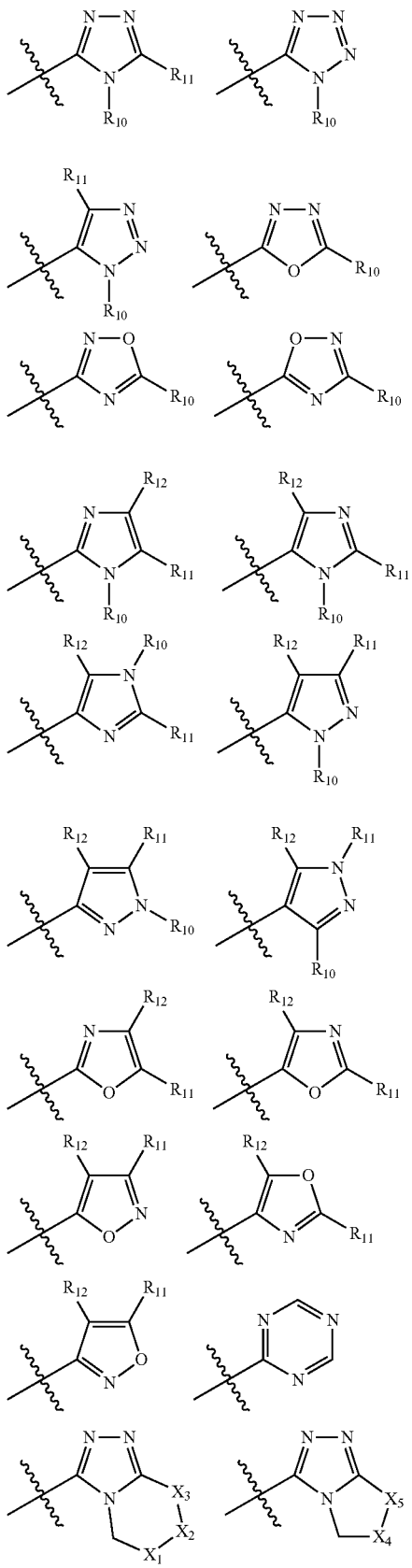

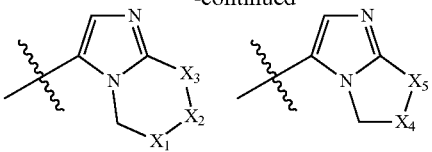

wherein $R_{10}$, $R_{11}$ and $R_{12}$ are each independently selected from hydrogen cyano or a (1-2C)alkyl group which is optionally substituted by one or more substituents selected from hydroxy and (1-2C)alkoxy;

and one of $X_1$, $X_2$ and $X_3$ is O or $NR_{13}$, wherein $R_{13}$ is hydrogen or a (1-2C)alkyl group;

and one of $X_4$ and $X_5$ is O or $NR_{14}$, wherein $R_{14}$ is hydrogen or a (1-2C)alkyl group;

(20) $R_1$ is a heteroaryl of the formula:

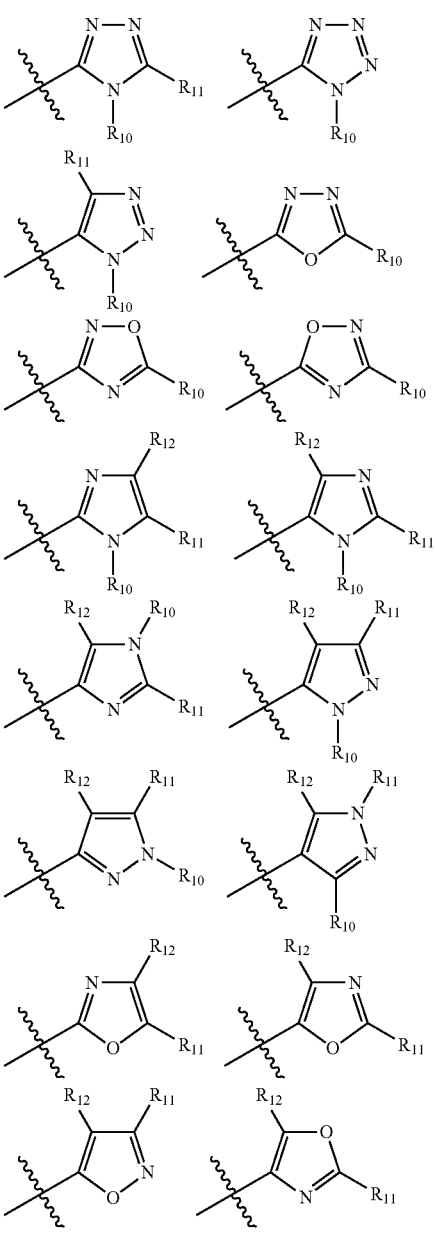

-continued

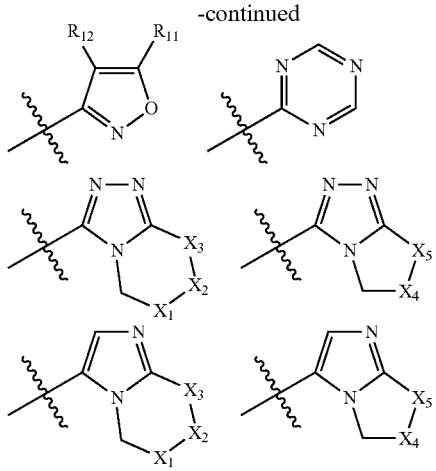

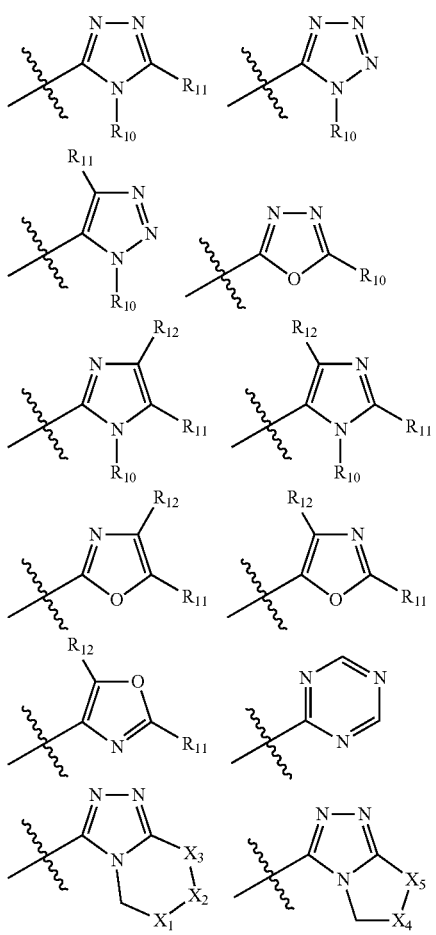

wherein $R_{10}$, $R_{11}$ and $R_{12}$ are each independently selected from hydrogen, cyano or a (1-2C)alkyl group which is optionally substituted by one or more substituents selected from hydroxy and (1-2C)alkoxy;

and one of $X_1$, $X_2$ and $X_3$ is O or $NR_{13}$, wherein $R_{13}$ is hydrogen or a (1-2C)alkyl group;

and one of $X_4$ and $X_5$ is O or $NR_{14}$, wherein $R_{14}$ is hydrogen or a (1-2C)alkyl group;

(21) $R_1$ is a heteroaryl of the formula:

-continued

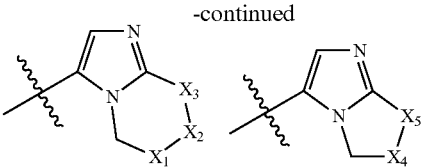

wherein $R_{10}$, $R_{11}$ and $R_{12}$ are each independently selected from hydrogen or a (1-2C)alkyl group which is optionally substituted by one or more substituents selected from hydroxy and (1-2C)alkoxy;

and one of $X_1$, $X_2$ and $X_3$ is O or $NR_{13}$, wherein $R_{13}$ is hydrogen or a (1-2C)alkyl group;

and one of $X_4$ and $X_5$ is O or $NR_{14}$, wherein $R_{14}$ is hydrogen or a (1-2C)alkyl group;

(22) $R_1$ is a heteroaryl of the formula:

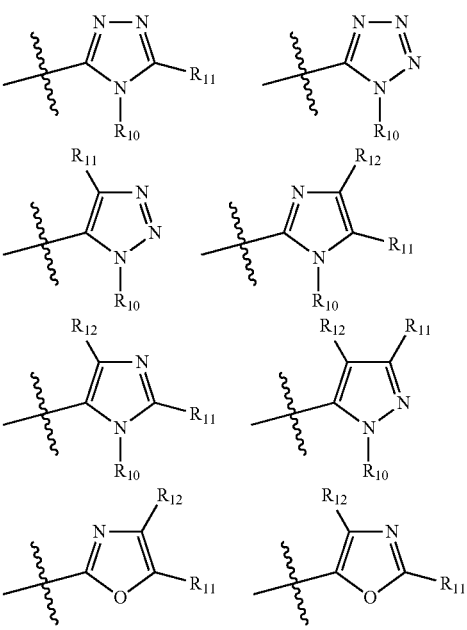

wherein $R_{10}$, $R_{11}$ and $R_{12}$ are each independently selected from hydrogen or a (1-2C)alkyl group which is optionally substituted by one or more substituents selected from hydroxy and (1-2C)alkoxy;

(23) $R_1$ is a 5-membered heteroaryl of the formula:

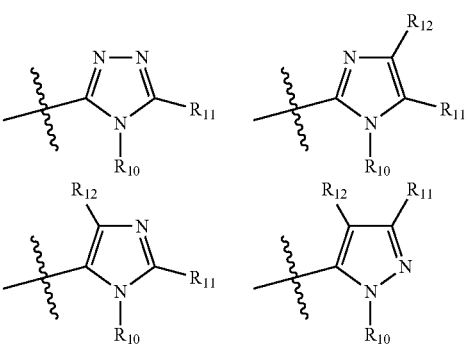

wherein $R_{10}$, $R_{11}$ and $R_{12}$ are each independently selected from hydrogen or a (1-2C)alkyl group which is optionally substituted by one or more substituents selected from hydroxy and (1-2C)alkoxy;

(24) $R_i$ is a 5-membered heteroaryl of the formula:

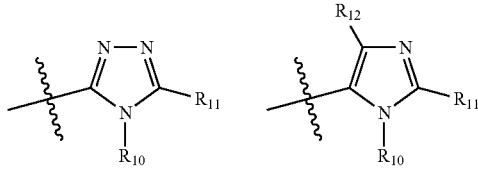

wherein $R_{10}$, $R_{11}$ and $R_{12}$ are each independently selected from hydrogen or a (1-2C)alkyl group which is optionally substituted by one or more substituents selected from hydroxy and (1-2C)alkoxy;

(25) $R_i$ is a 5-membered heteroaryl of the formula:

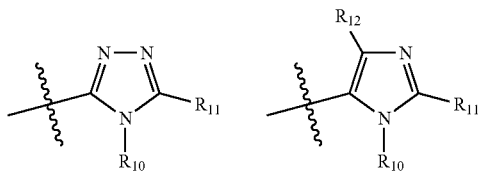

wherein $R_{10}$, $R_{11}$ and $R_{12}$ are each independently selected from hydrogen or a (1-2C)alkyl group;

(26) $R_1$ is a 5-membered heteroaryl of the formula:

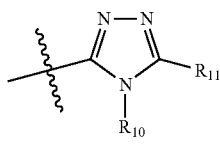

wherein $R_{10}$ and $R_{11}$ are each independently selected from hydrogen or a (1-2C)alkyl group which is optionally substituted by one or more substituents selected from hydroxy and (1-2C)alkoxy;

(27) $R_1$ is a 5-membered heteroaryl of the formula:

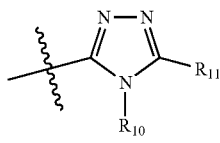

wherein $R_{10}$ and $R_{11}$ are each independently selected from hydrogen or a (1-2C)alkyl group;

(28) $R_i$ is a 5- or 6-membered heteroaryl of the formula:

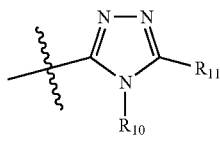

wherein $R_{10}$ is methyl and $R_{11}$ is hydrogen or methyl;

(29) $R_i$ is a 5-membered heteroaryl of the formula:

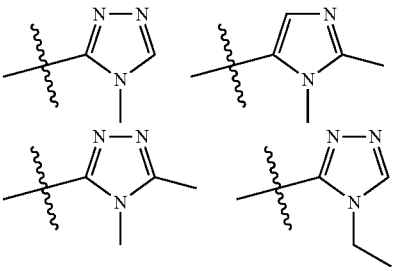

(30) $R_i$ is a triazole or imidazole ring optionally substituted with one or more substituents independently selected from halo, trifluoromethyl, difluoromethyl, trifluoromethoxy, difluoromethoxy, cyano, nitro, (1-4C)alkyl, $NR_aR_b$, $OR_a$, C(O)$R_a$, C(O)O$R_a$, OC(O)$R_a$, N($R_b$)O$R_a$, C(O)N($R_b$)$R_a$, N($R_b$)C(O)$R_a$, S(O)$_p$$R_a$ (where p is 0, 1 or 2), SO$_2$N($R_b$)$R_a$, or N($R_b$)SO$_2$$R_a$,
wherein $R_a$ and $R_b$ are each independently selected from H or (1-4C)alkyl, and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, $NR_cR_d$, $OR_c$, C(O)$R_c$, C(O)O$R_c$, OC(O)$R_c$, N($R_d$)O$R_c$, C(O)N($R_d$)$R_c$, N($R_d$)C(O)$R_c$, S(O)$_q$$R_c$ (where q is 0, 1 or 2), SO$_2$N($R_d$)$R_c$, or N($R_d$)SO$_2$$R_c$, wherein $R_c$ and $R_d$ are each independently selected from H or (1-4C)alkyl;
wherein the triazole or imidazole ring is optionally fused to a 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-4C)alkyl, $NR_kR_l$, $OR_k$, C(O)$R_k$, C(O)O$R_k$, OC(O)$R_k$, N($R_l$)O$R_k$, C(O)N($R_l$)$R_k$, N($R_l$)C(O)$R_k$, S(O)$_p$$R_k$ (where p is 0, 1 or 2), SO$_2$N($R_k$)$R_l$, or N($R_k$)SO$_2$$R_l$, wherein $R_k$ and $R_l$ are each independently selected from H or (1-4C)alkyl,
and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, $NR_mR_n$, $OR_m$, C(O)$R_m$, C(O)O$R_m$, OC(O)$R_m$, N($R_n$)O$R_m$, C(O)N($R_n$)$R_m$, N($R_n$)C(O)$R_m$, S(O)$_q$$R_m$ (where q is 0, 1 or 2), SO$_2$N($R_n$)$R_m$, or N($R_n$)SO$_2$$R_m$, wherein $R_m$ and $R_n$ are each independently selected from H or (1-4C)alkyl;

(31) $R_1$ is a triazole or imidazole ring optionally substituted with one or more substituents independently selected from halo, trifluoromethyl, difluoromethyl, trifluoromethoxy, difluoromethoxy, cyano, nitro, (1-4C)alkyl, $NR_aR_b$, $OR_a$, C(O)$R_a$, C(O)O$R_a$, OC(O)$R_a$, N($R_b$)O$R_a$, C(O)N($R_b$)$R_a$, N($R_b$)C(O)$R_a$, S(O)$_p$$R_a$ (where p is 0, 1 or 2), SO$_2$N($R_b$)$R_a$, or N($R_b$)SO$_2$$R_a$,
wherein $R_a$ and $R_b$ are each independently selected from H or (1-4C)alkyl, and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, $NR_cR_d$, $OR_c$, C(O)$R_c$, C(O)O$R_c$, OC(O)R$_c$, N(R$_d$)OR$_c$, C(O)N(R$_d$)R$_c$, N(R$_d$)C(O)R$_c$, S(O)$_q$R$_c$ (where q is 0, 1 or 2), SO$_2$N(R$_d$)R$_c$, or N(R$_d$)SO$_2$R$_c$, wherein R$_c$ and R$_d$ are each independently selected from H or (1-4C)alkyl;

(32) R$_1$ is a triazole or imidazole ring optionally substituted with one or more substituents independently selected from halo, trifluoromethyl, difluoromethyl, trifluoromethoxy, difluoromethoxy, cyano, nitro, (1-4C)alkyl, NR$_a$R$_b$, OR$_a$, C(O)R$_a$, C(O)OR$_a$, OC(O)R$_a$, N(R$_b$)OR$_a$, C(O)N(R$_b$)R$_a$, N(R$_b$)C(O)R$_a$, S(O)$_p$R$_a$ (where p is 0, 1 or 2), SO$_2$N(R$_b$)R$_a$, or N(R$_b$)SO$_2$R$_a$, wherein R$_a$ and R$_b$ are each independently selected from H or (1-4C)alkyl;

(33) R$_1$ is a triazole or imidazole ring optionally substituted with one or more substituents independently selected from halo, trifluoromethyl, difluoromethyl, trifluoromethoxy, difluoromethoxy, (1-4C)alkyl, NR$_a$R$_b$, OR$_a$, wherein R$_a$ and R$_b$ are each independently selected from H or (1-2C)alkyl;

(34) R$_1$ is a triazole or imidazole ring optionally substituted with (1-2C)alkyl;

(35) R$_1$ is a triazole ring optionally substituted with one or more substituents independently selected from halo, trifluoromethyl, difluoromethyl, trifluoromethoxy, difluoromethoxy, cyano, nitro, (1-4C)alkyl, NR$_a$R$_b$, OR$_a$, C(O)R$_a$, C(O)OR$_a$, OC(O)R$_a$, N(R$_b$)OR$_a$, C(O)N(R$_b$)R$_a$, N(R$_b$)C(O)R$_a$, S(O)$_p$R$_a$ (where p is 0, 1 or 2), SO$_2$N(R$_b$)R$_a$, or N(R$_b$)SO$_2$R$_a$,
wherein R$_a$ and R$_b$ are each independently selected from H or (1-4C)alkyl, and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, NR$_c$R$_d$, OR$_c$, C(O)R$_c$, C(O)OR$_c$, OC(O)R$_c$, N(R$_d$)OR$_c$, C(O)N(R$_d$)R$_c$, N(R$_d$)C(O)R$_c$, S(O)$_q$R$_c$ (where q is 0, 1 or 2), SO$_2$N(R$_d$)R$_c$, or N(R$_d$)SO$_2$R$_c$, wherein R$_c$ and R$_d$ are each independently selected from H or (1-4C)alkyl;
wherein the triazole or imidazole ring is optionally fused to a 4-, 5-, 6- or 7-membered heterocyclic ring, wherein the fused ring system is optionally substituted by one or more substituents independently selected from halo, trifluoromethyl, difluoromethyl, trifluoromethoxy, difluoromethoxy, cyano, nitro, (1-4C)alkyl, NR$_k$R$_l$, OR$_k$, C(O)R$_k$, C(O)OR$_k$, OC(O)R$_k$, N(R$_l$)OR$_k$, C(O)N(R$_l$)R$_k$, N(R$_l$)C(O)R$_k$, S(O)$_p$R$_k$ (where p is 0, 1 or 2), SO$_2$N(R$_k$)R$_l$, or N(R$_k$)SO$_2$R$_l$, wherein R$_k$ and R$_l$ are each independently selected from H or (1-4C)alkyl,
and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, NR$_m$R$_n$, OR$_m$, C(O)R$_m$, C(O)OR$_m$, OC(O)R$_m$, N(R$_n$)OR$_m$, C(O)N(R$_n$)R$_m$, N(R$_n$)C(O)R$_m$, S(O)$_q$R$_m$ (where q is 0, 1 or 2), SO$_2$N(R$_n$)R$_m$, or N(R$_n$)SO$_2$R$_m$, wherein R$_m$ and R$_n$ are each independently selected from H or (1-4C)alkyl;

(36) R$_1$ is a triazole ring optionally substituted with one or more substituents independently selected from halo, trifluoromethyl, difluoromethyl, trifluoromethoxy, difluoromethoxy, cyano, nitro, (1-4C)alkyl, NR$_a$R$_b$, OR$_a$, C(O)R$_a$, C(O)OR$_a$, OC(O)R$_a$, N(R$_b$)OR$_a$, C(O)N(R$_b$)R$_a$, N(R$_b$)C(O)R$_a$, S(O)$_p$R$_a$ (where p is 0, 1 or 2), SO$_2$N(R$_b$)R$_a$, or N(R$_b$)SO$_2$R$_a$,
wherein R$_a$ and R$_b$ are each independently selected from H or (1-4C)alkyl, and wherein any alkyl moiety present in the substituent group is optionally further substituted with one or more substituents selected from halo, trifluoromethyl, difluoromethyl, trifluoromethoxy, difluoromethoxy, cyano, nitro, (1-4C)alkyl, 4-7-membered heterocyclyl, NR$_c$R$_d$, OR$_c$, C(O)R$_c$, C(O)OR$_c$, OC(O)R$_c$, N(R$_d$)OR$_c$, C(O)N(R$_d$)R$_c$, N(R$_d$)C(O)R$_c$, S(O)$_q$R$_c$ (where q is 0, 1 or 2), SO$_2$N(R$_d$)R$_c$, or N(R$_d$)SO$_2$R$_c$, wherein R$_c$ and R$_d$ are each independently selected from H or (1-4C)alkyl;

(37) R$_1$ is a triazole ring optionally substituted with one or more substituents independently selected from halo, trifluoromethyl, difluoromethyl, trifluoromethoxy, difluoromethoxy, cyano, nitro, (1-4C)alkyl, NR$_a$R$_b$, OR$_a$, C(O)R$_a$, C(O)OR$_a$, OC(O)R$_a$, N(R$_b$)OR$_a$, C(O)N(R$_b$)R$_a$, N(R$_b$)C(O)R$_a$, S(O)$_p$R$_a$ (where p is 0, 1 or 2), SO$_2$N(R$_b$)R$_a$, or N(R$_b$)SO$_2$R$_a$, wherein R$_a$ and R$_b$ are each independently selected from H or (1-4C)alkyl;

(38) R$_1$ is a triazole ring optionally substituted with one or more substituents independently selected from halo, trifluoromethyl, difluoromethyl, trifluoromethoxy, difluoromethoxy, (1-4C)alkyl, NR$_a$R$_b$, OR$_a$, wherein R$_a$ and R$_b$ are each independently selected from H or (1-2C)alkyl;

(39) R$_1$ is a triazole ring optionally substituted with (1-2C)alkyl;

(40) R$_2$ is selected from chloro, (1-2C)alkoxy or (1-2C)fluoroalkoxy;

(41) R$_2$ is selected from chloro, methoxy, ethoxy, difluoromethoxy or trifluoromethoxy;

(42) R$_2$ is selected from methoxy, ethoxy, or difluoromethoxy;

(43) R$_2$ is methoxy;

(44) R$_2$ is ethoxy;

(45) R$_2$ is difluoromethoxy;

(46) either:
  (i) R$_3$ is selected from hydrogen or (1-2C)alkyl and R$_4$ is selected from (1-6C)alkyl, (3-9C)cycloalkyl, (3-9C)cycloalkyl-(1-2C)alkyl, aryl, aryl-(1-2C)alkyl, heterocyclyl, heterocyclyl-(1-2C)alkyl, heteroaryl, heteroaryl-(1-2C)alkyl, and
  wherein R$_4$ is optionally further substituted by one or more substituents selected from hydroxy, fluoro, chloro, cyano, CF$_3$, CHF$_2$, OCF$_3$, OCHF$_2$, (1-4C)alkyl, NR$_o$R$_p$, OR$_o$, C(O)R$_o$, C(O)OR$_p$, OC(O)R$_o$, N(R$_p$)OR$_o$, C(O)N(R$_p$)R$_o$, N(R$_p$)C(O)R$_o$, S(O)$_p$R$_o$ (where p is 0, 1 or 2), SO$_2$N(R$_p$)R$_o$, or N(R$_p$)SO$_2$R$_o$ or (3-6C)cycloalkyl, (3-6C)cycloalkyl-(1-2C)alkyl, wherein R$_o$ and R$_p$ are each independently selected from H or (1-4C)alkyl, (3-6C)cycloalkyl or (3-6C)cycloalkyl-(1-2C)alkyl; or
  (ii) R$_3$ and R$_4$ are linked such that, together with the nitrogen atom to which they are attached, they form a nitrogen-linked 4-, 5-6- or 7-membered heterocyclic ring,
    wherein said ring is optionally fused to a further 3-, 4-, 5- or 6-membered ring carbocyclic or heterocyclic ring, a 5- or 6-membered heteroaryl ring or a phenyl ring to form a bi-cyclic heterocyclic system, or
    linked through a spiro carbon atom to a further 4-, 5- or 6-membered ring carbocyclic or heterocyclic ring to form a spiro bicyclic ring system;
    and wherein the heterocyclic ring, bicyclic ring system or spiro bicyclic ring system is optionally substituted by one or more substituents independently selected from halo, trifluoromethyl, difluoromethyl, trifluoromethoxy, difluoromethoxy, cyano, nitro, (1-4C)alkyl, NR$_i$R$_j$, OR$_i$, C(O)R$_i$, C(O)OR$_i$, OC(O)R$_i$, N(R$_j$)OR$_i$, C(O)N(R$_j$)R$_i$, N(R$_j$)C(O)R$_i$, S(O)$_q$R$_i$ (where q is 0, 1 or 2), $SO_2N(R_j)R_i$, or $N(R_j)SO_2R_i$, wherein $R_i$ and $R_j$ are each independently selected from H or (1-4C)alkyl;

(47) either:
(i) $R_3$ is selected from hydrogen or methyl and $R_4$ is selected from (1-6C)alkyl, (3-6C)cycloalkyl, (3-6C)cycloalkyl-(1-2C)alkyl, a 4, 5 or 6-membered heterocyclyl, a 4, 5 or 6-membered heterocyclyl-(1-2C)alkyl, and wherein $R_4$ is optionally further substituted by one or more substituents selected from hydroxy, fluoro, chloro, cyano, $CF_3$, $CHF_2$, $OCF_3$, $OCHF_2$, (1-4C)alkyl, $NR_oR_p$, $OR_o$, $C(O)R_o$, $C(O)OR_p$, $OC(O)R_o$, $N(R_p)OR_o$, $C(O)N(R_p)R_o$, $N(R_p)C(O)R_o$, $S(O)_pR_o$ (where p is 0, 1 or 2), $SO_2N(R_p)R_o$, $N(R_p)SO_2R_o$ or (3-6C)cycloalkyl, wherein $R_o$ and $R_p$ are each independently selected from H or (1-4C)alkyl, (3-6C)cycloalkyl or (3-6C)cycloalkyl-(1-2C)alkyl; or
(ii) $R_3$ and $R_4$ are linked such that, together with the nitrogen atom to which they are attached, they form a nitrogen-linked 4-, 5-6- or 7-membered heterocyclic ring,
wherein said ring is optionally fused to a further 3-, 4-, 5- or 6-membered ring carbocyclic or heterocyclic ring to form a bi-cyclic heterocyclic system, or linked through a spiro carbon atom to a further 4-, 5- or 6-membered ring carbocyclic or heterocyclic ring to form a spiro bicyclic ring system;
and wherein the heterocyclic ring, bicyclic ring system or spiro bicyclic ring system is optionally substituted by one or more substituents independently selected from halo, trifluoromethyl, difluoromethyl, trifluoromethoxy, difluoromethoxy, cyano, nitro, (1-4C)alkyl, $NR_iR_j$, $OR_i$, $C(O)R_i$, $C(O)OR_i$, $OC(O)R_i$, $N(R_j)OR_i$, $C(O)N(R_j)R_i$, $N(R_j)C(O)R_i$, $S(O)_qR_i$ (where q is 0, 1 or 2), $SO_2N(R_j)R_i$, or $N(R_j)SO_2R_i$, wherein $R_i$ and $R_j$ are each independently selected from H or (1-4C)alkyl;

(48) either:
(i) $R_3$ is selected from hydrogen or methyl and $R_4$ is selected from (1-6C)alkyl, (3-6C)cycloalkyl, (3-6C)cycloalkyl-(1-2C)alkyl, a 4, 5 or 6-membered heterocyclyl, a 4, 5 or 6-membered heterocyclyl-(1-2C)alkyl, and wherein $R_4$ is optionally further substituted by one or more substituents selected from hydroxy, fluoro, chloro, cyano, $CF_3$, $CHF_2$, $OCF_3$, $OCHF_2$, (1-4C)alkyl, $NR_oR_p$, $OR_o$, $S(O)_pR_o$ (where p is 0, 1 or 2), or (3-6C)cycloalkyl, wherein $R_o$ and $R_p$ are each independently selected from H or (1-4C)alkyl, (3-6C)cycloalkyl or (3-6C)cycloalkyl-(1-2C)alkyl; or
(ii) $R_3$ and $R_4$ are linked such that, together with the nitrogen atom to which they are attached, they form a nitrogen-linked 4-, 5-6- or 7-membered heterocyclic ring,
wherein said ring is optionally fused to a further 3-, 4-, 5- or 6-membered ring carbocyclic or heterocyclic ring to form a bi-cyclic heterocyclic system, or linked through a spiro carbon atom to a further 4-, 5- or 6-membered ring carbocyclic or heterocyclic ring to form a spiro bicyclic ring system;
and wherein the heterocyclic ring, bicyclic ring system or spiro bicyclic ring system is optionally substituted by one or more substituents independently selected from halo, trifluoromethyl, difluoromethyl, trifluoromethoxy, difluoromethoxy, cyano, nitro, (1-4C)alkyl, $NR_iR_j$, $OR_i$, $C(O)R_i$, $S(O)_qR_i$ (where q is 0, 1 or 2), wherein $R_i$ and $R_j$ are each independently selected from H or (1-4C)alkyl;

(49) either:
(i) $R_3$ is selected from hydrogen and $R_4$ is selected from (1-6C)alkyl, (3-6C)cycloalkyl, (3-6C)cycloalkyl-(1-2C)alkyl, a 4, 5 or 6-membered heterocyclyl, a 4, 5 or 6-membered heterocyclyl-(1-2C)alkyl, and wherein $R_4$ is optionally further substituted by one or more substituents selected from hydroxy, fluoro, chloro, cyano, $CF_3$, $CHF_2$, $OCF_3$, $OCHF_2$, (1-4C)alkyl, $NR_oR_p$, $OR_o$, $S(O)_pR_o$ (where p is 0, 1 or 2), or (3-6C)cycloalkyl, wherein $R_o$ and $R_p$ are each independently selected from H or (1-4C)alkyl, (3-6C)cycloalkyl or (3-6C)cycloalkyl-(1-2C)alkyl; or
(ii) $R_3$ and $R_4$ are linked such that, together with the nitrogen atom to which they are attached, they form a nitrogen-linked 4-, 5-, or 6-membered heterocyclic ring,
wherein said ring is optionally linked through a spiro carbon atom to a further 4-, 5- or 6-membered ring carbocyclic or heterocyclic ring to form a spiro bicyclic ring system;
and wherein the heterocyclic ring, bicyclic ring system or spiro bicyclic ring system is optionally substituted by one or more substituents independently selected from halo, trifluoromethyl, difluoromethyl, trifluoromethoxy, difluoromethoxy, cyano, nitro, (1-4C)alkyl, $NR_iR_j$, $OR_i$, $C(O)R_i$, $S(O)_qR_i$ (where q is 0, 1 or 2), wherein $R_i$ and $R_j$ are each independently selected from H or (1-4C)alkyl;

(50) either:
(i) $R_3$ is selected from hydrogen and $R_4$ is selected from (1-6C)alkyl, (3-6C)cycloalkyl-(1-2C)alkyl, a 4, 5 or 6-membered heterocyclyl, a 4, 5 or 6-membered heterocyclyl-(1-2C)alkyl, and wherein $R_4$ is optionally further substituted by one or more substituents selected from hydroxy, fluoro, chloro, cyano, $CF_3$, $CHF_2$, $OCF_3$, $OCHF_2$, (1-4C)alkyl, $NR_oR_p$ or $OR_o$, wherein $R_o$ and $R_p$ are each independently selected from H or (1-4C)alkyl; or
(ii) $R_3$ and $R_4$ are linked such that, together with the nitrogen atom to which they are attached, they form a nitrogen-linked 4-, 5-, or 6-membered heterocyclic ring,
wherein said ring is optionally linked through a spiro carbon atom to a further 4-, 5- or 6-membered ring carbocyclic or heterocyclic ring to form a spiro bicyclic ring system;
and wherein the heterocyclic ring, bicyclic ring system or spiro bicyclic ring system is optionally substituted by one or more substituents independently selected from halo, trifluoromethyl, difluoromethyl, trifluoromethoxy, difluoromethoxy, cyano, nitro, (1-4C)alkyl, $NR_iR_j$, $OR_i$, $C(O)R_i$, $S(O)_qR_i$ (where q is 0, 1 or 2), wherein $R_i$ and $R_j$ are each independently selected from H or (1-4C)alkyl;

(51) either:
(i) $R_3$ is selected from hydrogen and $R_4$ is selected from (1-6C)alkyl, (3-6C)cycloalkyl-(1-2C)alkyl, a 4, 5 or 6-membered heterocyclyl, a 4, 5 or 6-membered heterocyclyl-(1-2C)alkyl, and wherein $R_4$ is optionally further substituted by one or more substituents selected from hydroxyl, (1-4C)alkyl or $OR_o$, wherein $R_o$ is selected from H or (1-2C)alkyl; or
(ii) $R_3$ and $R_4$ are linked such that, together with the nitrogen atom to which they are attached, they form a nitrogen-linked 4-, 5-, or 6-membered heterocyclic ring, wherein said ring is optionally linked through a spiro carbon atom to a further 4-, 5- or 6-membered ring carbocyclic or heterocyclic ring to form a spiro bicyclic ring system;

and wherein the heterocyclic ring, bicyclic ring system or spiro bicyclic ring system is optionally substituted by one or more substituents independently selected from halo, trifluoromethyl, cyano, (1-4C)alkyl, $NR_iR_j$, $OR_i$, wherein $R_i$ and $R_j$ are each independently selected from H or (1-2C)alkyl;

(52) $R_3$ is selected from hydrogen or (1-3C)alkyl and $R_4$ is selected from (1-6C)alkyl, (3-9C)cycloalkyl, (3-9C)cycloalkyl-(1-4C)alkyl, aryl, aryl-(1-4C)alkyl, heterocyclyl, heterocyclyl-(1-4C)alkyl, heteroaryl, heteroaryl-(1-4C)alkyl, and wherein $R_4$ is optionally further substituted by one or more substituents selected from hydroxy, fluoro, chloro, cyano, $CF_3$, $CHF_2$, $OCF_3$, $OCHF_2$, (1-4C)alkyl, $NR_oR_p$, $OR_o$, $C(O)R_o$, $C(O)OR_p$, $OC(O)R_o$, $N(R_p)OR_o$, $C(O)N(R_p)R_o$, $N(R_p)C(O)R_o$, $S(O)_pR_o$ (where p is 0, 1 or 2), $SO_2N(R_p)R_o$, or $N(R_p)SO_2R_o$ or (3-6C)cycloalkyl, (3-6C)cycloalkyl-(1-2C)alkyl, a 4, 5 or 6-membered heterocyclyl, a 4, 5 or 6-membered heterocyclyl-(1-2C)alkyl, wherein $R_o$ and $R_p$ are each independently selected from H or (1-4C)alkyl, (3-6C)cycloalkyl or (3-6C)cycloalkyl-(1-4C)alkyl;

(53) $R_3$ is selected from hydrogen and $R_4$ is selected from (1-6C)alkyl, (3-6C)cycloalkyl-(1-2C)alkyl, a 4, 5 or 6-membered heterocyclyl, a 4, 5 or 6-membered heterocyclyl-(1-2C)alkyl, and wherein $R_4$ is optionally further substituted by one or more substituents selected from hydroxyl, (1-4C)alkyl or $OR_o$, wherein $R_o$ is selected from H or (1-2C)alkyl

(54) $R_3$ and $R_4$ are linked such that, together with the nitrogen atom to which they are attached, they form a nitrogen-linked 4-, 5-6- or 7-membered heterocyclic ring; and wherein the heterocyclic ring is optionally substituted by one or more substituents independently selected from halo, trifluoromethyl, difluoromethyl, trifluoromethoxy, difluoromethoxy, cyano, nitro, (1-4C)alkyl, $NR_iR_j$, $OR_i$, $C(O)R_i$, $C(O)OR_i$, $OC(O)R_i$, $N(R_j)OR_i$, $C(O)N(R_j)R_i$, $N(R_j)C(O)R_i$, $S(O)_qR_i$ (where q is 0, 1 or 2), $SO_2N(R_j)R_i$, or $N(R_j)SO_2R_i$, wherein $R_i$ and $R_j$ are each independently selected from H or (1-4C)alkyl;

(55) $R_3$ and $R_4$ are linked such that, together with the nitrogen atom to which they are attached, they form a nitrogen-linked 4-, 5-6- or 7-membered heterocyclic ring, wherein said ring is fused to a further 3-, 4-, 5- or 6-membered ring carbocyclic or heterocyclic ring, a 5- or 6-membered heteroaryl ring or a phenyl ring to form a bi-cyclic heterocyclic system; and wherein the bicyclic ring system is optionally substituted by one or more substituents independently selected from halo, trifluoromethyl, difluoromethyl, trifluoromethoxy, difluoromethoxy, cyano, nitro, (1-4C)alkyl, $NR_iR_j$, $OR_i$, $C(O)R_i$, $C(O)OR_i$, $OC(O)R_i$, $N(R_j)OR_i$, $C(O)N(R_j)R_i$, $N(R_j)C(O)R_i$, $S(O)_qR_i$ (where q is 0, 1 or 2), $SO_2N(R_j)R_i$, or $N(R_j)SO_2R_i$, wherein $R_i$ and $R_j$ are each independently selected from H or (1-4C)alkyl;

(56) $R_3$ and $R_4$ are linked such that, together with the nitrogen atom to which they are attached, they form a nitrogen-linked 4-, 5-6- or 7-membered heterocyclic ring wherein said ring is fused to a further 3-, 4-, 5- or 6-membered ring carbocyclic or heterocyclic ring, a 5- or 6-membered heteroaryl ring or a phenyl ring to form a bi-cyclic heterocyclic system; and wherein the bicyclic ring system is optionally substituted by one or more substituents independently selected from halo, trifluoromethyl, difluoromethyl, trifluoromethoxy, difluoromethoxy, cyano, nitro, (1-4C)alkyl, $NR_iR_j$, $OR_i$, $C(O)R_i$, $C(O)OR_i$, $OC(O)R_i$, $N(R_j)OR_i$, $C(O)N(R_j)R_i$, $N(R_j)C(O)R_i$, $S(O)_qR_i$ (where q is 0, 1 or 2), $SO_2N(R_j)R_i$, or $N(R_j)SO_2R_i$, wherein $R_i$ and $R_j$ are each independently selected from H or (1-4C)alkyl

(57) $R_3$ and $R_4$ are linked such that, together with the nitrogen atom to which they are attached, they form a nitrogen-linked 4-, 5-6- or 7-membered heterocyclic ring wherein said ring is linked through a spiro carbon atom to a further 4-, 5- or 6-membered ring carbocyclic or heterocyclic ring to form a spiro bicyclic ring system;

and wherein the spiro bicyclic ring system is optionally substituted by one or more substituents independently selected from halo, trifluoromethyl, difluoromethyl, trifluoromethoxy, difluoromethoxy, cyano, nitro, (1-4C)alkyl, $NR_iR_j$, $OR_i$, $C(O)R_i$, $C(O)OR_i$, $OC(O)R_i$, $N(R_j)OR_i$, $C(O)N(R_j)R_i$, $N(R_j)C(O)R_i$, $S(O)_qR_i$ (where q is 0, 1 or 2), $SO_2N(R_j)R_i$, or $N(R_j)SO_2R_i$, wherein $R_i$ and $R_j$ are each independently selected from H or (1-4C)alkyl;

(58) $R_3$ and $R_4$ are linked such that, together with the nitrogen atom to which they are attached, they form a nitrogen-linked 4-, 5-6- or 7-membered heterocyclic ring wherein said ring is linked through a spiro carbon atom to a further 4-, 5- or 6-membered ring carbocyclic or heterocyclic ring to form a spiro bicyclic ring system;

and wherein the spiro bicyclic ring system is optionally substituted by one or more substituents independently selected from halo, trifluoromethyl, cyano, (1-4C)alkyl, $NR_iR_j$, $OR_i$, wherein $R_i$ and $R_j$ are each independently selected from H or (1-2C)alkyl.

Suitably, $R_1$ is as defined in any one of paragraphs (1) to (39) above. In an embodiment, $R_1$ is as defined in any one of paragraphs (12) to (39) above. In a particular embodiment, $R_1$ is as defined in any one of paragraphs (20) to (39) above.

Suitably, $R_2$ is as defined in any one of paragraphs (40) to (45) above. In an embodiment, $R_2$ is as defined in paragraph (42) above. In a particular embodiment, $R_1$ is as defined in (44) above.

Suitably, $R_3$ and $R_4$ are as defined in any one of paragraphs (46) to (58) above. In an embodiment, $R_3$ and $R_4$ are as defined in paragraph (49) above.

In an embodiment, $R_1$ is a triazole or imidazole that is optionally substituted as defined hereinbefore.

In a particular group of compounds of the invention:
$R_1$ is as defined in any one of paragraphs (1) to (39) above;
$R_2$ is as defined in any one of paragraphs (40) to (45) above; and
$R_3$ and $R_4$ each have any one of the definitions set out herein.

In a further group of compounds of the invention:
$R_1$ is as defined in any one of paragraphs (12) to (39) above;
$R_2$ is as defined in paragraph (42) above; and
$R_3$ and $R_4$ each have any one of the definitions set out herein.

In a further group of compounds of the invention:
$R_1$ is as defined in any one of paragraphs (20) to (39) above;
$R_2$ is as defined in paragraph (42) above; and
$R_3$ and $R_4$ each have any one of the definitions set out herein.

In a further group of compounds of the invention:
$R_1$ is as defined in any one of paragraphs (22) to (39) above;
$R_2$ is as defined in paragraph (42) above; and
$R_3$ and $R_4$ each have any one of the definitions set out herein.

In a further group of compounds of the invention:
R₁ is as defined in paragraph (25) above;
R₂ is as defined in paragraph (42) above; and
R₃ and R₄ each have any one of the definitions set out herein.

In a further group of compounds of the invention:
R₁ is as defined in paragraph (26) above;
R₂ is as defined in paragraph (42) above; and
R₃ and R₄ each have any one of the definitions set out herein.

In a further group of compounds of the invention:
R₁ is as defined in paragraph (27) above;
R₂ is as defined in paragraph (42) above; and
R₃ and R₄ each have any one of the definitions set out herein.

In a further group of compounds of the invention:
R₁ is as defined in any one of paragraphs (12) to (39) above;
R₂ is as defined in paragraph (43) above; and
R₃ and R₄ each have any one of the definitions set out herein.

In a further group of compounds of the invention:
R₁ is as defined in any one of paragraphs (12) to (39) above;
R₂ is as defined in paragraph (44) above; and
R₃ and R₄ each have any one of the definitions set out herein.

In a further group of compounds of the invention:
R₁ is as defined in any one of paragraphs (21) to (39) above;
R₂ is as defined in paragraph (43) above; and
R₃ and R₄ each have any one of the definitions set out herein.

In a further group of compounds of the invention:
R₁ is as defined in any one of paragraphs (21) to (39) above;
R₂ is as defined in paragraph (44) above; and
R₃ and R₄ each have any one of the definitions set out herein.

In a further group of compounds of the invention:
R₁ is as defined in paragraph (25) above;
R₂ is as defined in paragraph (43) above; and
R₃ and R₄ each have any one of the definitions set out herein.

In a further group of compounds of the invention:
R₁ is as defined in paragraph (25) above;
R₂ is as defined in paragraph (44) above; and
R₃ and R₄ each have any one of the definitions set out herein.

Particular compounds of the present invention include any one of the compounds exemplified in the present application, or a pharmaceutically acceptable salt or solvate thereof, and, in particular, any one of the following:

N2-(2-methoxy-4-(1-methyl-1H-1,2,3-triazol-5-yl)phenyl)-6-methyl-N8-neopentylpyrido[3,4-d]pyrimidine-2,8-diamine;
N2-(2-ethoxy-4-(4-methyl-4H-1,2,4-triazol-3-yl)phenyl)-6-methyl-N8-((3-methyltetrahydrofuran-3-yl)methyl)pyrido[3,4-d]pyrimidine-2,8-diamine;
1-(((2-((2-ethoxy-4-(4-methyl-4H-1,2,4-triazol-3-yl)phenyl)amino)-6-methylpyrido[3,4-d]pyrimidin-8-yl)amino)methyl)cyclobutanol;
1-(2-((2-ethoxy-4-(4-methyl-4H-1,2,4-triazol-3-yl)phenyl)amino)-6-methylpyrido[3,4-d]pyrimidin-8-yl)-3-methyl-azetidine-3-carbonitrile;
N-(2-ethoxy-4-(4-methyl-4H-1,2,4-triazol-3-yl)phenyl)-6-methyl-8-(7-oxa-2-azaspiro[3.5]nonan-2-yl)pyrido[3,4-d]pyrimidin-2-amine;
1-(2-((2-ethoxy-4-(4-methyl-4H-1,2,4-triazol-3-yl)phenyl)amino)-6-methylpyrido[3,4-d]pyrimidin-8-yl)piperidine-4-carbonitrile;
1-(2-((2-ethoxy-4-(4-methyl-4H-1,2,4-triazol-3-yl)phenyl)amino)-6-methylpyrido[3,4-d]pyrimidin-8-yl)-3-methyl-azetidin-3-ol;
N2-(2-ethoxy-4-(4-methyl-4H-1,2,4-triazol-3-yl)phenyl)-6-methyl-N8-((3-methyloxetan-3-yl)methyl)pyrido[3,4-d]pyrimidine-2,8-diamine;
N2-(2-ethoxy-4-(4-methyl-4H-1,2,4-triazol-3-yl)phenyl)-6-methyl-N8-(tetrahydro-2H-pyran-4-yl)pyrido[3,4-d]pyrimidine-2,8-diamine;
N-(2-ethoxy-4-(4-methyl-4H-1,2,4-triazol-3-yl)phenyl)-6-methyl-8-(2-oxa-7-azaspiro[4.4]nonan-7-yl)pyrido[3,4-d]pyrimidin-2-amine;
1-(((2-((2-ethoxy-4-(4-methyl-4H-1,2,4-triazol-3-yl)phenyl)amino)-6-methylpyrido[3,4-d]pyrimidin-8-yl)amino)methyl)cyclopropanol;
N2-(4-(1,2-dimethyl-1H-imidazol-5-yl)-2-methoxyphenyl)-6-methyl-N8-((3-methyltetrahydrofuran-3-yl)methyl)pyrido[3,4-d]pyrimidine-2,8-diamine;
N-(4-(1,2-dimethyl-1H-imidazol-5-yl)-2-methoxyphenyl)-6-methyl-8-(2-oxa-7-azaspiro[4.4]nonan-7-yl)pyrido[3,4-d]pyrimidin-2-amine;
1-(2-((4-(1,2-dimethyl-1H-imidazol-5-yl)-2-methoxyphenyl)amino)-6-methylpyrido[3,4-d]pyrimidin-8-yl)piperidine-4-carbonitrile;
1-(2-((4-(1,2-dimethyl-1H-imidazol-5-yl)-2-methoxyphenyl)amino)-6-methylpyrido[3,4-d]pyrimidin-8-yl)-3-methylazetidine-3-carbonitrile;
N-(2-ethoxy-4-(4-methyl-4H-1,2,4-triazol-3-yl)phenyl)-6-methyl-8-(1-oxa-6-azaspiro[3.3]heptan-6-yl)pyrido[3,4-d]pyrimidin-2-amine;
N2-(2-methoxy-4-(1-methyl-1H-pyrazol-3-yl)phenyl)-6-methyl-N8-neopentyl pyrido[3,4-d]pyrimidine-2,8-diamine;
8-(3,3-difluoroazetidin-1-yl)-N-(2-ethoxy-4-(4-methyl-4H-1,2,4-triazol-3-yl)phenyl)-6-methylpyrido[3,4-d]pyrimidin-2-amine;
N-(2-ethoxy-4-(4-methyl-4H-1,2,4-triazol-3-yl)phenyl)-8-(4-methoxypiperidin-1-yl)-6-methylpyrido[3,4-d]pyrimidin-2-amine;
N-(2-ethoxy-4-(4-methyl-4H-1,2,4-triazol-3-yl)phenyl)-8-(3-methoxypiperidin-1-yl)-6-methylpyrido[3,4-d]pyrimidin-2-amine;
N-(2-ethoxy-4-(4-methyl-4H-1,2,4-triazol-3-yl)phenyl)-6-methyl-8-(2-methylmorpholino)pyrido[3,4-d]pyrimidin-2-amine;
N-(2-ethoxy-4-(4-methyl-4H-1,2,4-triazol-3-yl)phenyl)-8-(4-methoxy-4-methylpiperidin-1-yl)-6-methylpyrido[3,4-d]pyrimidin-2-amine;
8-(3-azabicyclo[3.1.0]hexan-3-yl)-N-(2-ethoxy-4-(4-methyl-4H-1,2,4-triazol-3-yl)phenyl)-6-methylpyrido[3,4-d]pyrimidin-2-amine;
8-(3-(dimethylamino)azetidin-1-yl)-N-(2-ethoxy-4-(4-methyl-4H-1,2,4-triazol-3-yl)phenyl)-6-methylpyrido[3,4-d]pyrimidin-2-amine;
1-(2-((2-ethoxy-4-(4-methyl-4H-1,2,4-triazol-3-yl)phenyl)amino)-6-methylpyrido[3,4-d]pyrimidin-8-yl)piperidin-4-ol;
N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine;

1-(2-((2-ethoxy-4-(4-methyl-4H-1,2,4-triazol-3-yl)phenyl) amino)-6-methylpyrido[3,4-d]pyrimidin-8-yl)-3-methyl-pyrrolidin-3-ol;

1-(2-((2-ethoxy-4-(4-methyl-4H-1,2,4-triazol-3-yl)phenyl) amino)-6-methylpyrido[3,4-d]pyrimidin-8-yl)-4-methyl-piperidine-4-carbonitrile;

1-(2-((2-ethoxy-4-(4-methyl-4H-1,2,4-triazol-3-yl)phenyl) amino)-6-methylpyrido[3,4-d]pyrimidin-8-yl)pyrrolidine-3-carbonitrile;

N2-(2-methoxy-4-(1-methyl-1H-imidazol-2-yl)phenyl)-6-methyl-N8-neopentylpyrido[3,4-d]pyrimidine-2,8-diamine;

N2-(2-methoxy-4-(1-methyl-1H-pyrazol-5-yl)phenyl)-6-methyl-N8-neopentylpyrido[3,4-d]pyrimidine-2,8-diamine;

N2-(2-methoxy-4-(oxazol-2-yl)phenyl)-6-methyl-N8-neopentylpyrido[3,4-d]pyrimidine-2,8-diamine;

N-(2-ethoxy-4-(4-methyl-4H-1,2,4-triazol-3-yl)phenyl)-8-(3-methoxypyrrolidin-1-yl)-6-methylpyrido[3,4-d]pyrimidin-2-amine;

8-(3,3-dimethyl azetidin-1-yl)-N-(2-ethoxy-4-(4-methyl-4H-1,2,4-triazol-3-yl)phenyl)-6-methylpyrido[3,4-d]pyrimidin-2-amine;

1-(2-((2-ethoxy-4-(4-methyl-4H-1,2,4-triazol-3-yl)phenyl) amino)-6-methylpyrido[3,4-d]pyrimidin-8-yl)-3-methyl-pyrrolidine-3-carbonitrile;

8-(2,2-dimethyl azetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-6-methyl-8-(3-(trifluoromethyl)azetidin-1-yl)pyrido[3,4-d]pyrimidin-2-amine;

N-(2-ethoxy-4-(4-methyl-4H-1,2,4-triazol-3-yl)phenyl)-6-methyl-8-(2-azaspiro[3.3]heptan-2-yl)pyrido[3,4-d]pyrimidin-2-amine;

(R)—N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine;

(S)—N8-(3,3-dimethyl butan-2-yl)-N2-(2-ethoxy-4-(4-methyl-4H-1,2,4-triazol-3-yl)phenyl)-6-methylpyrido[3,4-d]pyrimidine-2,8-diamine;

N2-(2-ethoxy-4-(4-methyl-4H-1,2,4-triazol-3-yl)phenyl)-N8-((1-methoxycyclobutyl)methyl)-6-methylpyrido[3,4-d]pyrimidine-2,8-diamine;

N2-(2-ethoxy-4-(4-methyl-4H-1,2,4-triazol-3-yl)phenyl)-6-methyl-N8-(1-methylazetidin-3-yl)pyrido[3,4-d]pyrimidine-2,8-diamine;

N2-(2-ethoxy-4-(4-methyl-4H-1,2,4-triazol-3-yl)phenyl)-6-methyl-N8-(oxetan-3-ylmethyl)pyrido[3,4-d]pyrimidine-2,8-diamine;

N-(2-ethoxy-4-(4-methyl-4H-1,2,4-triazol-3-yl)phenyl)-6-methyl-8-(pyrrolidin-1-yl)pyrido[3,4-d]pyrimidin-2-amine;

N-(2-ethoxy-4-(4-methyl-4H-1,2,4-triazol-3-yl)phenyl)-6-methyl-8-(2-azaspiro[3.4]octan-2-yl)pyrido[3,4-d]pyrimidin-2-amine;

1-(2-((2-ethoxy-4-(4-methyl-4H-1,2,4-triazol-3-yl)phenyl) amino)-6-methylpyrido[3,4-d]pyrimidin-8-yl)-3-ethyl-azetidin-3-ol;

N2-(2-ethoxy-4-(4-methyl-4H-1,2,4-triazol-3-yl)phenyl)-6-methyl-N8-(1-methylpiperidin-4-yl)pyrido[3,4-d]pyrimidine-2,8-diamine;

8-(4-(dimethylamino) piperidin-1-yl)-N-(2-ethoxy-4-(4-methyl-4H-1,2,4-triazol-3-yl)phenyl)-6-methylpyrido[3,4-d]pyrimidin-2-amine;

N2-(2-ethoxy-4-(4-methyl-4H-1,2,4-triazol-3-yl)phenyl)-6-methyl-N8-((tetrahydro-2H-pyran-4-yl)methyl)pyrido[3,4-d]pyrimidine-2,8-diamine;

N2-(2-ethoxy-4-(4-methyl-4H-1,2,4-triazol-3-yl)phenyl)-6-methyl-N8-((4-methyltetrahydro-2H-pyran-4-yl)methyl) pyrido[3,4-d]pyrimidine-2,8-diamine;

1-(2-((2-ethoxy-4-(4-methyl-4H-1,2,4-triazol-3-yl)phenyl) amino)-6-methylpyrido[3,4-d]pyrimidin-8-yl)-4-ethylpiperidine-4-carbonitrile;

N2-(2-ethoxy-4-(4-methyl-4H-1,2,4-triazol-3-yl)phenyl)-6-methyl-N8-(2-(3-methyltetrahydrofuran-3-yl)ethyl) pyrido[3,4-d]pyrimidine-2,8-diamine;

N2-(2-ethoxy-4-(4-methyl-4H-1,2,4-triazol-3-yl)phenyl)-6-methyl-N8-(1-(tetrahydro-2H-pyran-4-yl)ethyl)pyrido[3,4-d]pyrimidine-2,8-diamine;

N2-(2-ethoxy-4-(4-methyl-4H-1,2,4-triazol-3-yl)phenyl)-6-methyl-N8-(pentan-3-yl)pyrido[3,4-d]pyrimidine-2,8-diamine;

N2-(2-ethoxy-4-(4-methyl-4H-1,2,4-triazol-3-yl)phenyl)-6-methyl-N8-(tetrahydrofuran-3-yl)pyrido[3,4-d]pyrimidine-2,8-diamine;

8-(3-ethoxy-3-methylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-ethyl-3-methoxyazetidin-1-yl)-6-methylpyrido[3,4-d] pyrimidin-2-amine;

8-(3-ethoxy-3-ethylazetidin-1-yl)-N-(2-ethoxy-4-(4-methyl-4H-1,2,4-triazol-3-yl)phenyl)-6-methylpyrido[3,4-d]pyrimidin-2-amine;

N-(2-ethoxy-4-(4-methyl-4H-1,2,4-triazol-3-yl)phenyl)-8-(3-isopropyl-3-methoxyazetidin-1-yl)-6-methylpyrido[3,4-d]pyrimidin-2-amine;

8-(3-ethoxy-3-isopropylazetidin-1-yl)-N-(2-ethoxy-4-(4-methyl-4H-1,2,4-triazol-3-yl)phenyl)-6-methylpyrido[3,4-d]pyrimidin-2-amine;

1-(2-((2-ethoxy-4-(4-methyl-4H-1,2,4-triazol-3-yl)phenyl) amino)-6-methylpyrido[3,4-d]pyrimidin-8-yl)-3-ethyl-azetidine-3-carbonitrile;

1-(2-((2-ethoxy-4-(4-methyl-4H-1,2,4-triazol-3-yl)phenyl) amino)-6-methylpyrido[3,4-d]pyrimidin-8-yl)-3-isopropylazetidine-3-carbonitrile;

1-(2-((2-ethoxy-4-(4-methyl-4H-1,2,4-triazol-3-yl)phenyl) amino)-6-methylpyrido[3,4-d]pyrimidin-8-yl)-2,2,3-trimethylazetidine-3-carbonitrile;

N-(2-ethoxy-4-(4-methyl-4H-1,2,4-triazol-3-yl)phenyl)-8-(3-methoxy-2,2-dimethylazetidin-1-yl)-6-methylpyrido [3,4-d]pyrimidin-2-amine;

N-(2-ethoxy-4-(4-methyl-4H-1,2,4-triazol-3-yl)phenyl)-8-(3-methoxy-2,2,3-trimethylazetidin-1-yl)-6-methylpyrido [3,4-d]pyrimidin-2-amine;

1-(2-((2-ethoxy-4-(4-methyl-4H-1,2,4-triazol-3-yl)phenyl) amino)-6-methylpyrido[3,4-d]pyrimidin-8-yl)-2,2-dim-ethylazetidine-3-carbonitrile;

N2-(2-methoxy-4-(4-methyl-4H-1,2,4-triazol-3-yl)phenyl)-6-methyl-N8-(1-methylpiperidin-4-yl)pyrido[3,4-d]pyrimidine-2,8-diamine;

8-(4-(dimethylamino)piperidin-1-yl)-N-(2-methoxy-4-(4-methyl-4H-1,2,4-triazol-3-yl)phenyl)-6-methylpyrido[3,4-d]pyrimidin-2-amine;

N2-(2-methoxy-4-(4-methyl-4H-1,2,4-triazol-3-yl)phenyl)-6-methyl-N8-((tetrahydro-2H-pyran-4-yl)methyl)pyrido [3,4-d]pyrimidine-2,8-diamine;

N2-(2-methoxy-4-(4-methyl-4H-1,2,4-triazol-3-yl)phenyl)-6-methyl-N8-((4-methyltetrahydro-2H-pyran-4-yl) methyl)pyrido[3,4-d]pyrimidine-2,8-diamine;

4-ethyl-1-(2-((2-methoxy-4-(4-methyl-4H-1,2,4-triazol-3-yl)phenyl)amino)-6-methylpyrido[3,4-d]pyrimidin-8-yl)piperidine-4-carbonitrile;

N2-(2-methoxy-4-(4-methyl-4H-1,2,4-triazol-3-yl)phenyl)-6-methyl-N8-(2-(3-methyltetrahydrofuran-3-yl)ethyl)pyrido[3,4-d]pyrimidine-2,8-diamine;

N2-(2-methoxy-4-(4-methyl-4H-1,2,4-triazol-3-yl)phenyl)-6-methyl-N8-(1-(tetrahydro-2H-pyran-4-yl)ethyl)pyrido[3,4-d]pyrimidine-2,8-diamine;

N2-(2-methoxy-4-(4-methyl-4H-1,2,4-triazol-3-yl)phenyl)-6-methyl-N8-(pentan-3-yl)pyrido[3,4-d]pyrimidine-2,8-diamine;

N2-(2-methoxy-4-(4-methyl-4H-1,2,4-triazol-3-yl)phenyl)-6-methyl-N8-(tetrahydrofuran-3-yl)pyrido[3,4-d]pyrimidine-2,8-diamine;

8-(3-ethoxy-3-methylazetidin-1-yl)-N-(2-methoxy-4-(4-methyl-4H-1,2,4-triazol-3-yl)phenyl)-6-methylpyrido[3,4-d]pyrimidin-2-amine;

8-(3-ethyl-3-methoxyazetidin-1-yl)-N-(2-methoxy-4-(4-methyl-4H-1,2,4-triazol-3-yl)phenyl)-6-methylpyrido[3,4-d]pyrimidin-2-amine;

8-(3-ethoxy-3-ethylazetidin-1-yl)-N-(2-methoxy-4-(4-methyl-4H-1,2,4-triazol-3-yl)phenyl)-6-methylpyrido[3,4-d]pyrimidin-2-amine;

8-(3-isopropyl-3-methoxyazetidin-1-yl)-N-(2-methoxy-4-(4-methyl-4H-1,2,4-triazol-3-yl)phenyl)-6-methylpyrido[3,4-d]pyrimidin-2-amine;

8-(3-ethoxy-3-isopropylazetidin-1-yl)-N-(2-methoxy-4-(4-methyl-4H-1,2,4-triazol-3-yl)phenyl)-6-methylpyrido[3,4-d]pyrimidin-2-amine;

3-ethyl-1-(2-((2-methoxy-4-(4-methyl-4H-1,2,4-triazol-3-yl)phenyl)amino)-6-methylpyrido[3,4-d]pyrimidin-8-yl)azetidine-3-carbonitrile;

3-isopropyl-1-(2-((2-methoxy-4-(4-methyl-4H-1,2,4-triazol-3-yl)phenyl)amino)-6-methylpyrido[3,4-d]pyrimidin-8-yl)azetidine-3-carbonitrile;

1-(2-((2-methoxy-4-(4-methyl-4H-1,2,4-triazol-3-yl)phenyl)amino)-6-methylpyrido[3,4-d]pyrimidin-8-yl)-2,2,3-trimethylazetidine-3-carbonitrile;

8-(3-methoxy-2,2-dimethylazetidin-1-yl)-N-(2-methoxy-4-(4-methyl-4H-1,2,4-triazol-3-yl)phenyl)-6-methylpyrido[3,4-d]pyrimidin-2-amine;

8-(3-methoxy-2,2,3-trimethylazetidin-1-yl)-N-(2-methoxy-4-(4-methyl-4H-1,2,4-triazol-3-yl)phenyl)-6-methylpyrido[3,4-d]pyrimidin-2-amine;

1-(2-((2-methoxy-4-(4-methyl-4H-1,2,4-triazol-3-yl)phenyl)amino)-6-methylpyrido[3,4-d]pyrimidin-8-yl)-2,2-dimethylazetidine-3-carbonitrile;

8-(3,3-dimethylazetidin-1-yl)-N-(2-methoxy-4-(1-methyl-1H-tetrazol-5-yl)phenyl)-6-methylpyrido[3,4-d]pyrimidin-2-amine;

1-(2-((2-methoxy-4-(1-methyl-1H-tetrazol-5-yl)phenyl)amino)-6-methylpyrido[3,4-d]pyrimidin-8-yl)-4-methylpiperidine-4-carbonitrile;

8-(3-methoxy-3-methylazetidin-1-yl)-N-(2-methoxy-4-(1-methyl-1H-tetrazol-5-yl)phenyl)-6-methylpyrido[3,4-d]pyrimidin-2-amine;

N-(2-methoxy-4-(1-methyl-1H-tetrazol-5-yl)phenyl)-8-(4-methoxypiperidin-1-yl)-6-methylpyrido[3,4-d]pyrimidin-2-amine;

N-(2-methoxy-4-(1-methyl-1H-tetrazol-5-yl)phenyl)-8-(4-methoxy-4-methylpiperidin-1-yl)-6-methylpyrido[3,4-d]pyrimidin-2-amine;

N-(2-methoxy-4-(1-methyl-1H-tetrazol-5-yl)phenyl)-6-methyl-8-(1-oxa-6-azaspiro[3.3]heptan-6-yl)pyrido[3,4-d]pyrimidin-2-amine;

1-(2-((2-methoxy-4-(1-methyl-1H-tetrazol-5-yl)phenyl)amino)-6-methylpyrido[3,4-d]pyrimidin-8-yl)-3-methylazetidine-3-carbonitrile;

N2-(2-methoxy-4-(1-methyl-1H-tetrazol-5-yl)phenyl)-6-methyl-N8-((3-methyltetrahydrofuran-3-yl)methyl)pyrido[3,4-d]pyrimidine-2,8-diamine;

N-(2-methoxy-4-(1-methyl-1H-tetrazol-5-yl)phenyl)-6-methyl-8-(2-oxa-7-azaspiro[4.4]nonan-7-yl)pyrido[3,4-d]pyrimidin-2-amine;

N2-(2-methoxy-4-(1-methyl-1H-tetrazol-5-yl)phenyl)-6-methyl-N8-(tetrahydro-2H-pyran-4-yl)pyrido[3,4-d]pyrimidine-2,8-diamine;

N-(2-methoxy-4-(1-methyl-1H-tetrazol-5-yl)phenyl)-6-methyl-8-(7-oxa-2-azaspiro[3.5]nonan-2-yl)pyrido[3,4-d]pyrimidin-2-amine;

N2-(2-methoxy-4-(1-methyl-1H-tetrazol-5-yl)phenyl)-6-methyl-N8-neopentylpyrido[3,4-d]pyrimidine-2,8-diamine;

N-(2-(difluoromethoxy)-4-(4-methyl-4H-1,2,4-triazol-3-yl)phenyl)-8-(3,3-dimethylazetidin-1-yl)-6-methylpyrido[3,4-d]pyrimidin-2-amine;

1-(2-((2-(difluoromethoxy)-4-(4-methyl-4H-1,2,4-triazol-3-yl)phenyl)amino)-6-methylpyrido[3,4-d]pyrimidin-8-yl)-4-methylpiperidine-4-carbonitrile;

N-(2-(difluoromethoxy)-4-(4-methyl-4H-1,2,4-triazol-3-yl)phenyl)-8-(3-methoxy-3-methylazetidin-1-yl)-6-methylpyrido[3,4-d]pyrimidin-2-amine;

N-(2-(difluoromethoxy)-4-(4-methyl-4H-1,2,4-triazol-3-yl)phenyl)-8-(4-methoxypiperidin-1-yl)-6-methylpyrido[3,4-d]pyrimidin-2-amine;

N-(2-(difluoromethoxy)-4-(4-methyl-4H-1,2,4-triazol-3-yl)phenyl)-8-(4-methoxy-4-methylpiperidin-1-yl)-6-methylpyrido[3,4-d]pyrimidin-2-amine;

N-(2-(difluoromethoxy)-4-(4-methyl-4H-1,2,4-triazol-3-yl)phenyl)-6-methyl-8-(1-oxa-6-azaspiro[3.3]heptan-6-yl)pyrido[3,4-d]pyrimidin-2-amine;

1-(2-((2-(difluoromethoxy)-4-(4-methyl-4H-1,2,4-triazol-3-yl)phenyl)amino)-6-methylpyrido[3,4-d]pyrimidin-8-yl)-3-methylazetidine-3-carbonitrile;

N2-(2-(difluoromethoxy)-4-(4-methyl-4H-1,2,4-triazol-3-yl)phenyl)-6-methyl-N8-((3-methyltetrahydrofuran-3-yl)methyl)pyrido[3,4-d]pyrimidine-2,8-diamine;

N-(2-(difluoromethoxy)-4-(4-methyl-4H-1,2,4-triazol-3-yl)phenyl)-6-methyl-8-(2-oxa-7-azaspiro[4.4]nonan-7-yl)pyrido[3,4-d]pyrimidin-2-amine;

N2-(2-(difluoromethoxy)-4-(4-methyl-4H-1,2,4-triazol-3-yl)phenyl)-6-methyl-N8-(tetrahydro-2H-pyran-4-yl)pyrido[3,4-d]pyrimidine-2,8-diamine;

N-(2-(difluoromethoxy)-4-(4-methyl-4H-1,2,4-triazol-3-yl)phenyl)-6-methyl-8-(7-oxa-2-azaspiro[3.5]nonan-2-yl)pyrido[3,4-d]pyrimidin-2-amine;

N2-(2-(difluoromethoxy)-4-(4-methyl-4H-1,2,4-triazol-3-yl)phenyl)-6-methyl-N8-neopentylpyrido[3,4-d]pyrimidine-2,8-diamine;

8-(3,3-dimethylazetidin-1-yl)-N-(4-(4-ethyl-4H-1,2,4-triazol-3-yl)-2-methoxyphenyl)-6-methylpyrido[3,4-d]pyrimidin-2-amine;

1-(2-((4-(4-ethyl-4H-1,2,4-triazol-3-yl)-2-methoxyphenyl)amino)-6-methylpyrido[3,4-d]pyrimidin-8-yl)-4-methylpiperidine-4-carbonitrile;

N-(4-(4-ethyl-4H-1,2,4-triazol-3-yl)-2-methoxyphenyl)-8-(3-methoxy-3-methylazetidin-1-yl)-6-methylpyrido[3,4-d]pyrimidin-2-amine;

N-(4-(4-ethyl-4H-1,2,4-triazol-3-yl)-2-methoxyphenyl)-8-(4-methoxypiperidin-1-yl)-6-methylpyrido[3,4-d]pyrimidin-2-amine;

N-(4-(4-ethyl-4H-1,2,4-triazol-3-yl)-2-methoxyphenyl)-8-(4-methoxy-4-methylpiperidin-1-yl)-6-methylpyrido[3,4-d]pyrimidin-2-amine;

N-(4-(4-ethyl-4H-1,2,4-triazol-3-yl)-2-methoxyphenyl)-6-methyl-8-(1-oxa-6-azaspiro[3.3]heptan-6-yl)pyrido[3,4-d]pyrimidin-2-amine;

1-(2-((4-(4-ethyl-4H-1,2,4-triazol-3-yl)-2-methoxyphenyl)amino)-6-methylpyrido[3,4-d]pyrimidin-8-yl)-3-methylazetidine-3-carbonitrile;

N2-(4-(4-ethyl-4H-1,2,4-triazol-3-yl)-2-methoxyphenyl)-6-methyl-N8-((3-methyltetrahydrofuran-3-yl)methyl)pyrido[3,4-d]pyrimidine-2,8-diamine;

N-(4-(4-ethyl-4H-1,2,4-triazol-3-yl)-2-methoxyphenyl)-6-methyl-8-(2-oxa-7-azaspiro[4.4]nonan-7-yl)pyrido[3,4-d]pyrimidin-2-amine;

N2-(4-(4-ethyl-4H-1,2,4-triazol-3-yl)-2-methoxyphenyl)-6-methyl-N8-(tetra hydro-2H-pyran-4-yl)pyrido[3,4-d]pyrimidine-2,8-diamine;

N-(4-(4-ethyl-4H-1,2,4-triazol-3-yl)-2-methoxyphenyl)-6-methyl-8-(7-oxa-2-azaspiro[3.5]nonan-2-yl)pyrido[3,4-d]pyrimidin-2-amine;

N2-(4-(4-ethyl-4H-1,2,4-triazol-3-yl)-2-methoxyphenyl)-6-methyl-N8-neopentylpyrido[3,4-d]pyrimidine-2,8-diamine;

8-(3,3-dimethyl azetidin-1-yl)-N-(2-ethoxy-4-(4-ethyl-4H-1,2,4-triazol-3-yl)phenyl)-6-methylpyrido[3,4-d]pyrimidin-2-amine;

1-(2-((2-ethoxy-4-(4-ethyl-4H-1,2,4-triazol-3-yl)phenyl)amino)-6-methylpyrido[3,4-d]pyrimidin-8-yl)-4-methylpiperidine-4-carbonitrile;

N-(2-ethoxy-4-(4-ethyl-4H-1,2,4-triazol-3-yl)phenyl)-8-(3-methoxy-3-methylazetidin-1-yl)-6-methylpyrido[3,4-d]pyrimidin-2-amine;

N-(2-ethoxy-4-(4-ethyl-4H-1,2,4-triazol-3-yl)phenyl)-8-(4-methoxypiperidin-1-yl)-6-methylpyrido[3,4-d]pyrimidin-2-amine;

N-(2-ethoxy-4-(4-ethyl-4H-1,2,4-triazol-3-yl)phenyl)-8-(4-methoxy-4-methylpiperidin-1-yl)-6-methylpyrido[3,4-d]pyrimidin-2-amine;

N-(2-ethoxy-4-(4-ethyl-4H-1,2,4-triazol-3-yl)phenyl)-6-methyl-8-(1-oxa-6-azaspiro[3.3]heptan-6-yl)pyrido[3,4-d]pyrimidin-2-amine;

1-(2-((2-ethoxy-4-(4-ethyl-4H-1,2,4-triazol-3-yl)phenyl)amino)-6-methylpyrido[3,4-d]pyrimidin-8-yl)-3-methylazetidine-3-carbonitrile;

N2-(2-ethoxy-4-(4-ethyl-4H-1,2,4-triazol-3-yl)phenyl)-6-methyl-N8-((3-methyltetrahydrofuran-3-yl)methyl)pyrido[3,4-d]pyrimidine-2,8-diamine;

N-(2-ethoxy-4-(4-ethyl-4H-1,2,4-triazol-3-yl)phenyl)-6-methyl-8-(2-oxa-7-azaspiro[4.4]nonan-7-yl)pyrido[3,4-d]pyrimidin-2-amine;

N2-(2-ethoxy-4-(4-ethyl-4H-1,2,4-triazol-3-yl)phenyl)-6-methyl-N8-(tetra hydro-2H-pyran-4-yl)pyrido[3,4-d]pyrimidine-2,8-diamine;

N-(2-ethoxy-4-(4-ethyl-4H-1,2,4-triazol-3-yl)phenyl)-6-methyl-8-(7-oxa-2-azaspiro[3.5]nonan-2-yl)pyrido[3,4-d]pyrimidin-2-amine;

N2-(2-ethoxy-4-(4-ethyl-4H-1,2,4-triazol-3-yl)phenyl)-6-methyl-N8-neopentylpyrido[3,4-d]pyrimidine-2,8-diamine;

N-(4-(4,5-dimethyl-4H-1,2,4-triazol-3-yl)-2-methoxyphenyl)-8-(3,3-dimethylazetidin-1-yl)-6-methylpyrido[3,4-d]pyrimidin-2-amine;

1-(2-((4-(4,5-dimethyl-4H-1,2,4-triazol-3-yl)-2-methoxyphenyl)amino)-6-methylpyrido[3,4-d]pyrimidin-8-yl)-4-methylpiperidine-4-carbonitrile;

N-(4-(4,5-dimethyl-4H-1,2,4-triazol-3-yl)-2-methoxyphenyl)-8-(3-methoxy-3-methylazetidin-1-yl)-6-methylpyrido[3,4-d]pyrimidin-2-amine;

N-(4-(4,5-dimethyl-4H-1,2,4-triazol-3-yl)-2-methoxyphenyl)-8-(4-methoxypiperidin-1-yl)-6-methylpyrido[3,4-d]pyrimidin-2-amine;

N-(4-(4,5-dimethyl-4H-1,2,4-triazol-3-yl)-2-methoxyphenyl)-8-(4-methoxy-4-methylpiperidin-1-yl)-6-methylpyrido[3,4-d]pyrimidin-2-amine;

N-(4-(4,5-dimethyl-4H-1,2,4-triazol-3-yl)-2-methoxyphenyl)-6-methyl-8-(1-oxa-6-azaspiro[3.3]heptan-6-yl)pyrido[3,4-d]pyrimidin-2-amine;

1-(2-((4-(4,5-dimethyl-4H-1,2,4-triazol-3-yl)-2-methoxyphenyl)amino)-6-methylpyrido[3,4-d]pyrimidin-8-yl)-3-methylazetidine-3-carbonitrile;

N2-(4-(4,5-dimethyl-4H-1,2,4-triazol-3-yl)-2-methoxyphenyl)-6-methyl-N8-((3-methyltetrahydrofuran-3-yl)methyl)pyrido[3,4-d]pyrimidine-2,8-diamine;

N-(4-(4,5-dimethyl-4H-1,2,4-triazol-3-yl)-2-methoxyphenyl)-6-methyl-8-(2-oxa-7-azaspiro[4.4]nonan-7-yl)pyrido[3,4-d]pyrimidin-2-amine;

N2-(4-(4,5-dimethyl-4H-1,2,4-triazol-3-yl)-2-methoxyphenyl)-6-methyl-N8-(tetrahydro-2H-pyran-4-yl)pyrido[3,4-d]pyrimidine-2,8-diamine;

N-(4-(4,5-dimethyl-4H-1,2,4-triazol-3-yl)-2-methoxyphenyl)-6-methyl-8-(7-oxa-2-azaspiro[3.5]nonan-2-yl)pyrido[3,4-d]pyrimidin-2-amine;

N2-(4-(4,5-dimethyl-4H-1,2,4-triazol-3-yl)-2-methoxyphenyl)-6-methyl-N8-neopentylpyrido[3,4-d]pyrimidine-2,8-diamine;

N-(4-(4,5-dimethyl-4H-1,2,4-triazol-3-yl)-2-ethoxyphenyl)-8-(3,3-dimethylazetidin-1-yl)-6-methylpyrido[3,4-d]pyrimidin-2-amine;

1-(2-((4-(4,5-dimethyl-4H-1,2,4-triazol-3-yl)-2-ethoxyphenyl)amino)-6-methylpyrido[3,4-d]pyrimidin-8-yl)-4-methylpiperidine-4-carbonitrile;

N-(4-(4,5-dimethyl-4H-1,2,4-triazol-3-yl)-2-ethoxyphenyl)-8-(3-methoxy-3-methyl azetidin-1-yl)-6-methylpyrido[3,4-d]pyrimidin-2-amine;

N-(4-(4,5-dimethyl-4H-1,2,4-triazol-3-yl)-2-ethoxyphenyl)-8-(4-methoxypiperidin-1-yl)-6-methylpyrido[3,4-d]pyrimidin-2-amine;

N-(4-(4,5-dimethyl-4H-1,2,4-triazol-3-yl)-2-ethoxyphenyl)-8-(4-methoxy-4-methylpiperidin-1-yl)-6-methylpyrido[3,4-d]pyrimidin-2-amine;

N-(4-(4,5-dimethyl-4H-1,2,4-triazol-3-yl)-2-ethoxyphenyl)-6-methyl-8-(1-oxa-6-azaspiro[3.3]heptan-6-yl)pyrido[3,4-d]pyrimidin-2-amine;

1-(2-((4-(4,5-dimethyl-4H-1,2,4-triazol-3-yl)-2-ethoxyphenyl)amino)-6-methylpyrido[3,4-d]pyrimidin-8-yl)-3-methylazetidine-3-carbonitrile;

N2-(4-(4,5-dimethyl-4H-1,2,4-triazol-3-yl)-2-ethoxyphenyl)-6-methyl-N8-((3-methyltetrahydrofuran-3-yl)methyl)pyrido[3,4-d]pyrimidine-2,8-diamine;

N-(4-(4,5-dimethyl-4H-1,2,4-triazol-3-yl)-2-ethoxyphenyl)-6-methyl-8-(2-oxa-7-azaspiro[4.4]nonan-7-yl)pyrido[3,4-d]pyrimidin-2-amine;

N2-(4-(4,5-dimethyl-4H-1,2,4-triazol-3-yl)-2-ethoxyphenyl)-6-methyl-N8-(tetra hydro-2H-pyran-4-yl)pyrido[3,4-d]pyrimidine-2,8-diamine;

N-(4-(4,5-dimethyl-4H-1,2,4-triazol-3-yl)-2-ethoxyphenyl)-6-methyl-8-(7-oxa-2-azaspiro[3.5]nonan-2-yl)pyrido[3,4-d]pyrimidin-2-amine;

N2-(4-(4,5-dimethyl-4H-1,2,4-triazol-3-yl)-2-ethoxyphenyl)-6-methyl-N8-neopentylpyrido[3,4-d]pyrimidine-2,8-diamine;

8-(3,3-dimethylazetidin-1-yl)-N-(2-methoxy-4-(1-methyl-1H-1,2,3-triazol-5-yl)phenyl)-6-methylpyrido[3,4-d]pyrimidin-2-amine;

1-(2-((2-methoxy-4-(1-methyl-1H-1,2,3-triazol-5-yl)phenyl)amino)-6-methylpyrido[3,4-d]pyrimidin-8-yl)-4-methylpiperidine-4-carbonitrile;

8-(3-methoxy-3-methylazetidin-1-yl)-N-(2-methoxy-4-(1-methyl-1H-1,2,3-triazol-5-yl)phenyl)-6-methylpyrido[3,4-d]pyrimidin-2-amine;

N-(2-methoxy-4-(1-methyl-1H-1,2,3-triazol-5-yl)phenyl)-8-(4-methoxypiperidin-1-yl)-6-methylpyrido[3,4-d]pyrimidin-2-amine;

N-(2-methoxy-4-(1-methyl-1H-1,2,3-triazol-5-yl)phenyl)-8-(4-methoxy-4-methylpiperidin-1-yl)-6-methylpyrido[3,4-d]pyrimidin-2-amine;

N-(2-methoxy-4-(1-methyl-1H-1,2,3-triazol-5-yl)phenyl)-6-methyl-8-(1-oxa-6-azaspiro[3.3]heptan-6-yl)pyrido[3,4-d]pyrimidin-2-amine;

1-(2-((2-methoxy-4-(1-methyl-1H-1,2,3-triazol-5-yl)phenyl)amino)-6-methylpyrido[3,4-d]pyrimidin-8-yl)-3-methylazetidine-3-carbonitrile;

N2-(2-methoxy-4-(1-methyl-1H-1,2,3-triazol-5-yl)phenyl)-6-methyl-N8-((3-methyltetrahydrofuran-3-yl)methyl)pyrido[3,4-d]pyrimidine-2,8-diamine;

N-(2-methoxy-4-(1-methyl-1H-1,2,3-triazol-5-yl)phenyl)-6-methyl-8-(2-oxa-7-azaspiro[4.4]nonan-7-yl)pyrido[3,4-d]pyrimidin-2-amine;

N2-(2-methoxy-4-(1-methyl-1H-1,2,3-triazol-5-yl)phenyl)-6-methyl-N8-(tetrahydro-2H-pyran-4-yl)pyrido[3,4-d]pyrimidine-2,8-diamine;

N-(2-methoxy-4-(1-methyl-1H-1,2,3-triazol-5-yl)phenyl)-6-methyl-8-(7-oxa-2-azaspiro[3.5]nonan-2-yl)pyrido[3,4-d]pyrimidin-2-amine;

N-(4-(1,2-dimethyl-1H-imidazol-5-yl)-2-methoxyphenyl)-8-(3,3-dimethylazetidin-1-yl)-6-methylpyrido[3,4-d]pyrimidin-2-amine;

1-(2-((4-(1,2-dimethyl-1H-imidazol-5-yl)-2-methoxyphenyl)amino)-6-methylpyrido[3,4-d]pyrimidin-8-yl)-4-methylpiperidine-4-carbonitrile;

N-(4-(1,2-dimethyl-1H-imidazol-5-yl)-2-methoxyphenyl)-8-(3-methoxy-3-methylazetidin-1-yl)-6-methylpyrido[3,4-d]pyrimidin-2-amine;

N-(4-(1,2-dimethyl-1H-imidazol-5-yl)-2-methoxyphenyl)-8-(4-methoxypiperidin-1-yl)-6-methylpyrido[3,4-d]pyrimidin-2-amine;

N-(4-(1,2-dimethyl-1H-imidazol-5-yl)-2-methoxyphenyl)-8-(4-methoxy-4-methylpiperidin-1-yl)-6-methylpyrido[3,4-d]pyrimidin-2-amine;

N-(4-(1,2-dimethyl-1H-imidazol-5-yl)-2-methoxyphenyl)-6-methyl-8-(1-oxa-6-azaspiro[3.3]heptan-6-yl)pyrido[3,4-d]pyrimidin-2-amine;

1-(2-((4-(1,2-dimethyl-1H-imidazol-5-yl)-2-methoxyphenyl)amino)-6-methylpyrido[3,4-d]pyrimidin-8-yl)-3-methylazetidine-3-carbonitrile;

N-(4-(1,2-dimethyl-1H-imidazol-5-yl)-2-methoxyphenyl)-6-methyl-8-(2-oxa-7-azaspiro[4.4]nonan-7-yl)pyrido[3,4-d]pyrimidin-2-amine;

N2-(4-(1,2-dimethyl-1H-imidazol-5-yl)-2-methoxyphenyl)-6-methyl-N8-(tetrahydro-2H-pyran-4-yl)pyrido[3,4-d]pyrimidine-2,8-diamine;

N-(4-(1,2-dimethyl-1H-imidazol-5-yl)-2-methoxyphenyl)-6-methyl-8-(7-oxa-2-azaspiro[3.5]nonan-2-yl)pyrido[3,4-d]pyrimidin-2-amine;

N-(4-(1,5-dimethyl-1H-imidazol-2-yl)-2-methoxyphenyl)-8-(3,3-dimethylazetidin-1-yl)-6-methylpyrido[3,4-d]pyrimidin-2-amine;

1-(2-((4-(1,5-dimethyl-1H-imidazol-2-yl)-2-methoxyphenyl)amino)-6-methylpyrido[3,4-d]pyrimidin-8-yl)-4-methylpiperidine-4-carbonitrile;

N-(4-(1,5-dimethyl-1H-imidazol-2-yl)-2-methoxyphenyl)-8-(3-methoxy-3-methylazetidin-1-yl)-6-methylpyrido[3,4-d]pyrimidin-2-amine;

N-(4-(1,5-dimethyl-1H-imidazol-2-yl)-2-methoxyphenyl)-8-(4-methoxypiperidin-1-yl)-6-methylpyrido[3,4-d]pyrimidin-2-amine;

N-(4-(1,5-dimethyl-1H-imidazol-2-yl)-2-methoxyphenyl)-8-(4-methoxy-4-methylpiperidin-1-yl)-6-methylpyrido[3,4-d]pyrimidin-2-amine;

N-(4-(1,5-dimethyl-1H-imidazol-2-yl)-2-methoxyphenyl)-6-methyl-8-(1-oxa-6-azaspiro[3.3]heptan-6-yl)pyrido[3,4-d]pyrimidin-2-amine;

1-(2-((4-(1,5-dimethyl-1H-imidazol-2-yl)-2-methoxyphenyl)amino)-6-methylpyrido[3,4-d]pyrimidin-8-yl)-3-methylazetidine-3-carbonitrile;

N2-(4-(1,5-dimethyl-1H-imidazol-2-yl)-2-methoxyphenyl)-6-methyl-N8-((3-methyltetrahydrofuran-3-yl)methyl)pyrido[3,4-d]pyrimidine-2,8-diamine;

N-(4-(1,5-dimethyl-1H-imidazol-2-yl)-2-methoxyphenyl)-6-methyl-8-(2-oxa-7-azaspiro[4.4]nonan-7-yl)pyrido[3,4-d]pyrimidin-2-amine;

N2-(4-(1,5-dimethyl-1H-imidazol-2-yl)-2-methoxyphenyl)-6-methyl-N8-(tetrahydro-2H-pyran-4-yl)pyrido[3,4-d]pyrimidine-2,8-diamine;

N-(4-(1,5-dimethyl-1H-imidazol-2-yl)-2-methoxyphenyl)-6-methyl-8-(7-oxa-2-azaspiro[3.5]nonan-2-yl)pyrido[3,4-d]pyrimidin-2-amine;

N2-(4-(1,5-dimethyl-1H-imidazol-2-yl)-2-methoxyphenyl)-6-methyl-N8-neopentylpyrido[3,4-d]pyrimidine-2,8-diamine;

8-(3,3-dimethylazetidin-1-yl)-N-(2-methoxy-4-(1-methyl-1H-imidazol-2-yl)phenyl)-6-methylpyrido[3,4-d]pyrimidin-2-amine;

1-(2-((2-methoxy-4-(1-methyl-1H-imidazol-2-yl)phenyl)amino)-6-methylpyrido[3,4-d]pyrimidin-8-yl)-4-methylpiperidine-4-carbonitrile;

8-(3-methoxy-3-methylazetidin-1-yl)-N-(2-methoxy-4-(1-methyl-1H-imidazol-2-yl)phenyl)-6-methylpyrido[3,4-d]pyrimidin-2-amine;

N-(2-methoxy-4-(1-methyl-1H-imidazol-2-yl)phenyl)-8-(4-methoxypiperidin-1-yl)-6-methylpyrido[3,4-d]pyrimidin-2-amine;

N-(2-methoxy-4-(1-methyl-1H-imidazol-2-yl)phenyl)-8-(4-methoxy-4-methylpiperidin-1-yl)-6-methylpyrido[3,4-d]pyrimidin-2-amine;

N-(2-methoxy-4-(1-methyl-1H-imidazol-2-yl)phenyl)-6-methyl-8-(1-oxa-6-azaspiro[3.3]heptan-6-yl)pyrido[3,4-d]pyrimidin-2-amine;

1-(2-((2-methoxy-4-(1-methyl-1H-imidazol-2-yl)phenyl)amino)-6-methylpyrido[3,4-d]pyrimidin-8-yl)-3-methylazetidine-3-carbonitrile;

N2-(2-methoxy-4-(1-methyl-1H-imidazol-2-yl)phenyl)-6-methyl-N8-((3-methyltetrahydrofuran-3-yl)methyl)pyrido[3,4-d]pyrimidine-2,8-diamine;

N-(2-methoxy-4-(1-methyl-1H-imidazol-2-yl)phenyl)-6-methyl-8-(2-oxa-7-azaspiro[4.4]nonan-7-yl)pyrido[3,4-d]pyrimidin-2-amine;

N2-(2-methoxy-4-(1-methyl-1H-imidazol-2-yl)phenyl)-6-methyl-N8-(tetra hydro-2H-pyran-4-yl)pyrido[3,4-d]pyrimidine-2,8-diamine;

N-(2-methoxy-4-(1-methyl-1H-imidazol-2-yl)phenyl)-6-methyl-8-(7-oxa-2-azaspiro[3.5]nonan-2-yl)pyrido[3,4-d]pyrimidin-2-amine;

8-(3,3-dimethylazetidin-1-yl)-N-(4-(2,4-dimethyloxazol-5-yl)-2-methoxyphenyl)-6-methylpyrido[3,4-d]pyrimidin-2-amine;

1-(2-((4-(2,4-dimethyloxazol-5-yl)-2-methoxyphenyl)amino)-6-methylpyrido[3,4-d]pyrimidin-8-yl)-4-methylpiperidine-4-carbonitrile;

N-(4-(2,4-dimethyloxazol-5-yl)-2-methoxyphenyl)-8-(3-methoxy-3-methylazetidin-1-yl)-6-methylpyrido[3,4-d]pyrimidin-2-amine;

N-(4-(2,4-dimethyloxazol-5-yl)-2-methoxyphenyl)-8-(4-methoxypiperidin-1-yl)-6-methylpyrido[3,4-d]pyrimidin-2-amine;

N-(4-(2,4-dimethyloxazol-5-yl)-2-methoxyphenyl)-8-(4-methoxy-4-methylpiperidin-1-yl)-6-methylpyrido[3,4-d]pyrimidin-2-amine;

N-(4-(2,4-dimethyloxazol-5-yl)-2-methoxyphenyl)-6-methyl-8-(1-oxa-6-azaspiro[3.3]heptan-6-yl)pyrido[3,4-d]pyrimidin-2-amine;

1-(2-((4-(2,4-dimethyloxazol-5-yl)-2-methoxyphenyl)amino)-6-methylpyrido[3,4-d]pyrimidin-8-yl)-3-methylazetidine-3-carbonitrile;

N2-(4-(2,4-dimethyloxazol-5-yl)-2-methoxyphenyl)-6-methyl-N8-((3-methyltetrahydrofuran-3-yl)methyl)pyrido[3,4-d]pyrimidine-2,8-diamine;

N-(4-(2,4-dimethyloxazol-5-yl)-2-methoxyphenyl)-6-methyl-8-(2-oxa-7-azaspiro[4.4]nonan-7-yl)pyrido[3,4-d]pyrimidin-2-amine;

N2-(4-(2,4-dimethyloxazol-5-yl)-2-methoxyphenyl)-6-methyl-N8-(tetra hydro-2H-pyran-4-yl)pyrido[3,4-d]pyrimidine-2,8-diamine;

N-(4-(2,4-dimethyloxazol-5-yl)-2-methoxyphenyl)-6-methyl-8-(7-oxa-2-azaspiro[3.5]nonan-2-yl)pyrido[3,4-d]pyrimidin-2-amine;

N2-(4-(2,4-dimethyloxazol-5-yl)-2-methoxyphenyl)-6-methyl-N8-neopentylpyrido[3,4-d]pyrimidine-2,8-diamine;

8-(3,3-dimethylazetidin-1-yl)-N-(4-(2,4-dimethyloxazol-5-yl)-2-ethoxyphenyl)-6-methylpyrido[3,4-d]pyrimidin-2-amine;

1-(2-((4-(2,4-dimethyloxazol-5-yl)-2-ethoxyphenyl)amino)-6-methylpyrido[3,4-d]pyrimidin-8-yl)-4-methylpiperidine-4-carbonitrile;

N-(4-(2,4-dimethyloxazol-5-yl)-2-ethoxyphenyl)-8-(3-methoxy-3-methylazetidin-1-yl)-6-methylpyrido[3,4-d]pyrimidin-2-amine;

N-(4-(2,4-dimethyloxazol-5-yl)-2-ethoxyphenyl)-8-(4-methoxypiperidin-1-yl)-6-methylpyrido[3,4-d]pyrimidin-2-amine;

N-(4-(2,4-dimethyloxazol-5-yl)-2-ethoxyphenyl)-8-(4-methoxy-4-methylpiperidin-1-yl)-6-methylpyrido[3,4-d]pyrimidin-2-amine;

N-(4-(2,4-dimethyloxazol-5-yl)-2-ethoxyphenyl)-6-methyl-8-(1-oxa-6-azaspiro[3.3]heptan-6-yl)pyrido[3,4-d]pyrimidin-2-amine;

1-(2-((4-(2,4-dimethyloxazol-5-yl)-2-ethoxyphenyl)amino)-6-methylpyrido[3,4-d]pyrimidin-8-yl)-3-methylazetidine-3-carbonitrile;

N2-(4-(2,4-dimethyloxazol-5-yl)-2-ethoxyphenyl)-6-methyl-N8-((3-methyltetrahydrofuran-3-yl)methyl)pyrido[3,4-d]pyrimidine-2,8-diamine;

N-(4-(2,4-dimethyloxazol-5-yl)-2-ethoxyphenyl)-6-methyl-8-(2-oxa-7-azaspiro[4.4]nonan-7-yl)pyrido[3,4-d]pyrimidin-2-amine;

N2-(4-(2,4-dimethyloxazol-5-yl)-2-ethoxyphenyl)-6-methyl-N8-(tetra hydro-2H-pyran-4-yl)pyrido[3,4-d]pyrimidine-2,8-diamine;

N-(4-(2,4-dimethyloxazol-5-yl)-2-ethoxyphenyl)-6-methyl-8-(7-oxa-2-azaspiro[3.5]nonan-2-yl)pyrido[3,4-d]pyrimidin-2-amine;

N2-(4-(2,4-dimethyloxazol-5-yl)-2-ethoxyphenyl)-6-methyl-N8-neopentylpyrido[3,4-d]pyrimidine-2,8-diamine;

8-(3,3-dimethylazetidin-1-yl)-N-(4-(2,5-dimethyloxazol-4-yl)-2-methoxyphenyl)-6-methylpyrido[3,4-d]pyrimidin-2-amine;

1-(2-((4-(2,5-dimethyloxazol-4-yl)-2-methoxyphenyl)amino)-6-methylpyrido[3,4-d]pyrimidin-8-yl)-4-methylpiperidine-4-carbonitrile;

N-(4-(2,5-dimethyloxazol-4-yl)-2-methoxyphenyl)-8-(3-methoxy-3-methylazetidin-1-yl)-6-methylpyrido[3,4-d]pyrimidin-2-amine;

N-(4-(2,5-dimethyloxazol-4-yl)-2-methoxyphenyl)-8-(4-methoxypiperidin-1-yl)-6-methylpyrido[3,4-d]pyrimidin-2-amine;

N-(4-(2,5-dimethyloxazol-4-yl)-2-methoxyphenyl)-8-(4-methoxy-4-methylpiperidin-1-yl)-6-methylpyrido[3,4-d]pyrimidin-2-amine;

N-(4-(2,5-dimethyloxazol-4-yl)-2-methoxyphenyl)-6-methyl-8-(1-oxa-6-azaspiro[3.3]heptan-6-yl)pyrido[3,4-d]pyrimidin-2-amine;

1-(2-((4-(2,5-dimethyloxazol-4-yl)-2-methoxyphenyl)amino)-6-methylpyrido[3,4-d]pyrimidin-8-yl)-3-methylazetidine-3-carbonitrile;

N2-(4-(2,5-dimethyloxazol-4-yl)-2-methoxyphenyl)-6-methyl-N8-((3-methyltetrahydrofuran-3-yl)methyl)pyrido[3,4-d]pyrimidine-2,8-diamine;

N-(4-(2,5-dimethyloxazol-4-yl)-2-methoxyphenyl)-6-methyl-8-(2-oxa-7-azaspiro[4.4]nonan-7-yl)pyrido[3,4-d]pyrimidin-2-amine;

N2-(4-(2,5-dimethyloxazol-4-yl)-2-methoxyphenyl)-6-methyl-N8-(tetra hydro-2H-pyran-4-yl)pyrido[3,4-d]pyrimidine-2,8-diamine;

N-(4-(2,5-dimethyloxazol-4-yl)-2-methoxyphenyl)-6-methyl-8-(7-oxa-2-azaspiro[3.5]nonan-2-yl)pyrido[3,4-d]pyrimidin-2-amine;

N2-(4-(2,5-dimethyloxazol-4-yl)-2-methoxyphenyl)-6-methyl-N8-neopentylpyrido[3,4-d]pyrimidine-2,8-diamine;

8-(3,3-dimethylazetidin-1-yl)-N-(4-(2,5-dimethyloxazol-4-yl)-2-ethoxyphenyl)-6-methylpyrido[3,4-d]pyrimidin-2-amine;

1-(2-((4-(2,5-dimethyloxazol-4-yl)-2-ethoxyphenyl)amino)-6-methylpyrido[3,4-d]pyrimidin-8-yl)-4-methylpiperidine-4-carbonitrile;

N-(4-(2,5-dimethyloxazol-4-yl)-2-ethoxyphenyl)-8-(3-methoxy-3-methylazetidin-1-yl)-6-methylpyrido[3,4-d]pyrimidin-2-amine;

N-(4-(2,5-dimethyloxazol-4-yl)-2-ethoxyphenyl)-8-(4-methoxypiperidin-1-yl)-6-methylpyrido[3,4-d]pyrimidin-2-amine;

N-(4-(2,5-dimethyloxazol-4-yl)-2-ethoxyphenyl)-8-(4-methoxy-4-methylpiperidin-1-yl)-6-methylpyrido[3,4-d]pyrimidin-2-amine;

N-(4-(2,5-dimethyloxazol-4-yl)-2-ethoxyphenyl)-6-methyl-8-(1-oxa-6-azaspiro[3.3]heptan-6-yl)pyrido[3,4-d]pyrimidin-2-amine;

1-(2-((4-(2,5-dimethyloxazol-4-yl)-2-ethoxyphenyl)amino)-6-methylpyrido[3,4-d]pyrimidin-8-yl)-3-methylazetidine-3-carbonitrile;

N2-(4-(2,5-dimethyloxazol-4-yl)-2-ethoxyphenyl)-6-methyl-N8-((3-methyltetrahydrofuran-3-yl)methyl)pyrido[3,4-d]pyrimidine-2,8-diamine;

N-(4-(2,5-dimethyloxazol-4-yl)-2-ethoxyphenyl)-6-methyl-8-(2-oxa-7-azaspiro[4.4]nonan-7-yl)pyrido[3,4-d]pyrimidin-2-amine;

N2-(4-(2,5-dimethyloxazol-4-yl)-2-ethoxyphenyl)-6-methyl-N8-(tetrahydro-2H-pyran-4-yl)pyrido[3,4-d]pyrimidine-2,8-diamine;

N-(4-(2,5-dimethyloxazol-4-yl)-2-ethoxyphenyl)-6-methyl-8-(7-oxa-2-azaspiro[3.5]nonan-2-yl)pyrido[3,4-d]pyrimidin-2-amine;

N2-(4-(2,5-dimethyloxazol-4-yl)-2-ethoxyphenyl)-6-methyl-N8-neopentylpyrido[3,4-d]pyrimidine-2,8-diamine;

or a pharmaceutically acceptable salt or solvate thereof.

The various functional groups and substituents making up the compounds of the present invention are typically chosen such that the molecular weight of the compound does not exceed 1000. More usually, the molecular weight of the compound will be less than 750, for example less than 700, or less than 650, or less than 600, or less than 550. More preferably, the molecular weight is less than 525 and, for example, is 500 or less.

Suitable or preferred features of any compounds of the present invention may also be suitable features of any other aspect.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, sulfuric, phosphoric, trifluoroacetic, formic, citric or maleic acid. In addition a suitable pharmaceutically acceptable salt of a compound of the invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation, for example a salt with methylamine, dimethylamine, trimethylamine, piperidine, morpholine or tris-(2-hydroxyethyl)amine.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 2001), for example by synthesis from optically active starting materials or by resolution of a racemic form. Some of the compounds of the invention may have geometric isomeric centres (E- and Z-isomers). It is to be understood that the present invention encompasses all optical, diastereoisomers and geometric isomers and mixtures thereof that possess Mps1 kinase inhibitory activity.

The present invention also encompasses compounds of the invention as defined herein which comprise one or more isotopic substitutions. For example, H may be in any isotopic form, including $^1H$, $^2H(D)$, and $^3H$ (T); C may be in any isotopic form, including $^{12}C$, $^{13}C$, and $^{14}C$; and O may be in any isotopic form, including $^{16}O$ and $^{18}O$; and the like.

It is also to be understood that certain compounds of the invention may exist in solvated as well as unsolvated forms such as, for example, hydrated forms. It is to be understood that the invention encompasses all such solvated forms that possess Mps1 kinase inhibitory activity.

It is also to be understood that certain compounds of the invention may exhibit polymorphism, and that the invention encompasses all such forms that possess Mps1 kinase inhibitory activity.

Compounds of the invention may exist in a number of different tautomeric forms and references to compounds of the invention include all such forms. For the avoidance of doubt, where a compound can exist in one of several tautomeric forms, and only one is specifically described or shown, all others are nevertheless embraced by compounds of the invention. Examples of tautomeric forms include keto-, enol-, and enolate-forms, as in, for example, the following tautomeric pairs: keto/enol (illustrated below), imine/enamine, amide/imino alcohol, amidine/amidine, nitroso/oxime, thioketone/enethiol, and nitro/aci-nitro.

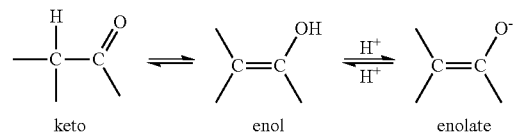

keto    enol    enolate

Compounds of the invention containing an amine function may also form N-oxides. A reference herein to a compound of the formula I that contains an amine function also includes the N-oxide. Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle. N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4$^{th}$ Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

The compounds of the invention may be administered in the form of a pro-drug which is broken down in the human or animal body to release a compound of the invention. A pro-drug may be used to alter the physical properties and/or the pharmacokinetic properties of a compound of the invention. A pro-drug can be formed when the compound of the invention contains a suitable group or substituent to which a property-modifying group can be attached. Examples of pro-drugs include in vivo cleavable ester derivatives that may be formed at a carboxy group or a hydroxy group in a compound of the invention and in-vivo cleavable amide derivatives that may be formed at a carboxy group or an amino group in a compound of the invention.

Accordingly, the present invention includes those compounds of the formula I as defined hereinbefore when made available by organic synthesis and when made available within the human or animal body by way of cleavage of a pro-drug thereof. Accordingly, the present invention includes those compounds of the formula I that are produced by organic synthetic means and also such compounds that are produced in the human or animal body by way of metabolism of a precursor compound, that is a compound of the formula I may be a synthetically-produced compound or a metabolically-produced compound.

A suitable pharmaceutically acceptable pro-drug of a compound of the formula I is one that is based on reasonable medical judgement as being suitable for administration to the human or animal body without undesirable pharmacological activities and without undue toxicity.

Various forms of pro-drug have been described, for example in the following documents:—
a) *Methods in Enzymology*, Vol. 42, p. 309-396, edited by K. Widder, et al. (Academic Press, 1985);
b) Design of Pro-drugs, edited by H. Bundgaard, (Elsevier, 1985);
c) A Textbook of Drug Design and Development, edited by Krogsgaard-Larsen and H. Bundgaard, Chapter 5 "Design and Application of Pro-drugs", by H. Bundgaard p. 113-191 (1991);
d) H. Bundgaard, *Advanced Drug Delivery Reviews*, 8, 1-38 (1992);
e) H. Bundgaard, et al., *Journal of Pharmaceutical Sciences*, 77, 285 (1988);
f) N. Kakeya, et al., *Chem. Pharm. Bull.*, 32, 692 (1984);
g) T. Higuchi and V. Stella, "Pro-Drugs as Novel Delivery Systems", A.C.S. Symposium Series, Volume 14; and
h) E. Roche (editor), "Bioreversible Carriers in Drug Design", Pergamon Press, 1987.

A suitable pharmaceutically acceptable pro-drug of a compound of the formula I that possesses a carboxy group is, for example, an in vivo cleavable ester thereof. An in vivo cleavable ester of a compound of the formula I containing a carboxy group is, for example, a pharmaceutically acceptable ester which is cleaved in the human or animal body to produce the parent acid. Suitable pharmaceutically acceptable esters for carboxy include $C_{1-6}$alkyl esters such as methyl, ethyl and tert-butyl, $C_{1-6}$alkoxymethyl esters such as methoxymethyl esters, $C_{1-6}$alkanoyloxymethyl esters such as pivaloyloxymethyl esters, 3-phthalidyl esters, $C_{3-8}$cycloalkylcarbonyloxy-$C_{1-6}$alkyl esters such as cyclopentylcarbonyloxymethyl and 1-cyclohexylcarbonyloxyethyl esters, 2-oxo-1,3-dioxolenylmethyl esters such as 5-methyl-2-oxo-1,3-dioxolen-4-ylmethyl esters and $C_{1-6}$alkoxycarbonyloxy-$C_{1-6}$alkyl esters such as methoxycarbonyloxymethyl and 1-methoxycarbonyloxyethyl esters.

A suitable pharmaceutically acceptable pro-drug of a compound of the formula I that possesses a hydroxy group is, for example, an in vivo cleavable ester or ether thereof. An in vivo cleavable ester or ether of a compound of the formula I containing a hydroxy group is, for example, a pharmaceutically acceptable ester or ether which is cleaved in the human or animal body to produce the parent hydroxy compound. Suitable pharmaceutically acceptable ester forming groups for a hydroxy group include inorganic esters such as phosphate esters (including phosphoramidic cyclic esters). Further suitable pharmaceutically acceptable ester forming groups for a hydroxy group include $C_{1-10}$alkanoyl groups such as acetyl, benzoyl, phenylacetyl and substituted benzoyl and phenylacetyl groups, $C_{1-10}$alkoxycarbonyl groups such as ethoxycarbonyl, N,N—$(C_{1-6})_2$carbamoyl, 2-dialkylaminoacetyl and 2-carboxyacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl. Suitable pharmaceutically acceptable ether forming groups for a hydroxy group include α-acyloxyalkyl groups such as acetoxymethyl and pivaloyloxymethyl groups.

A suitable pharmaceutically acceptable pro-drug of a compound of the formula I that possesses a carboxy group is, for example, an in vivo cleavable amide thereof, for example an amide formed with an amine such as ammonia, a $C_{1-4}$alkylamine such as methylamine, a $(C_{1-4}$alkyl$)_2$ amine such as dimethylamine, N-ethyl-N-methylamine or diethylamine, a $C_{1-4}$alkoxy-$C_{2-4}$alkylamine such as 2-methoxyethylamine, a phenyl-$C_{1-4}$ alkylamine such as benzylamine and amino acids such as glycine or an ester thereof.

A suitable pharmaceutically acceptable pro-drug of a compound of the formula I that possesses an amino group is, for example, an in vivo cleavable amide derivative thereof. Suitable pharmaceutically acceptable amides from an amino group include, for example an amide formed with $C_{1-10}$alkanoyl groups such as an acetyl, benzoyl, phenylacetyl and substituted benzoyl and phenylacetyl groups. Examples of ring substituents on the phenylacetyl and benzoyl groups include aminomethyl, N-alkylaminomethyl, N,N-dialkylaminomethyl, morpholinomethyl, piperazin-1-ylmethyl and 4-($C_{1-4}$alkyl)piperazin-1-ylmethyl.

The in vivo effects of a compound of the formula I may be exerted in part by one or more metabolites that are formed within the human or animal body after administration of a compound of the formula I. As stated hereinbefore, the in vivo effects of a compound of the formula I may also be exerted by way of metabolism of a precursor compound (a pro-drug).

It shall also be appreciated that compounds of formula I may also be covalently linked (at any suitable position) to other groups such as, for example, solubilising moieties (for example, PEG polymers), moieties that enable them to be bound to a solid support (such as, for example, biotin-containing moieties), and targeting ligands (such as antibodies or antibody fragments).

Synthesis

In the description of the synthetic methods described below and in the referenced synthetic methods that are used to prepare the staring materials, it is to be understood that all proposed reaction conditions, including choice of solvent, reaction atmosphere, reaction temperature, duration of the experiment and workup procedures, can be selected by a person skilled in the art.

It is understood by one skilled in the art of organic synthesis that the functionality present on various portions of the molecule must be compatible with the reagents and reaction conditions utilised.

Necessary starting materials may be obtained by standard procedures of organic chemistry. The preparation of such starting materials is described in conjunction with the following representative process variants and within the accompanying Examples.

Alternatively necessary starting materials are obtainable by analogous procedures to those illustrated which are within the ordinary skill of an organic chemist.

It will be appreciated that during the synthesis of the compounds of the invention in the processes defined below, or during the synthesis of certain starting materials, it may be desirable to protect certain substituent groups to prevent their undesired reaction. The skilled chemist will appreciate when such protection is required, and how such protecting groups may be put in place, and later removed.

For examples of protecting groups see one of the many general texts on the subject, for example, 'Protective Groups in Organic Synthesis' by Theodora Green (publisher: John Wiley & Sons). Protecting groups may be removed by any convenient method described in the literature or known to the skilled chemist as appropriate for the removal of the protecting group in question, such methods being chosen so as to effect removal of the protecting group with the minimum disturbance of groups elsewhere in the molecule.

Thus, if reactants include, for example, groups such as amino, carboxy or hydroxy it may be desirable to protect the group in some of the reactions mentioned herein.

By way of example, a suitable protecting group for an amino or alkylamino group is, for example, an acyl group, for example an alkanoyl group such as acetyl, an alkoxycarbonyl group, for example a methoxycarbonyl, ethoxycarbonyl or t-butoxycarbonyl group, an arylmethoxycarbonyl group, for example benzyloxycarbonyl, or an aroyl group, for example benzoyl. The deprotection conditions for the above protecting groups necessarily vary with the choice of protecting group. Thus, for example, an acyl group such as an alkanoyl or alkoxycarbonyl group or an aroyl group may be removed by, for example, hydrolysis with a suitable base such as an alkali metal hydroxide, for example lithium or sodium hydroxide. Alternatively an acyl group such as a tert-butoxycarbonyl group may be removed, for example, by treatment with a suitable acid as hydrochloric, sulfuric or phosphoric acid or trifluoroacetic acid and an arylmethoxycarbonyl group such as a benzyloxycarbonyl group may be removed, for example, by hydrogenation over a catalyst such as palladium-on-carbon, or by treatment with a Lewis acid for example $BF_3 \cdot OEt_2$. A suitable alternative protecting group for a primary amino group is, for example, a phthaloyl group which may be removed by treatment with an alkylamine, for example dimethylaminopropylamine, or with hydrazine.

A suitable protecting group for a hydroxy group is, for example, an acyl group, for example an alkanoyl group such as acetyl, an aroyl group, for example benzoyl, or an arylmethyl group, for example benzyl. The deprotection conditions for the above protecting groups will necessarily vary with the choice of protecting group. Thus, for example, an acyl group such as an alkanoyl or an aroyl group may be removed, for example, by hydrolysis with a suitable base such as an alkali metal hydroxide, for example lithium, sodium hydroxide or ammonia. Alternatively an arylmethyl group such as a benzyl group may be removed, for example, by hydrogenation over a catalyst such as palladium-on-carbon.

A suitable protecting group for a carboxy group is, for example, an esterifying group, for example a methyl or an ethyl group which may be removed, for example, by hydrolysis with a base such as sodium hydroxide, or for example a t-butyl group which may be removed, for example, by treatment with, for example an organic acid such as trifluoroacetic acid, or for example a benzyl group which may be removed, for example, by hydrogenation over a catalyst such as palladium-on-carbon.

Resins may also be used as a protecting group.

In a particular aspect, the present invention provides a method of synthesising a compound of the formula I, or a pharmaceutically acceptable salt or solvate thereof, the method comprising:

a) reacting a compound of formula A:

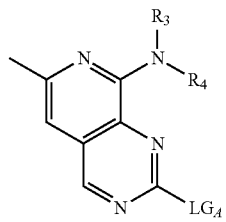

Formula A wherein $R_3$ and $R_4$ each have any one of the meanings as defined hereinbefore, and $LG_A$ is a suitable leaving group; with a compound of formula B:

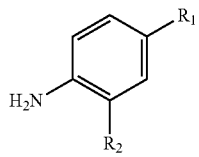

Formula B wherein $R_1$ and $R_2$ are as defined herein; and
b) optionally thereafter, and if necessary:
i) removing any protecting groups present;
ii) converting the compound formula I into another compound of formula I; and/or
iii) forming a pharmaceutically acceptable salt or solvate thereof.

$LG_A$ may be any suitable leaving group. Suitably $LG_A$ is a halogen or any other suitable leaving group (e.g. trifluoromethylsulphonate etc.). Suitably $LG_A$ may be chlorine, bromine or trifluoromethylsulphonate.

Suitably the coupling reaction between compound A and compound B takes place in the presence of a suitable solvent. Any suitable solvent or solvent mixture may be used for this reaction. A person skilled in the art will know how to select suitable solvents or solvent mixtures for use in these reactions. Examples of suitable solvents include DMA, 1,4-dioxane, toluene, DMF, tBuOH, THF and $H_2O$.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 80 to 160° C. or, more suitably 100 to 160° C. (depending on the solvent utilised), for a suitable time period of, for example, 2 hours to 7 days, or more suitably 2 to 10 hours either thermally or under microwave irradiation.

Suitably the coupling reaction between compound A and compound B takes place in the presence of a catalyst, suitably a palladium-derived catalyst, such as Pd or $Pd_2(dba)_3$ or by using an acid catalysis, such as trifluoroacetic acid.

Suitably the coupling reaction between compound A and compound B takes place in the presence of an organophosphorus compound, suitably an organophosphorus compound which serves as a suitable ligand to the catalyst. The organophosphorus compound may suitably be a phosphine-derivative, such as Xantphos.

Suitably the coupling reaction between compound A and compound B takes place in the presence of a base, for example a metal carbonate, such as cesium carbonate, or metal hydrides, such as sodium hydride.

The compound of formula A can be prepared by processes known in the art, and suitably by the processes described herein with reference to the examples.

The compound of formula B can be prepared by processes known in the art, and suitably by the processes described herein with reference to the examples.

A racemic compound of formula I may be separated using suitable chiral separation chromatography to furnish the desired enantiomers.

In another aspect, the present invention provides a method of synthesising a compound of the formula I, or a pharmaceutically acceptable salt or solvate thereof, the method comprising:
a) reacting a compound of formula C:

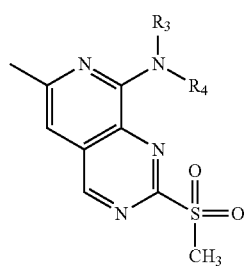

Formula C wherein $R_3$ and $R_4$ each have any one of the meanings as defined hereinbefore;
with a compound of formula B as defined hereinbefore, or a compound of formula D:

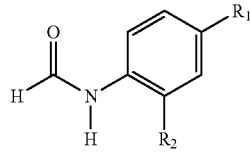

Formula D wherein $R_1$ and $R_2$ are as defined herein; and
b) optionally thereafter, and if necessary:
i) removing any protecting groups present;
ii) converting the compound formula I into another compound of formula I; and/or
iii) forming a pharmaceutically acceptable salt or solvate thereof.

Suitably the coupling reaction between compound C and compound B or D takes place in the presence of a suitable solvent. Any suitable solvent or solvent mixture may be used for this reaction. A person skilled in the art will know how to select suitable solvents or solvent mixtures for use in these reactions. Examples of suitable solvents include THF, TFE (1,2,3-trifluoroethanol) or DMF.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 30 to 170° C. or, more suitably 30 to 50° C. for compounds of formula D and 120 to 170 50° C. for compounds of formula B (depending on the solvent utilised), for a suitable time period of, for example, 2 hours to 7 days, or more suitably 2 to 10 hours either thermally or under microwave irradiation.

Suitably the coupling reaction between compound C and compounds B or D takes place in the presence of a catalyst, suitably a palladium-derived catalyst, such as Pd or $Pd_2(dba)_3$ or by using an acid catalysis, such as trifluoroacetic acid.

Suitably the coupling reaction between compound C and compounds B or D takes place in the presence of an organophosphorus compound, suitably an organophosphorus compound which serves as a suitable ligand to the catalyst. The organophosphorus compound may suitably be a phosphine-derivative, such as Xantphos.

Suitably the coupling reaction between compound C and compounds B or D takes place in the presence of a base, for example a metal carbonate, such as cesium carbonate, or metal hydrides, such as sodium hydride.

The compound of formula C can be prepared by processes known in the art, and suitably by the processes described herein with reference to the examples.

The compound of formula D can be prepared by processes known in the art, and suitably by the processes described herein with reference to the examples.

In another aspect, the present invention provides a method of synthesising a compound of the formula I, or a pharmaceutically acceptable salt or solvate thereof, the method comprising:
a) reacting a compound of formula E:

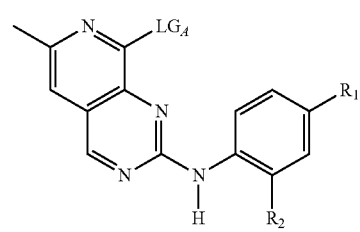

Formula E wherein $R_1$ and $R_2$ each have any one of the meanings as defined hereinbefore, and $LG_A$ is a suitable leaving group as hereinbefore defined;
with a compound of formula F:

$HNR_3R_4$  Formula F and
b) optionally thereafter, and if necessary:
i) removing any protecting groups present;
ii) converting the compound formula I into another compound of formula I; and/or
iii) forming a pharmaceutically acceptable salt or solvate thereof.

As described above, $LG_A$ may be any suitable leaving group. Suitably $LG_A$ is a halogen or any other suitable leaving group (e.g. trifluoromethylsulphonate etc.). Suitably $LG_A$ may be chlorine or bromine.

Suitably the coupling reaction between compound E and compound F takes place in the presence of a suitable solvent. Any suitable solvent or solvent mixture may be used for this reaction. A person skilled in the art will know how to select suitable solvents or solvent mixtures for use in these reactions. Examples of suitable solvents include dioxane, DMA, NMP, THF, or TFE.

A person skilled in the art will be able to select appropriate reaction conditions to use in order to facilitate this reaction. Suitably, the reaction is carried out in anhydrous conditions and in the presence of an inert atmosphere, such as argon or nitrogen. The reaction may also be carried out an elevated temperature, such as, for example, within the range of 100 to 140° C. (depending on the solvent utilised), for a suitable time period of, for example, 2 hours to 7 days, or more suitably 2 to 10 hours either thermally or under microwave irradiation.

Suitably the coupling reaction between compound E and compound F takes place in the presence of a catalyst, suitably a palladium-derived catalyst, such as Pd or $Pd_2(dba)_3$, $Pd(PPh_3)_4$ or $Pd(dppf)Cl_2$ or by using an acid catalysis, such as trifluoroacetic acid.

Suitably the coupling reaction between compound E and compound F takes place in the presence of an organophosphorus compound, suitably an organophosphorus compound which serves as a suitable ligand to the catalyst. The organophosphorus compound may suitably be a phosphine-derivative, such as Xantphos or DavePhos.

Suitably the coupling reaction between compound E and compound F takes place in the presence of a base, for example a metal carbonate, such as cesium carbonate, or metal hydrides, such as sodium hydride.

The compound of formula E can be prepared by processes known in the art and/or by the processes described herein with reference to the examples.

The compound of formula F can be prepared by processes known in the art, and/or by the processes described herein with reference to the examples.

The resultant compound of formula I can be isolated and purified using techniques well known in the art.

The processes defined herein may further comprise the step of subjecting the compound of formula I to a salt exchange, particularly in situations where the compound of formula I is formed as a mixture of different salt forms. The salt exchange suitably comprises immobilising the compound of formula I on a suitable solid support or resin, and eluting the compounds with an appropriate acid to yield a single salt of the compound of formula I.

In a further aspect of the invention, there is provided a compound of formula I obtainable by any one of the processes defined herein.

In a further aspect of the invention, there is provided a compound of formula I obtained by any one of the processes defined herein.

In a further aspect of the invention, there is provided a compound of formula I directly obtained by any one of the processes defined herein.

By way of example, particular synthetic schemes by which compounds of the invention can be prepared are shown below in Schemes 1 to 3:

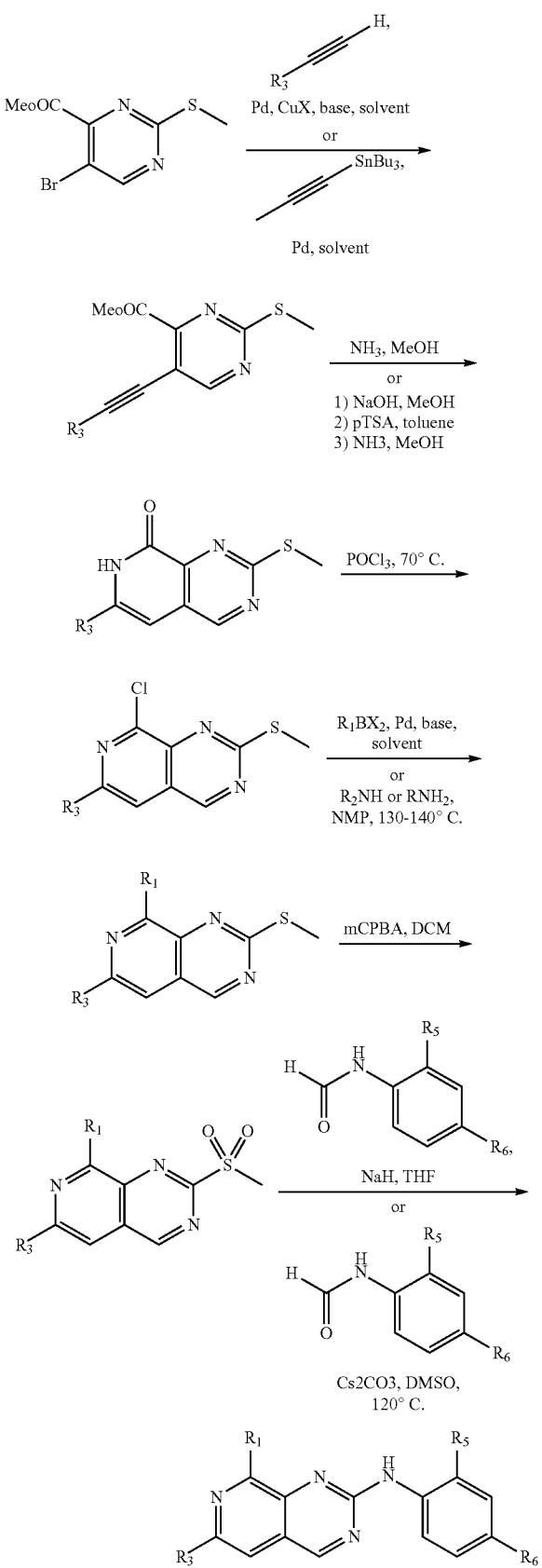

General Scheme 1

General Scheme 2

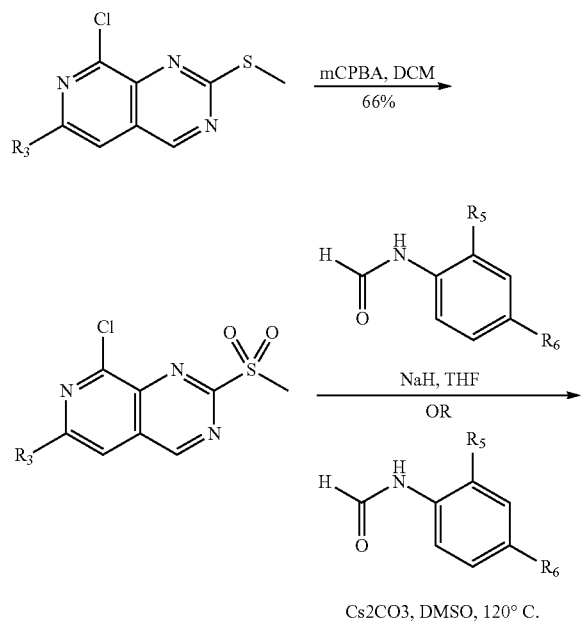

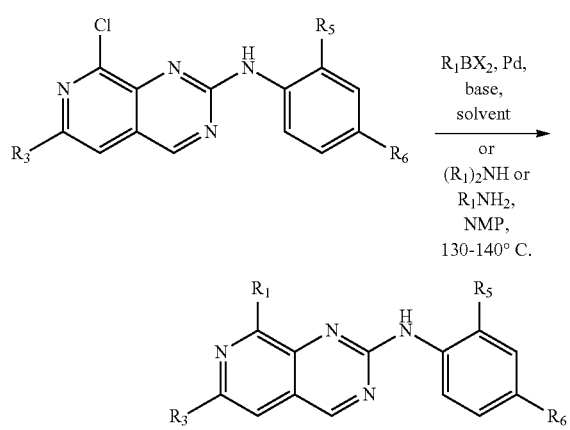

General Scheme 3

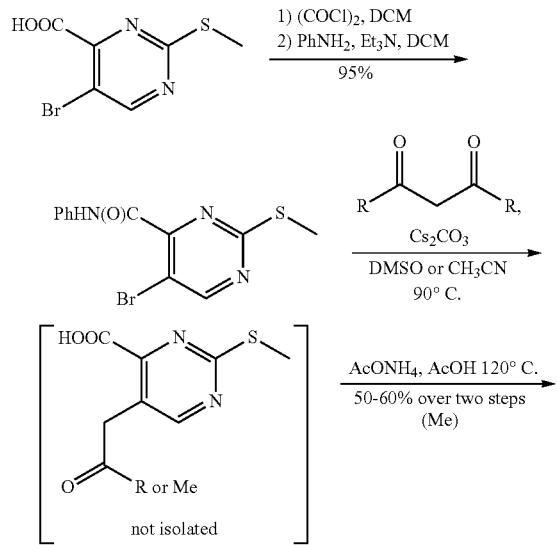

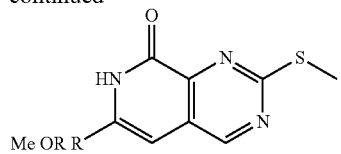

Biological Activity

The following biological assays may be used to measure the pharmacological effects of the compounds of the present invention.

Measurement of Inhibition of MPS1 Kinase

The enzyme reaction (total volume 10 μl) was carried out in black 384-well low volume plates containing full length MPS1 (12.5 nM or 3 nM), fluorescent labelled peptide [known as H236, which has the sequence: 5FAM-DHTG-FLTEYVATR-CONH$_2$] (5 μM), ATP (10 μM), either DMSO (1% v/v) or the test compound (in the range 0.25 nM-100 μM in 1% DMSO) and assay buffer (50 mM HEPES (pH 7.0), 0.02% NaN$_3$, 0.01% BSA, 0.1 mM Orthovandate, 10 μM MgCl$_2$, 1 μM DTT, Roche protease inhibitor). The reaction was carried out for 60 min at room temperature and stopped by the addition of buffer (10 μl) containing 20 mM EDTA, 0.05% (v/v) Brij-35, in 0.1M HEPES-buffered saline (Free acid, Sigma, UK). The plate was read on a Caliper EZ reader II (Caliper Life Sciences).

The reader provides a Software package ('Reviewer') which converts the peak heights into % conversion by measuring both product and substrate peak and also allows selection of control well which represent 0% and 100% inhibition, respectively. The % inhibition of the compounds is calculated relative to the means of selected control wells. IC$_{50}$s are determined by testing the compounds at a range of concentrations from 0.25 nM-100 μM. The % inhibitions at each concentration are then fitted to a 4 parameter logistic fit:

$$y=(a+((b-a)/(1+((c/x\hat{\ }d))))$$

where a=asym min, b=asym max, c=IC$_{50}$ and d=hill coefficient

In general, activity possessed by compounds of the formula I, may be demonstrated in the inhibition assay by an IC$_{50}$ value of less than 15 μM. Suitably compounds have an IC$_{50}$ value of less than 10 μM, suitably less than 1 μM, suitably less than 0.1 μM, and suitably less than 0.01 μM (i.e. less than 10 nM).

The activities of compounds of the invention in the above assay are shown in the accompanying example section.

Pharmaceutical Compositions

According to a further aspect of the invention there is provided a pharmaceutical composition which comprises a compound of the invention as defined hereinbefore, or a pharmaceutically acceptable salt or solvate thereof, in association with a pharmaceutically acceptable diluent or carrier.

The compositions of the invention may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous, intramuscular, intraperitoneal or intramuscular dosing or as a suppository for rectal dosing).

The compositions of the invention may be obtained by conventional procedures using conventional pharmaceutical excipients, well known in the art. Thus, compositions intended for oral use may contain, for example, one or more colouring, sweetening, flavouring and/or preservative agents.

An effective amount of a compound of the present invention for use in therapy of proliferative disease is an amount sufficient to symptomatically relieve in a warm-blooded animal, particularly a human the symptoms of infection, to slow the progression of infection, or to reduce in patients with symptoms of infection the risk of getting worse.

The amount of active ingredient that is combined with one or more excipients to produce a single dosage form will necessarily vary depending upon the host treated and the particular route of administration. For example, a formulation intended for oral administration to humans will generally contain, for example, from 0.5 mg to 0.5 g of active agent (more suitably from 0.5 to 100 mg, for example from 1 to 30 mg) compounded with an appropriate and convenient amount of excipients which may vary from about 5 to about 98 percent by weight of the total composition.

The size of the dose for therapeutic or prophylactic purposes of a compound of the formula I will naturally vary according to the nature and severity of the conditions, the age and sex of the animal or patient and the route of administration, according to well known principles of medicine.

In using a compound of the invention for therapeutic or prophylactic purposes it will generally be administered so that a daily dose in the range, for example, 0.1 mg/kg to 75 mg/kg body weight is received, given if required in divided doses. In general lower doses will be administered when a parenteral route is employed. Thus, for example, for intravenous or intraperitoneal administration, a dose in the range, for example, 0.1 mg/kg to 30 mg/kg body weight will generally be used. Similarly, for administration by inhalation, a dose in the range, for example, 0.05 mg/kg to 25 mg/kg body weight will be used. Oral administration may also be suitable, particularly in tablet form. Typically, unit dosage forms will contain about 0.5 mg to 0.5 g of a compound of this invention.

Therapeutic Uses and Applications

In one aspect, the present invention provides a compound of Formula I, or a pharmaceutically acceptable salt or solvate thereof, or a pharmaceutical composition as defined herein for use in therapy.

The compounds of the invention are capable of inhibiting Mps1 kinase activity. Thus, in another aspect, the present invention provides a method of inhibiting Mps1 kinase activity in a cell, the method comprising administering to said cell compound of formula I as defined herein, or a pharmaceutically acceptable salt or solvate thereof.

In a further aspect, the present invention provides a method of inhibiting Mps1 kinase in vitro or in vivo, said method comprising contacting a cell with an effective amount of a compound, or a pharmaceutically acceptable salt or solvate thereof, as defined herein.

In another aspect, the present invention provides a method of inhibiting Mps1 kinase activity in a human or animal subject in need of such inhibition, the method comprising administering to said subject an effective amount of a compound of formula I as defined herein, or a pharmaceutically acceptable salt or solvate thereof.

In another aspect, the present invention provides a compound of formula I as defined herein, or a pharmaceutically acceptable salt or solvate thereof for use in the treatment of disease or condition associated with Mps1 kinase activity.

In another aspect, the present invention provides the use of a compound of formula I as defined herein, or a pharmaceutically acceptable salt or solvate thereof, in the manufacture of a medicament for use in the treatment of disease or condition associated with Mps1 kinase activity.

In yet another aspect, the present invention provides a method of treating a proliferative disorder in a human or animal subject, the method comprising administering to said subject a therapeutically acceptable amount of a compound of formula I as defined herein, or a pharmaceutically acceptable salt or solvate thereof.

In yet another aspect, the present invention provides a compound of formula I as defined herein, or a pharmaceutically acceptable salt or solvate thereof, for use in the treatment of a proliferative disorder.

In yet another aspect, the present invention provides the use of a compound of formula I as defined herein, or a pharmaceutically acceptable salt or solvate thereof, in the manufacture of a medicament for use in the treatment of a proliferative disorder.

The term "proliferative disorder" are used interchangeably herein and pertain to an unwanted or uncontrolled cellular proliferation of excessive or abnormal cells which is undesired, such as, neoplastic or hyperplasticgrowth, whether in vitro or in vivo. Examples of proliferative conditions include, but are not limited to, pre-malignant and malignant cellular proliferation, including but not limited to, malignant neoplasms and tumours, cancers, leukemias, psoriasis, bone diseases, fibroproliferative disorders (e.g., of connective tissues), and atherosclerosis. Any type of cell may be treated, including but not limited to, lung, colon, breast, ovarian, prostate, liver, pancreas, brain, and skin.

The anti-proliferative effects of the compounds of the present invention have particular application in the treatment of human cancers by virtue of their Mps1 kinase inhibitory properties.

The anti-cancer effect may arise through one or more mechanisms, including but not limited to, the regulation of cell proliferation, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Therefore, in another aspect, the present invention provides a compound, or a pharmaceutically acceptable salt or solvate thereof, or a pharmaceutical composition as defined herein for use in the treatment of cancer.

In yet another aspect, the present invention provides the use of a compound, or a pharmaceutically acceptable salt or solvate thereof, as defined herein in the manufacture of a medicament for use in the treatment of cancer.

In yet another aspect, the present invention provides a method of treating cancer in a patient in need of such treatment, said method comprising administering to said patient a therapeutically effective amount of a compound, or a pharmaceutically acceptable salt or solvate thereof, or a pharmaceutical composition as defined herein.

The invention further provides a method of treatment of the human or animal body, the method comprising administering to a subject in need of treatment a therapeutically-effective amount of an active compound, preferably in the form of a pharmaceutical composition.

Routes of Administration

The compounds of the invention or pharmaceutical composition comprising the active compound may be administered to a subject by any convenient route of administration, whether systemically/peripherally or topically (ie. at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot or reservoir, for example, subcutaneously or intramuscularly.

Combination Therapies

The antiproliferative treatment defined hereinbefore may be applied as a sole therapy or may involve, in addition to the compound of the invention, conventional surgery or radiotherapy or chemotherapy. Such chemotherapy may include one or more of the following categories of anti-tumour agents:—

(i) other antiproliferative/antineoplastic drugs and combinations thereof, as used in medical oncology, such as alkylating agents (for example cis-platin, oxaliplatin, carboplatin, cyclophosphamide, nitrogen mustard, melphalan, chlorambucil, busulphan, temozolamide and nitrosoureas); antimetabolites (for example gemcitabine and antifolates such as fluoropyrimidines like 5-fluorouracil and tegafur, raltitrexed, methotrexate, cytosine arabinoside, and hydroxyurea); antitumour antibiotics (for example anthracyclines like adriamycin, bleomycin, doxorubicin, daunomycin, epirubicin, idarubicin, mitomycin-C, dactinomycin and mithramycin); antimitotic agents (for example vinca alkaloids like vincristine, vinblastine, vindesine and vinorelbine and taxoids like taxol and taxotere and polokinase inhibitors); and topoisomerase inhibitors (for example epipodophyllotoxins like etoposide and teniposide, amsacrine, topotecan and camptothecin);

(ii) cytostatic agents such as antioestrogens (for example tamoxifen, fulvestrant, toremifene, raloxifene, droloxifene and iodoxyfene), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) anti-invasion agents [for example c-Src kinase family inhibitors like 4-(6-chloro-2,3-methylenedioxyanilino)-7-[2-(4-methylpiperazin-1-yl)ethoxy]-5-tetrahydropyran-4-yloxyquinazoline (AZD0530; International Patent Application WO 01/94341), N-(2-chloro-6-methylphenyl)-2-{6-[4-(2-hydroxyethyl)piperazin-1-yl]-2-methylpyrimidin-4-ylamino}thiazole-5-carboxamide (dasatinib, BMS-354825; *J. Med. Chem.*, 2004, 47, 6658-6661) and bosutinib (SKI-606), and metalloproteinase inhibitors like marimastat, inhibitors of urokinase plasminogen activator receptor function or antibodies to Heparanase];

(iv) inhibitors of growth factor function: for example such inhibitors include growth factor antibodies and growth factor receptor antibodies (for example the anti-erbB2 antibody trastuzumab [Herceptin™], the anti-EGFR antibody panitumumab, the anti-erbB1 antibody cetuximab [Erbitux, C225] and any growth factor or growth factor receptor antibodies disclosed by Stern et al. Critical reviews in oncology/haematology, 2005, Vol. 54, pp 11-29); such inhibitors also include tyrosine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, ZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)-quinazolin-4-amine (CI 1033), erbB2 tyrosine kinase inhibitors such as lapatinib); inhibitors of the hepatocyte growth factor family; inhibitors of the insulin growth factor family; inhibitors of the platelet-derived growth factor family such as imatinib and/or nilotinib (AMN107); inhibitors of serine/threonine kinases (for example Ras/Raf signalling inhibitors such as farnesyl transferase inhibitors, for example sorafenib (BAY 43-9006), tipifarnib (R115777) and lonafarnib (SCH66336)), inhibitors of cell signalling through MEK and/or AKT kinases, c-kit inhibitors, abl kinase inhibitors, PI3 kinase inhibitors, Plt3 kinase inhibitors, CSF-1R kinase inhibitors, IGF receptor (insulin-like growth factor) kinase inhibitors; aurora kinase inhibitors (for example AZD1152, PH739358, VX-680, MLN8054, R763, MP235, MP529, VX-528 AND AX39459) and cyclin dependent kinase inhibitors such as CDK2 and/or CDK4 inhibitors;

(v) antiangiogenic agents such as those which inhibit the effects of vascular endothelial growth factor, [for example the anti-vascular endothelial cell growth factor antibody bevacizumab (Avastin™) and for example, a VEGF receptor tyrosine kinase inhibitor such as vandetanib (ZD6474), vatalanib (PTK787), sunitinib (SU11248), axitinib (AG-013736), pazopanib (GW 786034) and 4-(4-fluoro-2-methylindol-5-yloxy)-6-methoxy-7-(3-pyrrolidin-1-ylpropoxy) quinazoline (AZD2171; Example 240 within WO 00/47212), compounds such as those disclosed in International Patent Applications WO97/22596, WO 97/30035, WO 97/32856 and WO 98/13354 and compounds that work by other mechanisms (for example linomide, inhibitors of integrin αvβ3 function and angiostatin)];

(vi) vascular damaging agents such as Combretastatin A4 and compounds disclosed in International Patent Applications WO 99/02166, WO 00/40529, WO 00/41669, WO 01/92224, WO 02/04434 and WO 02/08213;

(vii) an endothelin receptor antagonist, for example zibotentan (ZD4054) or atrasentan;

(viii) antisense therapies, for example those which are directed to the targets listed above, such as ISIS 2503, an anti-ras antisense;

(ix) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine kinase or a bacterial nitroreductase enzyme and approaches to increase patient tolerance to chemotherapy or radiotherapy such as multi-drug resistance gene therapy; and (x) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

Such conjoint treatment may be achieved by way of the simultaneous, sequential or separate dosing of the individual components of the treatment. Such combination products employ the compounds of this invention within the dosage range described hereinbefore and the other pharmaceutically-active agent within its approved dosage range.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and another anti-tumour agent.

According to this aspect of the invention there is provided a combination suitable for use in the treatment of a cancer (for example a cancer involving a solid tumour) comprising a compound of the invention as defined hereinbefore, or a pharmaceutically acceptable salt or solvate thereof, and any one of the anti-tumour agents listed under (i)-(ix) above.

In a further aspect of the invention there is provided a compound of the invention or a pharmaceutically acceptable salt or solvate thereof, in combination with an anti-tumour agent selected from one listed under (i)-(ix) herein above.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

According to a further aspect of the invention there is provided a pharmaceutical composition which comprises a compound of the invention, or a pharmaceutically acceptable salt or solvate thereof in combination with an anti-tumour agent selected from one listed under (i)-(ix) herein above, in association with a pharmaceutically acceptable diluent or carrier.

EXAMPLES

General Experimental Methods

LC/MS analysis was performed on a Waters Alliance 2795 Separations Module and Waters 2487 dual wavelength absorbance detector coupled to a Waters/Micromass LCt time of flight mass spectrometer with ESI source. Analytical separation was carried out at 30° C. either on a Merck Chromolith SpeedROD column (RP-18e, 50×4.6 mm) using a flow rate of 2 mL/min in a 3.5 minute gradient elution with detection at 254 nm or on a Merck Purospher STAR column (RP-18e, 30×4 mm) using a flow rate of 1.5 mL/min in a 3.5 minute gradient elution with detection at 254 nm. The mobile phase was a mixture of MeOH (solvent A) and water (solvent B) both containing formic acid at 0.1%. Gradient elution was as follows: 1:9 (A/B) to 9:1 (A/B) over 2.25 min, 9:1 (A/B) for 0.75 min, and then reversion back to 1:9 (A/B) over 0.3 min, finally 1:9 (A/B) for 0.2 min (ESI-HRMS Method A).

LC/MS and HRMS analyses were performed on an Agilent 1200 series HPLC and diode array detector coupled to a 6210 time of flight mass spectrometer with dual multimode atmospheric pressure CI/ESI source. Analytical separation was carried out at 30° C. either on a Merck Chromolith SpeedROD column (RP-18e, 50×4.6 mm) using a flow rate of 2 mL/min in a 4 minute gradient elution with detection at 254 nm or on a Merck Purospher STAR column (RP-18e, 30×4 mm) using a flow rate of 1.5 mL/min in a 4 minute gradient elution with detection at 254 nm. The mobile phase was a mixture of MeOH (solvent A) and water (solvent B) both containing formic acid at 0.1%. Gradient elution was: 1:9 (A/B) to 9:1 (A/B) over 2.5 min, 9:1 (A/B) for 1 min, and then reversion back to 1:9 (A/B) over 0.3 min, finally 1:9 (A/B) for 0.2 min (Default method also referred to as ESI-HRMS Method B). The following references masses were used for HRMS analysis: caffeine $[M+H]^+$ 195.087652; (hexakis(1H,1H,3H-tetrafluoropentoxy)phosphazene $[M+H]^+$ 922.009798) and hexakis(2,2-difluoroethoxy)phosphazene $[M+H]+$ 622.02896 or reserpine $[M+H]^+$ 609.280657.

LC/MS and HRMS analysis was also performed on a Waters Acquity UPLC and diode array detector coupled to a Waters G2 QToF mass spectrometer fitted with a multimode ESI/APCI source. Analytical separation was carried out at 30° C. on a Phenomenex Kinetex XB-C18 column (30×2.1 mm, 1.7 u, 100 A) using a flow rate of 0.3 mL/min in a 4 minute gradient elution with detection at 254 nm. The mobile phase was a mixture of methanol (solvent A) and water containing formic acid at 0.1% (solvent B). Gradient elution was as follows: 1:9 (A/B) to 9:1 (A/B) over 3 min, 9:1 (A/B) for 0.5 min, and then reversion back to 1:9 (A/B) over 0.3 min, finally 1:9 (A/B) for 0.2 min(also referred to ESI-HRMS Method C). The following references masses were used for HRMS analysis: Leucine Enkephalin fragment ion $[M+H]^+$ 397.1876 $[C_{21}H_{25}N_4O_4+H]^+$ General HPLC Methods A) Fast2 mins: Analytical separation was carried out at 40° C. on a Merck Purospher STAR column (RP-18e, 30×4 mm) using a flow rate of 3 mL/min in a 2 minute gradient elution with detection at 254 nm. The mobile phase was a mixture of methanol (solvent A) and water containing formic acid at 0.1% (solvent B). Gradient elution was as follows: 1:9 (A/B) to 9:1 (A/B) over 1.25 min, 9:1 (A/B) for 0.5 min, and then reversion back to 1:9 (A/B) over 0.15 min, finally 1:9 (A/B) for 0.1 min B) Fast4 mins: Analytical separation was carried out at 30° C. on a Merck Purospher STAR column (RP-18e, 30×4 mm) using a flow rate of 1.5 mL/min in a 4 minute gradient elution with detection at 254 nm. The mobile phase was a mixture of methanol (solvent A) and water containing formic acid at 0.1% (solvent B). Gradient elution was as follows: 1:9 (A/B) to 9:1 (A/B) over 2.5 min, 9:1 (A/B) for 1 min, and then reversion back to 1:9 (A/B) over 0.3 min, finally 1:9 (A/B) for 0.2 min.

Example 1

N2-(2-methoxy-4-(1-methyl-1H-1,2,3-triazol-5-yl)phenyl)-6-methyl-N8-neopentylpyrido[3,4-d]pyrimidine-2,8-diamine

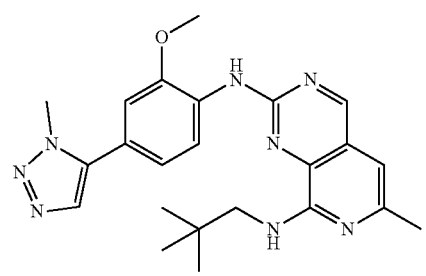 [SMILES: COc1cc(-c2cnnn2C)ccc1Nc1ncc2cc(C)nc(NCC(C)(C)C)c2n1]

Method 1

To a solution of 6-methyl-2-(methylsulfonyl)-N-neopentylpyrido[3,4-d]pyrimidin-8-amine (Preparation 4, 29 mg, 0.094 mmol) in DMSO (7 mL) was added N-(2-methoxy-4-(1-methyl-1H-1,2,3-triazol-5-yl)phenyl)formamide (Preparation 31, 22 mg, 0.094 mmol) and $Cs_2CO_3$ (61 mg, 0.188 mmol). The reaction was heated to 100° C. for 18 hours. The reaction mixture was diluted with EtOAc and water. The organic layer was washed with brine, dried ($MgSO_4$) and concentrated in vacuo. The residue was purified by elution through an SCX-2 cartridge using MeOH followed by 1M $NH_3$ in MeOH to afford the title compound (13.4 mg, 33%).

$^1$H NMR (500 MHz, MeOH-$d_4$): δ ppm 9.04 (s, 1H), 8.69 (d, J=8.5 Hz, 1H), 7.84 (s, 1H), 7.23 (d, J=2.0 Hz, 1H), 7.16 (d, J=8.5, 2.0 Hz, 1H), 6.71 (s, 1H), 4.16 (s, 3H), 4.05 (s, 3H), 3.47 (s, 2H), 2.44 (d, J=0.5 Hz, 3H), 1.09 (s, 9H).

HRMS (ESI) MS m/z calcd for $C_{23}H_{29}N_8O$ $[M+H]^+$ 433.2459, found 433.2449.

MPS1 IC50 (µM): 0.0005

Example 2

N2-(2-ethoxy-4-(4-methyl-4H-1,2,4-triazol-3-yl)phenyl)-6-methyl-N8-((3-methyltetrahydrofuran-3-yl)methyl)pyrido[3,4-d]pyrimidine-2,8-diamine

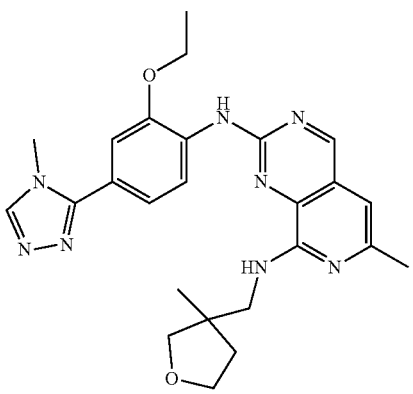 [SMILES: CCOc1cc(-c2nncn2C)ccc1Nc1ncc2cc(C)nc(NCC3(C)CCOC3)c2n1]

To a solution of 6-methyl-2-(methylsulfonyl)-N-((3-methyltetrahydrofuran-3-yl)methyl)pyrido[3,4-d]pyrimidin-8-amine (Preparation 5, 34 mg, 0.101 mmol) in DMSO (7 mL) was added N-(2-ethoxy-4-(4-methyl-4H-1,2,4-triazol-3-yl)phenyl)formamide (Preparation 32, 30 mg, 0.121 mmol) and $Cs_2CO_3$ (66 mg, 0.202 mmol). The reaction was heated to 100° C. for 18 hours. The reaction mixture was diluted with EtOAc and water. The organic layer was washed with brine, dried ($MgSO_4$) and concentrated in vacuo. The residue was purified by silica gel column chromatography eluting with 0-10% MeOH in DCM followed by elution through an SCX-2 cartridge using MeOH followed by 1M $NH_3$ in MeOH to afford the title compound (27.6 mg, 58%).

$^1$H NMR (500 MHz, MeOH-$d_4$): δ ppm 9.06 (s, 1H), 8.82 (d, J=8.5 Hz, 1H), 8.55 (s, 1H), 7.40-7.37 (m, 2H), 6.74 (s, 1H), 4.31 (q, J=7.0 Hz, 2H), 4.08 (td, J=8.5, 5.0 Hz, 1H), 3.93-3.90 (m, 2H), 3.87 (s, 3H), 3.71 (d, J=13.5 Hz, 1H), 3.64 (d, J=13.5 Hz, 1H), 3.52 (d, J=8.5 Hz, 1H), 2.45 (s, 3H), 2.08 (m, 1H), 1.82 (m, 1H), 1.56 (t, J=7.0 Hz, 3H), 1.29 (s, 3H).

HRMS (ESI) MS m/z calcd for $C_{25}H_{31}N_8O_2$ $[M+H]^+$ 475.2564, found 475.2549.

MPS1 IC50 (µM): 0.002

Example 3

1-(2-((2-ethoxy-4-(4-methyl-4H-1,2,4-triazol-3-yl)phenyl)amino)-6-methylpyrido[3,4-d]pyrimidin-8-yl)-3-methylazetidine-3-carbonitrile

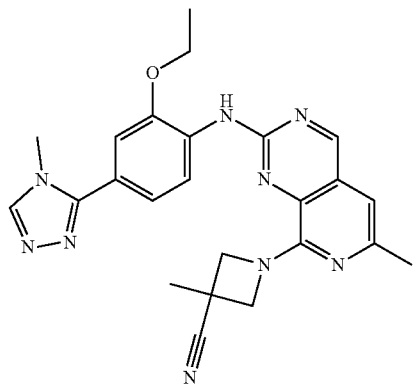 [SMILES: CCOc1cc(-c2nncn2C)ccc1Nc1ncc2cc(C)nc(N3CC(C)(C#N)C3)c2n1]

To a solution of 3-methyl-1-(6-methyl-2-(methylsulfonyl)pyrido[3,4-d]pyrimidin-8-yl)azetidine-3-carbonitrile (Preparation 7, 64 mg, 0.202 mmol) in DMSO (7 mL) was added N-(2-ethoxy-4-(4-methyl-4H-1,2,4-triazol-3-yl)phenyl)formamide (Preparation 32, 60 mg, 0.242 mmol) and $Cs_2CO_3$ (131 mg, 0.403 mmol). The reaction was heated to 100° C. for 18 hours. The reaction mixture was diluted with EtOAc and water. The organic layer was washed with brine, dried ($MgSO_4$) and concentrated in vacuo. The residue was purified by silica gel column chromatography eluting with 0-10% MeOH in DCM followed by elution through an SCX-2 cartridge using MeOH followed by 1M $NH_3$ in MeOH to afford the title compound (34.6 mg, 38%).

$^1$H NMR (500 MHz, MeOH-$d_4$): δ ppm 9.10 (s, 1H), 8.56 (s, 1H), 8.46 (d, J=8.5 Hz, 1H), 7.40 (dd, J=8.5, 2.0 Hz, 1H), 7.39 (d, J=2.0 Hz, 1H), 6.91 (s, 1H), 4.75 (d, J=9.0 Hz, 2H), 4.39 (d, J=9.0 Hz, 2H), 4.28 (q, J=7.0 Hz, 2H), 3.88 (s, 3H), 2.47 (s, 3H), 1.75 (s, 3H), 1.53 (t, J=7.0 Hz, 3H).

HRMS (ESI) MS m/z calcd for $C_{24}H_{26}N_9O$ $[M+H]^+$ 456.2255, found 456.2180.

MPS1 IC50 (µM): 0.003

Example 4

N-(2-ethoxy-4-(4-methyl-4H-1,2,4-triazol-3-yl)phenyl)-6-methyl-8-(7-oxa-2-azaspiro[3.5]nonan-2-yl)pyrido[3,4-d]pyrimidin-2-amine

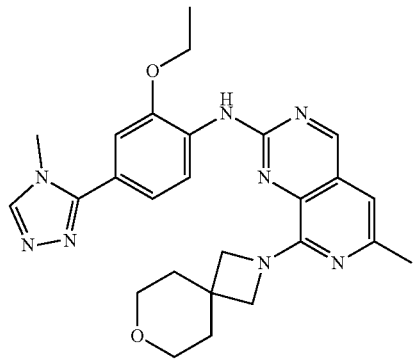 [SMILES: CCOc1cc(-c2nncn2C)ccc1Nc1ncc2cc(C)nc(N3CC4(CCOCC4)C3)c2n1]

To a solution of 2-(6-methyl-2-(methylsulfonyl)pyrido[3,4-d]pyrimidin-8-yl)-7-oxa-2-azaspiro[3.5]nonane (Preparation 8, 15 mg, 0.044 mmol) in DMSO (4 ml) was added N-(2-ethoxy-4-(4-methyl-4H-1,2,4-triazol-3-yl)phenyl)formamide (Preparation 32, 13 mg, 0.052 mmol) and Cs$_2$CO$_3$ (28 mg, 0.087 mmol). The reaction was heated to 100° C. for 18 hours. The reaction mixture was diluted with EtOAc and water. The organic layer was washed with brine, dried (MgSO$_4$) and concentrated in vacuo. The residue was purified by silica gel column chromatography eluting with 0-10% MeOH in DCM followed by elution through an SCX-2 cartridge using MeOH followed by 1M NH$_3$ in MeOH to afford the title compound (9.7 mg, 46%).

$^1$H NMR (500 MHz, MeOH-d$_4$): δ ppm 9.06 (s, 1H), 8.57 (d, J=8.5 Hz, 1H), 8.56 (s, 1H), 7.39 (d, J=2.0 Hz, 1H), 7.36 (dd, J=8.5, 2.0 Hz, 1H), 6.78 (s, 1H), 4.31-4.27 (m, 6H), 3.87 (s, 3H), 3.69 (app t, J=5.5 Hz, 4H), 2.44 (s, 3H), 1.89 (app t, J=5.5 Hz, 4H), 1.54 (t, J=7.0 Hz, 3H).

HRMS (ESI) MS m/z calcd for C$_{26}$H$_{31}$N$_8$O$_2$ [M+H]$^+$ 487.2564, found 487.2511.

MPS1 IC50 (μM): 0.002

Example 5

1-(2-((2-ethoxy-4-(4-methyl-4H-1,2,4-triazol-3-yl)phenyl)amino)-6-methylpyrido[3,4-d]pyrimidin-8-yl)piperidine-4-carbonitrile

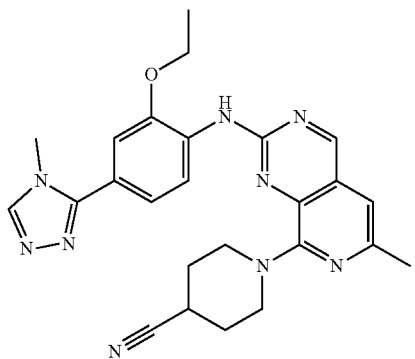 [SMILES: CCOc1cc(-c2nncn2C)ccc1Nc1ncc2cc(C)nc(N3CCC(C#N)CC3)c2n1]

To a solution of 1-(6-methyl-2-(methylsulfonyl)pyrido[3,4-d]pyrimidin-8-yl)piperidine-4-carbonitrile (Preparation 9, 22 mg, 0.067 mmol) in DMSO (5 mL) was added N-(2-ethoxy-4-(4-methyl-4H-1,2,4-triazol-3-yl)phenyl)formamide (Preparation 32, 20 mg, 0.081 mmol) and Cs$_2$CO$_3$ (44 mg, 0.135 mmol). The reaction was heated to 100° C. for 18 hours. The reaction mixture was diluted with EtOAc and water. The organic layer was washed with brine, dried (MgSO$_4$) and concentrated in vacuo. The residue was purified by silica gel column chromatography eluting with 0-10% MeOH in DCM followed by elution through an SCX-2 cartridge using MeOH followed by 1M NH$_3$ in MeOH to afford the title compound (14.7 mg, 47%).

$^1$H NMR (500 MHz, MeOH-d$_4$): δ ppm 9.16 (s, 1H), 8.84 (d, J=8.5 Hz, 1H), 8.56 (s, 1H), 7.41-7.39 (m, 2H), 7.07 (s, 1H), 4.31 (q, J=7.0 Hz, 2H), 4.20-4.15 (m, 2H), 3.89 (s, 3H), 3.69-3.64 (m, 2H), 3.10 (m, 1H), 2.51 (s, 3H), 2.24-2.18 (m, 2H), 2.12-2.07 (m, 2H), 1.56 (t, J=7.0 Hz, 3H).

HRMS (ESI) MS m/z calcd for C$_{25}$H$_{28}$N$_9$O [M+H]$^+$ 470.2411, found 470.2394.

MPS1 IC50 (μM): 0.003

Example 6

N2-(2-ethoxy-4-(4-methyl-4H-1,2,4-triazol-3-yl)phenyl)-6-methyl-N8-(tetrahydro-2H-pyran-4-yl)pyrido[3,4-d]pyrimidine-2,8-diamine

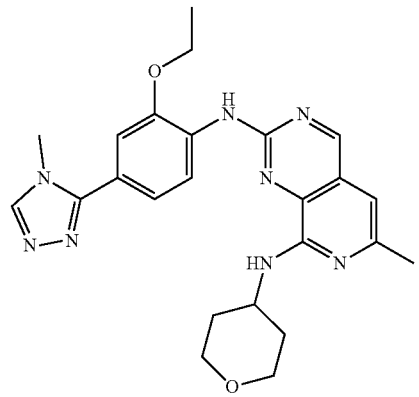 [SMILES: CCOc1cc(-c2nncn2C)ccc1Nc1ncc2cc(C)nc(NC3CCOCC3)c2n1]

To a solution of 6-methyl-2-(methylsulfonyl)-N-(tetrahydro-2H-pyran-4-yl)pyrido[3,4-d]pyrimidin-8-amine (Preparation 12, 19 mg, 0.059 mmol) in DMSO (5 mL) was added N-(2-ethoxy-4-(4-methyl-4H-1,2,4-triazol-3-yl)phenyl)formamide (Preparation 32, 17 mg, 0.071 mmol) and Cs$_2$CO$_3$ (38 mg, 0.118 mmol). The reaction was heated to 100° C. for 18 hours. The reaction mixture was diluted with EtOAc and water. The organic layer was washed with brine, dried (MgSO$_4$) and concentrated in vacuo. The residue was purified by silica gel column chromatography eluting with 0-10% MeOH in DCM followed by elution through an SCX-2 cartridge using MeOH followed by 1M NH$_3$ in MeOH to afford the title compound (15 mg, 55%).

$^1$H NMR (500 MHz, MeOH-d$_4$): δ ppm 9.06 (s, 1H), 8.70 (d, J=9.0 Hz, 1H), 8.56 (s, 1H), 7.41-7.38 (m, 2H), 6.75 (d, J=0.5 Hz, 1H), 4.60 (br s, 2H), 4.36 (m, 1H), 4.31 (q, J=7.0 Hz, 2H), 4.03 (dt, J=12.0, 2.5 Hz, 1H), 3.88 (s, 3H), 3.65 (td, J=12.0, 2.5 Hz, 1H), 2.45 (d, J=0.5 Hz, 3H), 2.16-2.12 (m, 2H), 1.77-1.69 (m, 2H), 1.56 (t, J=7.0 Hz, 3H).

HRMS (ESI) MS m/z calcd for C$_{24}$H$_{29}$N$_8$O$_2$ [M+H]$^+$ 461.2408, found 461.2388.

MPS1 IC50 (μM): 0.005

Example 7

N2-(4-(4,5-dimethyl-4H-1,2,4-triazol-3-yl)-2-ethoxyphenyl)-6-methyl-N8-neopentylpyrido[3,4-d]pyrimidine-2,8-diamine

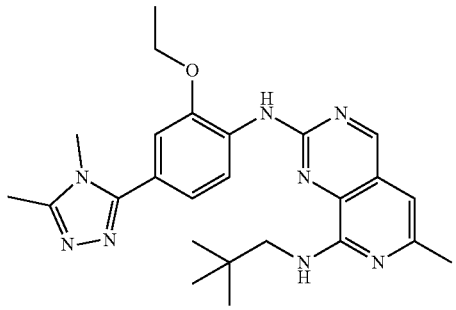

To 6-methyl-2-(methylsulfonyl)-N-neopentylpyrido[3,4-d]pyrimidin-8-amine (Preparation 4, 20 mg, 0.063 mmol) was added Cs$_2$CO$_3$ (28 mg, 0.086 mmol) and N-(2-ethoxy-4-(4-methyl-4H-1,2,4-triazol-3-yl)phenyl)formamide (Preparation 43, 15 mg, 0.058 mmol) in DMSO (2.0 ml). The reaction was heated to 100° C. for 18 hours. The reaction mixture was diluted with EtOAc and water. The aqueous layer was re-extracted with EtOAc and the combined organic layers were dried (MgSO$_4$) and concentrated in vacuo. The residue was purified by silica gel column chromatography eluting with 0-10% MeOH in DCM followed by elution through an SCX-2 cartridge using MeOH followed by 1M NH$_3$ in MeOH to afford the title compound (14.8 mg, 56%)

$^1$H NMR (500 MHz, MeOH-d$_4$): δ ppm 9.06 (s, 1H), 8.75 (d, J=8.5 Hz, 1H), 7.34 (d, J=1.9 Hz, 1H), 7.28 (dd, J=8.5, 1.9 Hz, 1H), 6.72 (s, 1H), 4.30 (q, J=7.2 Hz, 1H), 3.71 (s, 3H), 3.48 (s, 2H), 2.53 (s, 3H), 2.45 (s, 3H), 1.56 (t, J=7.2 Hz, 3H), 1.10 (s, 9H).

HRMS (ESI) MS m/z calcd C$_{25}$H$_{33}$N$_8$O [M+H]$^+$ 461.2772, found 461.2756.

MPS1 IC50 (μM): 0.004

Examples 8 to 26

The following Examples were prepared according to Method 1 (Example 1) above using the appropriate methylsulfonylpyridopyrimidine and the appropriate formamide as described. The crude reaction residues were purified as above or according to one of the following Purification Methods (PM):

Purification Method A: Silica gel column chromatography eluting with 0-10% MeOH in DCM followed by elution through an SCX-2 cartridge using MeOH followed by 1M NH$_3$ in MeOH.

Purification Method B: Silica gel column chromatography eluting with 0-10% MeOH in DCM.

Purification Method C: Silica gel column chromatography eluting with 0-30% EtOAc in cyclohexane.

Purification Method D: Silica gel column chromatography eluting with 0-5% MeOH in DCM.

Purification Method E: Silica gel column chromatography eluting with 0-10% MeOH in DCM followed by silica gel column chromatography eluting with 0-10% MeOH in EtOAc followed by elution through an SCX-2 cartridge using MeOH followed by 1M NH$_3$ in MeOH.

Purification Method F: Silica gel column chromatography eluting with 0-10% MeOH in DCM followed by silica gel column chromatography eluting with 3-10% MeOH in DCM.

| Example No | Name/Structure | Data | MPS1 IC50 (μM) |
|---|---|---|---|
| 8 | 1-(((2-((2-ethoxy-4-(4-methyl-4H-1,2,4-triazol-3-yl)phenyl)amino)-6-methylpyrido[3,4-d]pyrimidin-8-yl)amino)methyl)cyclobutanol 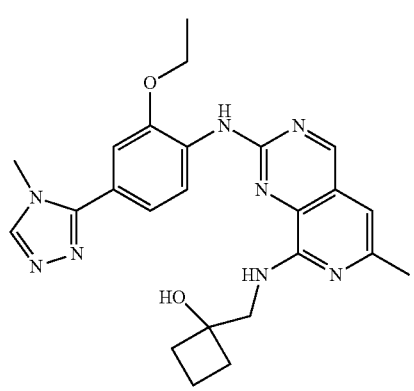 [SMILES: CCOc1cc(-c2nncn2C)ccc1Nc1ncc2cc(C)nc(NCC3(O)CCC3)c2n1] | $^1$H NMR (500 MHz, MeOH-d$_4$): δ ppm 9.07 (s, 1H), 8.80 (d, J = 8.5 Hz, 1H), 8.56 (s, 1H), 7.39 (dd, J = 8.5, 2.0 Hz, 1H), 7.38 (d, J = 2.0 Hz, 1H), 6.76 (d, J = 0.5 Hz, 1H), 4.30 (q, J = 7.0 Hz, 2H), 3.88 (s, 3H), 3.78 (s, 2H), 2.45 (d, J = 0.5 Hz, 3H), 2.22-2.10 (m, 4H), 1.80 (m, 1H), 1.68 (m, 1H), 1.56 (t, J = 7.0 Hz, 3H). HRMS (ESI) MS m/z calcd for C$_{24}$H$_{29}$N$_8$O$_2$ [M + H]$^+$ 461.2408, found 461.2391. Using 1-(((6-methyl-2-(methylsulfonyl)pyrido[3,4-d]pyrimidin-8-yl)amino)methyl)cyclobutanol (Preparation 6) and N-(2-ethoxy-4-(4-methyl-4H-1,2,4-triazol-3-yl)phenyl)formamide (Preparation 32). PM A. | 0.003 |

| Example No | Name/Structure | Data | MPS1 IC50 (μM) |
|---|---|---|---|
| 9 | 1-(2-((2-ethoxy-4-(4-methyl-4H-1,2,4-triazol-3-yl)phenyl)amino)-6-methylpyrido[3,4-d]pyrimidin-8-yl)-3-methylazetidin-3-ol 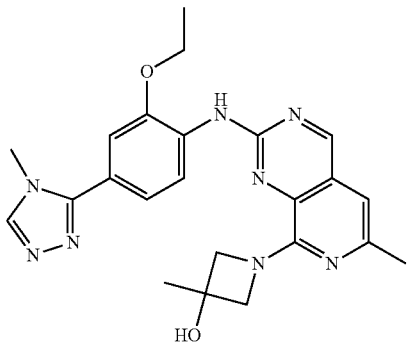 [SMILES: CCOc1cc(-c2nncn2C)ccc1Nc1ncc2cc(C)nc(N3CC(C)(O)C3)c2n1] | $^1$H NMR (500 MHz, MeOH-d$_4$): δ ppm 9.06 (s, 1H), 8.55 (s, 1H), 8.54 (d, J = 8.5 Hz, 1H), 7.39-7.36 (m, 2H), 6.80 (d, J = 0.5 Hz, 1H), 4.44-4.40 (m, 2H), 4.38-4.34 (m, 2H), 4.29 (q, J = 7.0 Hz, 2H), 3.87 (s, 3H), 2.45 (d, J = 0.5 Hz, 3H), 1.57 (s, 3H), 1.54 (t, J = 7.0 Hz, 3H). HRMS (ESI) MS m/z calcd for C$_{23}$H$_{27}$N$_8$O$_2$ [M + H]$^+$ 447.2251, found 447.2207. Using 3-methyl-1-(6-methyl-2-(methylsulfonyl)pyrido[3,4-d]pyrimidin-8-yl)azetidin-3-ol (Preparation 10) and N-(2-ethoxy-4-(4-methyl-4H-1,2,4-triazol-3-yl)phenyl)formamide (Preparation 32). PM A. | 0.004 |
| 10 | N2-(2-ethoxy-4-(4-methyl-4H-1,2,4-triazol-3-yl)phenyl)-6-methyl-N8-((3-methyloxetan-3-yl)methyl)pyrido[3,4-d]pyrimidine-2,8-diamine 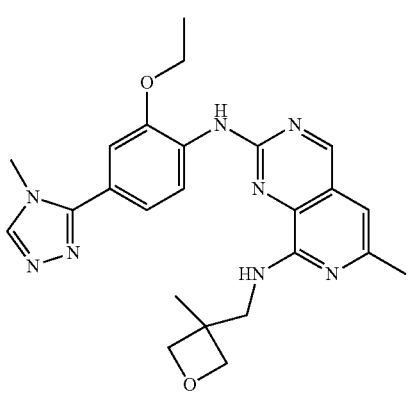 [SMILES: CCOc1cc(-c2nncn2C)ccc1Nc1ncc2cc(C)nc(NCC3(C)COC3)c2n1] | $^1$H NMR (500 MHz, MeOH-d$_4$): δ ppm 9.21 (s, 1H), 8.63 (d, J = 8.5 Hz, 1H), 8.57 (s, 1H), 7.41 (s, 1H), 7.40 (dd, J = 8.5, 2.0 Hz, 1H), 7.05 (s, 1H), 4.32 (d, J = 13.5 Hz, 1H), 4.30, (q, J = 7.0 Hz, 2H), 4.05 (dd, J = 13.5, 1.0 Hz, 1H), 3.88 (s, 3H), 3.69 (dd, J = 13.5, 1.0 Hz, 1H), 3.55 (d, J = 2.5 Hz, 2H), 3.47 (dd, J = 13.5, 1.0 Hz, 1H), 2.61 (s, 3H), 1.53 (t, J = 7.0 Hz, 3H), 1.19 (s, 3H). HRMS (ESI) MS m/z calcd for C$_{24}$H$_{29}$N$_8$O$_2$ [M + H]$^+$ 461.2408, found 461.2407. Using 6-methyl-N-((3-methyloxetan-3-yl)methyl)-2-(methylsulfonyl)pyrido[3,4-d]pyrimidin-8-amine (Preparation 11) and N-(2-ethoxy-4-(4-methyl-4H-1,2,4-triazol-3-yl)phenyl)formamide (Preparation 32). PM A. | No data |
| 11 | N2-(2-methoxy-4-(1-methyl-1H-pyrazol-3-yl)phenyl)-6-methyl-N8-neopentylpyrido[3,4-d]pyrimidine-2,8-diamine 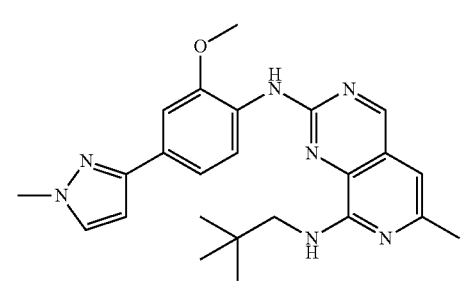 | $^1$H NMR (500 MHz, MeOH-d$_4$): δ ppm 9.00 (s, 1H), 8.52 (d, J = 8.5 Hz, 1H), 7.62 (d, J = 2.0 Hz, 1H), 7.50 (d, J = 2.0 Hz, 1H), 7.39 (dd, J = 8.5, 2.0 Hz, 1H), 6.69 (s, 1H), 6.63 (d, J = 2.0 Hz, 1H), 4.05 (s, 3H), 3.96 (s, 3H), 3.46 (s, 2H), 2.44 (s, 3H), 1.11 (s, 9H). HRMS (ESI) MS m/z calcd for C$_{24}$H$_{30}$N$_7$O [M + H]$^+$ 432.2506, found 432.2487. Using 6-methyl-2-(methylsulfonyl)-N-neopentylpyrido[3,4-d]pyrimidin-8-amine (Preparation 4) and N-(2-methoxy-4-(1-methyl-1H-pyrazol-3-yl)phenyl)formamide (Preparation 33). PM A. | 0.036 |

| Example No | Name/Structure | Data | MPS1 IC50 (μM) |
|---|---|---|---|
| 12 | N2-(2-methoxy-4-(1-methyl-1H-imidazol-2-yl)phenyl)-6-methyl-N8-neopentylpyrido[3,4-d]pyrimidine-2,8-diamine | $^1$H NMR (500 MHz, MeOH-$d_4$): δ ppm 9.03 (s, 1H), 8.66 (d, J = 8.5 Hz, 1H), 7.32 (d, J = 2.0 Hz, 1H), 7.24 (dd, J = 8.5, 2.0 Hz, 1H), 7.19 (d, J = 1.5 Hz, 1H), 7.05 (d, J = 1.5 Hz, 1H), 6.70 (d, J = 0.5 Hz, 1H), 4.05 (s, 3H), 3.82 (s, 3H), 3.46 (s, 2H), 2.44 (d, J = 0.5 Hz, 3H), 1.09 (s, 9H). HRMS (ESI) MS m/z calcd for $C_{24}H_{30}N_7O$ [M + H]$^+$ 433.2535, found 433.2512. Using 6-methyl-2-(methylsulfonyl)-N-neopentylpyrido[3,4-d]pyrimidin-8-amine (Preparation 4) and N-(2-methoxy-4-(1-methyl-1H-imidazol-2-yl)phenyl)formamide (Preparation 34). PM B. | 0.004 |
| 13 | N2-(2-methoxy-4-(1-methyl-1H-pyrazol-5-yl)phenyl)-6-methyl-N8-neopentylpyrido[3,4-d]pyrimidine-2,8-diamine | $^1$H NMR (500 MHz, MeOH-$d_4$): δ ppm 9.03 (s, 1H), 8.62 (d, J = 8.5 Hz, 1H), 7.52 (d, J = 2.0 Hz, 1H), 7.16 (d, J = 2.0 Hz, 1H), 7.09 (dd, J = 8.5, 2.0 Hz, 1H), 6.70 (d, J = 0.5 Hz, 1H), 6.39 (d, J = 2.0 Hz, 1H), 4.03 (s, 3H), 3.92 (s, 3H), 3.46 (s, 2H), 2.44 (d, J = 0.5 Hz, 3H), 1.09 (s, 9H). HRMS (ESI) MS m/z calcd for $C_{24}H_{30}N_7O$ [M + H]$^+$ 432.2506, found 432.2503. Using 6-methyl-2-(methylsulfonyl)-N-neopentylpyrido[3,4-d]pyrimidin-8-amine (Preparation 4) and N-(2-methoxy-4-(1-methyl-1H-pyrazol-5-yl)phenyl)formamide (Preparation 35). PM B. | 0.018 |
| 14 | N2-(2-methoxy-4-(oxazol-2-yl)phenyl)-6-methyl-N8-neopentylpyrido[3,4-d]pyrimidine-2,8-diamine | $^1$H NMR (500 MHz, MeOH-$d_4$): δ ppm 9.04 (s, 1H), 8.71 (d, J = 8.5 Hz, 1H), 7.98 (d, J = 1.0 Hz, 1H), 7.70 (d, J = 2.0 Hz, 1H), 7.67 (dd, J = 8.5, 2.0 Hz, 1H), 7.31 (d, J = 1.0 Hz, 1H), 6.70 (d, J = 0.5 Hz, 1H), 4.08 (s, 3H), 3.48 (s, 2H), 2.44 (d, J = 0.5 Hz, 3H), 1.12 (s, 9H). HRMS (ESI) MS m/z calcd for $C_{23}H_{27}N_6O_2$ [M + H]$^+$ 419.219, found 419.217. Using 6-methyl-2-(methylsulfonyl)-N-neopentylpyrido[3,4-d]pyrimidin-8-amine (Preparation 4) and N-(2-methoxy-4-(oxazol-2-yl)phenyl)formamide (Preparation 36). PM B. | 0.059 |

| Example No | Name/Structure | Data | MPS1 IC50 (μM) |
|---|---|---|---|
| 15 | N2-(2-(difluoromethoxy)-4-(4-methyl-4H-1,2,4-triazol-3-yl)phenyl)-6-methyl-N8-neopentylpyrido[3,4-d]pyrimidine-2,8-diamine 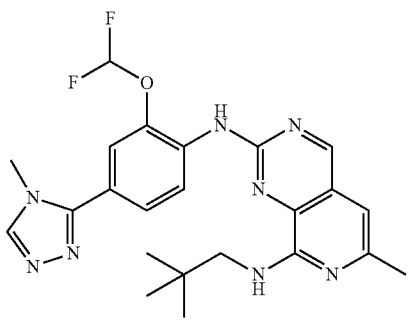 [SMILES: Cc1cc2cnc(Nc3ccc(-c4nncn4C)cc3OC(F)F)nc2c(NCC(C)(C)C)n1] | $^1$H NMR (500 MHz, DMSO-$d_6$): δ ppm 9.16 (s, 1H), 9.15 (s, 1H), 8.59 (s, 1H), 8.39 (d, J = 8.4 Hz, 1H), 7.67-7.60 (m, 2H), 7.28 (t, J = 73.5 Hz, 1H), 6.72 (s, 1H), 6.63 (t, J = 6.2 Hz, 1H), 3.78 (s, 3H), 3.37 (d, J = 6.0 Hz, 2H), 2.36 (s, 3H), 0.97 (s, 9H).<br>HRMS (ESI) MS m/z calcd for $C_{23}H_{27}F_2N_8O$ [M + H]$^+$ 469.2276, found 469.2263.<br>Using 6-methyl-2-(methylsulfonyl)-N-neopentylpyrido[3,4-d]pyrimidin-8-amine (Preparation 4) and N-(2-(Difluoromethoxy)-4-(4-methyl-4H-1,2,4-triazol-3-yl)phenyl)formamide (Preparation 38).<br>PM C. | 0.001 |
| 16 | N2-(2-methoxy-4-(1-methyl-1H-tetrazol-5-yl)phenyl)-6-methyl-N8-neopentylpyrido[3,4-d]pyrimidine-2,8-diamine 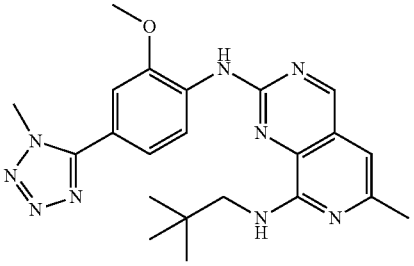 [SMILES: COc1cc(-c2nnnn2C)ccc1Nc1ncc2cc(C)nc(NCC(C)(C)C)c2n1] | $^1$H NMR (500 MHz, DMSO-$d_6$): δ ppm 9.17 (s, 1H), 8.66 (s, 1H), 8.58 (d, J = 8.4 Hz, 1H), 7.51 (d, J = 1.9 Hz, 1H), 7.46 (dd, J = 8.4, 1.9 Hz, 1H), 6.75-6.67 (m, 2H), 4.21 (s, 3H), 3.99 (s, 3H), 3.39 (d, J = 6.2 Hz, 2H), 2.36 (d, J = 0.8 Hz, 3H), 0.99 (s, 9H).<br>HRMS (ESI) MS m/z calcd for $C_{22}H_{28}N_9O$ [M + H]$^+$ 434.2417, found 434.2406.<br>Using 6-methyl-2-(methylsulfonyl)-N-neopentylpyrido[3,4-d]pyrimidin-8-amine (Preparation 4) and N-(2-methoxy-4-(1-methyl-1H-tetrazol-5-yl)phenyl)formamide (Preparation 39)<br>PM D. | 0.005 |
| 17 | N2-(4-(2,4-dimethyloxazol-5-yl)-2-methoxyphenyl)-6-methyl-N8-neopentylpyrido[3,4-d]pyrimidine-2,8-diamine 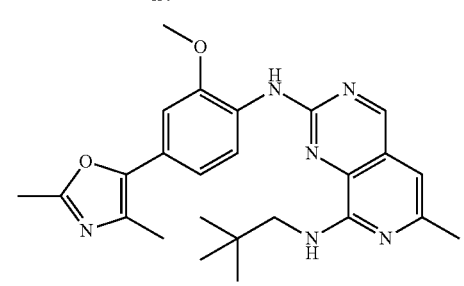 | $^1$H NMR (500 MHz, MeOH-$d_4$): δ ppm 8.97 (s, 1H), 8.55 (d, J = 8.5 Hz, 1H), 7.21 (s, 1H), 7.16 (d, J = 8.5 Hz, 1H), 6.66 (d, J = 0.5 Hz, 1H), 4.02 (s, 3H), 3.45 (s, 2H), 2.49 (s, 3H), 2.42 (s, 3H), 2.37 (s, 3H), 1.10 (s, 9H).<br>HRMS (ESI) MS m/z calcd for $C_{25}H_{31}N_6O_2$ [M + H]$^+$ 447.2508, found 447.2508.<br>Using 6-methyl-2-(methylsulfonyl)-N-neopentylpyrido[3,4-d]pyrimidin-8-amine (Preparation 4) and N-(4-(2,4-dimethyloxazol-5-yl)-2-methoxyphenyl)formamide (Preparation 40).<br>PM A. | 0.043 |

| Example No | Name/Structure | Data | MPS1 IC50 (μM) |
|---|---|---|---|
| 18 | N2-(4-(1,5-dimethyl-1H-imidazol-2-yl)-2-methoxyphenyl)-6-methyl-N8-neopentylpyrido[3,4-d]pyrimidine-2,8-diamine 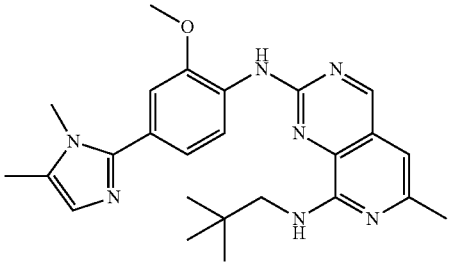 | ¹H NMR (500 MHz, MeOH-d₄): δ ppm 9.02 (s, 1H), 8.64 (d, J = 8.5 Hz, 1H), 7.28 (d, J = 2.0 Hz, 1H), 7.19 (dd, J = 8.5, 2.0 Hz, 1H), 6.83 (d, J = 1.0 Hz, 1H), 6.69 (d, J = 0.5 Hz, 1H), 4.04 (s, 3H), 3.68 (s, 3H), 3.48 (s, 2H), 2.43 (d, J = 0.5 Hz, 3H), 2.32 (d, J = 1.0 Hz, 3H), 1.09 (s, 9H). HRMS (ESI) MS /z calcd for C₂₅H₃₂N₇O [M + H]⁺ 446.2668, found 446.2670. Using 6-methyl-2-(methylsulfonyl)-N-neopentylpyrido[3,4-d]pyrimidin-8-amine (Preparation 4) and N-(4-(1,5-dimethyl-1H-imidazol-2-yl)-2-methoxyphenyl)formamide (Preparation 41). PM A. | 0.004 |
| 19 | N-(4-(1,2-dimethyl-1H-imidazol-5-yl)-2-methoxyphenyl)-8-(3,3-dimethylazetidin-1-yl)-6-methylpyrido[3,4-d]pyrimidin-2-amine 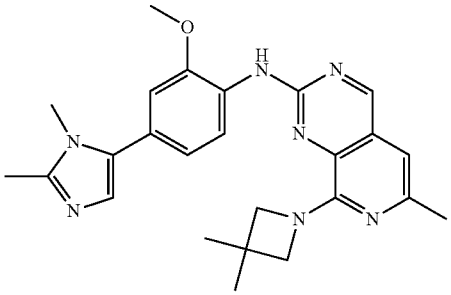 | ¹H NMR (500 MHz, MeOH-d₄): δ ppm 9.00 (s, 1H), 8.33 (d, J = 8.3 Hz, 1H), 7.06 (d, J = 1.7 Hz, 1H), 7.03 (dd, J = 8.3, 1.7 Hz, 1H), 6.90 (br s, 1H), 6.74 (s, 1H), 4.18 (br s, 4H), 3.99 (s, 3H), 3.62 (s, 3H), 2.45 (s, 3H), 2.43 (s, 3H), 1.36 (s, 6H). HRMS (ESI) MS m/z calcd C₂₅H₃₀N₇O [M + H]⁺ 444.2512, found 444.2516 Using 8-(3,3-dimethylazetidin-1-yl)-6-methyl-2-(methylsulfonyl)pyrido[3,4-d]pyrimidine (Preparation 13) and N-(4-(1,2-dimethyl-1H-imidazol-5-yl)-2-methoxyphenyl)formamide (Preparation 37) at 120° C. for 18 hours. PM A. | 0.005 |
| 20 | N-(4-(1,2-dimethyl-1H-imidazol-5-yl)-2-methoxyphenyl)-6-methyl-8-(7-oxa-2-azaspiro[3.5]nonan-2-yl)pyrido[3,4-d]pyrimidin-2-amine 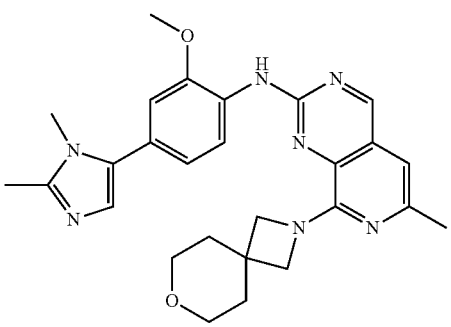 | ¹H NMR (500 MHz, MeOH-d₄): δ ppm 9.01 (s, 1H), 8.32 (d, J = 8.1 Hz, 1H), 7.08 (d, J = 1.6 Hz, 1H), 7.05 (dd, J = 8.1, 1.6 Hz, 1H), 6.90 (s, 1 H), 6.75 (s, 1H), 4.25 (br s, 4H), 3.90 (s, 3H), 3.69-3.66 (m, 4H), 3.63 (s, 3H), 2.45 (s, 3H), 2.43 (s, 3H), 1.87 (app t, J = 5.3 Hz, 4H). HRMS (ESI) MS m/z calcd C₂₇H₃₁N₇O₂ [M + H]⁺ 486.2617, found 486.2623. Using 2-(6-methyl-2-(methylsulfonyl)pyrido[3,4-d]pyrimidin-8-yl)-7-oxa-2-azaspiro[3.5]nonane (Preparation 8) and N-(4-(1,2-dimethyl-1H-imidazol-5-yl)-2-methoxyphenyl)formamide (Preparation 37) at 120° C. for 18 hours. PM E. | 0.012 |

| Example No | Name/Structure | Data | MPS1 IC50 (μM) |
|---|---|---|---|
| 21 | N2-(4-(4,5-dimethyl-4H-1,2,4-triazol-3-yl)-2-methoxyphenyl)-6-methyl-N8-neopentylpyrido[3,4-d]pyrimidine-2,8-diamine 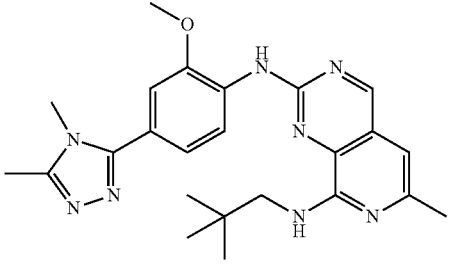 | $^1$H NMR (500 MHz, MeOH-d$_4$): δ ppm 9.04 (s, 1H), 8.74 (d, J = 8.3 Hz, 1H), 7.36 (d, J = 1.9 Hz, 1H), 7.28 (dd, J = 8.3, 1.9 Hz, 1H), 6.71 (d, J = 0.6 Hz, 1H), 4.06 (s, 3H), 3.72 (s, 3H), 3.47 (s, 2H), 2.54 (s, 3H), 2.44 (d, J = 0.6 Hz, 3H), 1.09 (s, 9H).<br>HRMS (ESI) MS m/z calcd C$_{24}$H$_{31}$N$_8$O [M + H]$^+$ 447.2621, found 447.2626.<br>Using 6-methyl-2-(methylsulfonyl)-N-neopentylpyrido[3,4-d]pyrimidin-8-amine (Preparation 4) and N-(4-(4,5-dimethyl-4H-1,2,4-triazol-3-yl)-2-methoxyphenyl)formamide (Preparation 37) at 120° C. for 18 hours. PM A. | 0.001 |
| 22 | N-(4-(4,5-dimethyl-4H-1,2,4-triazol-3-yl)-2-ethoxyphenyl)-8-(3,3-dimethylazetidin-1-yl)-6-methylpyrido[3,4-d]pyrimidin-2-amine 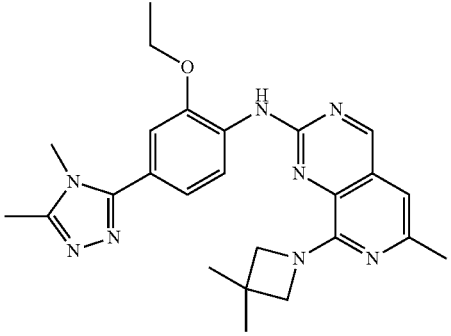 | $^1$H NMR (500 MHz, MeOH-d$_4$): δ ppm 9.06 (s, 1H), 8.50 (d, J = 8.2 Hz, 1H), 7.31 (d, J = 1.6 Hz, 1H), 7.28 (dd, J = 8.2, 1.6 Hz, 1H), 6.77 (s, 1H), 4.28 (q, J = 6.9 Hz, 2H) 4.24 (br s, 4H), 3.71 (s, 3H), 2.54 (s, 3H), 2.44 (s, 3H), 1.53 (t, J = 6.9 Hz, 3H), 1.38 (s, 6H).<br>HRMS (ESI) MS m/z calcd C$_{25}$H$_{31}$N$_8$O [M + H]$^+$ 459.2621, found 459.2660.<br>Using 8-(3,3-dimethylazetidin-1-yl)-6-methyl-2-(methylsulfonyl)pyrido[3,4-d]pyrimidine (Preparation 13) and N-(4-(4,5-dimethyl-4H-1,2,4-triazol-3-yl)-2-ethoxyphenyl)formamide (Preparation 43) at 120° C. for 18 hours. PM A. | 0.02 |
| 23 | N-(4-(4,5-dimethyl-4H-1,2,4-triazol-3-yl)-2-ethoxyphenyl)-6-methyl-8-(7-oxa-2-azaspiro[3.5]nonan-2-yl)pyrido[3,4-d]pyrimidin-2-amine 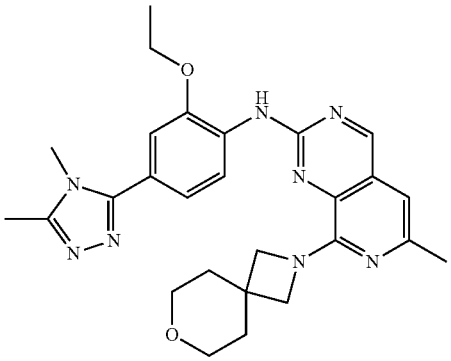 | $^1$H NMR (500 MHz, MeOH-d$_4$): δ ppm 9.05 (s, 1H), 8.56 (d, J = 8.2 Hz, 1H), 7.32 (d, J = 1.8 Hz, 1H), 7.30 (dd, J = 8.2, 1.8 Hz, 1H), 6.78 (s, 1H), 4.31-4.26 (m, 6H), 3.72 (s, 3H), 3.69 (app t, J = 5.0 Hz, 4H), 2.54 (s, 3H), 2.44 (s, 3H), 1.89 (app t, J = 5.0 Hz, 4H), 1.54 (t, J = 7.0 Hz, 3H).<br>HRMS (ESI) MS m/z calcd C$_{27}$H$_{33}$N$_8$O$_2$ [M + H]$^+$ 501.2726, found 501.2726.<br>Using 2-(6-methyl-2-(methylsulfonyl)pyrido[3,4-d]pyrimidin-8-yl)-7-oxa-2-azaspiro[3.5]nonane (Preparation 8) and N-(4-(4,5-dimethyl-4H-1,2,4-triazol-3-yl)-2-ethoxyphenyl)formamide (Preparation 43) at 120° C. for 18 hours. PM B. | 0.004 |

| Example No | Name/Structure | Data | MPS1 IC50 (μM) |
|---|---|---|---|
| 24 | N-(2-ethoxy-4-(4-ethyl-4H-1,2,4-triazol-3-yl)phenyl)-6-methyl-8-(7-oxa-2-azaspiro[3.5]nonan-2-yl)pyrido[3,4-d]pyrimidin-2-amine | $^1$H NMR (500 MHz, MeOH-d$_4$): δ ppm 9.06 (s, 1H), 8.67 (s, 1H), 8.57 (d, J = 8.2 Hz, 1H), 7.33 (d, J = 1.7 Hz, 1H), 7.29 (dd, J = 8.2, 1.7 Hz, 1H), 6.78 (s, 1H), 4.30-4.23 (m, 8H), 3.70-3.68 (m, 4H), 2.44 (s, 3H), 1.89 (br t, J = 5.2 Hz, 4H), 1.54 (t, J = 7.0 Hz, 3H), 1.46 (t, J = 7.4 Hz, 3H).<br>HRMS (ESI) MS m/z calcd C$_{27}$H$_{33}$N$_8$O$_2$ [M + H]$^+$ 501.2721, found 501.2706<br>Using 2-(6-methyl-2-(methylsulfonyl)pyrido[3,4-d]pyrimidin-8-yl)-7-oxa-2-azaspiro[3.5]nonane (Preparation 8) and N-(2-ethoxy-4-(4-ethyl-4H-1,2,4-triazol-3-yl)phenyl)formamide (Preparation 44). PM F. | 0.002 |
| 25 | 8-(3,3-dimethylazetidin-1-yl)-N-(2-ethoxy-4-(4-ethyl-4H-1,2,4-triazol-3-yl)phenyl)-6-methylpyrido[3,4-d]pyrimidin-2-amine | $^1$H NMR (500 MHz, MeOH-d$_4$): δ ppm 9.05 (s, 1H), 8.67 (s, 1H), 8.55 (d, J = 8.3 Hz, 1H), 7.31 (d, J = 1.7 Hz, 1H), 7.28 (dd, J = 8.3, 1.7 Hz, 1H), 6.77 (s,1 H), 4.30-4.21 (m, 8H), 2.44 (s, 3H), 1.54 (t, J = 7.0 Hz, 3H), 1.44 (t, J = 7.4 Hz, 3H), 1.37 (s, 6H).<br>HRMS (ESI) MS m/z calcd C$_{25}$H$_{31}$N$_8$O [M + H]$^+$ 459.2615, found 459.2601.<br>Using 8-(3,3-dimethylazetidin-1-yl)-6-methyl-2-(methylsulfonyl)pyrido[3,4-d]pyrimidine (Preparation 13) and N-(2-ethoxy-4-(4-ethyl-4H-1,2,4-triazol-3-yl)phenyl)formamide (Preparation 44). PM A. | 0.006 |
| 26 | N2-(2-ethoxy-4-(4-ethyl-4H-1,2,4-triazol-3-yl)phenyl)-6-methyl-N8-neopentylpyrido[3,4-d]pyrimidine-2,8-diamine | $^1$H NMR (500 MHz, MeOH-d$_4$): δ ppm 9.06 (s, 1H), 8.77 (d, J = 8.4 Hz, 1H), 8.66 (s, 1H), 7.34 (d, J = 1.7 Hz, 1H), 7.27 (dd, J = 8.4, 1.7 Hz, 1H), 6.72 (s, 1H), 4.30 (q, J = 7.0 Hz, 2H), 4.24 (q, J = 7.4 Hz, 2H), 3.48 (s, 2H), 2.44 (s, 3H), 1.56 (t, J = 7.0 Hz, 3H), 1.44 (t, J = 7.4 Hz, 3H), 1.10 (s, 9H).<br>HRMS (ESI) MS m/z calcd C$_{25}$H$_{33}$N$_8$O [M + H]$^+$ 461.2772, found 461.2752.<br>Using 6-methyl-2-(methylsulfonyl)-N-neopentylpyrido[3,4-d]pyrimidin-8-amine (Preparation 4) and N-(2-ethoxy-4-(4-ethyl-4H-1,2,4-triazol-3-yl)phenyl)formamide (Preparation 44). PM A. | 0.006 |

Example 27

N-(2-ethoxy-4-(4-methyl-4H-1,2,4-triazol-3-yl)phenyl)-6-methyl-8-(2-oxa-7-azaspiro[4.4]nonan-7-yl)pyrido[3,4-d]pyrimidin-2-amine

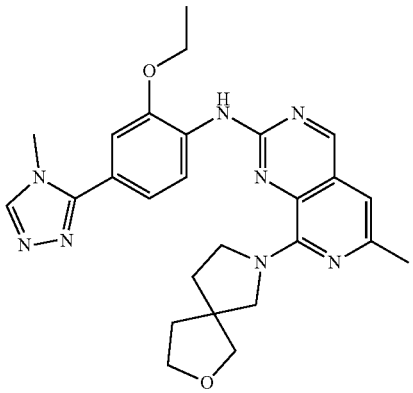 [SMILES: CCOc1cc(-c2nncn2C)ccc1Nc1ncc2cc(C)nc(N3CCC4(CCOC4)C3)c2n1]

Method 2

To a solution of 8-chloro-N-(2-ethoxy-4-(4-methyl-4H-1,2,4-triazol-3-yl)phenyl)-6-methylpyrido[3,4-d]pyrimidin-2-amine (Preparation 1, 25 mg, 0.063 mmol) in NMP (3 mL) was added 2-oxa-7-azaspiro[4.4]nonane (16 mg, 0.126 mmol) and triethylamine (0.044 mL, 0.316 mmol). The reaction was heated to 100° C. in a closed cap vial for 18 hours. The reaction mixture was diluted with EtOAc and water. The organic layer was washed with brine, dried (MgSO$_4$) and concentrated in vacuo. The residue was purified by silica gel column chromatography eluting with 0-50% EtOAc in cyclohexane to afford the title compound (20.4 mg, 66%).

$^1$H NMR (500 MHz, MeOH-d$_4$): δ ppm 9.03 (s, 1H), 8.56 (s, 1H), 8.50 (d, J=8.5 Hz, 1H), 7.38 (d, J=2.0 Hz, 1H), 7.35 (dd, J=8.5, 2.0 Hz, 1H), 6.75 (s, 1H), 4.28 (q, J=7.0 Hz, 2H), 4.17-4.14 (m, 2H), 4.07-4.01 (m, 2H), 3.96-3.88 (m, 2H), 3.87 (s, 3H), 3.74 (ABq, J=9.0 Hz, 2H), 2.44 (s, 3H), 2.08-1.98 (m, 4H), 1.54 (t, J=7.0 Hz, 3H).

HRMS (ESI) MS m/z calcd for C$_{26}$H$_{31}$N$_8$O$_2$ [M+H]+ 487.2564, found 487.2572.

MPS1 IC50 (μM): 0.004

Example 28

1-(2-((2-ethoxy-4-(4-methyl-4H-1,2,4-triazol-3-yl)phenyl)amino)-6-methylpyrido[3,4-d]pyrimidin-8-yl)-4-methylpiperidine-4-carbonitrile

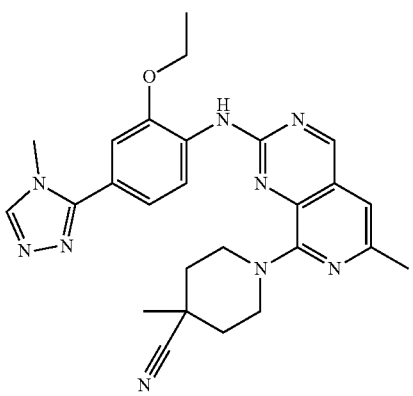 [SMILES: CCOc1cc(-c2nncn2C)ccc1Nc1ncc2cc(C)nc(N3CCC(C)(C#N)CC3)c2n1]

To a solution of 8-chloro-N-(2-ethoxy-4-(4-methyl-4H-1,2,4-triazol-3-yl)phenyl)-6-methylpyrido[3,4-d]pyrimidin-2-amine (Preparation 1, 25 mg, 0.063 mmol) in NMP (2 mL) was added 4-methylpiperidine-4-carbonitrile (20 mg, 0.126 mmol) and triethylamine (0.044 mL, 0.316 mmol). The reaction was heated to 100° C. in a closed cap vial for 18 hours. Further 4-methylpiperidine-4-carbonitrile hydrochloride (40 mg, 0.252 mmol) was added and the reaction heated at 120° C. for a further 5 hours. The reaction mixture was diluted with EtOAc and water. The organic layer was dried (MgSO$_4$) and concentrated in vacuo. The residue was purified by silica gel column chromatography eluting with 0-50% EtOAc in cyclohexane followed by elution through an SCX-2 cartridge using MeOH followed by 1M NH$_3$ in MeOH. The residue was further purified by silica gel column chromatography eluting with 0-15% MeOH in EtOAc followed by elution through an SCX-2 cartridge using MeOH followed by 1M NH$_3$ in MeOH to afford the title compound (5.1 mg, 17%).

$^1$H NMR (500 MHz, MeOH-d$_4$): δ ppm 9.13 (s, 1H), 8.80 (d, J=8.5 Hz, 1H), 8.56 (s, 1H), 7.38 (d, J=2.0 Hz, 1H), 7.36 (dd, J=8.5, 2.0 Hz, 1H), 7.04 (s, 1H), 4.70 (br d, J=13.0 Hz, 2H), 4.29 (q, J=7.0 Hz, 2H), 3.88 (s, 3H), 3.26 (t, J=13.0 Hz, 2H), 2.50 (s, 3H), 2.10 (br d, J=13.0 Hz, 2H), 1.92 (td, J=13.0, 3.5 Hz, 2H), 1.56 (t, J=7.0 Hz, 3H), 1.51 (s, 3H).

HRMS (ESI) MS m/z calcd for C$_{26}$H$_{31}$N$_9$O [M+2H]/2+ 242.632, found 242.6321.

MPS1 IC50 (μM): 0.002

Example 29

8-(3,3-dimethylazetidin-1-yl)-N-(2-ethoxy-4-(4-methyl-4H-1,2,4-triazol-3-yl)phenyl)-6-methylpyrido[3,4-d]pyrimidin-2-amine

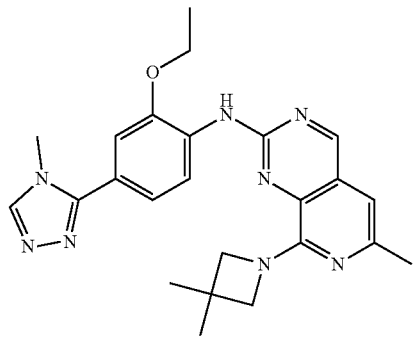 [SMILES: CCOc1cc(-c2nncn2C)ccc1Nc1ncc2cc(C)nc(N3CC(C)(C)C3)c2n1]

To a solution of 8-chloro-N-(2-ethoxy-4-(4-methyl-4H-1,2,4-triazol-3-yl)phenyl)-6-methylpyrido[3,4-d]pyrimidin-2-amine (Preparation 1, 20 mg, 0.051 mmol) in NMP (1 mL) was added 3,3-dimethylazetidine hydrochloride (25 mg, 0.202 mmol) and triethylamine (0.057 mL, 0.404 mmol). The reaction was heated to 100° C. in a closed cap vial for 18 hours. The reaction was diluted with EtOAc and water. The aqueous layer was re-extracted with EtOAc and the combined organic layers were dried (MgSO$_4$) and concentrated in vacuo. The residue was purified by silica gel column chromatography eluting with 0-10% MeOH in DCM to afford the title compound (15.7 mg, 70%).

$^1$H NMR (500 MHz, MeOH-d$_4$): δ ppm 9.05 (s, 1H), 8.56 (d, J=8.5 Hz, 1H), 8.56 (s, 1H), 7.37 (d, J=1.5 Hz, 1H), 7.34 (dd, J=8.5, 1.5 Hz, 1H), 6.77 (s, 1H), 4.29 (q, J=7.0 Hz, 2H), 4.21 (br s, 4H), 3.87 (s, 3H), 2.44 (s, 3H), 1.54 (t, J=7.0 Hz, 3H), 1.38 (s, 6H).

HRMS (ESI) MS m/z calcd for C$_{24}$H$_{30}$N$_8$O [M+2H]/2+ 223.1266, found 223.1261.

MPS1 IC50 (μM): 0.002

Example 30

N-(2-ethoxy-4-(4-methyl-4H-1,2,4-triazol-3-yl)phenyl)-8-(3-methoxy-3-methylazetidin-1-yl)-6-methylpyrido[3,4-d]pyrimidin-2-amine

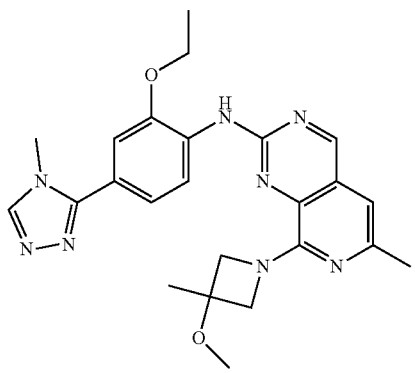 [SMILES: CCOc1cc(-c2nncn2C)ccc1Nc1ncc2cc(C)nc(N3CC(C)(OC)C3)c2n1]

A mixture of 8-chloro-N-(2-ethoxy-4-(4-methyl-4H-1,2,4-triazol-3-yl)phenyl)-6-methylpyrido[3,4-d]pyrimidin-2-amine (Preparation 1, 26 mg, 0.066 mmol), triethylamine (110 µL, 0.795 mmol) and 3-methoxy-3-methylazetidine hydrochloride (48 mg, 0.349 mmol) in NMP (0.5 mL) was stirred at 130° C. in a closed cap vial for 18 hours. The reaction was quenched with saturated aqueous $NaHCO_3$ solution and extracted with EtOAc. The combined organic layers were washed with water and brine, dried ($MgSO_4$) and concentrated in vacuo. The residue was purified by silica gel column chromatography eluting with 0-5% MeOH in DCM to afford the title compound (18 mg, 60%).

$^1$H NMR (500 MHz, DMSO-$d_6$): δ ppm 9.17 (s, 1H), 8.57 (s, 1H), 8.45 (s, 1H), 8.25 (d, J=8.2 Hz, 1H), 7.39 (d, J=1.8 Hz, 1H), 7.36 (dd, J=8.2, 1.8 Hz, 1H), 6.84 (s, 1H), 4.33-4.18 (br m, 4H), 4.15 (br d, J=8.6 Hz, 2H), 3.78 (s, 3H), 3.21 (s, 3H), 2.38 (s, 3H), 1.46 (s, 3H), 1.40 (t, J=6.9 Hz, 3H).

HRMS (ESI) MS m/z calcd for $C_{24}H_{29}N_8O_2$ [M+H]$^+$ 461.2408, found 461.2385.

MPS1 IC50 (µM): 0.002

Examples 31 to 62

The following Examples were prepared according to Method 2 (Example 27) above using either 8-chloro-N-(2-ethoxy-4-(4-methyl-4H-1,2,4-triazol-3-yl)phenyl)-6-methylpyrido[3,4-d]pyrimidin-2-amine (Preparation 1) or 8-chloro-N-(4-(1,2-dimethyl-1H-imidazol-5-yl)-2-methoxyphenyl)-6-methylpyrido[3,4-d]pyrimidin-2-amine (Preparation 2) or 8-chloro-N-(2-(difluoromethoxy)-4-(4-methyl-4H-1,2,4-triazol-3-yl)phenyl)-6-methylpyrido[3,4-d]pyrimidin-2-amine (Preparation 3) and the appropriate amine as described. Where necessary further equivalents of amine were added and/or the reaction continued heating to enable maximum yields. The crude reaction residues were purified as above or according to one of the following Purification Methods (PM): Purification Method A: Silica gel column chromatography eluting with 0-10% MeOH in DCM or EtOAc followed by further chromatography eluting with 0-20% MeOH in EtOAc.

Purification Method B: Following the described chromatography the residue was eluted through an SCX-2 cartridge using MeOH followed by 1M $NH_3$ in MeOH followed by further silica gel column chromatography eluting with 0-10% MeOH in DCM.

Purification Method C: Following the described chromatography the residue was eluted through an SCX-2 cartridge using MeOH followed by 1M $NH_3$ in MeOH.

Purification Method D: Reverse phase column chromatography eluting with water followed by elution through an SCX-2 cartridge using MeOH followed by 1M $NH_3$ in MeOH.

Purification Method E: Silica gel column chromatography eluting with 0-10% MeOH in DCM followed by elution through an SCX-2 cartridge using MeOH followed by 1M $NH_3$ in MeOH.

Purification Method F: Silica gel column chromatography eluting with 0-10% MeOH in DCM or EtOAc.

Purification Method G: Silica gel column chromatography eluting with 0-5% MeOH in DCM.

| Example No | Name/Structure | Data | MPS1 IC50 (µM) |
|---|---|---|---|
| 31 | 1-(((2-((2-ethoxy-4-(4-methyl-4H-1,2,4-triazol-3-yl)phenyl)amino)-6-methylpyrido[3,4-d]pyrimidin-8-yl)amino)methyl)cyclopropanol 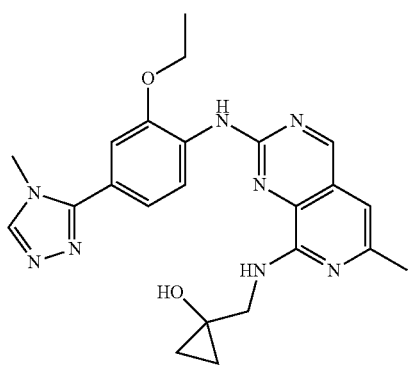 [SMILES: CCOc1cc(-c2nncn2C)ccc1Nc1ncc2cc(C)nc(NCC3(O)CC3)c2n1] | $^1$H NMR (500 MHz, MeOH-$d_4$): δ ppm 9.05 (s, 1H), 8.79 (d, J = 9.0 Hz, 1H), 8.55 (s, 1H), 7.40-7.37 (m, 2H), 6.74 (s, 1H), 4.30 (q, J = 7.0 Hz, 2H), 3.87 (s, 3H), 3.75 (s, 2H), 2.42 (s, 3H), 1.56 (t, J = 7.0 Hz, 3H), 0.82-0.79 (m, 2H), 0.77-0.74 (m, 2H). HRMS (ESI) MS m/z calcd for $C_{23}H_{27}N_8O_2$ [M + H]$^+$ 448.2279, found 44.2283. Using (1-aminomethyl)cyclopropanol. PM A. | 0.008 |

| Example No | Name/Structure | Data | MPS1 IC50 (μM) |
|---|---|---|---|
| 32 | N2-(4-(1,2-dimethyl-1H-imidazol-5-yl)-2-methoxyphenyl)-6-methyl-N8-((3-methyltetrahydrofuran-3-yl)methyl)pyrido[3,4-d]pyrimidine-2,8-diamine | $^1$H NMR (500 MHz, MeOH-$d_4$): δ ppm 9.02 (s, 1H), 8.63 (d, J = 8.5 Hz, 1H), 7.09-7.07 (m, 2H), 6.90 (s, 1H), 6.72 (s, 1H), 4.06 (td, J = 8.5, 5.5 Hz, 1H), 4.02 (s, 3H), 3.93-3.88 (m, 2H), 3.63 (s, 3H), 3.63 (d, J = 13.5 Hz, 1H), 3.69 (d, J = 13.5 Hz, 1H), 3.52 (d, J = 8.5 Hz, 1H), 2.45 (s, 3H), 2.44 (s, 3H), 2.06 (m, 1H), 1.81 (m, 1H), 1.28 (s, 3H). HRMS (ESI) MS m/z calcd for $C_{26}H_{33}N_7O_2$ [M + 2H]/2$^+$ 237.6342, found 237.6345. Using (3-methyltetrahydrofuran-3-yl)methanamine for 60 hours. PM B. | 0.002 |
| 33 | N-(4-(1,2-dimethyl-1H-imidazol-5-yl)-2-methoxyphenyl)-6-methyl-8-(2-oxa-7-azaspiro[4.4]nonan-7-yl)pyrido[3,4-d]pyrimidin-2-amine | $^1$H NMR (500 MHz, MeOH-$d_4$): δ ppm 8.99 (s, 1H), 8.26 (d, J = 8.0 Hz, 1H), 7.06 (d, J = 1.5 Hz, 1H), 7.04 (dd, J = 8.0, 1.5 Hz, 1H), 6.90 (s, 1H), 6.72 (s, 1H), 4.11 (q, J = 8.5 Hz, 2H), 4.04-3.97 (m, 2H), 3.99 (s, 3H), 3.94-3.85 (m, 2H), 3.71 (q, J = 8.5 Hz, 2H), 3.63 (s, 3H), 2.45 (s, 3H), 2.43 (s, 3H), 2.05-1.97 (m, 4H). HRMS (ESI) MS m/z calcd for $C_{27}H_{33}N_7O_2$ [M + 2H]/2$^+$ 243.6342, found 243.6348. Using 2-oxa-7-azaspiro[4.4]nonane for 60 hours. PM B. | 0.005 |
| 34 | 1-(2-((4-(1,2-dimethyl-1H-imidazol-5-yl)-2-methoxyphenyl)amino)-6-methylpyrido[3,4-d]pyrimidin-8-yl)piperidine-4-carbonitrile | $^1$H NMR (500 MHz, MeOH-$d_4$): δ ppm 9.11 (s, 1H), 8.63 (d, J = 8.5 Hz, 1H), 7.09-7.07 (m, 2H), 7.04 (d, J = 0.5 Hz, 1H), 6.91 (s, 1H), 4.20-4.41 (m, 2H), 4.02 (s, 3H), 3.64 (s, 3H), 3.64-3.60 (m, 2H), 3.08 (m, 1H), 2.50 (s, 3H), 2.45 (s, 3H), 2.21-2.15 (m, 2H), 2.09-2.04 (m, 2H). HRMS (ESI) MS m/z calcd for $C_{26}H_{29}N_8O$ [M + H]$^+$ 470.2487, found 470.2468. Using piperidine-4-carbonitrile for 60 hours. PM B. | 0.003 |

| Example No | Name/Structure | Data | MPS1 IC50 (μM) |
|---|---|---|---|
| 35 | 1-(2-((4-(1,2-dimethyl-1H-imidazol-5-yl)-2-methoxyphenyl)amino)-6-methylpyrido[3,4-d]pyrimidin-8-yl)-3-methylazetidine-3-carbonitrile 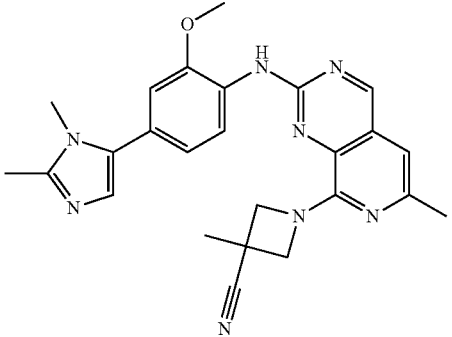 | $^1$H NMR (500 MHz, MeOH-d$_4$): δ ppm 9.06 (s, 1H), 8.24 (d, J = 8.5 Hz, 1H), 7.09 (dd, J = 8.5, 2.0 Hz, 1H), 7.08 (d, J = 2.0 Hz, 1H), 6.91 (s, 1H), 6.88 (s, 1H), 4.72 (d, J = 9.0 Hz, 2H), 4.35 (d, J = 9.0 Hz, 2H), 3.99 (s, 3H), 3.64 (s, 3H), 2.45 (br s, 6H), 1.72 (s, 3H). HRMS (ESI) MS m/z calcd for C$_{25}$H$_{28}$N$_8$O [M + 2H]/2$^+$ 228.6201, found 228.6192. Using 3-methylazetidine-3-carbonitrile hydrochloride for 60 hours. PM B. | 0.002 |
| 36 | N-(2-ethoxy-4-(4-methyl-4H-1,2,4-triazol-3-yl)phenyl)-6-methyl-8-(1-oxa-6-azaspiro[3.3]heptan-6-yl)pyrido[3,4-d]pyrimidin-2-amine 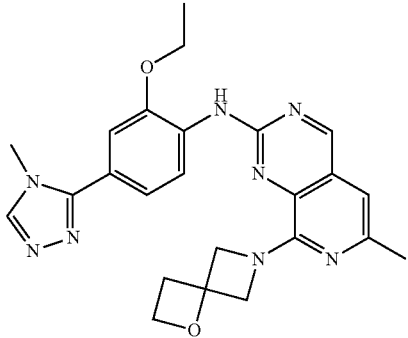 [SMILES: CCOc1cc(-c2nncn2C)ccc1Nc1ncc2cc(C)nc(N3CC4(CCO4)C3)c2n1] | $^1$H NMR (500 MHz, MeOH-d$_4$): δ ppm 9.07 (s, 1H), 8.57 (app t, J = 4.0 Hz, 2H), 7.44 (dd, J = 8.5, 2.0 Hz, 1H), 7.39 (d, J = 2.0 Hz, 1H), 6.83 (s, 1H), 4.71 (br d, J = 11.0 Hz, 2H), 4.60-4.57 (m, 4H), 4.29 (q, J = 7.0 Hz, 2H), 3.89 (s, 3H), 2.96 (t, J = 7.5 Hz, 2H), 2.45 (s, 3H), 1.55 (t, J = 7.0 Hz, 3H). HRMS (ESI) MS m/z calcd for C$_{24}$H$_{27}$N$_8$O$_2$ [M + H]$^+$ 459.2251, found 459.2226. Using 1-oxa-6-azaspiro[3.3]heptane oxalate. | 0.002 |
| 37 | 1-(2-((2-ethoxy-4-(4-methyl-4H-1,2,4-triazol-3-yl)phenyl)amino)-6-methylpyrido[3,4-d]pyrimidin-8-yl)-3-methylpyrrolidin-3-ol 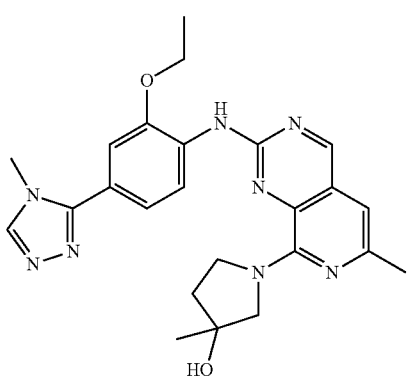 [SMILES: CCOc1cc(-c2nncn2C)ccc1Nc1ncc2cc(C)nc(N3CCC(C)(O)C3)c2n1] | $^1$H NMR (500 MHz, MeOH-d$_4$): δ ppm 9.02 (s, 1H), 8.55 (s, 1H), 8.53 (d, J = 8.0 Hz, 1H), 7.37 (d, J = 2.0 Hz, 1H), 7.35 (dd, J = 8.0, 2.0 Hz, 1H), 6.73 (s, 1H), 4.29 (q, J = 7.0 Hz, 2H), 4.19-4.13 (m, 2H), 4.09-4.00 (m, 2H), 3.87 (s, 3H), 2.44 (s, 3H), 2.06-1.97 (m, 2H), 1.54 (t, J = 7.0 Hz, 3H), 1.48 (s, 3H). HRMS (ESI) MS m/z calcd for C$_{24}$H$_{29}$N$_8$O$_2$ [M + H]$^+$ 461.2408, found 461.2393. Using 3-methylpyrrolidin-3-ol hydrochloride at 120° C. for 18 hours. PM C. | 0.003 |

| Example No | Name/Structure | Data | MPS1 IC50 (μM) |
|---|---|---|---|
| 38 | 1-(2-((2-ethoxy-4-(4-methyl-4H-1,2,4-triazol-3-yl)phenyl)amino)-6-methylpyrido[3,4-d]pyrimidin-8-yl)pyrrolidine-3-carbonitrile 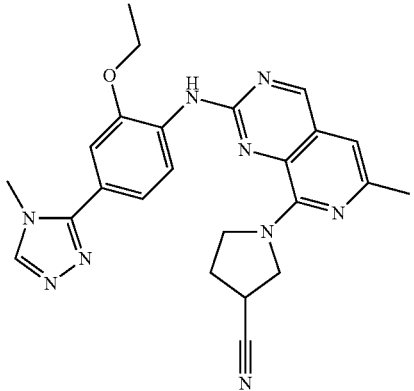 | $^1$H NMR (500 MHz, MeOH-d$_4$): δ ppm 9.07 (s, 1H), 8.55 (s, 1H), 8.46 (d, J = 8.0 Hz, 1H), 7.40 (d, J = 2.0 Hz, 1H), 7.39 (dd, J = 8.0, 2.0 Hz, 1H), 6.84 (s, 1H), 4.38 (d, J = 7.0 Hz, 2H), 4.29 (q, J = 7.0 Hz, 2H), 4.15 (m, 1H), 4.01 (m, 1H), 3.87 (s, 3H), 3.44 (m, 1H), 2.46 (s, 3H), 2.42 (m, 1H), 2.29 (m, 1H), 1.54 (t, J = 7.0 Hz, 3H). HRMS (ESI) MS m/z calcd for C$_{24}$H$_{27}$N$_9$O [M + 2H]/2$^+$ 228.6164, found 228.6162. Using pyrrolidine-3-carbonitrile hydrochloride for 60 hours. PM E. | 0.003 |
| 39 | N-(2-ethoxy-4-(4-methyl-4H-1,2,4-triazol-3-yl)phenyl)-8-(3-methoxypyrrolidin-1-yl)-6-methylpyrido[3,4-d]pyrimidin-2-amine 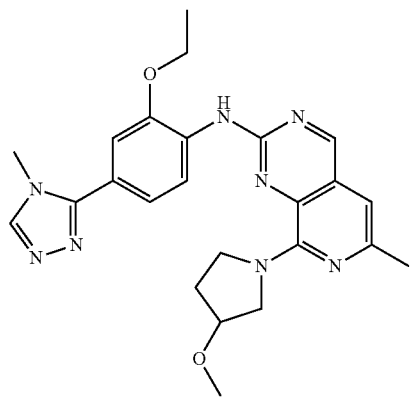 [SMILES: CCOc1cc(-c2nncn2C)ccc1Nc1ncc2cc(C)nc(N3CCC(OC)C3)c2n1] | $^1$H NMR (500 MHz, MeOH-d$_4$): δ ppm 9.04 (s, 1H), 8.55 (s, 1H), 8.50 (d, J = 8.5 Hz, 1H), 7.37 (d, J = 2.0 Hz, 1H), 7.36 (dd, J = 8.5, 2.0 Hz, 1H), 6.76 (s, 1H), 4.29 (d, J = 7.0 Hz, 2H), 4.14 (q, J = 7.0 Hz, 2H), 4.09-4.04 (m, 2H), 4.01 (m, 1H), 3.87 (s, 3H), 3.38 (s, 3H), 2.44 (s, 3H), 2.16 (m, 1H), 2.09 (m, 1H), 1.54 (t, J = 7.0 Hz, 3H). HRMS (ESI) MS m/z calcd for C$_{24}$H$_{29}$N$_8$O$_2$ [M + H]$^+$ 462.2436, found 462.2413. Using 3-methoxypyrrolidine hydrochloride. PM F. | 0.003 |

| Example No | Name/Structure | Data | MPS1 IC50 (µM) |
|---|---|---|---|
| 40 | N-(2-ethoxy-4-(4-methyl-4H-1,2,4-triazol-3-yl)phenyl)-6-methyl-8-(3-(trifluoromethyl)azetidin-1-yl)pyrido[3,4-d]pyrimidin-2-amine 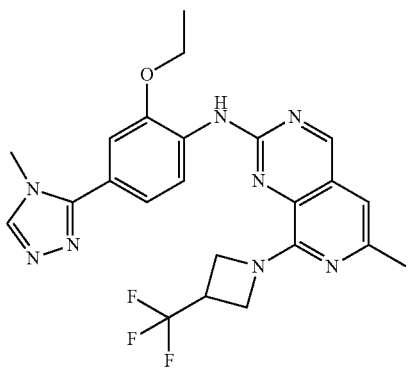 [SMILES: CCOc1cc(-c2nncn2C)ccc1Nc1ncc2cc(C)nc(N3CC(C(F)(F)F)C3)c2n1] | $^1$H NMR (500 MHz, MeOH-d$_4$): δ ppm 9.08 (s, 1H), 8.55 (s, 1H), 8.45 (d, J = 8.5 Hz, 1H), 7.37 (d, J = 2.0 Hz, 1H), 7.32 (dd, J = 8.5, 2.0 Hz, 1H), 6.85 (s, 1H), 4.66 (app t, J = 9.5 Hz, 2H), 4.50 (dd, J = 9.5, 5.5 Hz, 2H), 4.28 (d, J = 7.0 Hz, 2H), 3.85 (s, 3H), 3.59 (m, 1H), 2.46 (d, J = 0.5 Hz, 3H), 1.53 (t, J = 7.0 Hz, 3H). HRMS (ESI) MS m/z calcd for C$_{23}$H$_{24}$F$_3$N$_8$O [M + H]$^+$ 485.202, found 485.2022. Using 3-(trifluoromethyl)azetidine. PM A. | 0.005 |
| 41 | 1-(2-((2-ethoxy-4-(4-methyl-4H-1,2,4-triazol-3-yl)phenyl)amino)-6-methylpyrido[3,4-d]pyrimidin-8-yl)-3-ethylazetidin-3-ol 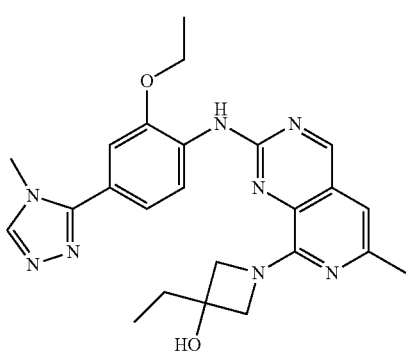 [SMILES: CCOc1cc(-c2nncn2C)ccc1Nc1ncc2cc(C)nc(N3CC(O)(CC)C3)c2n1] | $^1$H NMR (500 MHz, MeOH-d$_4$): δ ppm 9.04 (s, 1H), 8.55 (s, 1H), 8.54 (d, J = 8.5 Hz, 1H), 7.37 (d, J = 1.5 Hz, 1H), 7.34 (dd, J = 8.5, 1.5 Hz, 1H), 6.77 (s, 1H), 4.44 (br d, J = 9.5 Hz, 2H), 4.29 (br d, J = 9.5 Hz, 2H), 4.28 (d, J = 7.0 Hz, 2H), 3.86 (s, 3H), 2.44 (s, 3H), 1.86 (q, J = 7.5 Hz, 2H), 1.54 (t, J = 7.0 Hz, 3H), 1.04 (t, J = 7.5 Hz, 3H). HRMS (ESI) MS m/z calcd for C$_{24}$H$_{30}$N$_8$O$_2$ [M + 2H]/2$^+$ 231.6254, found 231.6243. Using 3-ethyl-3-hydroxy azetidine. PM A. | 0.004 |
| 42 | 8-(2,2-dimethylazetidin-1-yl)-N-(2-ethoxy-4-(4-methyl-4H-1,2,4-triazol-3-yl)phenyl)-6-methylpyrido[3,4-d]pyrimidin-2-amine 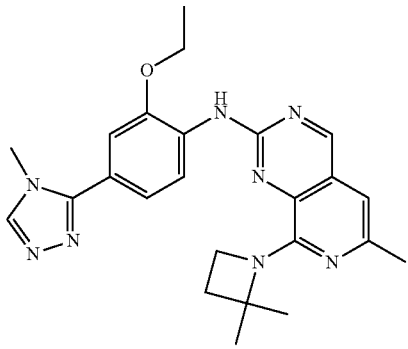 [SMILES: CCOc1cc(-c2nncn2C)ccc1Nc1ncc2cc(C)nc(N3CCC3(C)C)c2n1] | $^1$H NMR (500 MHz, MeOH-d$_4$): δ ppm 8.98 (s, 1H), 8.54 (s, 1H), 8.52 (d, J = 8.0 Hz, 1H), 7.35 (d, J = 2.0 Hz, 1H), 7.33 (dd, J = 8.0, 2.0 Hz, 1H), 6.65 (s, 1H), 4.70-4.66 (m, 2H), 4.27 (d, J = 7.0 Hz, 2H), 3.85 (s, 3H), 2.39 (s, 3H), 2.22 (dd, J = 9.0, 7.5 Hz, 2H), 1.71 (s, 6H), 1.54 (t, J = 7.0 Hz, 3H). HRMS (ESI) MS m/z calcd for C$_{24}$H$_{29}$N$_8$O [M + H]$^+$ 445.2459, found 445.2461. Using 2,2-dimethylazetidine. PM F. | 0.010 |

| Example No | Name/Structure | Data | MPS1 IC50 (μM) |
|---|---|---|---|
| 43 | 1-(2-((2-ethoxy-4-(4-methyl-4H-1,2,4-triazol-3-yl)phenyl)amino)-6-methylpyrido[3,4-d]pyrimidin-8-yl)-3-methylpyrrolidine-3-carbonitrile 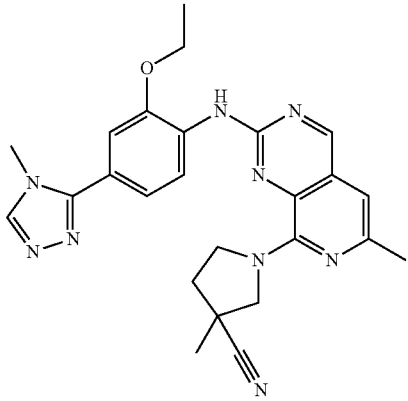 [SMILES: CCOc1cc(-c2nncn2C)ccc1Nc1ncc2cc(C)nc(N3CCC(C)(C#N)C3)c2n1] | $^1$H NMR (500 MHz, MeOH-d$_4$): δ ppm 9.07 (s, 1H), 8.55 (s, 1H), 8.45 (d, J = 8.0 Hz, 1H), 7.39 (d, J = 2.0 Hz, 1H), 7.37 (dd, J = 8.0, 2.0 Hz, 1H), 6.84 (s, 1H), 4.61 (d, J = 12.0 Hz, 1H), 4.28 (d, J = 7.0 Hz, 2H), 4.18 (m, 1H), 4.11 (m, 1H), 4.01 (d, J = 12.0 Hz, 1H), 3.87 (s, 3H), 2.45 (s, 3H), 2.47 (m, 1H), 2.12 (m, 1H), 1.56 (s, 3H), 1.54 (t, J = 7.0 Hz, 3H). HRMS (ESI) MS m/z calcd for C$_{25}$H$_{29}$N$_9$O [M + 2H]/2$^+$ 235.6242, found 235.6243. Using 3-cyano-3-methyl pyrrolidine hydrochloride. PM F. | 0.003 |
| 44 | N-(2-ethoxy-4-(4-methyl-4H-1,2,4-triazol-3-yl)phenyl)-6-methyl-8-(2-azaspiro[3.4]octan-2-yl)pyrido[3,4-d]pyrimidin-2-amine 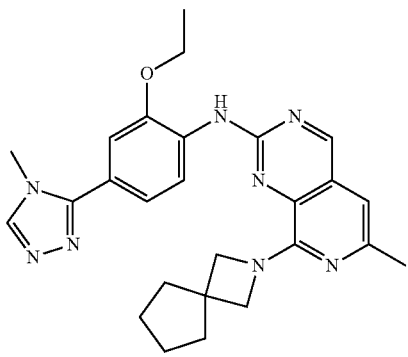 | $^1$H NMR (500 MHz, MeOH-d$_4$): δ ppm 9.04 (s, 1H), 8.56 (d, J = 8.0 Hz, 1H), 8.55 (s, 1H), 7.37 (d, J = 2.0 Hz, 1H), 7.32 (dd, J = 8.5, 2.0 Hz, 1H), 6.76 (s, 1H), 4.35 (br s, 4H), 4.28 (d, J = 7.0 Hz, 2H), 3.86 (s, 3H), 2.44 (s, 3H), 1.92-1.89 (m, 4H), 1.71-1.68 (m, 4H), 1.54 (t, J = 7.0 Hz, 3H). HRMS (ESI) MS m/z calcd for C$_{26}$H$_{32}$N$_8$O [M + 2H]/2$^+$ 235.1344, found 235.1336. Using 2-azaspiro[3.4]octane. PM F. | 0.002 |
| 45 | 8-(3,3-difluoroazetidin-1-yl)-N-(2-ethoxy-4-(4-methyl-4H-1,2,4-triazol-3-yl)phenyl)-6-methylpyrido[3,4-d]pyrimidin-2-amine 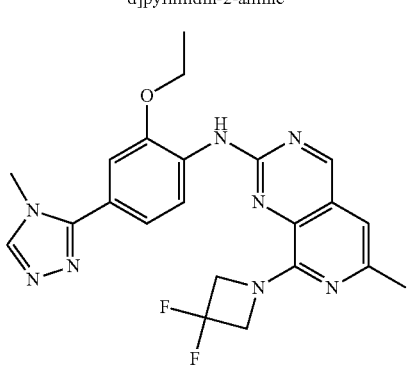 | $^1$H NMR (500 MHz, MeOH-d$_4$): δ ppm 9.24 (s, 1H), 8.62 (s, 1H), 8.57 (s, 1H), 8.15 (d, J = 8.8 Hz, 1H), 7.44-7.33 (m, 2H), 7.02 (m, 1H), 4.68 (t, J = 12.6 Hz, 4H), 4.25-4.15 (m, 2H), 3.79 (s, 3H), 2.43 (s, 3H), 1.39 (t, J = 7.0 Hz, 3H). HRMS (ESI) MS m/z calcd for C$_{22}$H$_{24}$F$_2$N$_8$O [M + 2H]/2$^+$ 227.1015, found 227.1021. Using 3,3-difluoroazetidine hydrochloride at 130° C. PM F. | 0.006 |

| Example No | Name/Structure | Data | MPS1 IC50 (μM) |
|---|---|---|---|
| 46 | N-(2-ethoxy-4-(4-methyl-4H-1,2,4-triazol-3-yl)phenyl)-8-(4-methoxypiperidin-1-yl)-6-methylpyrido[3,4-d]pyrimidin-2-amine 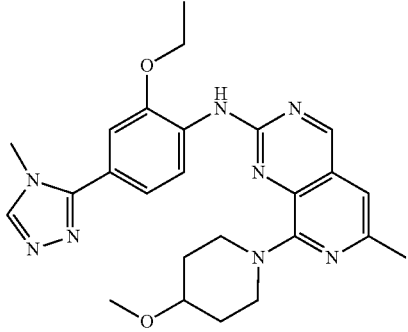 [SMILES: CCOc1cc(-c2nncn2C)ccc1Nc1ncc2cc(C)nc(N3CCC(OC)CC3)c2n1] | $^1$H NMR (500 MHz, DMSO-d$_6$): δ ppm 9.24 (d, J = 1.5 Hz, 1H), 8.62-8.49 (m, 2H), 8.45 (s, 1H), 7.41 (s, 1H), 7.36 (d, J = 8.5 Hz, 1H), 7.05 (s, 1H), 4.37-4.10 (m, 4H), 3.79 (s, 3H), 3.45 (m, 1H), 3.34 (s, 2H), 3.30 (s, 3H), 2.43 (s, 3H), 2.10-1.97 (m, 2H), 1.70-1.57 (m, 2H), 1.43 (t, J = 6.9 Hz, 3H).<br>HRMS (ESI) MS m/z calcd for C$_{25}$H$_{31}$N$_8$O$_2$ [M + H]$^+$ 475.2564, found 475.2540.<br>Using 4-methoxypiperidine hydrochloride at 130° C.<br>PM F. | 0.003 |
| 47 | Racemic-N-(2-ethoxy-4-(4-methyl-4H-1,2,4-triazol-3-yl)phenyl)-8-(3-methoxypiperidin-1-yl)-6-methylpyrido[3,4-d]pyrimidin-2-amine 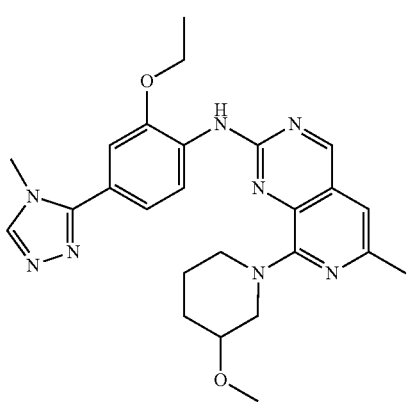 [SMILES: CCOc1cc(-c2nncn2C)ccc1Nc1ncc2cc(C)nc(N3CCCC(OC)C3)c2n1] | $^1$H NMR (500 MHz, DMSO-d$_6$): δ ppm 9.24 (s, 1H), 8.60-8.51 (m, 2H), 8.43 (s, 1H), 7.44-7.34 (m, 2H), 7.04 (d, J = 1.0 Hz, 1H), 4.43 (d, J = 10.9 Hz, 1H), 4.30 (d, J = 13.1 Hz, 1H), 4.24 (q, J = 6.9 Hz, 2H), 3.79 (s, 3H), 3.45 (m, 1H), 3.28 (m, 1H), 3.22 (s, 3H), 3.14 (dd, J = 12.4, 8.5 Hz, 1H), 2.43 (s, 3H), 2.09 (m, 1H), 1.87 (m, 1H), 1.66 (m, 1H), 1.50-1.35 (m, 4H).<br>HRMS (ESI) MS m/z calcd for C$_{25}$H$_{31}$N$_8$O$_2$ [M + H]$^+$ 475.2564, found 475.2547.<br>Using racemic-3-methoxpiperidine hydrochloride at 130° C.<br>PM F. | 0.006 |
| 48 | Racemic-N-(2-ethoxy-4-(4-methyl-4H-1,2,4-triazol-3-yl)phenyl)-6-methyl-8-(2-methylmorpholino)pyrido[3,4-d]pyrimidin-2-amine 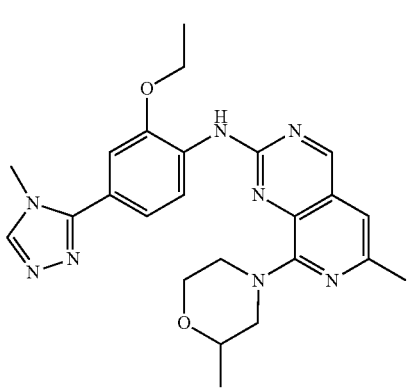 [SMILES: CCOc1cc(-c2nncn2C)ccc1Nc1ncc2cc(C)nc(N3CCOC(C)C3)c2n1] | $^1$H NMR (500 MHz, DMSO-d$_6$): δ ppm 9.26 (s, 1H), 8.57 (s, 1H), 8.49 (s, 1H), 8.47 (d, J = 8.3 Hz, 1H), 7.42 (d, J = 1.9 Hz, 1H), 7.37 (dd, J = 8.3, 1.8 Hz, 1H), 7.09 (s, 1H), 4.60 (d, J = 12.5 Hz, 1H), 4.50 (d, J = 12.9 Hz, 1H), 4.24 (q, J = 7.0 Hz, 2H), 3.95 (d, J = 13.0 Hz, 1H), 3.87-3.71 (m, 5H), 2.95 (td, J = 12.2, 3.1 Hz, 1H), 2.62 (dd, J = 12.6, 10.2 Hz, 1H), 2.44 (s, 3H), 1.42 (t, J = 6.9 Hz, 3H), 1.13 (d, J = 6.2 Hz, 3H).<br>HRMS (ESI) MS m/z calcd for C$_{24}$H$_{29}$N$_8$O$_2$ [M + H]$^+$ 461.2408, found 461.2390.<br>Using racemic-2-methylmorpholine hydrochloride at 130° C.<br>PM B. | 0.003 |

| Example No | Name/Structure | Data | MPS1 IC50 (μM) |
|---|---|---|---|
| 49 | N-(2-ethoxy-4-(4-methyl-4H-1,2,4-triazol-3-yl)phenyl)-8-(4-methoxy-4-methylpiperidin-1-yl)-6-methylpyrido[3,4-d]pyrimidin-2-amine 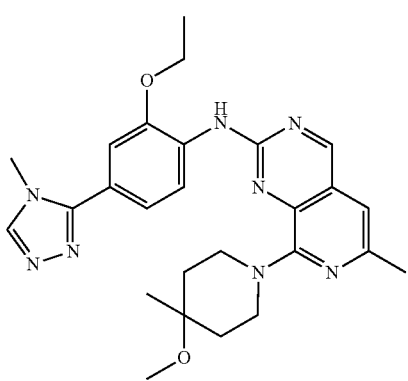 [SMILES: CCOc1cc(-c2nncn2C)ccc1Nc1ncc2cc(C)nc(N3CCC(C)(OC)CC3)c2n1] | $^1$H NMR (500 MHz, DMSO-d$_6$): δ ppm 9.23 (d, J = 3.1 Hz, 1H), 8.62-8.51 (m, 2H), 8.43 (d, J = 3.7 Hz, 1H), 7.40 (s, 1H), 7.36 (d, J = 8.2 Hz, 1H), 7.03 (s, 1H), 4.24 (q, J = 6.9 Hz, 2H), 4.17 (d, J = 12.3 Hz, 2H), 3.79 (s, 3H), 3.44-3.36 (m, 2H), 3.16 (s, 3H), 2.43 (s, 3H), 1.85 (d, J = 13.6 Hz, 2H), 1.76-1.65 (m, 2H), 1.43 (t, J = 6.9 Hz, 3H), 1.19 (s, 3H). HRMS (ESI) MS m/z calcd for C$_{26}$H$_{34}$N$_8$O$_2$ [M + 2H]/2$^+$ 245.1397, found 245.1397. Using 4-methoxy-4-methylpiperidine at 130° C. PM F. | 0.003 |
| 50 | 8-(3-azabicyclo[3.1.0]hexan-3-yl)-N-(2-ethoxy-4-(4-methyl-4H-1,2,4-triazol-3-yl)phenyl)-6-methylpyrido[3,4-d]pyrimidin-2-amine 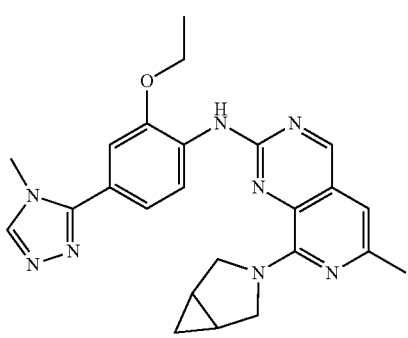 [SMILES: CCOc1cc(-c2nncn2C)ccc1Nc1ncc2cc(C)nc(N3CC4CC4C3)c2n1] | $^1$H NMR (500 MHz, DMSO-d$_6$): δ ppm 9.13 (d, J = 1.0 Hz, 1H), 8.57 (s, 1H), 8.44 (s, 1H), 8.15 (d, J = 8.2 Hz, 1H), 7.39 (s, 1H), 7.37 (dd, J = 8.1, 1.8 Hz, 1H), 6.80 (s, 1H), 4.41 (d, J = 11.6 Hz, 2H), 4.21 (q, J = 6.9 Hz, 2H), 3.80 (s, 3H), 3.69 (d, J = 11.4 Hz, 2H), 2.36 (s, 3H), 1.68-1.60 (m, 2H), 1.39 (t, J = 6.9 Hz, 3H), 0.68 (td, J = 7.6, 4.3 Hz, 1H), 0.19 (q, J = 4.1 Hz, 1H). HRMS (ESI) MS m/z calcd for C$_{24}$H$_{27}$N$_8$O [M + H]$^+$ 443.2302, found 443.2281. Using 3-azabicyclo[3.1.0]hexane hydrochloride at 130° C. PM F. | 0.002 |
| 51 | 8-(3-(dimethylamino)azetidin-1-yl)-N-(2-ethoxy-4-(4-methyl-4H-1,2,4-triazol-3-yl)phenyl)-6-methylpyrido[3,4-d]pyrimidin-2-amine 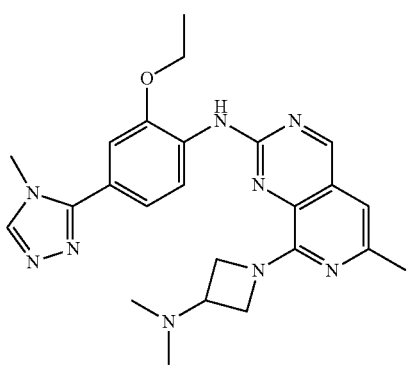 [SMILES: CCOc1cc(-c2nncn2C)ccc1Nc1ncc2cc(C)nc(N3CC(N(C)C)C3)c2n1] | $^1$H NMR (500 MHz, DMSO-d$_6$): δ ppm 9.16 (d, J = 1.2 Hz, 1H), 8.56 (s, 1H), 8.43 (s, 1H), 8.27 (d, J = 8.2 Hz, 1H), 7.39 (d, J = 1.9 Hz, 1H), 7.35 (dd, J = 8.3, 1.8 Hz, 1H), 6.82 (s, 1H), 4.38 (br s, 2H), 4.21 (q, J = 7.0 Hz, 2H), 4.12 (br s, 2H), 3.78 (s, 3H), 3.15 (br s, 1H), 2.37 (s, 3H), 2.12 (s, 6H), 1.40 (t, J = 6.9 Hz, 3H). HRMS (ESI) MS m/z calcd for C$_{24}$H$_{30}$N$_9$O [M + H]$^+$ 460.2568, found 460.2545. Using N,N-dimethylazetidin-3-amine dihydrochloride at 130° C. PM F. | 0.006 |

| Example No | Name/Structure | Data | MPS1 IC50 (μM) |
|---|---|---|---|
| 52 | 1-(2-(2-ethoxy-4-(4-methyl-4H-1,2,4-triazol-3-yl)phenylamino)-6-methylpyrido[3,4-d]pyrimidin-8-yl)piperidin-4-ol 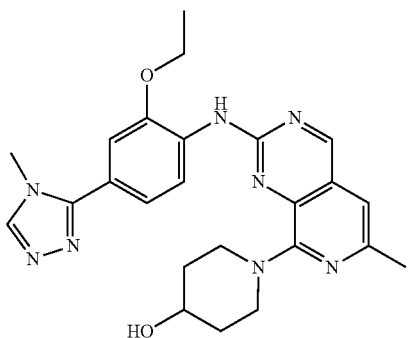 [SMILES: CCOc1cc(-c2nncn2C)ccc1Nc1ncc2cc(C)nc(N3CCC(O)CC3)c2n1] | $^1$H NMR (500 MHz, DMSO-d$_6$): δ ppm 9.24 (s, 1H), 8.61 (d, J = 8.4 Hz, 1H), 8.57 (s, 1H), 8.42 (s, 1H), 7.40 (s, 1H), 7.37 (dd, J = 8.4, 1.9 Hz, 1H), 7.03 (s, 1H), 4.74 (d, J = 4.4 Hz, 1H), 4.37 (d, J = 12.1 Hz, 2H), 4.24 (q, J = 6.9 Hz, 2H), 3.79 (s, 3H), 3.71 (m, 1H), 3.26-3.14 (m, 2H), 2.42 (s, 3H), 1.97-1.88 (m, 2H), 1.68-1.55 (m, 2H), 1.43 (t, J = 6.9 Hz, 3H). HRMS (ESI) MS m/z calcd for C$_{24}$H$_{29}$N$_8$O$_2$ [M + H]$^+$ 461.2408, found 461.2390. Using piperidin-4-ol hydrochloride at 130° C. PM F. | 0.002 |
| 53 | (R)-N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine 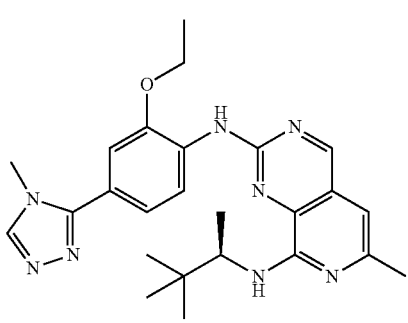 [SMILES: CCOc1cc(-c2nncn2C)ccc1Nc1ncc2cc(C)nc(N[C@H](C)C(C)(C)C)c2n1] | $^1$H NMR (500 MHz, DMSO-d$_6$): δ ppm 9.15 (s, 1H), 8.57 (s, 1H), 8.43 (d, J = 8.3 Hz, 1H), 7.41 (d, J = 1.9 Hz, 1H), 7.31 (dd, J = 8.2, 1.9 Hz, 1H), 6.72 (d, J = 1.0 Hz, 1H), 6.43 (d, J = 9.5 Hz, 1H), 4.23 (q, J = 6.9 Hz, 2H), 4.13 (dq, J = 9.4, 6.6 Hz, 1H), 3.78 (s, 3H), 2.38 (s, 3H), 1.41 (t, J = 6.9 Hz, 3H), 1.16 (d, J = 6.6 Hz, 3H), 1.00 (s, 9H). HRMS (ESI) MS m/z calcd for C$_{25}$H$_{33}$N$_8$O [M + H]$^+$ 461.2777, found 461.2772. Using (R)-3,3-dimethylbutan-2-amine at 130° C. for 48 hours. PM F. | 0.005 |
| 54 | (S)-N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine 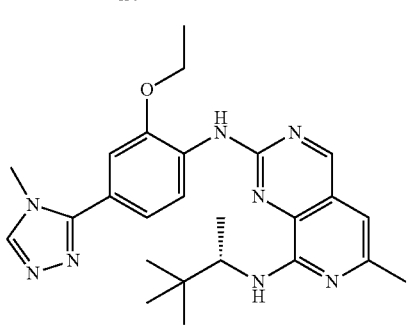 [SMILES: CCOc1cc(-c2nncn2C)ccc1Nc1ncc2cc(C)nc(N[C@@H](C)C(C)(C)C)c2n1] | $^1$H NMR (500 MHz, DMSO-d$_6$): δ ppm 9.15 (s, 1H), 8.57 (s, 1H), 8.43 (d, J = 8.3 Hz, 1H), 7.41 (d, J = 1.9 Hz, 1H), 7.31 (dd, J = 8.2, 1.9 Hz, 1H), 6.72 (d, J = 1.0 Hz, 1H), 6.43 (d, J = 9.5 Hz, 1H), 4.23 (q, J = 6.9 Hz, 2H), 4.13 (dq, J = 9.4, 6.6 Hz, 1H), 3.78 (s, 3H), 2.38 (s, 3H), 1.41 (t, J = 6.9 Hz, 3H), 1.16 (d, J = 6.6 Hz, 3H), 1.00 (s, 9H). HRMS (ESI) MS m/z calcd for C$_{25}$H$_{33}$N$_8$O [M + H]$^+$ 461.2777, found 461.2777. Using (S)-3,3-dimethylbutan-2-amine at 130° C. for 48 hours. PM F. | 0.004 |

| Example No | Name/Structure | Data | MPS1 IC50 (μM) |
|---|---|---|---|
| 55 | N-(2-ethoxy-4-(4-methyl-4H-1,2,4-triazol-3-yl)phenyl)-6-methyl-8-(2-azaspiro[3.3]heptan-2-yl)pyrido[3,4-d]pyrimidin-2-amine 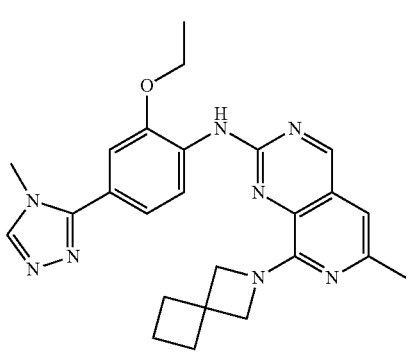 [SMILES: CCOc1cc(-c2nncn2C)ccc1Nc1ncc2cc(C)nc(N3CC4(CCC4)C3)c2n1] | $^1$H NMR (500 MHz, DMSO-d$_6$): δ ppm 9.15 (s, 1H), 8.58 (s, 1H), 8.39 (s, 1H), 8.32 (d, J = 8.1 Hz, 1H), 7.44-7.33 (m, 2H), 6.80 (s, 1H), 4.31 (br s, 4H), 4.22 (q, J = 6.9 Hz, 2H), 3.80 (s, 3H), 2.37 (s, 3H), 2.19 (t, J = 7.6 Hz, 4H), 1.88-1.73 (m, 2H), 1.42 (t, J = 6.9 Hz, 3H). HRMS (ESI) MS m/z calcd for C$_{25}$H$_{29}$N$_8$O [M + H]$^+$ 457.2464, found 457.2473. Using 2-azaspiro[3.3]heptane hydrochloride at 130° C. PM F. | 0.004 |
| 56 | N-(2-ethoxy-4-(4-methyl-4H-1,2,4-triazol-3-yl)phenyl)-6-methyl-8-(pyrrolidin-1-yl)pyrido[3,4-d]pyrimidin-2-amine 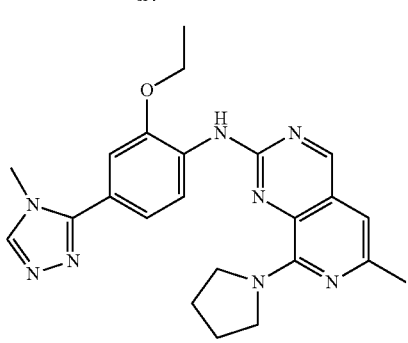 | $^1$H NMR (500 MHz, DMSO-d$_6$): δ ppm 9.13 (s, 1H), 8.56 (s, 1H), 8.34 (s, 1H), 8.23 (d, J = 8.2 Hz, 1H), 7.39-7.29 (m, 2H), 6.76 (d, J = 0.8 Hz, 1H), 4.21 (q, J = 6.9 Hz, 2H), 3.88 (s, 4H), 3.78 (s, 3H), 2.37 (s, 3H), 1.94-1.83 (m, 4H), 1.41 (t, J = 6.9 Hz, 3H). HRMS (ESI) MS m/z calcd for C$_{23}$H$_{27}$N$_8$O [M + H]$^+$ 431.2308, found 431.2315. Using pyrrolidine at 130° C. for 24 hours. PM F. | 0.006 |
| 57 | N2-(2-ethoxy-4-(4-methyl-4H-1,2,4-triazol-3-yl)phenyl)-6-methyl-N8-(oxetan-3-ylmethyl)pyrido[3,4-d]pyrimidine-2,8-diamine 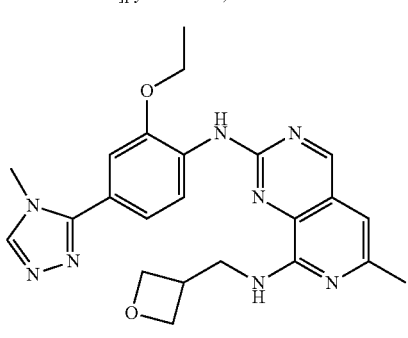 | $^1$H NMR (500 MHz, DMSO-d$_6$): δ ppm 9.15 (s, 1H), 8.56 (s, 1H), 8.36 (s, 1H), 8.32 (d, J = 8.1 Hz, 1H), 7.45-7.29 (m, 2H), 6.79 (s, 1H), 4.77 (t, J = 5.3 Hz, 1H), 4.38 (br s, 2H), 4.22 (q, J = 6.9 Hz, 2H), 4.11 (br s, 2H), 3.78 (s, 3H), 3.59 (t, J = 5.9 Hz, 2H), 2.81 (m, 1H), 2.37 (s, 3H), 1.42 (t, J = 6.9 Hz, 3H). HRMS (ESI) MS m/z calcd for C$_{23}$H$_{27}$N$_8$O$_2$ [M + H]$^+$ 447.2257, found 447.2260. Using oxetan-3-ylmethanamine at 130° C. for 24 hours. PM F. | 0.003 |

| Example No | Name/Structure | Data | MPS1 IC50 (μM) |
|---|---|---|---|
| 58 | N2-(2-ethoxy-4-(4-methyl-4H-1,2,4-triazol-3-yl)phenyl)-6-methyl-N8-(1-methylazetidin-3-yl)pyrido[3,4-d]pyrimidine-2,8-diamine 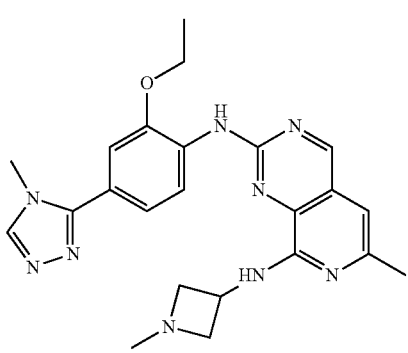 [SMILES: CCOc1cc(-c2nncn2C)ccc1Nc1ncc2cc(C)nc(NC3CN(C)C3)c2n1] | $^1$H NMR (500 MHz, MeOH-d$_4$): δ ppm 8.93 (m, 1H), 8.84 (d, J = 7.0 Hz, 1H), 8.55 (s, 1H), 7.37-7.34 (m, 2H), 6.17 (s, 1H), 4.29 (q, J = 7.0 Hz, 2H), 4.13 (m, 1H), 3.86 (d, J = 2.0 Hz, 3H), 2.91-2.79 (m, 4H), 2.44 (d, J = 1.0 Hz, 3H), 2.34 (s, 3H), 1.55 (t, J = 7.0 Hz, 3H). HRMS (ESI) MS m/z calcd for $C_{23}H_{28}N_9O$ [M + H]$^+$ 446.2417, found 446.2421. Using 1-methylazetidin-3-amine. PM D. | 0.518 |
| 59 | N2-(2-ethoxy-4-(4-methyl-4H-1,2,4-triazol-3-yl)phenyl)-N8-((1-methoxycyclobutyl)methyl)-6-methylpyrido[3,4-d]pyrimidine-2,8-diamine 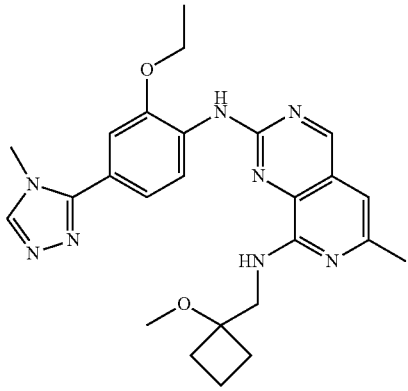 [SMILES: CCOc1cc(-c2nncn2C)ccc1Nc1ncc2cc(C)nc(NCC3(OC)CCC3)c2n1] | $^1$H NMR (500 MHz, MeOH-d$_4$): δ ppm 9.04 (s, 1H), 8.72 (d, J = 8.5 Hz, 1H), 8.55 (s, 1H), 7.38 (d, J = 2.0 Hz, 1H), 7.34 (dd, J = 8.5, 2.0 Hz, 1H), 6.74 (s, 1H), 4.30 (d, J = 7.0 Hz, 2H), 3.87 (s, 3H), 3.86 (s, 2H), 3.34 (s, 3H), 2.46 (s, 3H), 2.30-2.23 (m, 2H), 2.06-2.01 (m, 2H), 1.84 (m, 1H), 1.77 (m, 1H), 1.56 (t, J = 7.0 Hz, 3H). HRMS (ESI) MS m/z calcd for $C_{25}H_{31}N_8O_2$ [M + H]$^+$ 475.2570, found 475.2571. Using (1-methoxycyclobutyl)methanamine hydrochloride at 120° C. for 4 days. PM E. | 0.004 |
| 60 | N-(2-ethoxy-4-(4-methyl-4H-1,2,4-triazol-3-yl)phenyl)-8-(3-ethyl-3-methoxyazetidin-1-yl)-6-methylpyrido[3,4-d]pyrimidin-2-amine 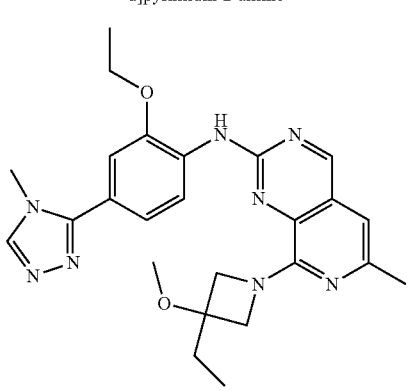 | $^1$H NMR (500 MHz, DMSO-d$_6$): δ ppm 9.15 (s, 1H), 8.55 (s, 1H), 8.43 (s, 1H), 8.25 (d, J = 8.3 Hz, 1H), 7.38 (d, J = 1.8 Hz, 1H), 7.32 (dd, J = 8.3, 1.8 Hz, 1H), 6.82 (d, J = 1.0 Hz, 1H), 4.27-4.03 (m, 6H), 3.77 (s, 3H), 3.16 (s, 3H), 2.37 (s, 3H), 1.82 (q, J = 7.3 Hz, 2H), 1.39 (t, J = 6.9 Hz, 3H), 0.83 (t, J = 7.2 Hz, 3H). HRMS (ESI) MS m/z calcd for $C_{25}H_{31}N_8O_2$ [M + H]$^+$ 475.2570, found 475.2567. Using 3-ethyl-3-methoxyazetidine hydrochloride (Preparation 66) at 130° C. for 18 hours. PM G. | 0.003 |

| Example No | Name/Structure | Data | MPS1 IC50 (μM) |
|---|---|---|---|
| 61 | 8-(3-ethoxy-3-methylazetidin-1-yl)-N-(2-ethoxy-4-(4-methyl-4H-1,2,4-triazol-3-yl)phenyl)-6-methylpyrido[3,4-d]pyrimidin-2-amine 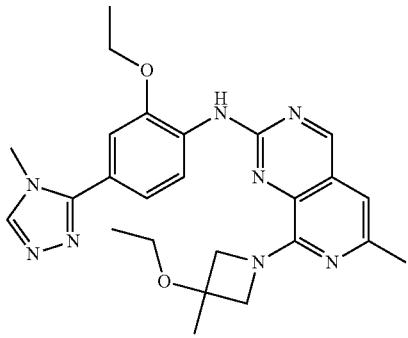 [SMILES: CCOc1cc(-c2nncn2C)ccc1Nc1ncc2cc(C)nc(N3CC(C)(OCC)C3)c2n1] | $^1$H NMR (500 MHz, DMSO-d$_6$): δ ppm 9.15 (s, 1H), 8.56 (s, 1H), 8.44 (s, 1H), 8.23 (d, J = 8.3 Hz, 1H), 7.38 (d, J = 1.8 Hz, 1H), 7.34 (dd, J = 8.3, 1.8 Hz, 1H), 6.82 (s, 1H), 4.34-4.09 (m, 6H), 3.78 (s, 3H), 3.43 (q, J = 7.0 Hz, 2H), 2.37 (s, 3H), 1.47 (s, 3H), 1.39 (t, J = 6.9 Hz, 3H), 1.11 (t, J = 7.0 Hz, 3H). HRMS (ESI) MS m/z calcd for C$_{25}$H$_{31}$N$_8$O$_2$ [M + H]$^+$ 475.2570, found 475.2575. Using 3-ethoxy-3-methylazetidine hydrochloride (Preparation 67) at 130° C. for 18 hours. PM F. | 0.004 |
| 62 | N-(2-(difluoromethoxy)-4-(4-methyl-4H-1,2,4-triazol-3-yl)phenyl)-8-(3,3-dimethylazetidin-1-yl)-6-methylpyrido[3,4-d]pyrimidin-2-amine 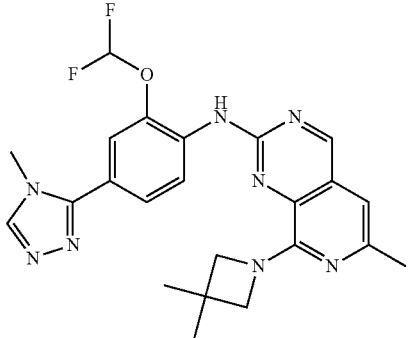 [SMILES: Cc1cc2cnc(Nc3ccc(-c4nncn4C)cc3OC(F)F)nc2c(N2CC(C)(C)C2)n1] | $^1$H NMR (500 MHz, CDCl$_3$): δ ppm 8.98 (s, 1H), 8.77 (d, J = 8.5 Hz, 1H), 8.24 (s, 1H), 7.74 (s, 1H), 7.64-7.55 (m, 2H), 6.71 (t, J = 72.9 Hz, 1H), 6.67 (s, 1H), 4.24 (s, 4H), 3.84 (s, 3H), 2.50 (s, 3H), 1.39 (s, 6H). HRMS (ESI) MS m/z calcd for C$_{23}$H$_{25}$F$_2$N$_8$O [M + H]$^+$ 467.2119, found 467.2117. Using 3,3-dimethylazetidine hydrochloride at 130° C. for 60 hours. PM G. | 0.016 |

Preparation 1

8-chloro-N-(2-ethoxy-4-(4-methyl-4H-1,2,4-triazol-3-yl)phenyl)-6-methylpyrido[3,4-d]pyrimidin-2-amine

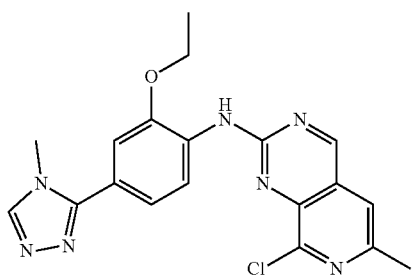 [SMILES: CCOc1cc(-c2nncn2C)ccc1Nc1ncc2cc(C)nc(Cl)c2n1]

To a solution of N-(2-ethoxy-4-(4-methyl-4H-1,2,4-triazol-3-yl)phenyl)formamide (Preparation 32, 1.88 g, 7.63 mmol) in THF (70 mL) was added sodium hydride (60% w/w, 500 mg, 12.50 mmol) at 0° C. The reaction was stirred at room temperature for 30 minutes before cooling to 0° C. 8-chloro-6-methyl-2-(methylsulfonyl)pyrido[3,4-d]pyrimidine (Preparation 24, 2.50 g, 9.70 mmol) was added and the reaction was stirred whilst warming to room temperature for 18 hours. A solution of aqueous 2M NaOH and MeOH were added (25 mL each) and the resulting mixture stirred at room temperature for 1 hour before concentrating in vacuo. The residue was partitioned between DCM and water. The aqueous layer was extracted with DCM and the combined organic layers were dried (MgSO$_4$) and concentrated in vacuo. The residue was purified by silica gel column chromatography eluting with 0-6% MeOH in DCM to afford the title compound (3.24 g, quant).

$^1$H NMR (500 MHz, DMSO-d$_6$): δ ppm 9.46 (s, 1H), 8.85 (d, J=8.3 Hz, 1H), 8.79 (s, 1H), 8.56 (s, 1H), 7.74 (d, J=1.0 Hz, 1H), 7.49-7.36 (m, 2H), 4.25 (q, J=7.0 Hz, 2H), 3.80 (s, 3H), 2.58 (s, 3H), 1.43 (t, J=6.9 Hz, 3H).

HRMS (ESI) MS m/z calcd for C$_{19}$H$_{19}$ClN$_7$O [M+H]$^+$ 396.1339, found 396.1335.

Preparation 2

8-chloro-N-(4-(1,2-dimethyl-1H-imidazol-5-yl)-2-methoxyphenyl)-6-methylpyrido[3,4-d]pyrimidin-2-amine

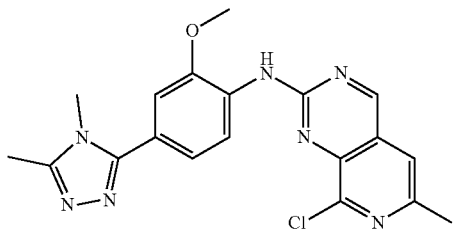

To a solution of N-(4-(1,2-dimethyl-1H-imidazol-5-yl)-2-methoxyphenyl)formamide (Preparation 37, 280 mg, 1.087 mmol) in THF (10 mL) was added sodium hydride (71 mg, 1.782 mmol) at 0° C. and the reaction was stirred at room temperature for 30 minutes before cooling to 0° C. 8-chloro-6-methyl-2-(methysulfonyl)pyrido[3,4-d]pyrimidine (Preparation 24, 333 mg, 1.087 mmol) was added and the reaction was stirred at room temperature for 18 hours. Aqueous NaOH (2M) and MeOH were added (25 mL each) and the resulting mixture stirred at room temperature for 1 hour before concentrating in vacuo. The residue was partitioned between DCM and water. The aqueous layer was extracted with DCM and the combined organic layers were dried (MgSO$_4$) and concentrated in vacuo. The residue was purified by reverse phase column chromatography eluting with water and MeOH to afford the title compound (230 mg, 54%).

$^1$H NMR (500 MHz, MeOH-d$_4$): δ ppm 9.29 (s, 1H), 9.09 (d, J=8.0 Hz, 1H), 7.62 (d, J=0.5 Hz, 1H), 7.12 (dd, J=8.0, 2.0 Hz, 1H), 7.09 (d, J=2.0 Hz, 1H), 6.91 (s, 1H), 4.04 (s, 3H), 3.64 (s, 3H), 2.63 (s, 3H), 2.45 (s, 3H).

HRMS (ESI) MS m/z calcd for C$_{20}$H$_{20}$N$_6$ClO [M+H]$^+$ 396.141, found 396.1389.

Preparation 3

8-chloro-N-(2-(difluoromethoxy)-4-(4-methyl-4H-1,2,4-triazol-3-yl)phenyl)-6-methylpyrido[3,4-d]pyrimidin-2-amine

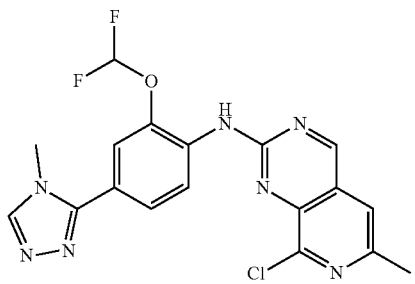 [SMILES: Cc1cc2cnc(Nc3ccc(-c4nncn4C)cc3OC(F)F)nc2c(Cl)n1]

A solution of N-(2-(difluoromethoxy)-4-(4-methyl-4H-1,2,4-triazol-3-yl)phenyl)formamide (Preparation 38, 102 mg, 0.380 mmol) in THF (3.5 mL) was treated with sodium hydride (60% w/w, 25 mg, 0.625 mmol) at 0° C. The reaction was stirred at room temperature for 30 min before cooling to 0° C. 8-chloro-6-methyl-2-(methylsulfonyl)pyrido[3,4-d]pyrimidine (Preparation 24, 122 mg, 0.473 mmol) was added and the reaction stirred at room temperature for 18 hours. Aqueous NaOH (2M, 0.5 mL) and MeOH (0.5 mL) were added and the resulting mixture stirred at room temperature for 2 hours before concentrating in vacuo. The residue was partitioned between DCM and water. The aqueous layer was extracted with DCM and the combined organics were dried (MgSO$_4$) and concentrated in vacuo. The residue was purified by silica gel column chromatography eluting with 0-7% MeOH in EtOAc to afford the title compound (30 mg, 19%).

$^1$H NMR (500 MHz, CDCl$_3$): δ ppm 9.37 (d, J=8.6 Hz, 1H), 9.19 (s, 1H), 8.24 (s, 1H), 8.19 (s, 1H), 7.71 (m, 1H), 7.63 (dd, J=8.6, 2.0 Hz, 1H), 7.43 (d, J=0.9 Hz, 1H), 6.76 (t, J=72.7 Hz, 1H), 3.87 (s, 3H), 2.71 (d, J=0.8 Hz, 3H).

HRMS (ESI) MS m/z calcd for C$_{18}$H$_{15}$ClF$_2$N7O [M+H]$^+$ 418.0995, found 418.0990.

Preparation 4

6-methyl-2-(methylsulfonyl)-N-neopentylpyrido[3,4-d]pyrimidin-8-amine

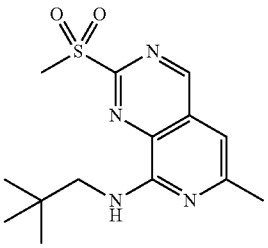 [SMILES: Cc1cc2cnc(S(C)(=O)=O)nc2c(NCC(C)(C)C)n1]

To a cooled (0° C.) solution of 6-methyl-2-(methylthio)-N-neopentylpyrido[3,4-d]pyrimidin-8-amine (Preparation 14, 133 mg, 0.481 mmol) in DCM (30 mL) was added mCPBA (77% w/w, 259 mg, 1.155 mmol). The reaction mixture was stirred for 18 hours whilst warming slowly to room temperature. Further mCPBA (30 mg) was added and the reaction continued for 2 hours. The reaction was diluted with DCM and saturated aqueous NaHCO$_3$ solution. The organic layer was collected, washed with brine, dried (MgSO$_4$) and concentrated in vacuo. The residue was purified by silica gel column chromatography eluting with 0-10% MeOH in DCM to afford the title compound (140 mg, 94%).

$^1$H NMR (500 MHz, Acetone-d$_6$): δ ppm 9.45 (s, 1H), 7.41 (br s, 1H), 6.95 (s, 1H), 3.59 (d, J=6.0 Hz, 2H), 3.44 (s, 3H), 2.51 (d, J=0.5 Hz, 3H), 1.03 (s, 9H).

HRMS (ESI) MS m/z calcd for C$_{14}$H$_{21}$N$_4$O$_2$S [M+H]$^+$ 309.138, found 309.1364.

The following Preparations were prepared according to the method described for Preparation 4 using the appropriate methylthiopyridopyrimidine as described below:

| Preparation No | Name/Structure | Data |
|---|---|---|
| 5 | 6-methyl-2-(methylsulfonyl)-N-((3-methyltetrahydrofuran-3-yl)methyl)pyrido[3,4-d]pyrimidin-8-amine | $^1$H NMR (500 MHz, MeOH-d$_4$): δ ppm 9.41 (s, 1H), 6.93 (s, 1H), 4.00 (td, J = 8.5, 6.0 Hz, 1H), 3.91 (td, J = 8.5, 6.0 Hz, 1H), 3.84 (d, J = 8.5 Hz, 1H), 3.83 (d, J = 13.5 Hz, 1H), 3.68 (d, J = 13.5 Hz, 1H), 3.47 (d, J = 8.5 Hz, 1H), 3.46 (s, 3H), 2.53 (d, J = 0.5 Hz, 3H), 2.06 (m, 1H), 1.73 (m, 1H), 1.23 (s, 3H).<br>HRMS (ESI) MS m/z calcd for C$_{15}$H$_{21}$N$_4$O$_3$S [M + H]$^+$ 337.1329, found 337.1319.<br>Using 6-methyl-N-((3-methyltetrahydrofuran-3-yl)methyl)-2-(methylthio)pyrido[3,4-d]pyrimidin-8-amine (Preparation 15). |
| 6 | 1-(((6-methyl-2-(methylsulfonyl)pyrido[3,4-d]pyrimidin-8-yl)amino)methyl)cyclobutanol | $^1$H NMR (500 MHz, MeOH-d$_4$): δ ppm 9.43 (s, 1H), 6.97 (d, J = 0.5 Hz, 1H), 3.84 (s, 2H), 3.46 (s, 3H), 2.53 (d, J = 0.5 Hz, 3H), 2.22-2.17 (m, 2H), 2.13-2.06 (m, 2H), 1.79 (m, 1H), 1.67 (m, 1H).<br>HRMS (ESI) MS m/z calcd for C$_{14}$H$_{19}$N$_4$O$_3$S [M + H]$^+$ 323.1172, found 323.1158.<br>Using 1-(((6-methyl-2-(methylthio)pyrido[3,4-d]pyrimidin-8-yl)amino)methyl)cyclobutanol (Preparation 16). |
| 7 | 3-methyl-1-(6-methyl-2-(methylsulfonyl)pyrido[3,4-d]pyrimidin-8-yl)azetidine-3-carbonitrile | $^1$H NMR (500 MHz, MeOH-d$_4$): δ ppm 9.46 (s, 1H), 7.08 (s, 1H), 4.54 (br s, 2H), 3.44 (s, 3H), 2.56 (s, 3H), 1.80 (s, 3H).<br>HRMS (ESI) MS m/z calcd for C$_{14}$H$_{16}$N$_5$O$_2$S [M + H]$^+$ 318.1019, found 318.1009.<br>Using 3-methyl-1-(6-methyl-2-(methylthio)pyrido[3,4-d]pyrimidin-8-yl)azetidine-3-carbonitrile (Preparation 17). |

| Preparation No | Name/Structure | Data |
|---|---|---|
| 8 | 2-(6-methyl-2-(methylsulfonyl)pyrido[3,4-d]pyrimidin-8-yl)-7-oxa-2-azaspiro[3.5]nonane 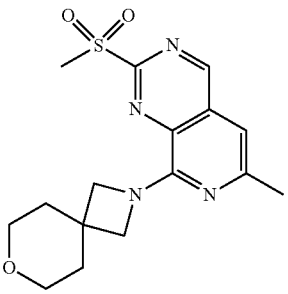 | $^1$H NMR (500 MHz, MeOH-d$_4$): δ ppm 9.38 (s, 1H), 6.94 (s, 1H), 4.29 (br s, 4H), 3.73 (app t, J = 5.5 Hz, 4H), 3.43 (s, 3H), 2.53 (s, 3H), 1.92 (app t, J = 5.5 Hz, 4H). HRMS (ESI) MS m/z calcd for C$_{16}$H$_{21}$N$_4$O$_3$S [M + H]$^+$ 349.1329, found 349.1318. Using 2-(6-methyl-2-(methylthio)pyrido[3,4-d]pyrimidin-8-yl)-7-oxa-2-azaspiro[3.5]nonane (Preparation 18). |
| 9 | 1-(6-methyl-2-(methylsulfonyl)pyrido[3,4-d]pyrimidin-8-yl)piperidine-4-carbonitrile 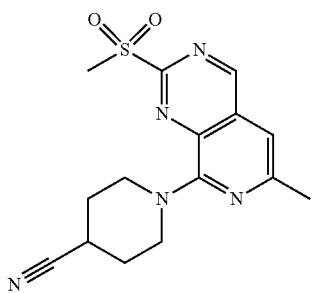 | $^1$H NMR (500 MHz, MeOH-d$_4$): δ ppm 9.48 (s, 1H), 7.15 (s, 1H), 4.55-4.51 (m, 2H), 3.97-3.92 (m, 2H), 3.43 (s, 3H), 3.15 (m, 1H), 2.57 (s, 3H), 2.19-2.13 (m, 2H), 2.04-1.98 (m, 2H). HRMS (ESI) MS m/z calcd for C$_{15}$H$_{18}$N$_5$O$_2$S [M + H]$^+$ 332.1176, found 332.1164. Using 1-(6-methyl-2-(methylthio)pyrido[3,4-d]pyrimidin-8-yl)piperidine-4-carbonitrile (Preparation 19). |
| 10 | 3-methyl-1-(6-methyl-2-(methylsulfonyl)pyrido[3,4-d]pyrimidin-8-yl)azetidin-3-ol 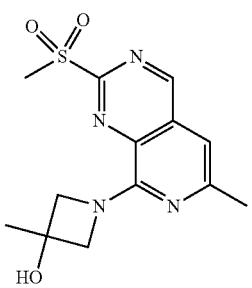 | $^1$H NMR (500 MHz, MeOH-d$_4$): δ ppm 9.39 (s, 1H), 6.95 (s, 1H), 5.30 (br s, 2H), 4.43 (br s, 2H), 3.41 (s, 3H), 2.53 (s, 3H), 1.60 (s, 3H). HRMS (ESI) MS m/z calcd for C$_{13}$H$_{17}$N$_4$O$_3$S [M + H]$^+$ 309.1016, found 309.1006. Using 3-methyl-1-(6-methyl-2-(methylthio)pyrido[3,4-d]pyrimidin-8-yl)azetidin-3-ol (Preparation 20). |

-continued

| Preparation No | Name/Structure | Data |
|---|---|---|
| 11 | 6-methyl-N-((3-methyloxetan-3-yl)methyl)-2-(methylsulfonyl)pyrido[3,4-d]pyrimidin-8-amine 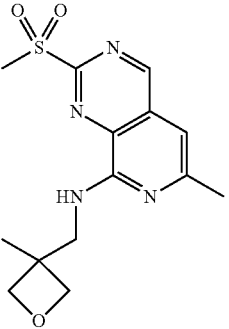 | $^1$H NMR (500 MHz, MeOH-d$_4$): δ ppm 9.42 (s, 1H), 6.95 (s, 1H), 4.77 (d, J = 6.0 Hz, 2H), 4.41 (d, J = 6.0 Hz, 2H), 3.89 (s, 2H), 3.46 (s, 3H), 2.53 (s, 3H), 1.43 (s, 3H).<br>HRMS (ESI) MS m/z calcd for C$_{14}$H$_{19}$N$_4$O$_3$S [M + H]$^+$ 323.1172, found 323.1165.<br>Using 6-methyl-N-((3-methyloxetan-3-yl)methyl)-2-(methylthio)pyrido[3,4-d]pyrimidin-8-amine (Preparation 21). |
| 12 | 6-methyl-2-(methylsulfonyl)-N-(tetrahydro-2H-pyran-4-yl)pyrido[3,4-d]pyrimidin-8-amine 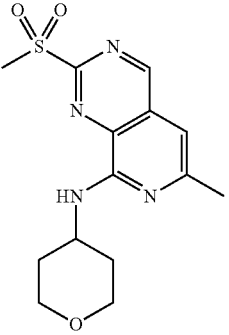 | $^1$H NMR (500 MHz, MeOH-d$_4$): δ ppm 9.39 (s, 1H), 6.92 (s, 1H), 4.44 (m, 1H), 4.07-4.03 (m, 2H), 3.62 (td, J = 12.0, 2.0 Hz, 2H), 3.45 (s, 3H), 2.54 (s, 3H), 2.10-2.06 (m, 2H), 1.82-1.74 (m, 2H).<br>HRMS (ESI) MS m/z calcd for C$_{14}$H$_{19}$N$_4$O$_3$S [M + H]$^+$ 323.1172, found 323.1158.<br>Using 6-methyl-2-(methylthio)-N-(tetrahydro-2H-pyran-4-yl)pyrido[3,4-d]pyrimidin-8-amine (Preparation 22). |
| 13 | 8-(3,3-dimethylazetidin-1-yl)-6-methyl-2-(methylsulfonyl)pyrido[3,4-d]pyrimidine 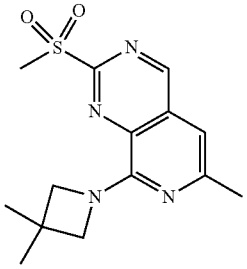 | $^1$H NMR (500 MHz, MeOH-d$_4$): δ ppm 9.37 (s, 1H), 6.91 (s, 1H), 4.53-4.09 (br m, 4H), 3.41 (s, 3H), 2.52 (s, 3H), 1.41 (s, 6H).<br>HRMS (ESI) MS m/z calcd C$_{14}$H$_{19}$N$_4$SO$_2$ [M + H]$^+$ 307.1229, found 307.1225.<br>Using 8-(3,3-dimethylazetidin-1-yl)-6-methyl-2-(methylthio)pyrido[3,4-d]pyrimidine (Preparation 23). |

Preparation 14

6-methyl-2-(methylthio)-N-neopentylpyrido[3,4-d]pyrimidin-8-amine

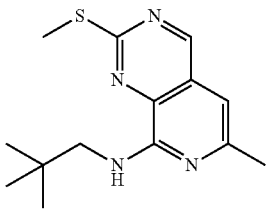 [SMILES: CSc1ncc2cc(C)nc(NCC(C)(C)C)c2n1]

To a solution of 8-chloro-6-methyl-2-(methylthio)pyrido[3,4-d]pyrimidine (Preparation 25, 500 mg, 2.215 mmol) in NMP (20 mL) was added neopentylamine (0.52 mL, 4.43 mmol) and triethylamine (1.56 mL, 11.08 mmol). The reaction mixture was heated to 100° C. for 36 hours. The reaction mixture was diluted with EtOAc and water, dried (MgSO$_4$) and concentrated in vacuo. The residue was purified by silica gel column chromatography eluting with 0-50% EtOAc in cyclohexane to afford the title compound (548 mg, 89%).

$^1$H NMR (500 MHz, MeOH-d$_4$): δ ppm 9.02 (s, 1H), 6.71 (d, J=0.5 Hz, 1H), 3.47 (s, 2H), 2.66 (s, 3H), 2.44 (d, J=0.5 Hz, 3H), 1.05 (s, 9H).

HRMS (ESI) MS m/z calcd for C$_{14}$H$_{21}$N$_4$S [M+H]$^+$ 277.1481, found 277.1467.

The following Preparations were prepared according to the method described for Preparation 14 using 8-chloro-6-methyl-2-(methythio)pyrido[3,4-d]pyrimidine (Preparation 25) and the appropriate amine as described below:

| Preparation No | Name/Structure | Data |
|---|---|---|
| 15 | 6-methyl-N-((3-methyltetrahydrofuran-3-yl)methyl)-2-(methylthio)pyrido[3,4-d]pyrimidin-8-amine | $^1$H NMR (500 MHz, MeOH-d$_4$): δ ppm 9.00 (s, 1H), 6.73 (d, J = 0.5 Hz, 1H), 4.02 (td, J = 8.5, 6.5 Hz, 1H), 3.89 (td, J = 8.5, 6.5 Hz, 1H), 3.84 (d, J = 8.5 Hz, 1H), 3.67 (d, J = 1.0 Hz, 2H), 3.47 (d, J = 8.5 Hz, 1H), 2.66 (s, 3H), 2.44 (d, J = 0.5 Hz, 3H), 1.76 (m, 1H), 1.24 (s, 3H). HRMS (ESI) MS m/z calcd for C$_{15}$H$_{21}$N$_4$OS [M + H]$^+$ 305.1431, found 305.1425. Using (3-methyltetrahydrofuran-3-yl)methanamine. |
| 16 | 1-(((6-methyl-2-(methylthio)pyrido[3,4-d]pyrimidin-8-yl)amino)methyl)cyclobutanol | $^1$H NMR (500 MHz, MeOH-d$_4$): δ ppm 9.04 (s, 1H), 6.77 (d, J = 0.5 Hz, 1H), 3.77 (s, 2H), 2.67 (s, 3H), 2.45 (d, J = 0.5 Hz, 3H), 2.19-2.06 (m, 4H), 1.78 (m, 1H), 1.65 (m, 1H). HRMS (ESI) MS m/z calcd for C$_{14}$H$_{19}$N$_4$OS [M + H]$^+$ 291.1274, found 291.1266. Using 1-(aminomethyl)cyclobutanol. |

| Preparation No | Name/Structure | Data |
|---|---|---|
| 17 | 3-methyl-1-(6-methyl-2-(methylthio)pyrido[3,4-d]pyrimidin-8-yl)azetidine-3-carbonitrile 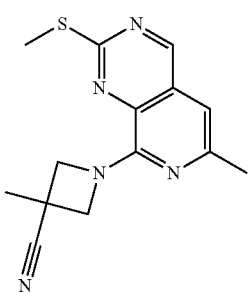 | $^1$H NMR (500 MHz, MeOH-d$_4$): δ ppm 9.05 (s, 1H), 6.89 (app s, 1H), 4.83 (br d, J = 7.5 Hz, 2H), 4.48 (br d, J = 7.5 Hz, 2H), 2.64 (s, 3H), 2.47 (d, J = 0.5 Hz, 3H), 1.78 (s, 3H).<br>HRMS (ESI) MS m/z calcd for C$_{14}$H$_{16}$N$_5$S [M + H]$^+$ 268.1121, found 268.1119.<br>Using 3-methylazetidine-3-carbonitrile hydrochloride. |
| 18 | 2-(6-methyl-2-(methylthio)pyrido[3,4-d]pyrimidin-8-yl)-7-oxa-2-azaspiro[3.5]nonane 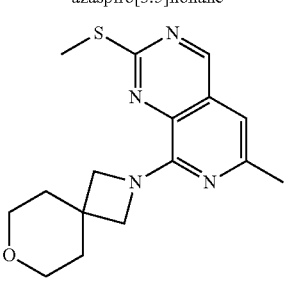 | $^1$H NMR (500 MHz, MeOH-d$_4$): δ ppm 9.00 (s, 1H), 6.76 (app s, 1H), 4.33 (br s, 4H), 3.71 (app t, J = 5.0 Hz, 4H), 2.65 (s, 3H), 2.44 (d, J = 0.5 Hz, 3H), 1.90 (app t, J = 5.0 Hz, 4H).<br>HRMS (ESI) MS m/z calcd for C$_{16}$H$_{21}$N$_4$OS [M + H]$^+$ 317.1431, found 317.1422.<br>Using 7-oxa-2-azaspiro[3.5]nonane. |
| 19 | 1-(6-methyl-2-(methylthio)pyrido[3,4-d]pyrimidin-8-yl)piperidine-4-carbonitrile 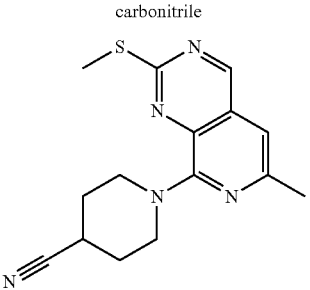 | $^1$H NMR (500 MHz, MeOH-d$_4$): δ ppm 9.10 (s, 1H), 7.01 (d, J = 0.5 Hz, 1H), 4.37-4.33 (m, 2H), 3.77 (ddd, J = 14.0, 8.5, 3.0 Hz, 2H), 3.11 (m, 1H), 2.64 (s, 3H), 2.50 (d, J = 0.5 Hz, 3H), 2.18-2.13 (m, 2H), 2.04-1.98 (m, 2H).<br>HRMS (ESI) MS m/z calcd for C$_{15}$H$_{18}$N$_5$S [M + H]$^+$ 300.1277, found 300.1266.<br>Using piperidine-4-carbonitrile. |
| 20 | 3-methyl-1-(6-methyl-2-(methylthio)pyrido[3,4-d]pyrimidin-8-yl)azetidin-3-ol 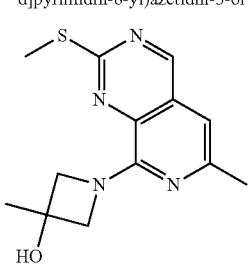 | $^1$H NMR (500 MHz, MeOH-d$_4$): δ ppm 9.00 (s, 1H), 6.77 (app s, 1H), 4.43 (br s, 4H), 2.64 (s, 3H), 2.45 (d, J = 0.5 Hz, 3H), 1.58 (s, 3H).<br>HRMS (ESI) MS m/z calcd for C$_{13}$H$_{17}$N$_4$OS [M + H]$^+$ 278.1144, found 278.1139.<br>Using 3-methylazetidin-3-ol hydrochloride. |

-continued

| Preparation No | Name/Structure | Data |
|---|---|---|
| 21 | 6-methyl-N-((3-methyloxetan-3-yl)methyl)-2-(methylthio)pyrido[3,4-d]pyrimidin-8-amine 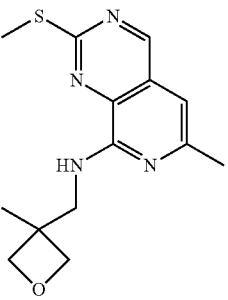 | $^1$H NMR (500 MHz, MeOH-d$_4$): δ ppm 9.03 (s, 1H), 6.76 (d, J = 0.5 Hz, 1H), 4.75 (d, J = 6.0 Hz, 2H), 4.41 (d, J = 6.0 Hz, 2H), 3.81 (s, 2H), 2.67 (s, 3H), 2.45 (d, J = 0.5 Hz, 3H), 1.42 (s, 3H). HRMS (ESI) MS m/z calcd for C$_{14}$H$_{19}$N$_4$OS [M + H]$^+$ 291.1274, found 291.1265. Using (3-methyloxetan-3-yl)methanamine. |
| 22 | 6-methyl-2-(methylthio)-N-(tetrahydro-2H-pyran-4-yl)pyrido[3,4-d]pyrimidin-8-amine 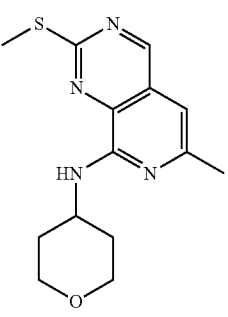 | $^1$H NMR (500 MHz, MeOH-d$_4$): δ ppm 9.02 (s, 1H), 6.75 (d, J = 0.5 Hz, 1H), 4.36 (m, 1H), 4.03 (td, J = 11.0, 2.5 Hz, 2H), 3.62 (td, J = 11.0, 2.5 Hz, 2H), 2.67 (s, 3H), 2.45 (d, J = 0.5 Hz, 3H), 2.11-2.07 (m, 2H), 1.77-1.76 (m, 2H). HRMS (ESI) MS m/z calcd for C$_{14}$H$_{19}$N$_4$OS [M + H]$^+$ 291.1274, found 291.1268. Using tetrahydro-2H-pyran-4-amine. |
| 23 | 8-(3,3-dimethylazetidin-1-yl)-6-methyl-2-(methylthio)pyrido[3,4-d]pyrimidine 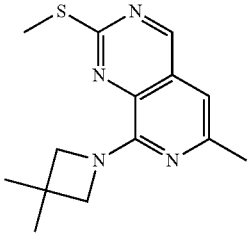 | $^1$H NMR (500 MHz, MeOH-d$_4$): δ ppm 8.99 (s, 1H), 6.73 (s, 1H), 4.26 (br s, 4H), 2.63 (s, 3H), 2.43 (s, 3H), 1.39 (s, 6H). HRMS (ESI) MS m/z calcd C$_{14}$H$_{19}$N$_4$S [M + H]$^+$ 275.1330, found 275.1332. Using 3,3-dimethylazetidine hydrochloride. |

Preparation 24

8-chloro-6-methyl-2-(methylsulfonyl)pyrido[3,4-d]pyrimidine

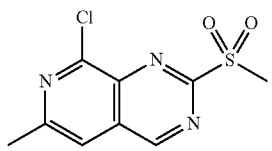

A suspension of 8-chloro-6-methyl-2-(methylthio)pyrido[3,4-d]pyrimidine (Preparation 25, 1.13 g, 5.01 mmol) in DCM (50 mL) was treated with mCPBA (77% w/w, 2.60 g, 11.57 mmol) at 0° C. and stirred whilst warming to room temperature for 18 hours. The reaction was quenched with water and extracted with DCM. The combined organic layers were washed with saturated aqueous NaHCO$_3$ solution, dried (MgSO$_4$) and concentrated in vacuo. The residue was purified by silica gel column chromatography eluting with 0-70% EtOAc in cyclohexane to afford the title compound (972 mg, 75%).

$^1$H NMR (500 MHz, MeOH-d$_4$): δ ppm 9.82 (s, 1H), 7.96 (d, J=0.5 Hz, 1H), 3.54 (s, 3H), 2.78 (d, J=0.5 Hz, 3H).

HRMS (ESI) MS m/z calcd for C$_9$H$_9$ClN$_3$O$_2$S [M+H]$^+$ 258.0099, found 258.0092.

Preparation 25

8-chloro-6-methyl-2-(methythio)pyrido[3,4-d]pyrimidine

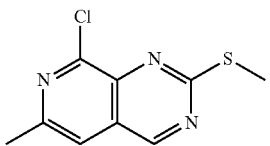

A solution of 6-methyl-2-(methylthio)pyrido[3,4-d]pyrimidin-8(7H)-one (Preparation 26, 100 mg, 0.483 mmol) in POCl$_3$ (5 mL) was heated to 70° C. for 1 hour. The reaction mixture was concentrated in vacuo. The residue was partitioned between EtOAc and washed with water, dried (MgSO$_4$) and concentrated in vacuo. The residue was purified by silica gel column chromatography eluting with 0-20% EtOAc in cyclohexane to afford the title compound (28.4 mg, 52%).

$^1$H NMR (500 MHz, CDCl$_3$): δ ppm 9.16 (s, 1H), 7.43 (s, 1H), 2.75 (s, 3H), 2.71 (s, 3H).

HRMS (ESI) MS m/z calcd for C$_9$H$_9$ClN$_3$S [M+H]$^+$ 226.0206, found 226.0204.

Preparation 26

6-methyl-2-(methythio)pyrido[3,4-d]pyrimidin-8(7H)-one

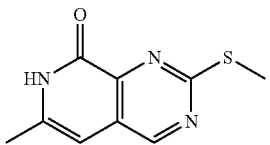

To a solution of 2-(methylthio)-5-(prop-1-yn-1-yl)pyrimidine-4-carboxamide (Preparation 27, 270 mg, 1.303 mmol) in toluene (30 mL) was added pTSA (50 mg, 0.261 mmol). The reaction mixture was heated to 90° C. for 18 hours. The reaction mixture was concentrated in vacuo. The residue was dissolved in NH$_3$ in MeOH (7M, 10 mL) and heated to 80° C. for 18 hours. The reaction mixture was concentrated in vacuo. The residue was purified by silica gel column chromatography eluting with 0-5% MeOH in DCM to afford the title compound (150 mg, 56%).

Alternatively

A suspension of pentane-2,4-dione (5.10 mL, 49.7 mmol), copper iodide (487 mg, 2.56 mmol), 5-bromo-2-(methylthio)-N-phenylpyrimidine-4-carboxamide, (Preparation 30, 8.00 g, 24.68 mmol) and Cs$_2$CO$_3$ (16.17 g, 49.6 mmol) in MeCN (70 mL) was heated to 85° C. for 18 hours. The reaction was treated with AcOH (70 mL) and AcONH$_4$ (28 g, 364 mmol) and heated to 85° C. for 5 hours. The reaction was partitioned between saturated aqueous NaHCO$_3$ and CHCl$_3$. The aqueous layers were extracted with CHCl$_3$. The combined organic layers were washed with water and brine, dried (MgSO$_4$) and concentrated in vacuo. The residue was purified by silica gel column chromatography eluting with 20-100% EtOAc in cyclohexane followed by 0-20% MeOH in EtOAc to afford the title compound (3.22 g, 63%).

$^1$H NMR (500 MHz, CDCl$_3$): δ ppm 10.52 (br s, 1H), 8.91 (s, 1H), 6.28 (s, 1H), 2.72 (s, 3H), 2.45 (s, 3H).

HRMS (ESI) MS m/z calcd for C$_9$H$_{10}$N$_3$SO [M+H]$^+$ 208.0545, found 208.0550.

Preparation 27

2-(methylthio)-5-(prop-1-yn-1 yl)pyrimidine-4-carboxamide

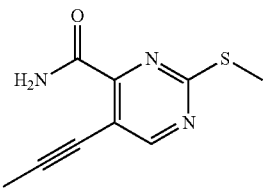

A solution of methyl 2-(methylthio)-5-prop-1-yn-1-yl)pyrimidine-4-carboxylate (Preparation 28, 410 mg, 1.845 mmol) in NH$_3$ in MeOH (7M, 12 mL) was heated to 120° C. for 18 hours. The reaction mixture was concentrated in vacuo. The residue was purified by silica gel column chromatography eluting with 0-5% MeOH in DCM to afford the title compound (280 mg, 73%).

$^1$H NMR (500 MHz, CDCl$_3$): δ ppm 8.74 (s, 1H), 7.52 (br s, 1H), 5.61 (br s, 1H), 2.61 (s, 3H), 2.19 (s, 3H).

LCMS (ESI) Rt=1.87 minutes, MS m/z 208.27 [M+H]$^+$

Preparation 28

Methyl 2-(methylthio)-5-prop-1-yn-1 yl)pyrimidine-4-carboxylate

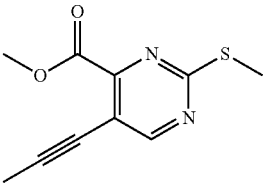

To a solution of methyl 5-bromo-2-(methylthio)pyrimidine-4-carboxylate (Preparation 29, 1.0 g, 3.80 mmol) in DMF (10 mL) was added tributylpropynyl tin (1.4 mL, 4.56 mmol) and Pd(PPh$_3$)$_4$ (132 mg, 0.114 mmol). The reaction mixture was heated to 110° C. under microwave irradiation for 30 minutes. The reaction mixture was diluted with EtOAc, washed with saturated aqueous NaHCO$_3$ and water, dried (MgSO$_4$) and concentrated in vacuo. The residue was purified by silica gel column chromatography eluting with 50-100% DCM in cyclohexane to afford the title compound (414 mg, 49%).

$^1$H NMR (500 MHz, CDCl$_3$): δ ppm 8.67 (s, 1H), 4.00 (s, 3H), 2.61 (s, 3H), 2.14 (s, 3H).

HRMS (ESI) MS m/z calcd for C$_9$H$_8$N$_2$O$_2$S [M+H]$^+$ 209.0379, found 209.038.

Preparation 29

Methyl 5-bromo-2-(methylthio)pyrimidine-4-carboxylate

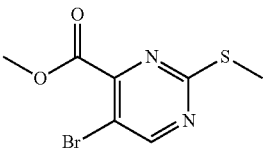

A solution of 5-bromo-2-(methylthio)pyrimidine-4-carboxylic acid (7.64 g, 30.7 mmol) in MeOH (60 mL) was treated with sulfuric acid (2 mL) and heated to reflux for 24 hours. The mixture was poured onto ice water and extracted with DCM. The organic layer was washed with saturated aqueous $NaHCO_3$, dried ($MgSO_4$) and concentrated in vacuo to afford the title compound (6.42 g, 80%).

$^1$H NMR (500 MHz, $CDCl_3$): δ ppm 8.72 (s, 1H), 4.01 (s, 3H), 2.58 (s, 3H).

LCMS (ESI) Rt=2.35 minutes, MS m/z 263 [M+H]$^+$

Preparation 30

5-bromo-2-(methylthio)-N-phenylpyrimidine-4-carboxamide

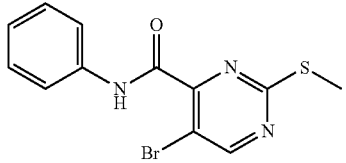 [SMILES: CSc1ncc(Br)c(C(=O)Nc2ccccc2)n1]

To a solution of 5-bromo-2-(methylthio)pyrimidine-4-carboxylic acid (20.1 g, 81 mmol) in DCM (300 mL) was added catalytic DMF (1 drop) and oxalyl chloride (8.6 mL, 102 mmol) at 0° C. The reaction was stirred at room temperature for 18 hours before concentrating in vacuo. The residue was dissolved in DCM and treated with aniline (12 mL, 132 mmol) and triethylamine (24 mL, 173 mmol) at 0° C. The reaction was stirred at room temperature for 3 days. The reaction was quenched with 0.5M HCl and extracted with DCM. The combined organic layers were washed with water and brine, dried ($MgSO_4$) and concentrated in vacuo to afford the title compound (24.91 g, 95%).

$^1$H NMR (500 MHz, $CDCl_3$): δ ppm 9.64 (br s, 1H), 8.86 (s, 1H), 7.75 (dd, J=8.6, 1.1 Hz, 2H), 7.42 (dd, J=8.5, 7.4 Hz, 2H), 7.22 (t, J=7.5 Hz, 1H), 2.66 (s, 3H).

HRMS (ESI) MS m/z calcd for $C_{12}H_{11}BrN_3OS$ [M+H]$^+$ 325.9780, found 325.9767.

Preparation 31

N-(2-methoxy-4-(1-methyl-1H-1,2,3-triazol-5-yl)phenyl)formamide

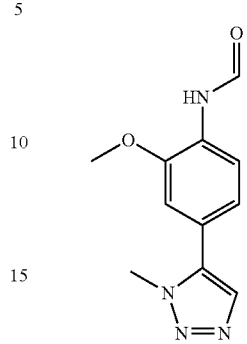

A solution of 2-methoxy-4-(1-methyl-1H-1,2,3-triazol-5-yl)aniline (Preparation 52, 25 mg, 0.122 mmol) in formic acid (3 mL) was heated to 100° C. for 1.5 hours. The reaction mixture was concentrated in vacuo. The residue was diluted with saturated aqueous $NaHCO_3$ and EtOAc. The aqueous layer was re-extracted with DCM. The combined organic layers were dried ($MgSO_4$) and concentrated in vacuo to afford the title compound (20 mg, 70%).

$^1$H NMR (500 MHz, MeOH-$d_4$): δ ppm 8.43 (d, J=8.5 Hz, 1H), 8.39 (s, 1H), 7.83 (s, 1H), 7.20 (d, J=2.0 Hz, 1H), 7.14 (dd, J=8.5, 2.0 Hz, 1H), 4.13 (s, 3H), 3.99 (s, 3H).

HRMS (ESI) MS m/z calcd for $C_{11}H_{13}N_4O_2$ [M+H]$^+$ 233.1033, found 233.1032.

The following Preparations were prepared according to the method described for Preparation 31 using the appropriate aniline as described below. Following concentration the residues were treated as above or according to one of the Purification Methods (PM) below:

Purification Method A: Azeotrope with toluene followed by silica gel column chromatography eluting with 0-85% EtOAc in cyclohexane.

Purification Method B: Azeotrope with toluene followed by silica gel column chromatography eluting with 0-10% MeOH in DCM Purification Method C: Azeotrope with toluene followed by purified by silica gel column chromatography eluting with 0-20% MeOH in DCM.

Purification Method D: Further material was obtained by acidifying the aqueous layer with 0.5M HCl and extracting with DCM, drying ($MgSO_4$) and concentrating in vacuo.

| Preparation No | Name/Structure | Data |
|---|---|---|
| 32 | N-(2-ethoxy-4-(4-methyl-4H-1,2,4-triazol-3-yl)phenyl)formamide | $^1$H NMR (500 MHz, Acetone-$d_6$): δ ppm 9.22 (br s, 1H), 8.55 (d, J = 8.5 Hz, 1H), 8.52 (s, 1H), 8.36 (s, 1H), 7.41 (d, J = 1.5 Hz, 1H), 7.31 (dd, J = 8.5, 1.5 Hz, 1H), 4.25 (q, J = 7.0 Hz, 2H), 3.88 (s, 3H), 1.45 (t, J = 7.0 Hz, 3H). HRMS (ESI) MS m/z calcd for $C_{12}H_{16}N_4O_2$ [M + H]$^+$ 247.1195, found 247.1195. Using 2-ethoxy-4-(4-methyl-4H-1,2,4-triazol-3-yl)aniline (Preparation 54). |

| Preparation No | Name/Structure | Data |
|---|---|---|
| 33 | N-(2-methoxy-4-(1-methyl-1H-pyrazol-3-yl)phenyl)formamide 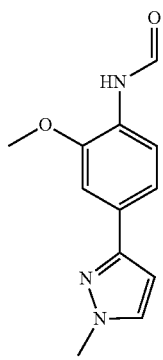 | $^1$H NMR (500 MHz, MeOH-d$_4$): δ ppm 8.35 (s, 1H), 8.25 (d, J = 8.3 Hz, 1H), 7.62 (d, J = 2.3 Hz, 1H), 7.48 (d, J = 1.8 Hz, 1H), 7.34 (dd, J = 8.3, 1.8 Hz, 1H), 6.64 (d, J = 2.3 Hz, 1H), 4.00 (s, 3H), 3.95 (s, 3H). <br> HRMS (ESI) MS m/z calcd for C$_{12}$H$_{14}$N$_3$O$_2$ [M + H]$^+$ 232.1081, found 232.1079. <br> Using 2-methoxy-4-(1-methyl-1H-pyrazol-3-yl)aniline (Preparation 45). <br> PM A. |
| 34 | N-(2-methoxy-4-(1-methyl-1H-imidazol-2-yl)phenyl)formamide 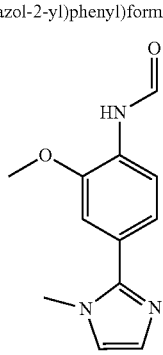 | $^1$H NMR (500 MHz, MeOH-d$_4$): δ ppm 8.46 (d, J = 8.3 Hz, 1H), 8.41 (s, 1H), 7.35 (dd, J = 11.4, 1.7 Hz, 2H), 7.25 (dd, J = 7.7, 1.7 Hz, 2H), 4.01 (s, 3H), 3.86 (s, 3H). <br> HRMS (ESI) MS m/z calcd for C$_{12}$H$_{14}$N$_3$O$_2$ [M + H]$^+$ 232.1081, found 232.1082. <br> Using 2-methoxy-4-(1-methyl-1H-imidazol-2-yl)aniline (Preparation 46). <br> PM B. |
| 35 | N-(2-methoxy-4-(1-methyl-1H-pyrazol-5-yl)phenyl)formamide 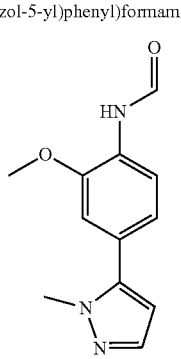 | $^1$H NMR (500 MHz, MeOH-d$_4$): δ ppm 8.42-8.32 (m, 2H), 7.51 (d, J = 1.9 Hz, 1H), 7.13 (d, J = 1.8 Hz, 1H), 7.07 (dd, J = 8.2, 1.8 Hz, 1H), 6.40 (d, J = 2.0 Hz, 1H), 3.98 (s, 3H), 3.91 (s, 3H). <br> HRMS (ESI) MS m/z calcd for C$_{12}$H$_{14}$N$_3$O$_2$ [M + H]$^+$ 232.1081, found 232.1091. <br> Using 2-methoxy-4-(1-methyl-1H-pyrazol-5-yl)aniline (Preparation 47). <br> PM A. |
| 36 | N-(2-methoxy-4-(oxazol-2-yl)phenyl)formamide 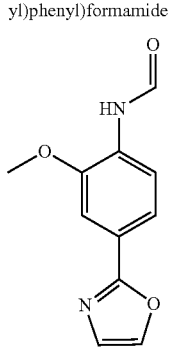 | $^1$H NMR (500 MHz, MeOH-d$_4$): δ ppm 8.43 (d, J = 8.4 Hz, 1H), 8.40 (s, 1H), 7.99 (d, J = 0.9 Hz, 1H), 7.68 (d, J = 1.8 Hz, 1H), 7.64 (dd, J = 8.4, 1.8 Hz, 1H), 7.32 (d, J = 0.9 Hz, 1H), 4.03 (s, 3H). <br> HRMS (ESI) MS m/z calcd for C$_{11}$H$_{11}$N$_2$O$_3$ [M + H]$^+$ 219.0764, found 219.0765. <br> Using 2-methoxy-4-(oxazol-2-yl)aniline (Preparation 48). <br> PM A. |

| Preparation No | Name/Structure | Data |
| --- | --- | --- |
| 37 | N-(4-(1,2-dimethyl-1H-imidazol-5-yl)-2-methoxyphenyl)formamide | $^1$H NMR (500 MHz, MeOH-d$_4$): δ ppm 8.36 (s, 1H), 8.31 (d, J = 8.5 Hz, 1H), 7.05 (d, J = 1.5 Hz, 1H), 6.99 (dd, J = 8.5, 1.5 Hz, 1H), 6.89 (s, 1H), 3.96 (s, 3H), 3.59 (s, 3H), 2.43 (s, 3H). HRMS (ESI) MS m/z calcd for C$_{13}$H$_{16}$N$_3$O$_2$ [M + H]$^+$ 246.1237, found 246.1233. Using 4-(1,2-dimethyl-1H-imidazol-5-yl)-2-methoxyaniline (Preparation 53). PM D. |
| 38 | N-(2-(difluoromethoxy)-4-(4-methyl-4H-1,2,4-triazol-3-yl)phenyl)formamide | $^1$H NMR (500 MHz, MeOH-d$_4$): δ ppm 8.59-8.55 (m, 2H), 8.43 (s, 1H), 7.64 (s, 1H), 7.61 (dd, J = 8.5, 2.0 Hz, 1H), 7.01 (t, J = 72.8 Hz, 1H), 3.84 (s, 3H). HRMS (ESI) MS m/z calcd for C$_{11}$H$_{11}$F$_2$N$_4$O$_2$ [M + H]$^+$ 269.0850, found 269.0854. Using 2-(Difluoromethoxy)-4-(4-methyl-4H-1,2,4-triazol-3-yl)aniline (Preparation 62). PM B. |
| 39 | N-(2-methoxy-4-(1-methyl-1H-tetrazol-5-yl)phenyl)formamide | $^1$H NMR (500 MHz, MeOH-d$_4$): δ ppm 8.53 (d, J = 8.4 Hz, 1H), 8.42 (s, 1H), 7.48 (d, J = 1.9 Hz, 1H), 7.41 (dd, J = 8.4, 1.9 Hz, 1H), 4.23 (s, 3H), 4.02 (s, 3H). HRMS (ESI) MS m/z calcd for C$_{10}$H$_{12}$N$_5$O$_2$ [M + H]$^+$ 234.0991, found 234.0992. Using 2-methoxy-4-(1-methyl-1H-tetrazol-5-yl)aniline (Preparation 49). PM A. |

| Preparation No | Name/Structure | Data |
|---|---|---|
| 40 | N-(4-(2,4-dimethyloxazol-5-yl)-2-methoxyphenyl)formamide 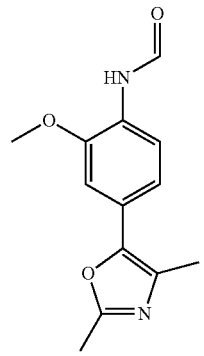 | $^1$H NMR (500 MHz, MeOH-d4): δ ppm 8.35 (s, 1H), 8.32 (d, J = 8.4 Hz, 1H), 7.20 (d, J = 1.8 Hz, 1H), 7.17 (dd, J = 8.4, 1.9 Hz, 1H), 3.98 (s, 3H), 2.48 (s, 3H), 2.36 (s, 3H). HRMS (ESI) MS m/z calcd for $C_{13}H_{15}N_2O_3$ [M + H]$^+$ 247.1082, found 247.1085. Using 4-(2,4-dimethyloxazol-5-yl)-2-methoxyaniline (Preparation 50). PM A. |
| 41 | N-(4-(1,5-dimethyl-1H-imidazol-2-yl)-2-methoxyphenyl)formamide 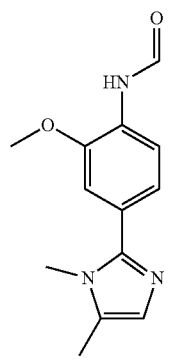 | LCMS (ESI) Rt = 0.50 minutes, MS m/z 246 [M + H]$^+$. Using 4-(1,5-dimethyl-1H-imidazol-2-yl)-2-methoxyaniline (Preparation 51). PM B. |
| 42 | N-(4-(4,5-dimethyl-4H-1,2,4-triazol-3-yl)-2-methoxyphenyl)formamide 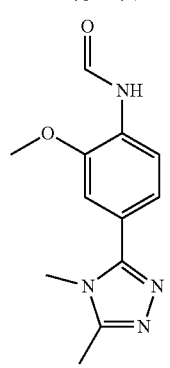 | $^1$H NMR (500 MHz, MeOH-d$_4$): δ ppm 8.47 (d, J = 8.3 Hz, 1H), 8.40 (s, 1H), 7.33 (d, J = 1.8 Hz, 1H), 7.24 (dd, J = 8.3, 1.8 Hz, 1H), 4.00 (s, 3H), 3.68 (s, 3H), 2.52 (s, 3H), HRMS (ESI) MS m/z calcd for $C_{12}H_{15}N_4O_2$ [M + H]$^+$ 247.1195, found 247.1195 Using 4-(4,5-dimethyl-4H-1,2,4-triazol-3-yl)-2-methoxyaniline (Preparation 61). PM C. |

-continued

| Preparation No | Name/Structure | Data |
|---|---|---|
| 43 | N-(4-(4,5-dimethyl-4H-1,2,4-triazol-3-yl)-2-ethoxyphenyl)formamide | $^1$H NMR (500 MHz, MeOH-$d_4$): δ ppm 8.46 (d, J = 8.2 Hz, 1H), 8.42 (s, 1H), 7.30 (d, J = 1.7 Hz, 1H), 7.22 (dd, J = 8.2, 1.7 Hz, 1H), 4.24 (q, J = 7.0 Hz, 2H), 3.68 (s, 3H), 2.52 (s, 3H), 1.51 (t, J = 7.0 Hz, 3H). HRMS (ESI) MS m/z calcd for $C_{13}H_{17}N_4O_2$ [M + H]$^+$ 261.1352, found 261.1345. Using 4-(4,5-dimethyl-4H-1,2,4-triazol-3-yl)-2-ethoxyaniline (Preparation 59). PM B. |
| 44 | N-(2-ethoxy-4-(4-ethyl-4H-1,2,4-triazol-3-yl)phenyl)formamide | $^1$H NMR (500 MHz, MeOH-$d_4$): δ ppm 8.65 (s, 1H), 8.47 (d, J = 8.0 Hz, 1H), 8.43 (s, 1H), 7.30 (d, J = 1.7 Hz, 1H), 7.22 (dd, J = 8.0, 1.7 Hz, 1H), 4.26-4.19 (m, 4H), 1.51 (t, J = 7.0 Hz, 3H), 1.41 (t, J = 7.0 Hz, 3H). HRMS (ESI) MS m/z calcd for $C_{13}H_{17}N_4O_2$ [M + H]$^+$ 261.1352, found 261.1352. Using 2-ethoxy-4-(4-ethyl-4H-1,2,4-triazol-3-yl)aniline (Preparation 60). PM C. |

Preparation 45

2-methoxy-4-(1-methyl-1H-pyrazol-3-yl)aniline

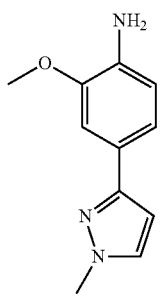

To a solution of 2-methoxy-4-(4,4,5,5-tetramethyl-1,3,2-dioxaborolan-2-yl)aniline (310 mg, 1.244 mmol) and 3-bromo-1-methyl-1H-pyrazole (154 mg, 0.957 mmol) in THF (3 mL) was added Pd(dppf)Cl$_2$.DCM (40 mg, 0.049 mmol) and 2M aqueous Na$_2$CO$_3$ (1 mL) and the reaction was heated to 65° C. for 18 hours. The reaction was diluted with EtOAc and water. The aqueous layer was extracted with EtOAc, the combined organic layers were washed with water and brine, dried (MgSO$_4$) and concentrated in vacuo. The residue was purified by silica gel column chromatography eluting with 0-60% EtOAc in cyclohexane to afford the title compound (34 mg, 18%).

$^1$H NMR (500 MHz, CDCl$_3$): δ ppm 7.33 (d, J=18.8 Hz, 2H), 7.28 (d, J=1.2 Hz, 2H), 7.20 (d, J=7.9 Hz, 1H), 6.74 (dd, J=7.9, 1.2 Hz, 1H), 6.45 (dd, J=2.2, 1.2 Hz, 1H), 3.95 (m, 6H), 3.85 (br s, 2H).

HRMS (ESI) MS m/z calcd for $C_{11}H_{14}N_3O$ [M+H]$^+$ 204.1131, found 204.1141.

The following Preparations were prepared according to the method described for Preparation 45 using the appropriate aniline and heterocycle as described below. The crude reaction residues were purified as above or according to one of the following Purification Methods (PM):

Purification Method A: Silica gel column chromatography eluting with 0-5% MeOH in DCM.

Purification Method B: Silica gel column chromatography eluting with 0-15% EtOAc in cyclohexane.

Purification Method C: Silica gel column chromatography eluting with 0-10% MeOH in DCM.

| Preparation No | Name/Structure | Data |
|---|---|---|
| 46 | 2-methoxy-4-(1-methyl-1H-imidazol-2-yl)aniline | $^1$H NMR (500 MHz, CDCl$_3$): δ ppm 7.18 (d, J = 1.8 Hz, 1H), 7.10 (d, J = 1.3 Hz, 1H), 6.99 (dd, J = 8.0, 1.8 Hz, 1H), 6.95 (s, 1H), 6.76 (d, J = 8.0 Hz, 1H), 3.98 (br s, 2H), 3.92 (s, 3H), 3.75 (s, 3H).<br>HRMS (ESI) MS m/z calcd for C$_{11}$H$_{14}$N$_3$O [M + H]$^+$ 204.1131, found 204.1139.<br>Using 2-methoxy-4-(4,4,5,5-tetramethyl-1,3,2-dioxaborolan-2-yl)aniline and 2-bromo-1-methyl-1H-imidazole at 110° C. under microwave irradiation.<br>PM A. |
| 47 | 2-methoxy-4-(1-methyl-1H-pyrazol-5-yl)aniline | $^1$H NMR (500 MHz, CDCl$_3$): δ ppm 7.51 (d, J = 1.9 Hz, 1H), 6.86 (dd, J = 7.9, 1.8 Hz, 1H), 6.83 (s, 1H), 6.79 (d, J = 7.9 Hz, 1H), 6.26 (d, J = 1.9 Hz, 1H), 3.98 br (s, 2H), 3.91 (s, 3H), 3.90 (s, 3H).<br>HRMS (ESI) MS m/z calcd for C$_{11}$H$_{14}$N$_3$O [M + H]$^+$ 204.1131, found 204.1140.<br>Using 4-bromo-2-methoxyaniline and 1-methyl-1H-pyrazol-5-ylboronic acid with Pd(PPh$_3$)$_4$ at 70° C. |
| 48 | 2-methoxy-4-(oxazol-2-yl)aniline | $^1$H NMR (500 MHz, CDCl$_3$): δ ppm 7.65 (d, J = 0.8 Hz, 1H), 7.57-7.49 (m, 2H), 7.19 (d, J = 0.9 Hz, 1H), 6.76 (d, J = 8.0 Hz, 1H), 4.11 (br s, 2H), 3.96 (s, 3H).<br>HRMS (ESI) MS m/z calcd for C$_{10}$H$_{11}$N$_2$O$_2$ [M + H]$^+$ 191.0815, found 191.0825.<br>Using 2-methoxy-4-(4,4,5,5-tetramethyl-1,3,2-dioxaborolan-2-yl)aniline and 2-bromooxazole hydrochloride with Pd(PPh$_3$)$_4$ at 110° C. under microwave irradiation.<br>PM B. |
| 49 | 2-methoxy-4-(1-methyl-1H-tetrazol-5-yl)aniline | $^1$H NMR (500 MHz, CDCl$_3$): δ ppm 7.31 (d, J = 1.8 Hz, 1H), 7.11 (dd, J = 8.0, 1.9 Hz, 1H), 6.81 (d, J = 8.1 Hz, 1H), 4.21 (br s, 2H), 4.18 (s, 3H), 3.94 (s, 3H).<br>HRMS (ESI) MS m/z calcd for C$_9$H$_{12}$N$_5$O [M + H]$^+$ 206.1042, found 206.1046.<br>Using 2-methoxy-4-(4,4,5,5-tetramethyl-1,3,2-dioxaborolan-2-yl)aniline and 5-bromo-1-methyl-1H-tetrazole. |

| Preparation No | Name/Structure | Data |
|---|---|---|
| 50 | 4-(2,4-dimethyloxazol-5-yl)-2-methoxyaniline 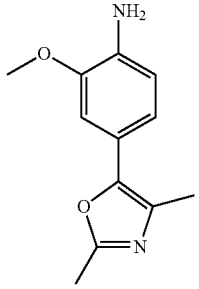 | $^1$H NMR (500 MHz, CDCl$_3$): δ ppm 7.04-6.97 (m, 2H), 6.76 (d, J = 8.5 Hz, 1H), 3.93 (s, 5H), 2.47 (s, 3H), 2.35 (s, 3H). HRMS (ESI) MS m/z calcd for C$_{12}$H$_{15}$N$_2$O$_2$ [M + H]$^+$ 219.1133, found 219.1128. Using 2-methoxy-4-(4,4,5,5-tetramethyl-1,3,2-dioxaborolan-2-yl)aniline and 5-bromo-2,4-dimethyloxazole. |
| 51 | 4-(1,5-dimethyl-1H-imidazol-2-yl)-2-methoxyaniline 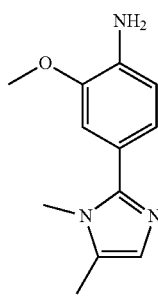 | LCMS (ESI) Rt = 0.87 minutes, MS m/z 218 [M + H]$^+$. Using 2-methoxy-4-(4,4,5,5-tetramethyl-1,3,2-dioxaborolan-2-yl)aniline and 2-bromo-1,5-dimethyl-1H-imidazole with Pd(PPh$_3$)$_4$ at 100 ° C. under microwave irradiation. PM C. |

Preparation 52

2-methoxy-4-(1-methyl-1H-1,2,3-triazol-5-yl)aniline

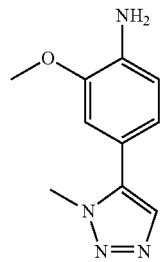

A suspension of 2-methoxy-4-(4,4,5,5-tetramethyl-1,3,2-dioxaborolan-2-yl)aniline (122 mg, 0.490 mmol), 5-iodo-1-methyl-1H-1,2,3-triazole (93 mg, 0.445 mmol), CsF (203 mg, 1.335 mmol) and Pd(PPh$_3$)$_4$ (51.4 mg, 0.045 mmol) in DME/MeOH (3:1, 4 mL) was heated to 150° C. for 1 hour under microwave irradiation. The reaction mixture was filtered and purified by silica gel column chromatography eluting with 50-70% EtOAc in cyclohexane to afford the title compound (75 mg, 83%).

$^1$H NMR (500 MHz, CDCl$_3$): δ ppm 7.67 (s, 1H), 6.85-6.84 (m, 2H), 6.80 (d, J=1.5 Hz, 1H), 4.06 (s, 3H), 3.91 (s, 3H).

HRMS (ESI) MS m/z calcd for C$_{10}$H$_{13}$N$_4$O [M+H]$^+$ 205.1084, found 205.1093.

Preparation 53

4-(1,2-dimethyl-1H-imidazol-5-yl)-2-methoxyaniline

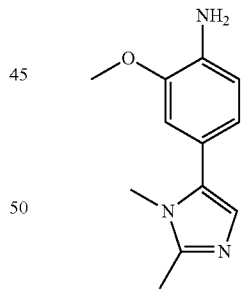

A suspension of 2-methoxy-4-(4,4,5,5-tetramethyl-1,3,2-dioxaborolan-2-yl)aniline (925 mg, 3.71 mmol), 5-bromo-1,2-dimethylimidazole (650 mg, 3.71 mmol), CsF (1.7 g, 11.14 mmol) and Pd(PPh$_3$)$_4$ (86 mg, 0.074 mmol) in DME/MeOH (2:1, 18 mL) was heated to 150° C. for 10 minutes under microwave irradiation. The reaction mixture was diluted with EtOAc and water. The aqueous layer was basified by addition of 2M aqueous Na$_2$CO$_3$ and extracted with EtOAc. The combined organic layers were washed with brine, dried (MgSO$_4$) and concentrated in vacuo. The residue was purified by reverse phase column chromatography eluting with 100% water to afford the title compound (800 mg, 99%).

¹H NMR (500 MHz, MeOH-d₄) δ ppm 6.84 (d, J=2.0 Hz, 1H), 6.81 (s, 1H), 6.78 (d, J=2.0 Hz, 1H), 6.75 (s, 1H), 3.88 (s, 3H), 3.53 (s, 3H), 2.41 (s, 3H).

HRMS (ESI) MS m/z calcd for $C_{12}H_{16}N_3O$ [M+H]⁺ 218.1288, found 218.1200.

Preparation 54

2-Ethoxy-4-(4-methyl-4H-1,2,4-triazol-3-yl)aniline

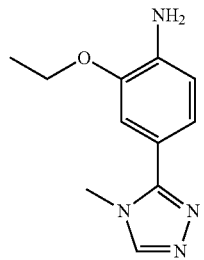 [SMILES: CCOc1cc(-c2nncn2C)ccc1[N+](=O)[O-]]

To a solution 3-(3-ethoxy-4-nitrophenyl)-4-methyl-4H-1,2,4-triazole (Preparation 55, 748 mg 3.19 mmol) in EtOH (50 mL) was added 10% Pd/C (130 mg, 0.123 mmol). The reaction was stirred in an atmosphere of hydrogen (1 atm) at room temperature for 18 hours. The reaction mixture was filtered through Celite and concentrated in vacuo to afford the title compound (539 mg, 83%).

¹H NMR (500 MHz, MeOH-d₄) δ ppm 8.49 (s, 1H), 7.15 (d, J=2.0 Hz, 1H), 7.08 (dd, J=8.0, 2.0 Hz, 1H), 6.87 (d, J=8.0 Hz, 1H), 4.15 (q, J=7.0 Hz, 2H), 3.80 (s, 3H), 1.47 (t, J=7.0 Hz, 3H).

HRMS (ESI) MS m/z calcd for $C_{11}H_{14}N_4O$ [M+H]⁺ 249.0988, found 249.0992.

Preparation 55

3-(3-Ethoxy-4-nitrophenyl)-4-methyl-4H-1,2,4-triazole

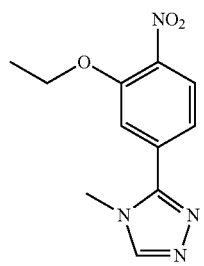

To a cooled (0° C.) suspension of 5-(3-ethoxy-4-nitrophenyl)-4-methyl-4H-1,2,4-triazole-3-thiol (Preparation 56, 1.16 g 4.14 mmol) in DCM (11.8 mL) was added a solution of 35% hydrogen peroxide (0.91 mL, 12.2 mmol) in acetic acid (6 mL) dropwise. The reaction was stirred at room temperature for 70 minutes. DCM (50 mL) was added followed by 2M NaOH (48 mL) to obtain a neutral pH. The aqueous layer was extracted with DCM. The combined organic layers were dried (Na₂SO₄) and concentrated in vacuo. The residue was purified by silica gel column chromatography eluting with 5-10% EtOH in DCM to afford the title compound (607 mg, 60%).

¹H NMR (500 MHz, DMSO-d₆): δ ppm 8.66 (s, 1H), 8.03 (d, J=8.5 Hz, 1H), 7.65 (d, J=1.6 Hz, 1H), 7.47 (dd, J=1.6, 8.5 Hz, 1H), 4.31 (q, J=7.3 Hz, 2H), 3.81 (s, 3H), 1.36 (t, J=6.9 Hz, 3H).

HRMS (ESI) MS m/z calcd for $C_{11}H_{13}N_4O_3$ [M+H]⁺ 249.0988, found 249.0985.

Alternatively

To a suspension of 3-ethoxy-N-methyl-4-nitrobenzamide (Preparation 58, 609 mg, 2.72 mmol) in DCE (12 mL) was added thionyl chloride (0.79 mL, 10.86 mmol). The mixture was stirred at 90° C. under microwave irradiation for 3 hours. The reaction mixture was concentrated in vacuo and the resulting orange oil was dried in vacuo for 1 hour. Formyl hydrazide (196 mg, 3.26 mmol) in DMF (10 mL) was added and the reaction heated at 110° C. under microwave irradiation for 1 hour. Brine was added to the reaction mixture. The resulting precipitate was filtered, washed with water and dried in vacuo to afford the title compound (290 mg, 43%).

Preparation 56

5-(3-Ethoxy-4-nitrophenyl)-4-methyl-4H-1,2,4-triazole-3-thiol

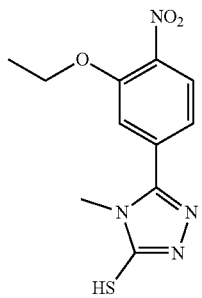 [SMILES: CCOc1cc(-c2nnc(S)n2C)ccc1[N+](=O)[O-]]

To a solution of 3-ethoxy-4-nitrobenzohydrazide (Preparation 57, 1287 mg 5.72 mmol) in THF (26 mL) was added a solution of methyl isothiocyanate (422 mg 5.78 mmol) in THF (5 mL). Triethylamine (102 uL, 0.71 mmol) was added and the reaction was stirred at room temperature for 22 hours. The reaction was concentrated in vacuo and the residue dissolved in 1M NaOH (85 mL). The reaction was stirred at 45° C. for 2.5 hours. The reaction was filtered through Celite and the filtrate extracted with ether. The aqueous was acidified using concentrated HCl and extracted with EtOAc. The combined organic layer was washed with water and brine, dried (Na₂SO₄) and concentrated in vacuo to afford the title compound (1.16 g, 72%).

¹H NMR (500 MHz, DMSO-d₆): δ ppm 14.11 (brs, 1H), 8.03 (d, J=8.5 Hz, 1H), 7.66 (d, J=1.6 Hz, 1H), 7.44 (dd, J=1.9, 8.5 Hz, 1H), 4.29 (q, J=6.9 Hz, 2H), 3.56 (s, 3H), 1.35 (t, J=6.9 Hz, 3H).

HRMS (ESI) MS m/z calcd for $C_{11}H_{12}N_4O_3S$ [M+H]⁺ 475.2570, found 475.2571.

Preparation 57

3-Ethoxy-4-nitrobenzohydrazide

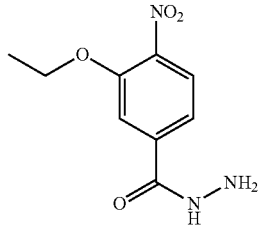 [SMILES: CCOc1cc(C(=O)NN)ccc1[N+](=O)[O-]]

To a cooled (0° C.) solution of 3-ethoxy-4-nitrobenzoic acid (PCT Int Appl. 2008003958, 1.06 g, 5.02 mmol) in THF (10 mL) and triethylamine (0.86 mL, 6.1 mmol) was added ethyl chloroformate (0.56 mL, 5.85 mmol) dropwise. The reaction was stirred at 0° C. for 15 minutes. Hydrazine hydrate (1.27 mL, 26 mmol) was added in one portion and the reaction stirred for 5 minutes and then at room temperature for 1 hour. The reaction was concentrated in vacuo, partitioned between EtOAc and saturated aqueous NaHCO$_3$. The organic layer was washed with brine, dried (Na$_2$SO$_4$) and concentrated in vacuo to afford the title compound (1.07 g, 95%).

$^1$H NMR (500 MHz, DMSO-d$_6$): δ ppm 10.05 (br s, 1H, NH), 7.92 (d, J=8.3 Hz, 1H), 7.69 (d, J=1.7 Hz, 1H), 7.51 (dd, J=8.3, 1.7 Hz, 1H), 4.70 (br s, 2H), 4.27 (q, J=6.9 Hz, 2H), 1.35 (t, J=6.9 Hz, 3H).

HRMS (ESI) MS m/z calcd for C$_9$H$_{11}$N$_3$O$_4$ [M+H]$^+$ 226.0822, found 226.0828.

Preparation 58

3-Ethoxy-N-methyl-4-nitrobenzamide

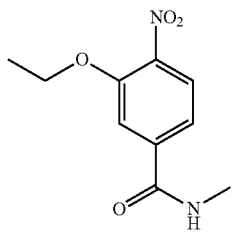 [SMILES: CCOc1cc(C(=O)NC)ccc1[N+](=O)[O-]]

To a suspension of 3-ethoxy-4-nitrobenzoic acid (PCT Int Appl. 2008003958, 2.57 g, 12.2 mmol), methanamine hydrochloride (1.32 g, 19.5 mmol), 1H-benzo[d][1,2,3]triazol-1-ol hydrate (3.73 g, 24.4 mmol) and N1-((ethylimino)methylene)-N3,N3-dimethylpropane-1,3-diamine hydrochloride (4.67 g, 24.4 mmol) in DCM (50 mL) was added N-ethyl-N-isopropylpropan-2-amine (10.6 mL, 60.9 mmol). The resulting solution was stirred at room temperature for 18 hours. The organic phase was washed with water, citric acid solution, saturated aqueous NaHCO$_3$ and brine, dried (Na$_2$SO$_4$) and concentrated in vacuo to afford the title compound (2.41 g, 88%).

$^1$H NMR (500 MHz, CDCl$_3$): δ ppm 7.83 (d, J=8.3 Hz, 1H), 7.60 (d, J=1.7 Hz, 1H), 7.25 (dd, J=8.3, 1.7 Hz, 1H), 6.23 (s, broad, 1H), 4.26 (q, J=7.0 Hz, 2H), 3.05 (d, J=4.9 Hz, 3H), 1.50 (t, J=7.0 Hz, 3H).

LCMS (ESI) Rt=1.09 minutes, MS m/z 225 [M+H]$^+$.

Preparation 59

4-(4,5-dimethyl-4H-1,2,4-triazol-3-yl)-2-ethoxyaniline

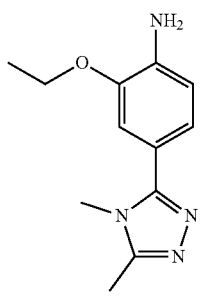 [SMILES: CCOc1cc(-c2nnc(C)n2C)ccc1N]

To a solution of 4-bromo-2-ethoxyaniline (150 mg, 0.694 mmol) in toluene (2 ml) in a microwave vial was added 3,4-dimethyl-triazole (135 mg, 1.39 mmol), Pd(OAc)$_2$ (16 mg, 0.069 mmol), K$_2$CO$_3$ (585 mg, 4.23 mmol), pivalic acid (47 mg, 0.458 mmol) and PCy$_3$.HBF$_4$ (51 mg, 0.139 mmol). The reaction was flushed with nitrogen, sealed and heated to 110° C. for 18 hours. The reaction mixture was concentrated in vacuo. The residue was purified by silica gel column chromatography eluting with 0-20% MeOH in EtOAc to afford the title compound (51 mg, 32%).

$^1$H NMR (500 MHz, MeOH-d$_4$) 7.08 (d, J=1.7 Hz, 1H), 7.02 (dd, J=8.0, 1.7 Hz, 1H), 6.87 (d, J=8.0 Hz, 1H), 4.14 (q, J=7.0 Hz, 2H), 3.64 (s, 3H), 2.49 (s, 3H), 1.47 (t, J=7.0 Hz, 3H).

HRMS (ESI) MS m/z calcd for C$_{12}$H$_{17}$N$_4$O [M+H]$^+$ 233.1402, found 233.1402.

Preparation 60

2-ethoxy-4-(4-ethyl-4H-1,2,4-triazol-3-yl)aniline

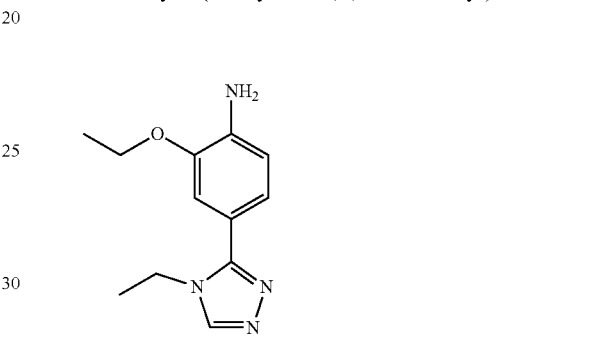

To a solution of 4-bromo-2-ethoxyaniline (75 mg, 0.347 mmol) in toluene (1 ml) in a microwave vial was added 4-ethyl-4H-1,2,4-triazole (50 mg, 0.521 mmol), Pd(OAc)$_2$ (8 mg, 0.035 mmol), K$_2$CO$_3$ (293 mg, 2.12 mmol), pivalic acid (23 mg, 0.229 mmol) and PCy$_3$.HBF$_4$ (26 mg, 0.069 mmol). The reaction was flushed with nitrogen, sealed and heated to 110° C. for 18 hours. The reaction mixture was concentrated in vacuo. The residue was purified by silica gel column chromatography eluting with 0-20% MeOH in EtOAc to afford the title compound (51 mg, 63%).

$^1$H NMR (500 MHz, MeOH-d$_4$): δ ppm 8.57 (s, 1H), 7.08 (d, J=1.8 Hz, 1H), 7.01 (dd, J=8.0, 1.8 Hz, 1H), 6.87 (d, J=8.0 Hz, 1H), 4.20-4.11 (m, 4H), 1.47 (t, J=7.0 Hz, 3H), 1.40 (t, J=7.2 Hz, 3H).

LCMS (ESI) Rt=1.04 minutes, MS m/z 263.0838 [M+H]$^+$.

Alternatively

To a solution of 3-(3-ethoxy-4-nitrophenyl)-4-ethyl-4H-1,2,4-triazole (Preparation 63, 410 mg, 1.563 mmol) in EtOH (25 ml) was added 10% Pd/C (83 mg, 0.078 mmol). The reaction was stirred in an atmosphere of hydrogen (1 atm) at room temperature for 18 hours. 10% Pd/C (83 mg, 0.078 mmol) was added and the reaction mixture stirred in an atmosphere of hydrogen for a further 24 hours. The reaction mixture was filtered through Celite, washed with EtOH and concentrated in vacuo to afford the title compound (280 mg, 77%).

The following Preparations were prepared according to the method described for Preparation 59 using the appropriate aniline and heterocycle as described below. The crude reaction residues were purified as above or according to one of the following Purification Methods (PM): Purification Method A: Silica gel column chromatography eluting with 0-7% MeOH in EtOAc.

| Preparation No | Name/Structure | Data |
| --- | --- | --- |
| 61 | 4-(4,5-dimethyl-4H-1,2,4-triazol-3-yl)-2-methoxyaniline<br>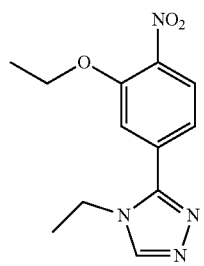 | $^1$H NMR (500 MHz, MeOH-d$_4$): δ ppm 7.10 (d, J = 1.7 Hz, 1H), 7.02 (dd, J = 8.0, 1.7 Hz, 1H), 6.85 (d, J = 8.0 Hz, 1H), 3.91 (s, 3H), 3.64 (s, 3H), 2.49 (s, 3H).<br>HRMS (ESI) MS m/z calcd for C$_{11}$H$_{15}$N$_4$O [M + H]$^+$ 219.1246, found 219.1252.<br>Using 4-bromo-2-methoxyaniline and 3,4-dimethyl-triazole. |
| 62 | 2-(difluoromethoxy)-4-(4-methyl-4H-1,2,4-triazol-3-yl)aniline<br>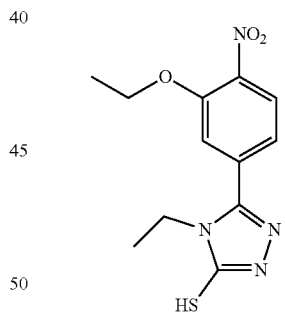 | LCMS (ESI) Rt = 1.07 minutes, MS m/z 241 [M + H]$^+$.<br>Using 4-bromo-2-(difluoromethoxy)aniline and 4-methyl-4H-1,2,4-triazole.<br>PM A. |

Preparation 63

3-(3-ethoxy-4-nitrophenyl)-4-ethyl-4H-1,2,4-triazole

To a cooled (0° C.) suspension of 5-(3-ethoxy-4-nitrophenyl)-4-ethyl-4H-1,2,4-triazole-3-thiol (Preparation 64, 1.0 g, 3.40 mmol) in DCM (11.5 ml) was added a solution of 35% hydrogen peroxide (1.0 ml, 10.19 mmol) in acetic acid (4.67 ml, 82 mmol) dropwise. The reaction was stirred at room temperature for 3 hours. DCM (12 ml) was added, followed by 1M NaOH to obtain a neutral pH. The aqueous layer was re-extracted with DCM. The combined organic layers were dried (MgSO$_4$) and concentrated in vacuo. The residue was purified by silica gel column chromatography eluting with 0-10% MeOH in DCM to afford the title compound (410 mg, 46%).

$^1$H NMR (500 MHz, MeOH-d$_4$) δ ppm 8.73 (s, 1H), 7.97 (d, J=8.1 Hz, 1H), 7.57 (d, J=1.7 Hz, 1H), 7.37 (dd, J=8.1, 1.7 Hz, 1H), 4.30 (q, J=6.9 Hz, 2H), 4.24 (q, J=7.4 Hz, 2H), 1.47 (t, J=6.9 Hz, 3H), 1.43 (t, J=7.4 Hz, 3H).

HRMS (ESI) MS m/z calcd for C$_2$H$_4$BrN$_4$ [M+H]$^+$ 162.9619, found 162.9640.

Preparation 64

5-(3-ethoxy-4-nitrophenyl)-4-ethyl-4H-1,2,4-triazole-3-thiol

To a solution of 3-ethoxy-4-nitrobenzohydrazide (Preparation 57, 1.5 g, 6.66 mmol) in THF (32 ml) was added ethyl isothiocyanate (1.0 ml, 11.32 mmol), followed by triethylamine (0.11 ml, 0.799 mmol). The reaction mixture was stirred at room temperature for 18 hours. Ethyl isothiocyanate (2 ml, 22.64 mmol) added and the reaction stirred for a further 24 hours. Ethyl isothiocyanate (2 ml, 22.64 mmol) added and the reaction stirred for a further 72 hours. The reaction was concentrated in vacuo and the residue redissolved in 1M NaOH (15 ml). The reaction was stirred at 45° C. for 4 hours. The reaction was filtered through Celite and the filtrate extracted with ether. The aqueous layer was acidified with 1M HCl and extracted with EtOAc. The combined organic layer was washed with water and brine, dried (MgSO$_4$) and concentrated in vacuo to afford the title compound (1.0 g, 51%).

$^1$H NMR (500 MHz, MeOH-d$_4$) δ ppm 7.96 (d, J=8.2 Hz, 1H), 7.56 (d, J=1.6 Hz, 1H), 7.37 (dd, J=8.2, 1.6 Hz, 1H), 4.29 (q, J=6.9 Hz, 2H), 4.21 (q, J=7.0 Hz, 2H), 1.47 (t, J=6.9 Hz, 3H), 1.30 (t, J=7.0 Hz, 3H).

HRMS (ESI) MS m/z calcd for C$_{12}$H$_{15}$N$_4$O$_3$S [M+H]$^+$ 295.0865, found 295.0857.

Preparation 65

5-bromo-1-methyl-1H-tetrazole

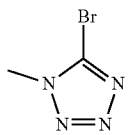

A suspension of zinc bromide (1.20 g, 5.33 mmol) and 1-methyl-1H-tetrazole-5-thiol (302 mg, 2.60 mmol) in AcOH (6 mL) was heated to 40° C. When homogeneous, AcOOH (39% w/w in AcOH, 2.65 mL, 15.64 mmol) was added. The resulting mixture was heated to 80° C. for 18 hours. The reaction was diluted with water, NaHCO$_3$ (solid) was added until pH 6/7 was reached and the resulting solution was extracted with EtOAc. The combined organics were washed with 1M Na$_2$SO$_3$, saturated aqueous NaHCO$_3$, water and brine, dried (MgSO$_4$) and concentrated in vacuo to afford the title compound (276 mg, 65%).

$^1$H NMR (500 MHz, CDCl$_3$): δ ppm 4.10 (s, 3H).

HRMS (ESI) MS m/z calcd for C$_2$H$_4$BrN$_4$ [M+H]$^+$ 162.9619, found 162.9640.

Preparation 66

3-ethyl-3-methoxyazetidine hydrochloride

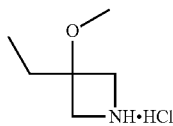

A solution of 1-benzhydryl-3-ethyl-3-methoxyazetidine (Preparation 68, 340 mg, 1.208 mmol) was dissolved in acetonitrile (8 mL), treated with 1-chloroethyl chloroformate (175 μL, 1.628 mmol) at 0° C. and then refluxed for 1 hour. The mixture was concentrated in vacuo, redissolved in MeOH (8 mL) and refluxed for 1.5 hours. The solution was concentrated in vacuo, the residue dissolved in water (8 mL) and washed with cyclohexane twice. The aqueous layer was concentrated in vacuo and co-evaporated with EtOH (three times) and DCM (twice) to afford the title compound (173 mg, 95%).

$^1$H NMR (500 MHz, DMSO-d$_6$): δ ppm 9.29 (br s, 1H), 9.17 (br s, 1H), 3.83 (br s, 2H), 3.73 (br s, 2H), 3.13 (s, 3H), 1.84 (q, J=7.3 Hz, 2H), 0.77 (t, J=7.3 Hz, 3H).

The following Preparation was prepared according to the method described for Preparation 66 using the appropriate azetidine as described below. The crude reaction residue was purified as above.

| Preparation No | Name/Structure | Data |
|---|---|---|
| 67 | 3-methyl-3-ethoxyazetidine hydrochloride 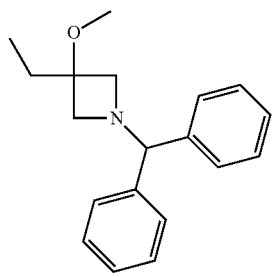 [SMILES: CCC1(OC)CN(C(c2ccccc2)c2ccccc2)C1] | $^1$H NMR (500 MHz, DMSO-d$_6$): δ ppm 9.25 (br s, 1H), 9.07 (br s, 1H), 3.91-3.82 (m, 2H), 3.80-3.68 (m, 2H), 3.39 (q, J = 7.0 Hz, 2H), 1.46 (s, 3H), 1.12 (t, J = 7.0 Hz, 3H). Using 1-benzhydryl-3-ethoxy-3-methylazetidine (Preparation 69). |

Preparation 68

1-benzhydryl-3-ethyl-3-methoxyazetidine

A solution of 1-benzhydryl-3-ethylazetidin-3-ol (Preparation 70, 490 mg, 1.833 mmol) in DMF (10 mL) was cooled to 0° C., treated with sodium hydride (60% w/w in mineral oil, 115 mg, 2.88 mmol) and stirred at room temperature for 90 minutes. The mixture was cooled to 0° C., treated with methyl iodide (150 μL, 2.41 mmol) and stirred at room temperature for 2.5 hours. The reaction was quenched with water and extracted with EtOAc. The combined organics were washed with water and brine, dried (MgSO$_4$) and concentrated in vacuo. The residue was purified by silica gel column chromatography eluting with 0-5% EtOAc in cyclohexane to afford the title compound (347 mg, 67%).

$^1$H NMR (500 MHz, CDCl$_3$): δ ppm 7.48-7.42 (m, 4H), 7.32-7.26 (m, 4H), 7.23-7.17 (m, 2H), 4.42 (s, 1H), 3.17 (s, 3H), 3.16-3.12 (m, 2H), 3.00 (d, J=8.6 Hz, 2H), 1.88 (q, J=7.4 Hz, 2H), 0.92 (t, J=7.4 Hz, 3H).

HRMS (ESI) MS m/z calcd for C$_{19}$H$_{24}$NO [M+H]$^+$ 282.1858, found 282.1860.

The following Preparation was prepared according to the method described for Preparation 68 using the appropriate azetidinol and alkylating reagent as described below. The crude reaction residue was purified as above.

| Preparation No | Name/Structure | Data |
|---|---|---|
| 69 | 1-benzhydryl-3-ethoxy-3-methylazetidine 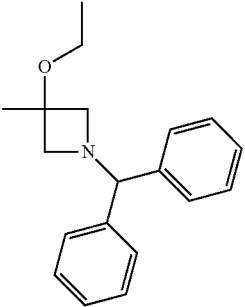 | $^1$H NMR (500 MHz, CDCl$_3$): δ ppm 7.47-7.39 (m, 4H), 7.31-7.24 (m, 4H), 7.22-7.14 (m, 2H), 4.41 (s, 1H), 3.37 (q, J = 7.0 Hz, 2H), 3.18-3.09 (m, 2H), 3.03-2.92 (m, 2H), 1.54 (s, 3H), 1.19 (t, J = 7.0 Hz, 3H). HRMS (ESI) MS m/z calcd for C$_{19}$H$_{24}$NO [M + H]$^+$ 282.1858, found 282.1845. Using 1-benzhydryl-3-methylazetidin-3-ol (Preparation 71) and ethyl bromide at room temperature for 18 hours. |

Preparation 70

1-benzhydryl-3-ethylazetidin-3-ol

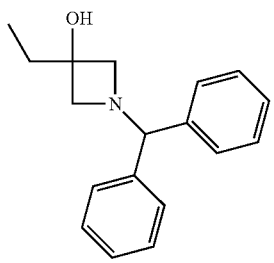 [SMILES: CCC1(O)CN(C(c2ccccc2)c2ccccc2)C1]

A solution of 1-benzhydrylazetidin-3-one (500 mg, 2.107 mmol) in THF (10 mL) was treated with EtMgCl (2M in THF, 2.2 ml, 4.40 mmol) at 0° C. and stirred at room temperature for 1 hour. The mixture was quenched with saturated aqueous NH$_4$Cl and extracted with EtOAc. The combined organics were washed with water and brine, dried (MgSO$_4$) and concentrated in vacuo. The residue was purified by silica gel column chromatography eluting with 0-20% EtOAc in cyclohexane to afford the title compound (492 mg, 87%).

$^1$H NMR (500 MHz, CDCl$_3$): δ ppm 7.50-7.37 (m, 4H), 7.32-7.25 (m, 4H), 7.25-7.15 (m, 2H), 4.39 (s, 1H), 3.23 (d, J=8.9 Hz, 2H), 2.97 (d, J=8.8 Hz, 2H), 1.93 (s, 1H), 1.83 (q, J=7.4 Hz, 2H), 0.99 (t, J=7.4 Hz, 3H).

HRMS (ESI) MS m/z calcd for C$_{18}$H$_{22}$NO [M+H]$^+$ 268.1701, found 268.1699.

The following Preparation was prepared according to the method described for Preparation 70 using the appropriate magnesium reagent as described below. The crude reaction residue was purified as above.

| Preparation No | Name/Structure | Data |
|---|---|---|
| 71 | 1-benzhydryl-3-methylazetidin-3-ol 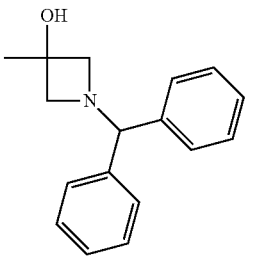 | $^1$H NMR (500 MHz, CDCl$_3$): δ ppm 7.48-7.36 (m, 4H), 7.32-7.24 (m, 4H), 7.22-7.16 (m, 2H), 4.37 (s, 1H), 3.23-3.18 (m, 2H), 3.01-2.97 (m, 2H), 1.97 (br s, 1H), 1.54 (s 3H). HRMS (ESI) MS m/z calcd for C$_{17}$H$_{20}$NO [M + H]$^+$ 254.1545, found 254.1553. Using MeMgBr (3M in Et$_2$O) |

The invention claimed is:
1. A compound selected from:
(S)-N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine

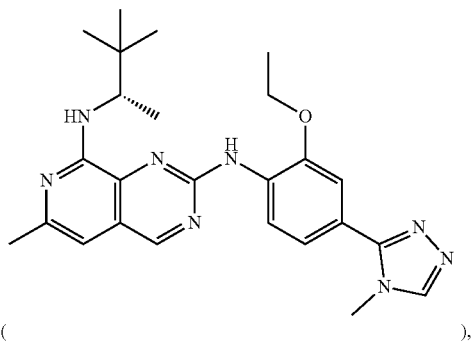 [SMILES: CCOc1cc(-c2nncn2C)ccc1Nc1ncc2cc(C)nc(N[C@@H](C)C(C)(C)C)c2n1]

( ), and
N2-(4-(4,5-dimethyl-4H-1,2,4-triazol-3-yl)-2-ethoxyphenyl)-6-methyl-N8-neopentylpyrido[3,4-d]pyrimidine-2,8-diamine

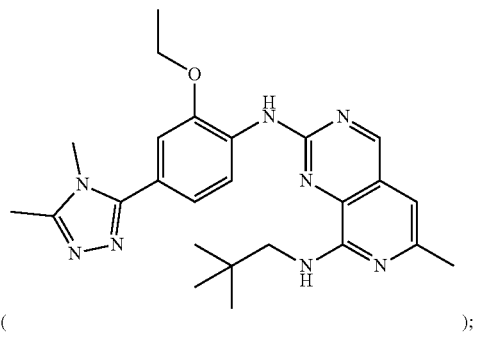

( );

or a pharmaceutically acceptable salt or solvate thereof.

2. A pharmaceutical composition comprising a compound according to claim 1, or a pharmaceutically acceptable salt or solvate thereof, in admixture with a pharmaceutically acceptable diluent or carrier.

3. A compound according to claim 1, wherein said compound is N2-(4-(4,5-dimethyl-4H-1,2,4-triazol-3-yl)-2-ethoxyphenyl)-6-methyl-N8-neopentylpyrido [3,4-d]pyrimidine-2, 8-diamine

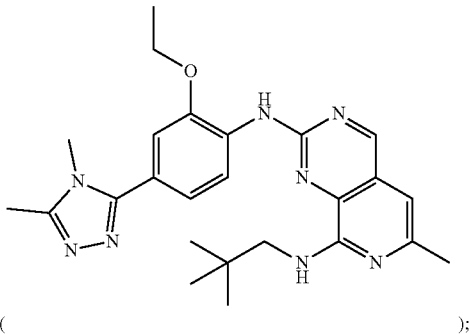

( );

or a pharmaceutically acceptable salt thereof.

4. A compound according to claim 1, wherein said compound is (S)-N8-(3,3-dimethylbutan-2-yl)-N2-(2-ethoxy-4-(4-methyl-4H-1,2,4-triazol-3-yl)phenyl)-6-methylpyrido[3,4-d]pyrimidine-2,8-diamine[H]

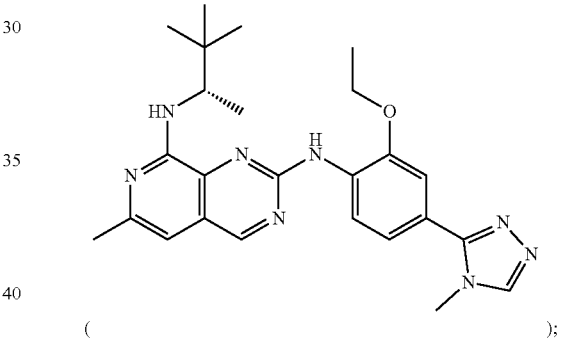

( );

or a pharmaceutically acceptable salt thereof.

* * * * *